(12) United States Patent
Jayawickreme et al.

(10) Patent No.: US 11,548,853 B2
(45) Date of Patent: Jan. 10, 2023

(54) ISOQUINOLINE COMPOUNDS AND THEIR USE IN TREATING AHR IMBALANCE

(71) Applicant: Dermavant Sciences GmbH, Basel (CH)

(72) Inventors: Channa K. Jayawickreme, Morrisville, NC (US); Susan H. Smith, Pennsburg, PA (US); Cunyu Zhang, Devon, PA (US); William Zuercher, Mies (CH)

(73) Assignee: DERMAVANT SCIENCES GMBH, Basel (CH)

(*) Notice: Subject to any disclaimer, the term of this patent is extended or adjusted under 35 U.S.C. 154(b) by 0 days.

(21) Appl. No.: 17/587,812

(22) Filed: Jan. 28, 2022

(65) Prior Publication Data
US 2022/0153703 A1 May 19, 2022

Related U.S. Application Data

(62) Division of application No. 17/332,805, filed on May 27, 2021, now Pat. No. 11,267,788.

(60) Provisional application No. 63/052,561, filed on Jul. 16, 2020, provisional application No. 63/052,574, filed on Jul. 16, 2020.

(51) Int. Cl.
| | | |
|---|---|---|
| A61K 31/47 | (2006.01) | |
| C07D 217/20 | (2006.01) | |
| A61P 29/00 | (2006.01) | |
| A61K 9/00 | (2006.01) | |

(52) U.S. Cl.
CPC .......... *C07D 217/20* (2013.01); *A61K 9/0014* (2013.01); *A61K 31/47* (2013.01); *A61P 29/00* (2018.01)

(58) Field of Classification Search
CPC .... C07D 217/20; A61K 9/0014; A61K 31/47; A61P 29/00

USPC ......................................................... 514/307
See application file for complete search history.

(56) References Cited

U.S. PATENT DOCUMENTS

| | | |
|---|---|---|
| 5,919,970 A | 7/1999 | Song et al. |
| 6,316,495 B1 | 11/2001 | Kun et al. |
| 6,897,206 B2 | 5/2005 | Sackeyfio et al. |
| 9,604,997 B2 | 3/2017 | Jordan et al. |
| 10,626,094 B2 | 4/2020 | Bottini et al. |
| 2006/0128702 A1 | 6/2006 | Pal et al. |
| 2007/0155813 A1 | 7/2007 | Kitamura et al. |
| 2010/0092547 A1 | 4/2010 | Prendergast |
| 2010/0120810 A1 | 5/2010 | Leblond et al. |

(Continued)

FOREIGN PATENT DOCUMENTS

WO 2011156626 A1 12/2011

OTHER PUBLICATIONS

Liu M, et.al. Emerging Biological Functions of IL-17A: A New Target in Chronic Obstructive Pulmonary Disease?Front. Pharmacol. 2021; 12:695957. doi:10.3389/fphar.2021.695957.

(Continued)

*Primary Examiner* — Taylor V Oh
(74) *Attorney, Agent, or Firm* — DLA Piper LLP (US)

(57) ABSTRACT

The present invention is directed to novel compounds of Formula (I), or a pharmaceutically acceptable salt, solvate or hydrate thereof. Pharmaceutical compositions comprising a compound of Formula (I), or a pharmaceutically acceptable salt, solvate or hydrate thereof, are also described. The invention is also directed to use of the compounds of Formula (I) for treating a condition in a mammal associated with AhR imbalance, such as an inflammatory disease or disorder.

23 Claims, 38 Drawing Sheets

(56) References Cited

U.S. PATENT DOCUMENTS

| | | |
|---|---|---|
| 2012/0322988 A1 | 12/2012 | Shichiri |
| 2013/0116278 A1 | 5/2013 | Lavoie et al. |
| 2018/0264042 A1 | 9/2018 | Lait et al. |
| 2021/0111345 A1 | 4/2021 | Stoessel et al. |

OTHER PUBLICATIONS

Fujino S, Andoh A, Bamba S, Ogawa A, Hata K, Araki Y, Bamba T, Fujiyama Y. Increased expression of interleukin 17 in inflammatory bowel disease. Gut. Jan. 2003; 52(1):65-70. doi: 10.1136/gut.52.1.65. PMID: 12477762; PMCID: PMC1773503.

Agneta Rannug How the AHR Became Important in Intestinal Homeostasis—A Diurnal FICZ/AHR/CYP1A1 Feedback Controls Both Immunity and Immunopathology; Int J. Mol Sci. 2020, 21, 5681; doi:10.3390/ijms21165681.

Cannon et al. Targeting AhR as a Novel Therapeutic Modality against Inflammator Diseases; Int. J. Mol. Sci. 2022, 23, 288. doi.org/10.3390/ijms23010288.

Jeremy A. Goettel et al. "AHR Activation Is Protective against Colitis Driven by T Cells in Humanized Mice," Cell Reports; 17, 1318-1329 Oct. 25, 2016 doi:10.1016/j.celrep.2016.09.082.

Aneta Grycová et al "Targeting the Aryl Hydrocarbon Receptor with Microbial Metabolite Mimics Alleviates Experimental Colitis in Mice" J. Med. Chem. 2022, 65 (9), 6859-6868 Apr. 13, 2022; doi:10.1021/acs.imedchem.2c00208.

Van Monteleone et al. "Aryl Hydrocarbon Receptor-Induced Signals Up-regulate IL-22 Production and Inhibit Inflammation in the Gastrointestinal Tract" Gastroenterology 2011;141:237-248 doi:10.1053/j.gastro.2011.04.007.

Nicholas Dopkins et al. "Tryptamine Attenuates Experimental Multiple Sclerosis Through Activation of Aryl Hydrocarbon Receptor" Front Pharmacol 11:619265. doi:10.3389/fphar.2020.619265.

Veit Rothhammer et al. "Type I interferons and microbial metabolites of tryptophan modulate astrocyte activity and CNS inflammation via the aryl hydrocarbon receptor" Nat Med. Jun. 2016 ; 22(6): 586-597. doi:10.1038/nm.4106.

Lina Zhang, et al. "Suppression of Experimental Autoimmune Uveoretinitis by Inducing Differentiation of Regulatory T Cells via Activation of Aryl Hydrocarbon Receptor" Investigative Ophthalmology & Visual Science, Apr. 2010, 51 (4) 2109-2117.

Peng Hu et al. "Aryl Hydrocarbon Receptor Deficiency Causes Dysregulated Cellular Matrix Metabolism and Age-related Macular Degeneration-Like Pathology" Oct. 2013; 110(43) E4069-E4078 doi: 10.1073/pnas .1307574110.

Lindsey F. Nugent et al. "ITE, A Novel Endogenous Nontoxic Aryl Hydrocarbon Receptor Ligand, Efficiently Suppresses EAU and T-Cell-Mediated Immunity" Invest Ophthalmol Vis Sci. 2013; 54:7463-7469. DOI:10.1167/iovs.12-11479.

Soo-Young Kim et al. "Deletion of Aryl Hydrocarbon Receptor AHR in Mice Leads to Subretinal Accumulation of Microglia and RPE Atrophy" Invest Ophthalmol Vis Sci. 2014; 55: 6031-6040. DOI:10.1167/iovs.14-15091.

Chaokui Wang et al. "Decreased Expression of the Aryl Hydrocarbon Receptor in Ocular Behcet's Disease" Hindawi Publishing Corporation; Mediators of Inflammation; 2014, Article ID 195094, 11 pages doi:10.1155/2014/195094.

Mayur Choudhary, et al. "Aryl hydrocarbon receptor knock-out exacerbates choroidal neovascularization via multiple pathogenic pathways" J Pathol 2015; 235: 101-112 DOI: 10.1002/path.4433.

Mark A. Gutierrez et al. "A Novel Ahr Ligand, 2AI, Protects the Retina From Environmental Stress" Scientific Reports 6:29025 DOI:10.1038/srep29025 1-11.

Hong Lan Jin et al. "Crosstalk between Aryl Hydrocarbon Receptor and Glucocorticoid Receptor in Human Retinal Pigment Epithelial Cells" Hindawi International Journal of Endocrinology vol. 2017, Article ID 5679517, 9 pages; doi:10.1155/2017/5679517.

Mayur Choudhary et al. "The Aryl Hydrocarbon Receptor: A Mediator and Potential Therapeutic Target for Ocular and Non-Ocular Neurodegenerative Diseases" Int. J. Mol Sci. 2020, 21, 6777; doi:10.3390/ijms21186777.

Huijun He et al. "Glycyrrhizin Protects Against Sodium Iodate-Induced RPE And Retinal Injury Though Activation Of AKT And Nrf2/HO-1 Pathway"; J Cell Mol Med. 2019; 23:3495-3504.

Khan and Langman "Indole-3-Carbinol Regulates Microglia Homeostasis And Protects The Retina From Degeneration" Journal of Neuroinflammation (2020) 17:327 1-14 doi:10.1186/s12974-020-01999-8.

Di Meglio et al., "Activation of the Aryl Hydrocarbon Receptor Dampens the Severity of Inflammatory Skin Conditions," Immunity, Jun. 19, 2014; 40(6): 989-1001.

International Search Report and Written Opinion for International PCT Application No. PCT/US2021/034599 dated Oct. 4, 2021.

Liao et al., "Enantioselective Total Syntheses of (−)-Taiwaniaquinone H and (−)-Taiwaniaquinol B by Iridium-Catalyzed Borylation and Palladium-Catalyzed Asymmetric α-Arylation," J. Am. Chem. Soc. 2011, 133, 2088-2091.

Smith et al. "Development of a Topical Treatment for Psoriasis Targeting RORγ: From Bench to Skin," Plos One, Feb. 12, 2016, pp. 1-18.

Smith et al., "Tapinarof is a Natural AhR Agonist that Resolves Skin Inflammation in Mice and Humans," Journal of Investigative Dermatology (2017) 137, 2110-2119.

ISOQUINOLINE COMPOUNDS AND THEIR USE IN TREATING AHR IMBALANCE

CROSS REFERENCE TO RELATED APPLICATION

The present application is a Divisional of U.S. application Ser. No. 17/332,805, entitled "ISOQUINOLINE COMPOUNDS AND THEIR USE IN TREATING AhR IMBALANCE", filed May 27, 2021, now U.S. Pat. No. 11,267,788, which claims benefit of and priority to U.S. Provisional No. 63/052,561 entitled "ISOQUINOLINE COMPOUNDS AND THEIR USE IN TREATING AhR IMBALANCE," filed Jul. 16, 2020; and U.S. Provisional No. 63/052,574 entitled "ISOQUINOLINE COMPOUNDS AND THEIR USE IN TREATING AhR IMBALANCE," filed Jul. 16, 2020; the contents of which are hereby incorporated by reference in their entirety.

SUMMARY OF THE INVENTION

Various embodiments provide compounds and compositions, and methods for the treatment and prevention of conditions associated with AhR imbalance, AhR mediated diseases and inflammatory disorders comprising administering such compounds and compositions. Compounds described herein bind and activates the Aryl hydrocarbon Receptor (AhR), providing a novel class of anti-inflammatory compounds with AhR-dependent cytokine modulation useful for the treatment of inflammatory disease states.

Some embodiments disclosed herein are directed to a compound of Formula (I) or a salt, solvate or hydrate thereof

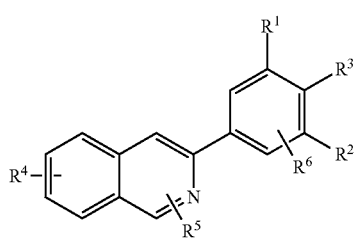

(I)

wherein each of $R^1$ and $R^2$ is independently selected from the group consisting of OH, $OR^7$, and H, provided that at least one of $R^1$ and $R^2$ is —OH or —$OR^7$;

$R^7$ is independently selected from the group consisting of optionally substituted $C_{1-6}$ alkyl, optionally substituted $C_{3-6}$ cycloalkyl, optionally substituted aryl, aryl $C_{1-6}$ alkyl and acyl;

$R^3$ is selected from the group consisting of optionally substituted $C_{1-6}$ alkyl, optionally substituted $C_{2-6}$ alkenyl, optionally substituted $C_{2-6}$ alkynyl, optionally substituted aryl, optionally substituted aryl $C_{1-6}$ alkyl, optionally substituted $C_{3-6}$ cycloalkyl, optionally substituted $C_{4-6}$ cycloalkenyl, halo, cyano, —$C(O)OR^8$, —$NR^9R^{10}$, —$S(O)_2NR^9R^{10}$, —$C(O)R^{11}$, —$OR^{12}$, —$S(O)_nR^{13}$, and optionally substituted heterocyclyl;

$R^8$ is selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl;

each of $R^9$ and $R^{10}$ is independently selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl, or alternatively, $R^9$ and $R^{10}$ together with the nitrogen atom to which they are attached form a 5-7 membered cyclic saturated or unsaturated ring;

$R^{11}$ is independently selected from the group consisting of H, optionally substituted $C_{1-6}$ alkyl, optionally substituted $C_{2-6}$ alkenyl, optionally substituted $C_{2-6}$ alkynyl, optionally substituted aryl, optionally substituted aryl $C_{1-6}$ alkyl, optionally substituted $C_{3-6}$ cycloalkyl, —$NR^9R^{10}$, and —$OR^{12}$;

each of $R^{12}$ and $R^{13}$ is independently selected from the group consisting of H, optionally substituted alkyl, optionally substituted alkenyl, optionally substituted alkynyl, optionally substituted aryl, optionally substituted aryl $C_{1-6}$ alkyl, and optionally substituted $C_{3-6}$ cycloalkyl;

$R^6$ is selected from the group consisting of H, halo, hydroxyl, alkoxy, optionally substituted $C_{1-6}$ alkyl, halogenated alkyl; optionally substituted $C_{2-6}$ alkenyl, optionally substituted $C_{2-6}$ alkynyl, and optionally substituted aryl $C_{1-6}$ alkyl;

n is an integer having a value of 0, 1 or 2;
s is an integer having a value of 0, 1 or 2;
t is an integer having a value of 0 to 6;

$R^5$ is selected from the group consisting of H, halo, optionally substituted $C_{1-6}$ alkyl, —$C(O)OR^{14}$, —$C(O)NR^{15}R^{16}$, aryl and —$C_{1-6}$ alkylaryl;

$R^{14}$ is selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl;

each of $R^{15}$ and $R^{16}$ is independently selected from the group consisting of H, optionally substituted $C_{1-6}$ alkyl, optionally substituted $C_{3-6}$ cycloalkyl, optionally substituted aryl, optionally substituted aryl $C_{1-6}$ alkyl, and optionally substituted $C_{3-6}$ cycloalkyl; alternatively $R^{15}$ and $R^{16}$ together with the nitrogen to which they are attached, form a 5-7 membered cyclic saturated or unsaturated ring;

$R^4$ is selected from the group consisting of H, halo, cyano, optionally substituted $C_{1-6}$ alkyl, optionally substituted $C_{2-6}$ alkenyl, optionally substituted $C_{2-6}$ alkynyl, optionally substituted aryl, optionally substituted aryl $C_{1-6}$ alkyl, optionally substituted $C_{3-6}$ cycloalkyl, —$(CR^{18}R^{19})_tCOOR^8$, —$(CR^{18}R^{19})_tOC(O)R^8$, —$(CR^{18}R^{19})_tNR^9R^{10}$, —$(CR^{18}R^{19})_tC(O)NR^9R^{10}$, —$(CR^{18}R^{19})_tNR^9C(O)R^8$, —$(CR^{18}R^{19})_tS(O)_2NR^9R^{10}$, —$(CR^{18}R^{19})_tCOR^{11}$, —$(CR^{18}R^{19})_tCH(O)$, —$(CR^{18}R^{19})_tOR^{12}$, —$(CR^{18}R^{19})_tS(O)_rR^{13}$, optionally substituted heterocyclic, and optionally substituted heterocyclic $C_{1-6}$ alkyl; and each of $R^{18}$ and $R^{19}$ is independently selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl.

Some embodiments are directed to a compound selected from the group consisting of:

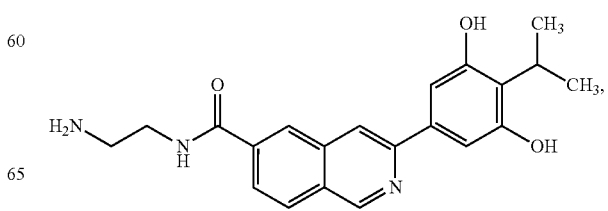

-continued

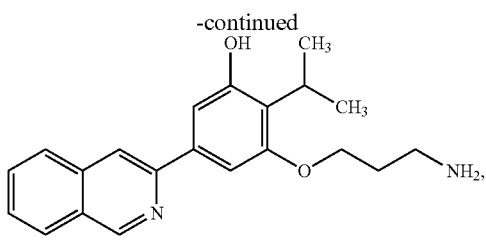

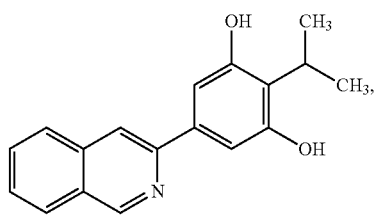

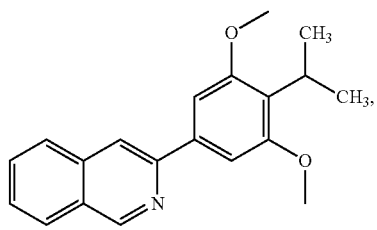

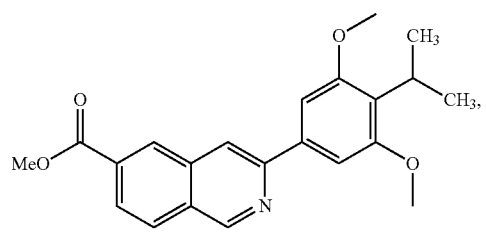

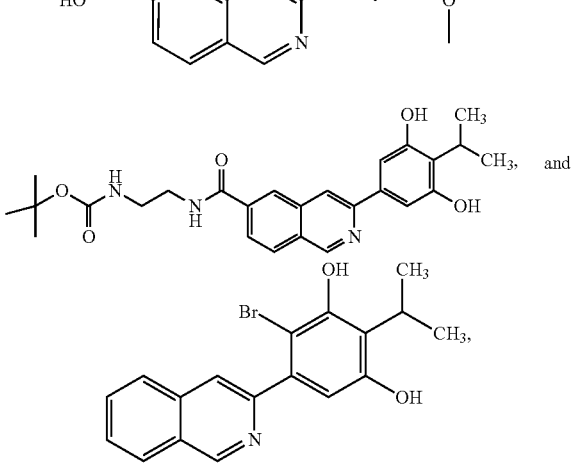

or a salt, solvate or hydrate thereof.

Some embodiments are directed to a compound of the formula

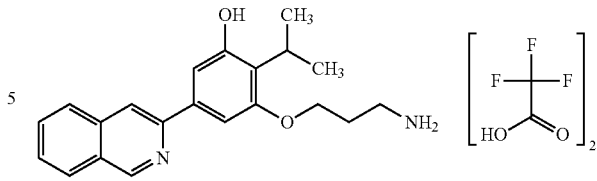

Some embodiments are directed to a compound of the formula

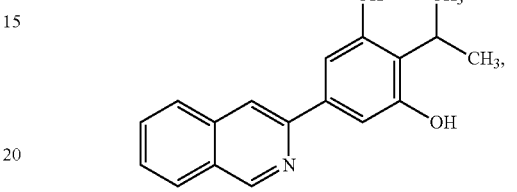

or a pharmaceutically acceptable salt, solvate of hydrate thereof.

Some embodiments are directed to 2-isopropyl-5-(isoquinolin-3-yl)benzene-1,3-diol, or a pharmaceutically acceptable salt solvate of hydrate thereof.

Some embodiments describe a compound of Formula (II) or a salt solvate or hydrate thereof:

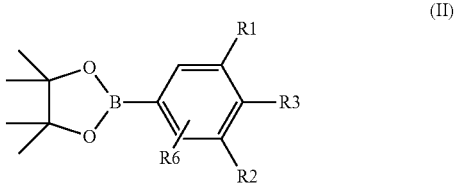

wherein each $R^1$ and $R^2$ is independently selected from the group consisting of OH, $OR^7$, and H, provided that at least one of $R^1$ and $R^2$ is OH or $OR^7$;

$R^7$ is independently selected from the group consisting of optionally substituted $C_{1-6}$ alkyl, optionally substituted $C_{3-6}$ cycloalkyl, optionally substituted aryl, optionally substituted aryl $C_{1-6}$ alkyl, and acyl;

$R^3$ is selected from optionally substituted $C_{1-6}$ alkyl, optionally substituted $C_{2-6}$ alkenyl, optionally substituted $C_{2-6}$ alkynyl, optionally substituted aryl, optionally substituted aryl $C_{1-6}$ alkyl, optionally substituted $C_{3-6}$ cycloalkyl, optionally substituted $C_{4-6}$ cycloalkenyl, halo, cyano, —C(O)$OR^8$, —$NR^9R^{10}$, —$S(O)_2NR^9R^{10}$, —C(O)$R^{11}$, —$OR^{12}$, —S(O). $R^{13}$ and optionally substituted heterocyclic ring;

n is an integer having a value of 0, 1 or 2;

$R^6$ is H;

$R^8$ is selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl;

each of $R^9$ and $R^{10}$ is independently selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl; alternatively, $R^9$ and $R^{10}$ together with the nitrogen atom to which they are attached, form a 5-7 membered cyclic saturated or unsaturated ring;

$R^{11}$ is selected from the group consisting of H, optionally substituted $C_{1-6}$ alkyl, optionally substituted $C_{2-6}$ alkenyl, optionally substituted $C_{2-6}$ alkynyl, optionally substituted aryl, optionally substituted aryl $C_{1-6}$ alkyl, optionally substituted $C_{3-6}$ cycloalkyl; —$NR^9R^{10}$, and —$OR^{12}$;

each of $R^{12}$ and $R^{13}$ is independently is selected from the group consisting of H, optionally substituted alkyl, optionally substituted alkenyl, optionally substituted alkynyl, optionally substituted aryl, optionally substituted aryl $C_{1-6}$ alkyl, and optionally substituted $C_{3-6}$ cycloalkyl; and $R^6$ is selected from the group consisting of halo, hydroxyl, alkoxy, optionally substituted $C_{1-6}$ alkyl, halogenated alkyl, optionally substituted $C_{2-6}$ alkenyl, optionally substituted $C_{2-6}$ alkynyl, and optionally substituted aryl $C_{1-6}$ alkyl.

Some embodiments herein describe a pharmaceutical composition comprising: a compound according to any embodiment described herein, or a pharmaceutically acceptable salt, solvate or hydrate thereof; and a pharmaceutically acceptable carrier or diluent.

Some embodiments describe a method of treating or preventing a condition in a mammal associated with AhR imbalance, comprising administering to the mammal a therapeutically effective amount of any compound or pharmaceutical composition described herein.

Some embodiments describe a method of treating or preventing an inflammatory disorder in a subject, comprising administering to the subject a therapeutically effective amount of any compound or pharmaceutical composition described herein. In some embodiments the inflammatory disorder is selected from the group consisting of psoriasis, atopic dermatitis, vitiligo, acne, neovascular (dry) AMD, neovascular (wet) AMD, uveitis or other inflammatory eye conditions, radiation dermatitis, COPD, asthma, multiple sclerosis (MS), and inflammatory bowel disease. In some embodiments the inflammatory disorder is psoriasis or atopic dermatitis. In some embodiments the compound or a pharmaceutical composition described herein is administered topically.

Some embodiments describe a method of treating or preventing psoriasis or atopic dermatitis in a subject in need thereof, comprising administering to the subject an effective amount of 2-isopropyl-5-(isoquinolin-3-yl)benzene-1,3-diol, or a pharmaceutically acceptable salt, solvate or hydrate thereof.

Some embodiments describe a process for preparing a compound of Formula

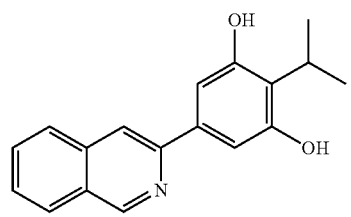

8 or a pharmaceutically acceptable salt, solvate or hydrate thereof, comprising:

a) preparing a compound of Formula 5

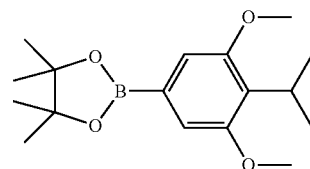

5 or a pharmaceutically acceptable salt, solvate or hydrate thereof, comprising
1) alkylating 2,6-dihydroxyacetophenone or a pharmaceutically acceptable salt, solvate or hydrate thereof, to form a compound of Formula 2

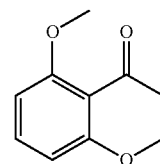

2 or a pharmaceutically acceptable salt, solvate or hydrate thereof;
2) treating the ketone of Formula 2 or a pharmaceutically acceptable salt, solvate or hydrate thereof with a Grignard reagent, followed by elimination of water under acidic conditions to form a compound of Formula 3

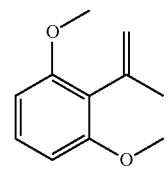

3 or a pharmaceutically acceptable salt, solvate or hydrate thereof;
3) hydrogenating the compound of Formula 3 or a pharmaceutically acceptable salt, solvate or hydrate thereof to form a compound of Formula 4

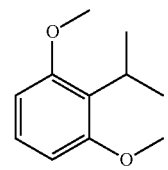

4 or a pharmaceutically acceptable salt, solvate or hydrate thereof; and
4) borylating the compound of Formula 4 or a pharmaceutically acceptable salt, solvate or hydrate thereof to form the compound of Formula 5
or a pharmaceutically acceptable salt, solvate or hydrate thereof;

b) preparing a compound of Formula 6

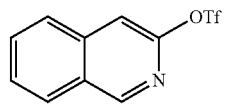

or a pharmaceutically acceptable salt, solvate or hydrate thereof comprising treating isoquinoline-3-ol with a triflating agent; and c) coupling the compound of Formula 6 or a pharmaceutically acceptable salt, solvate or hydrate thereof with the compound of Formula 5 or a pharmaceutically acceptable salt, solvate or hydrate thereof to form a compound of Formula 7

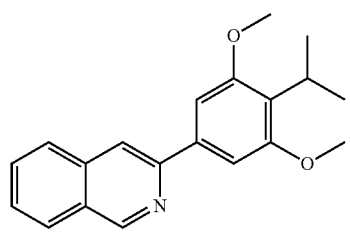

or a pharmaceutically acceptable salt, solvate or hydrate thereof; and d) demethylating the compound of Formula 7 to form the compound of Formula 8. or a pharmaceutically acceptable salt, solvate or hydrate thereof; wherein steps a and b can be done in either order or simultaneously in different reaction vessels.

DESCRIPTION OF THE DRAWINGS

FIGS. 1A to 1G shows the BioMAP profile of 2-isopropyl-5-(isoquinolin-3-yl)benzene-1,3-diol alone at concentrations of 1.0 µM, 0.33 µM, 0.11 µM, and 0.037 µM, FIGS. 1O to 1U shows the BioMAP profile of 2-isopropyl-5-(isoquinolin-3-yl)benzene-1,3-diol at 1 µM (light gray) overlaid with tapinarof (1 µM; dark gray). The shaded grey area represents normal variation. Common analytes outside normal variation are annotated.

FIG. 2A shows suppression of IL-17A in human peripheral blood CD4+ T-cells by 2-isopropyl-5-(isoquinolin-3-yl)benzene-1,3-diol (triangle) and tapinarof (circle) in a dose dependent manner under Th17 polarizing conditions. Points represent percent maximum expression of protein compared to Th17 from six combined donors; 3 biological replicates per treatment. Error bars represent standard error of mean. FIG. 2B shows cell viability in human peripheral blood CD4+ T-cells under Th17 polarizing conditions and increasing concentrations of 2-isopropyl-5-(isoquinolin-3-yl)benzene-1,3-diol (diamond) and tapinarof (circle) over 5 days. Data are mean±standard error from 3 to 9 experimental data points. FIG. 2C shows cell viability in human primary keratinocytes. Cell viability was quantitated after treatment with increasing concentrations of 2-isopropyl-5-(isoquinolin-3-yl)benzene-1,3-diol (triangle) and tapinarof (circle) for two days. Error bars represent mean±standard error of 10-15 biological replicates.

FIG. 3A shows the relative expression of CYP1A1 mRNA transcripts after 24 hours using qRT-PCR. FIG. 3B shows relative expression of IL-17A mRNA transcripts after 24 hours using qRT-PCR. Data are represented as the mean from 3 or 4 biological replicates±standard error. Student's t-test was used to determine statistical significance, *p<0.05.

In FIG. 5A plot the diamond represents vehicle (60% EtOH 40% water)+vanicream; the square represents vehicle+imiquimod (5%); the X represents 0.3% 2-isopropyl-5-(isoquinolin-3-yl)benzene-1,3-diol (60% EtOH 40% water)+imiquimod (5%). The other lines have no relevance to the present application and are thus not identified. In FIG. 5B the epidermal thickness was measured on histology sections of back skin taken on the last day of treatment. The triangle bar represents the vehicle (60% EtOH 40% water)+vanicream; the oval bar represents vehicle+imiquimod (5%); the solid bar represents 0.3% 2-isopropyl-5-(isoquinolin-3-yl)benzene-1,3-diol (60% EtOH 40% water)+imiquimod (5%). In FIG. 5C plot the diamond represents vehicle (60% EtOH 40% water)+vanicream; the square represents vehicle+imiquimod (5%); the X represents 0.1% 2-isopropyl-5-(isoquinolin-3-yl)benzene-1,3-diol (60% EtOH 40% water)+imiquimod (5%) and the circle represents 0.3% 2-isopropyl-5-(isoquinolin-3-yl)benzene-1,3-diol (60% EtOH 40% water)+imiquimod (5%). In FIG. 5D the the epidermal thickness was measured on histology sections of back skin taken on the last day of treatment. The triangle bar represents the vehicle (60% EtOH 40% water)+vanicream; the oval bar represents vehicle+imiquimod (5%); the square bar represents 0.1% 2-isopropyl-5-(isoquinolin-3-yl)benzene-1,3-diol (60% EtOH 40% water)+imiquimod (5%); and the solid bar represents 0.3% 2-isopropyl-5-(isoquinolin-3-yl)benzene-1,3-diol (60% EtOH 40% water)+imiquimod (5%). In FIG. 5E, a second 9-day IMQ study was performed using 0.1% cream formulation 1 (square), 0.5% cream formulation 1 (X), and 1% cream formulation 1 (star). 0% cream formulation 1+vanicream is represented by a diamond and 0% cream formulation 1+imiquimod is represented by a circle. In FIG. 5F the the epidermal thickness was measured on histology sections of back skin taken on the last day of treatment. The triangle bar represents the vehicle (0% cream formulation 1)+vanicream; the oval bar represents vehicle+imiquimod (5%); the square bar represents 0.1% cream formulation 1+imiquimod (5%); the solid bar represents 0.5% 2 cream formulation 1+imiquimod (5%) and the star bar represents 1% cream formulation 1+imiquimod.

FIG. 6A shows a schematic of experimental design. Mice were sensitized to DNFB on day 1 and challenged with DNFB every 2-3 days starting 5 days later. Topical formulations of 2-isopropyl-5-(isoquinolin-3-yl)benzene-1,3-diol were applied daily beginning at day 5. FIG. 6B shows measures of epidermal thickness and FIG. 6C shows measures of dermal thickness in response to topical application of 1% 2-isopropyl-5-(isoquinolin-3-yl) benzene-1,3-diol or 0.3% 2-isopropyl-5-(isoquinolin-3-yl) benzene-1,3-diol in 60% ethanolic solutions (60% EtOH, 40% water) twice per day (BID). In FIGS. 6B and 6C the squared bar represents solvent (acetone/olive oil (4:1 vol:vol)+vehicle (60% EtOH, 40% water), the diamond bar represents 0.15% DNFB (in acetone/olive oil (4:1 vol:vol)+vehicle (60% EtOH, 40% water), the star bar represents 0.15% DNFB (in acetone/olive oil (4:1 vol:vol)+1% 2-isopropyl-5-(isoquinolin-3-yl)benzene-1,3-diol in ethanolic solution (60% EtOH, 40% water), the solid bar represents 0.15% DNFB (in acetone/olive oil (4:1 vol:vol))+0.3% 2-isopropyl-5-(isoquinolin-3-yl)benzene-1,3-diol in ethanolic solution (60% EtOH, 40% water), and the hexagon bar represents 0.15% DNFB (in acetone/olive oil (4:1 vol:vol). FIG. 6D shows measures of epidermal thickness and FIG. 6E show dermal thickness in response to topical application of 0% cream formulation 1 or 0% cream formulation 1 once per day. In FIGS. 6D and 6E the squared bar represents acetone/olive oil (4:1 vol:vol)+vehicle (60% EtOH, 40% water), the diamond bar represents 0.15% DNFB (in acetone/olive oil (4:1 vol:vol))+vehicle (60% EtOH, 40% water), the circle bar represents 0.15% DNFB (in acetone/olive oil (4:1 vol:vol)+0% cream formulation 1, the solid bar represents 0.15% DNFB (in acetone/olive oil (4:1 vol:vol))+ 0.3% cream formulation 1, and the hexagon bar represents 0.15% DNFB (in acetone/olive oil (4:1 vol:vol)) and 0.05% clobetasol cream. One-way ANOVA was used to determine statistical significance. *$p<0.05$, ***$p<0.001$, n=12 per treatment group.

In FIG. 12A, 2-isopropyl-5-(isoquinolin-3-yl)benzene-1,3-diol is administered intravenously (1 mg/kg). In FIG. 12B the solid square represents the subcutaneous administration of 10 mg/kg of 2-isopropyl-5-(isoquinolin-3-yl)benzene-1,3-diol in 30% Captisol; the open square represents the subcutaneous administration of 25 mg/kg of 2-isopropyl-5-(isoquinolin-3-yl)benzene-1,3-diol in 30% Captisol; the solid triangle represents the subcutaneous administration of 10 mg/kg of 2-isopropyl-5-(isoquinolin-3-yl)benzene-1,3-diol in 30% Cavitron and the open triangle represents the subcutaneous administration of 25 mg/kg of 2-isopropyl-5-(isoquinolin-3-yl)benzene-1,3-diol in 30% Cavitron. In FIG. 12C the solid circle represents the topical administration of 1% cream formulation 1 of 2-isopropyl-5-(isoquinolin-3-yl)benzene-1,3-diol (20 mg/kg) and the open square in FIG. 12C represents a topical formulation of 1% gel formulation 1 of 2-isopropyl-5-(isoquinolin-3-yl)benzene-1,3-diol (20 mg/kg).

In FIG. 13A the solid line, open circle is the epidermis/upper dermis of minipig subject one treated with a 1% cream formulation 1 of 2-isopropyl-5-(isoquinolin-3-yl)benzene-1,3-diol; the dash line, open circle is the dermis of minipig subject one treated with a 1% cream formulation 1 of 2-isopropyl-5-(isoquinolin-3-yl)benzene-1,3-diol; the solid line, solid circle is the epidermis/upper dermis of minipig subject two treated with a 1% cream formulation 1 of 2-isopropyl-5-(isoquinolin-3-yl)benzene-1, 3-diol; and the dash line, solid circle is the dermis of minipig subject two treated with a 1% cream formulation 1 of 2-isopropyl-5-(isoquinolin-3-yl)benzene-1,3-diol. In FIG. 13B the solid line, solid circle is the epidermis/upper dermis of minipig subject one hundred one treated with a 1% gel formulation 1 of 2-isopropyl-5-(isoquinolin-3-yl)benzene-1, 3-diol; the dash line, solid circle is the dermis of minipig subject one hundred one treated with a 1% gel formulation 1 of 2-isopropyl-5-(isoquinolin-3-yl)benzene-1,3-diol; the solid line, open circle is the epidermis/upper dermis of minipig subject one hundred two treated with a 1% gel formulation 1 of 2-isopropyl-5-(isoquinolin-3-yl)benzene-1, 3-diol; and the dash line, open circle is the dermis of minipig subject one hundred two treated with a 1% gel formulation 1 of 2-isopropyl-5-(isoquinolin-3-yl)benzene-1,3-diol.

DETAILED DESCRIPTION OF THE INVENTION

Figure 1A:
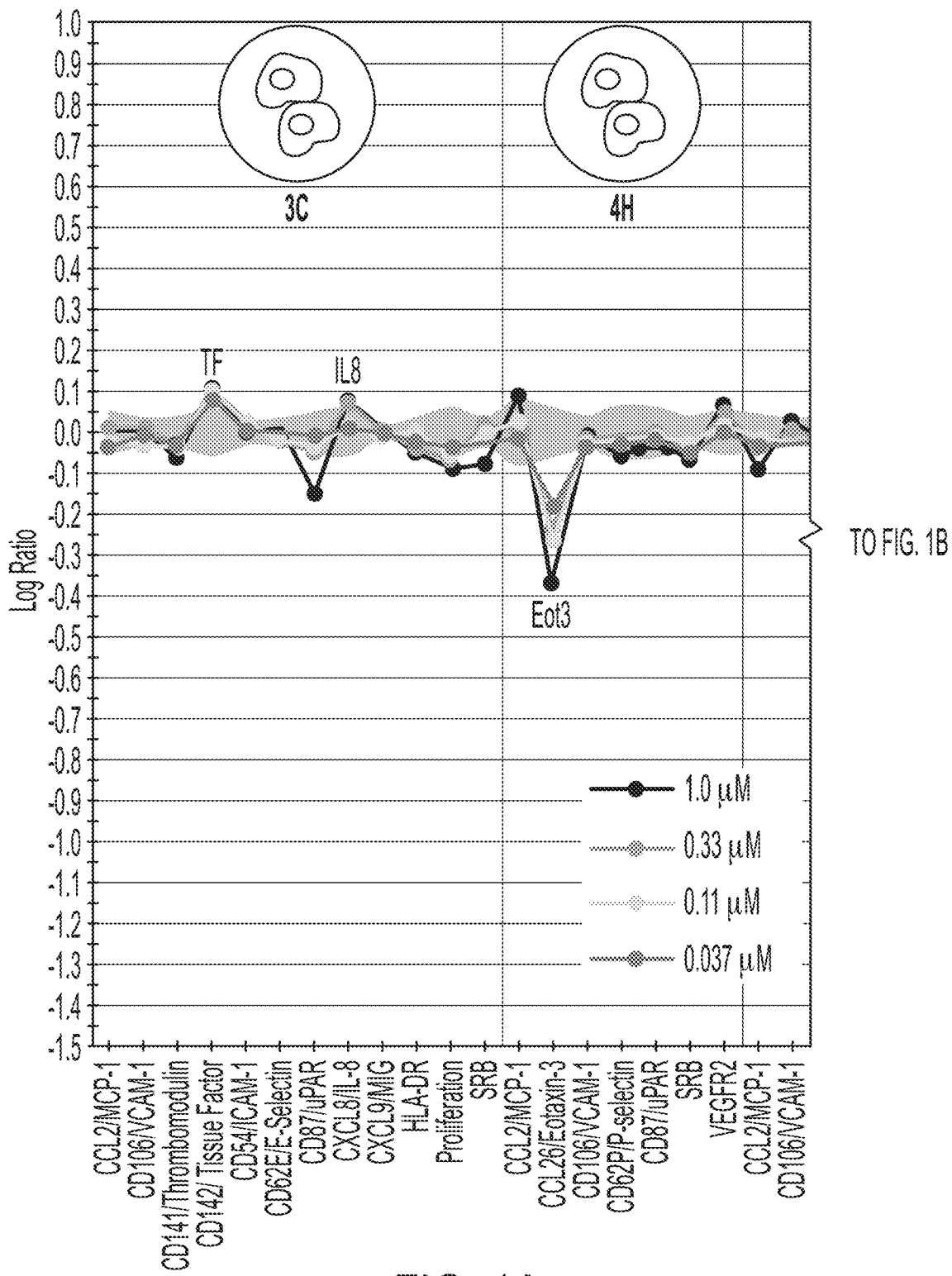
FIGS. 1A to 1U show the BioMAP profile of 2-isopropyl-5-(isoquinolin-3-yl)benzene-1,3-diol compared to tapinarof and F1CZ.
Figure 1B:
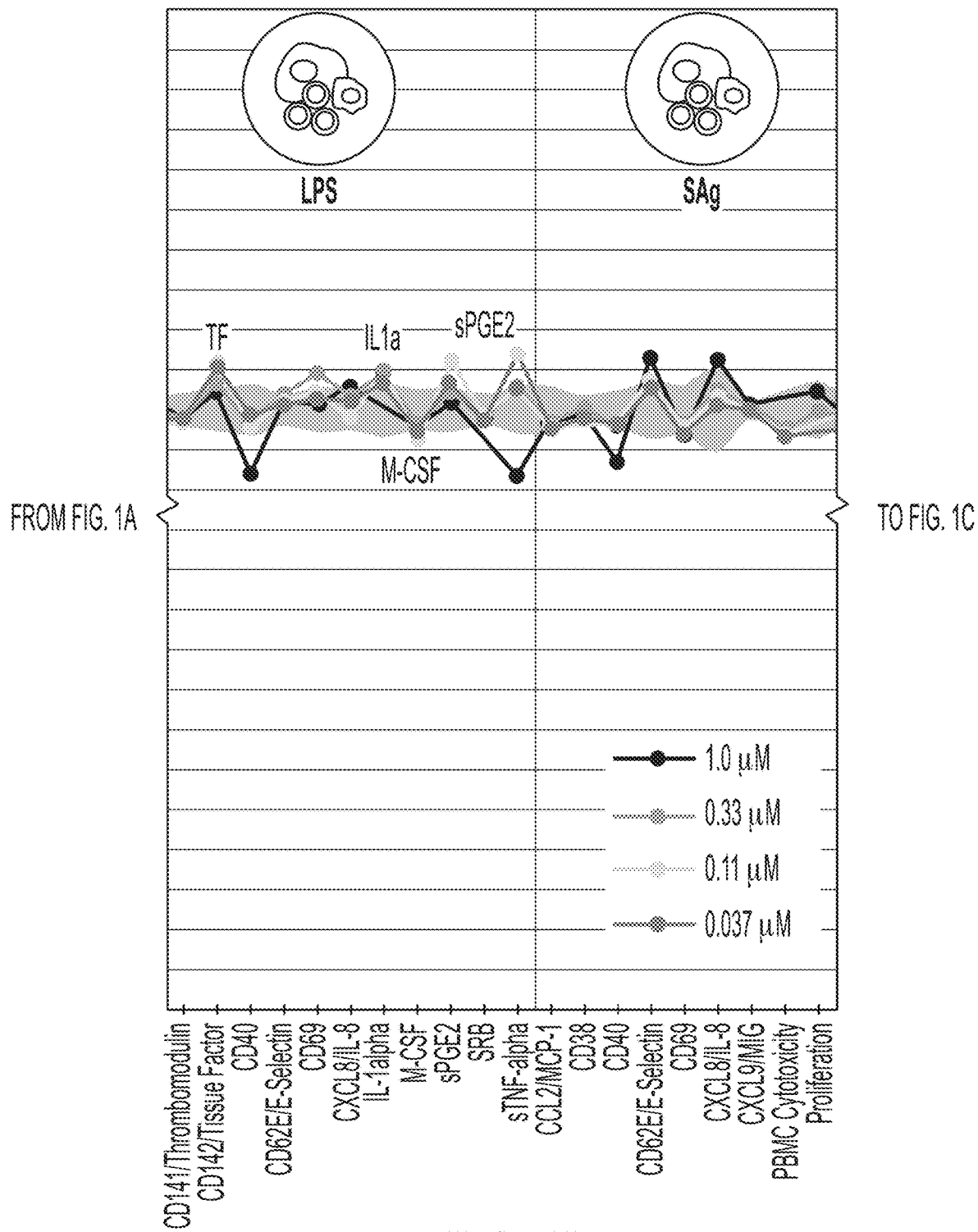
Figure 1C:
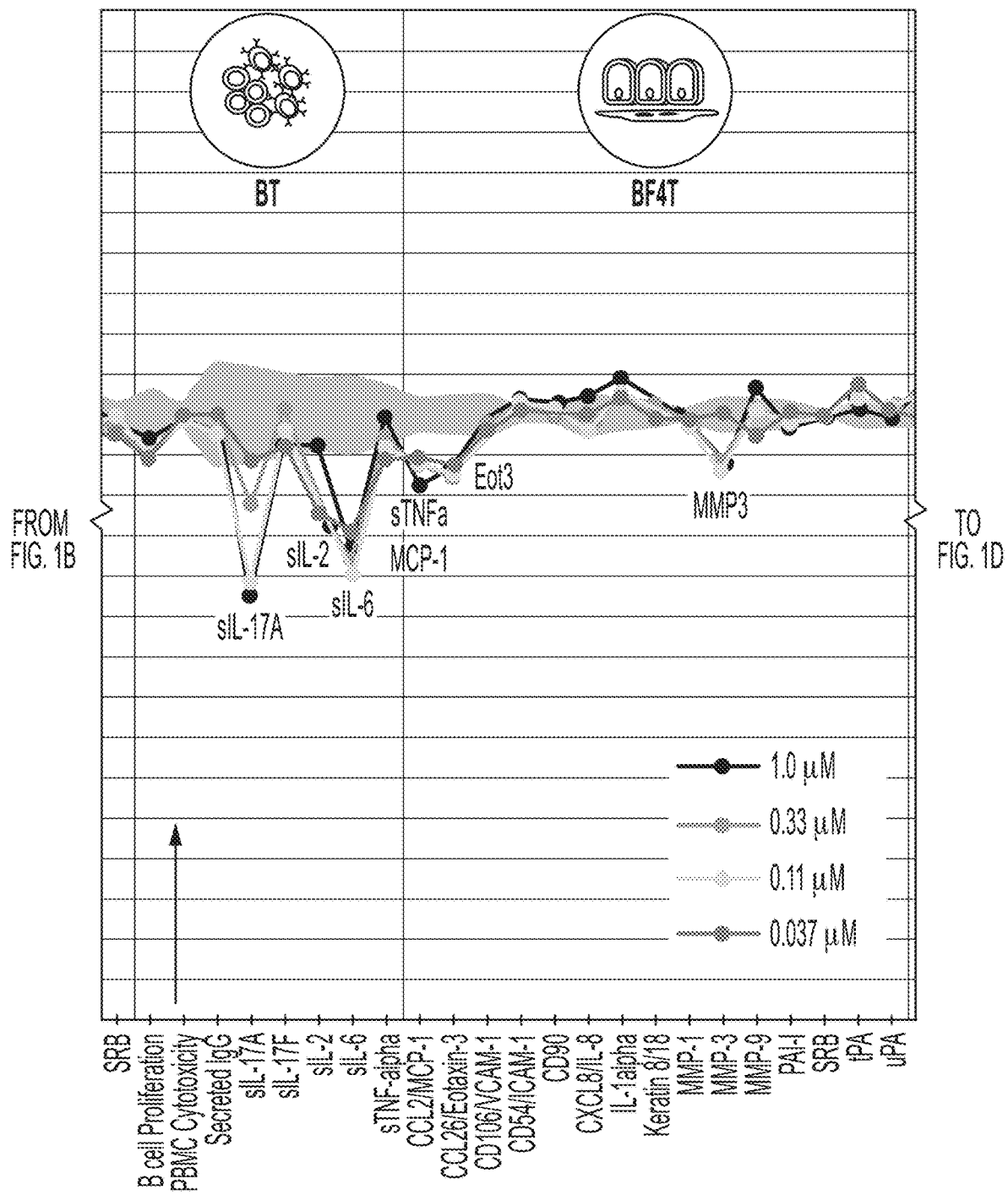
Figure 1D:
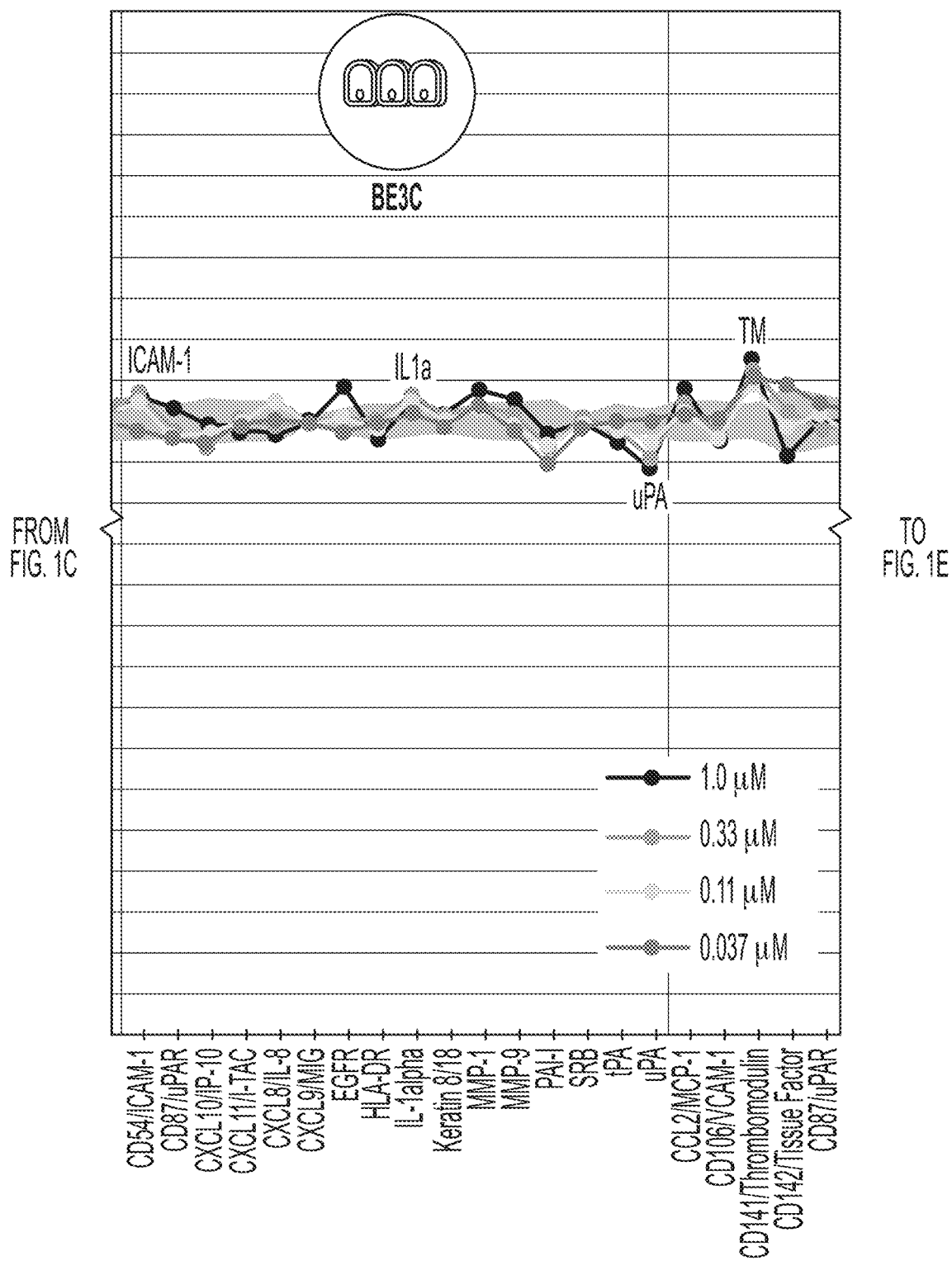
Figure 1E:
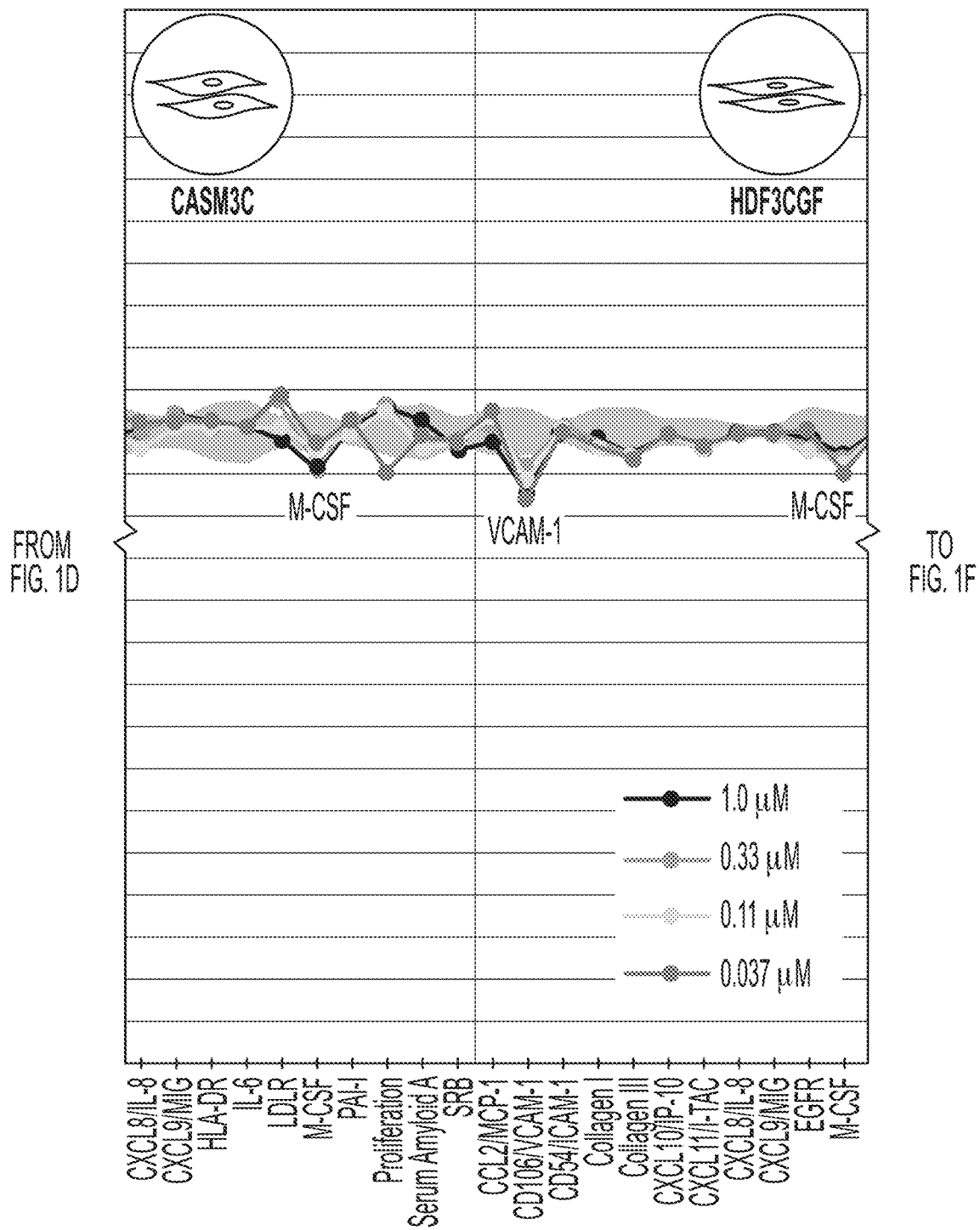
Figure 1F:
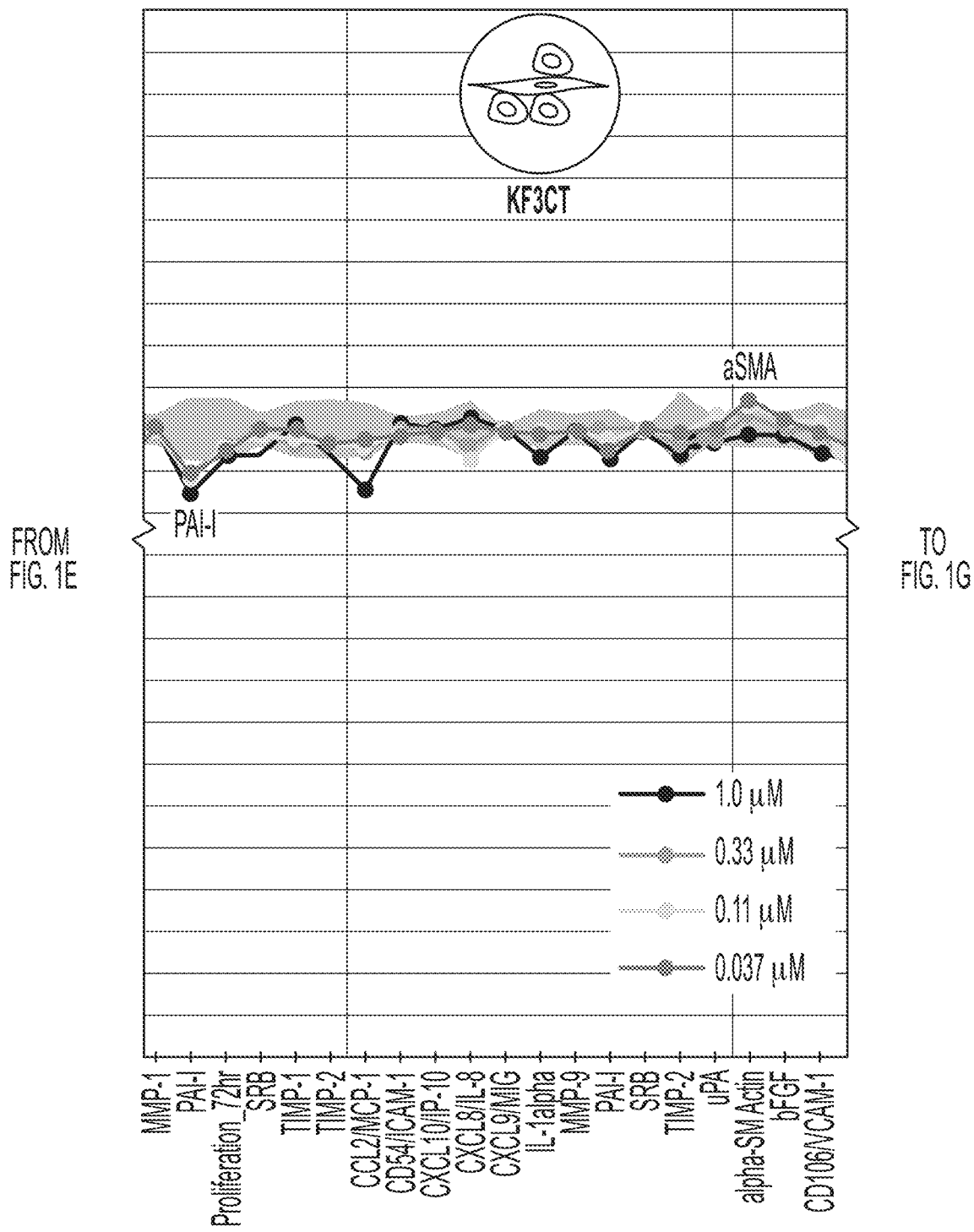
Figure 1G:
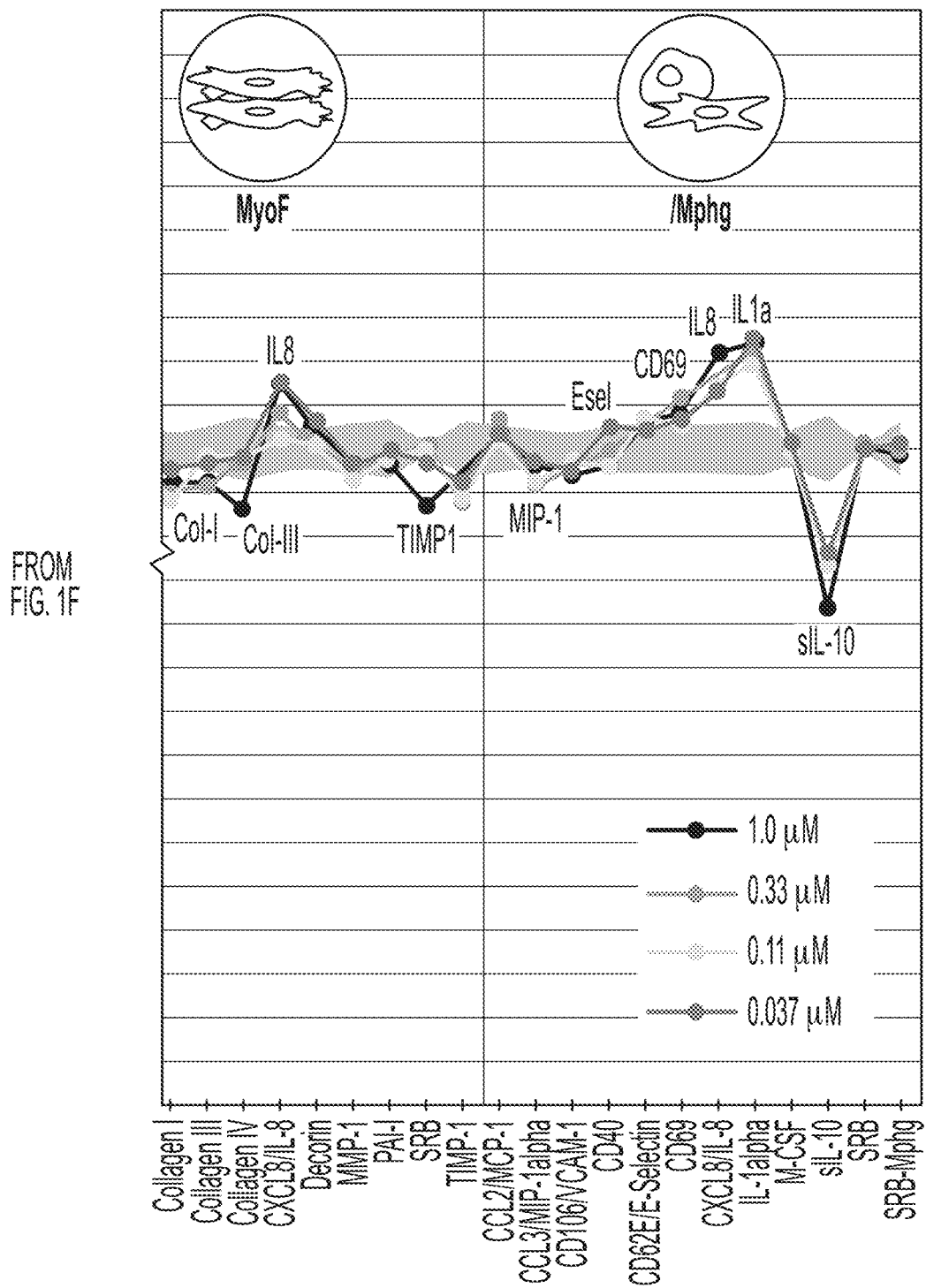
Figure 1H:
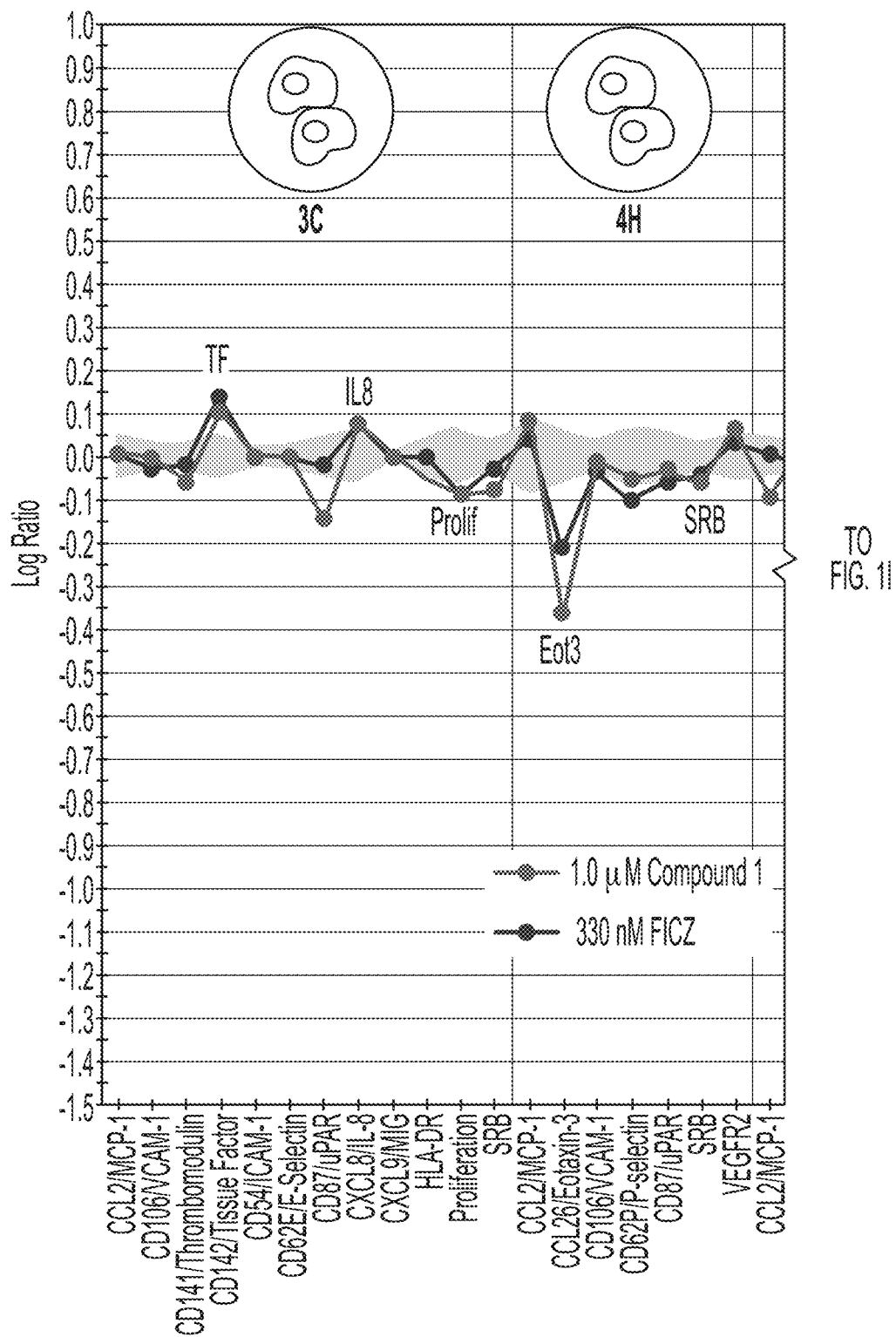
FIGS. 1H to 1N shows the BioMAP profile of 2-isopropyl-5-(isoquinolin-3-yl)benzene-1,3-diol at 1 µM (light gray) overlaid with FICZ (330 nM; dark gray)
Figure 1I:
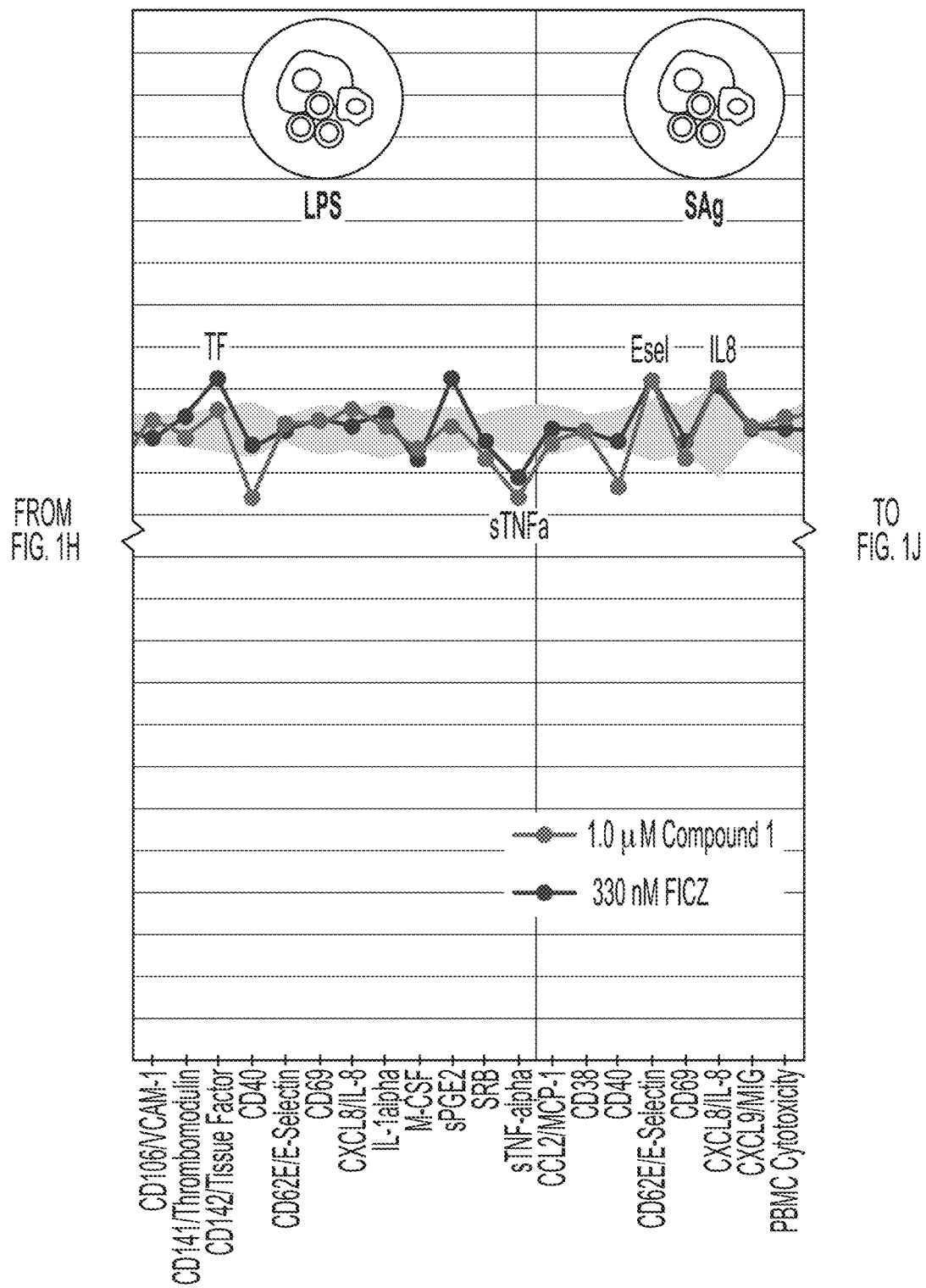
Figure 1J:
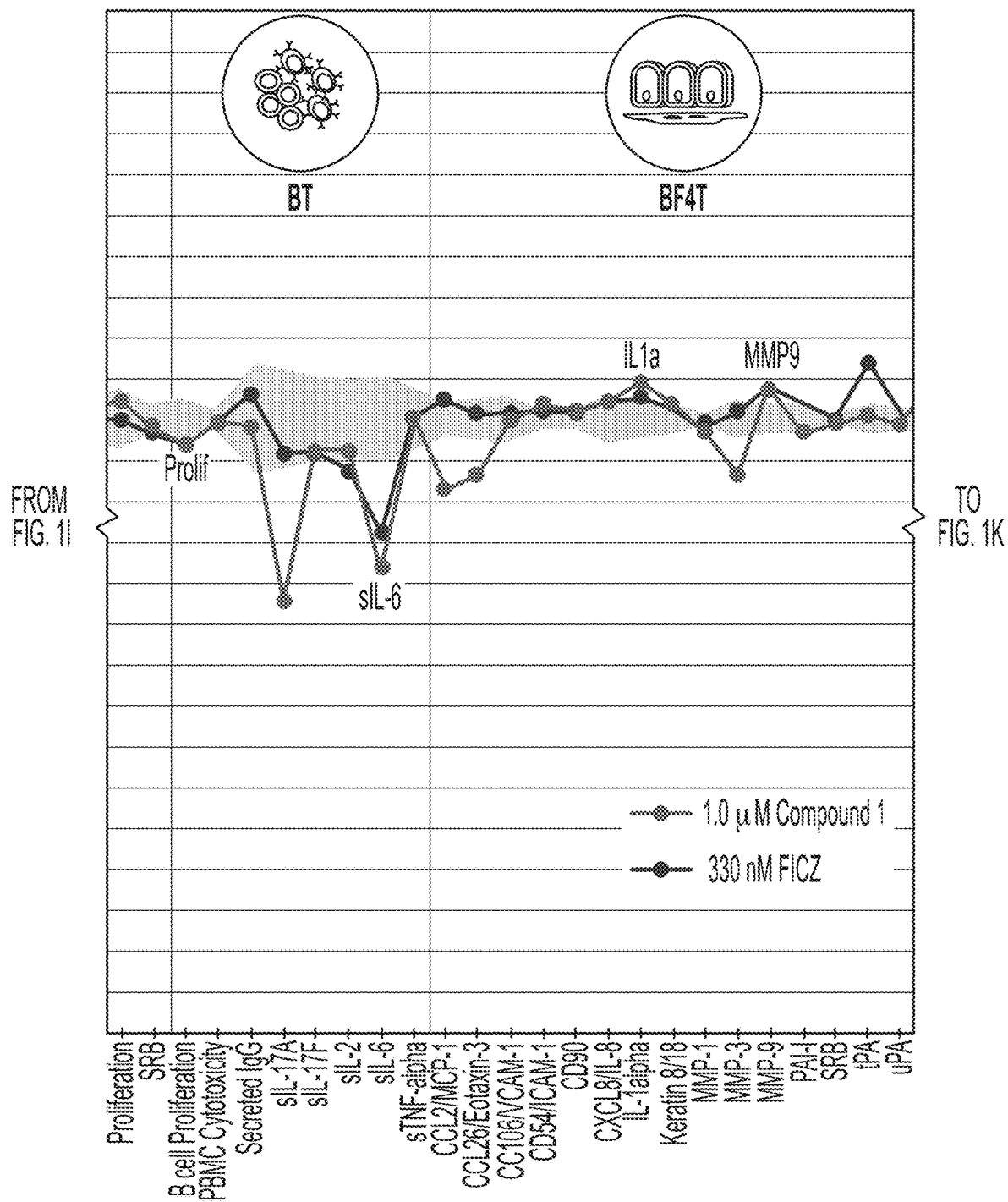
Figure 1K:
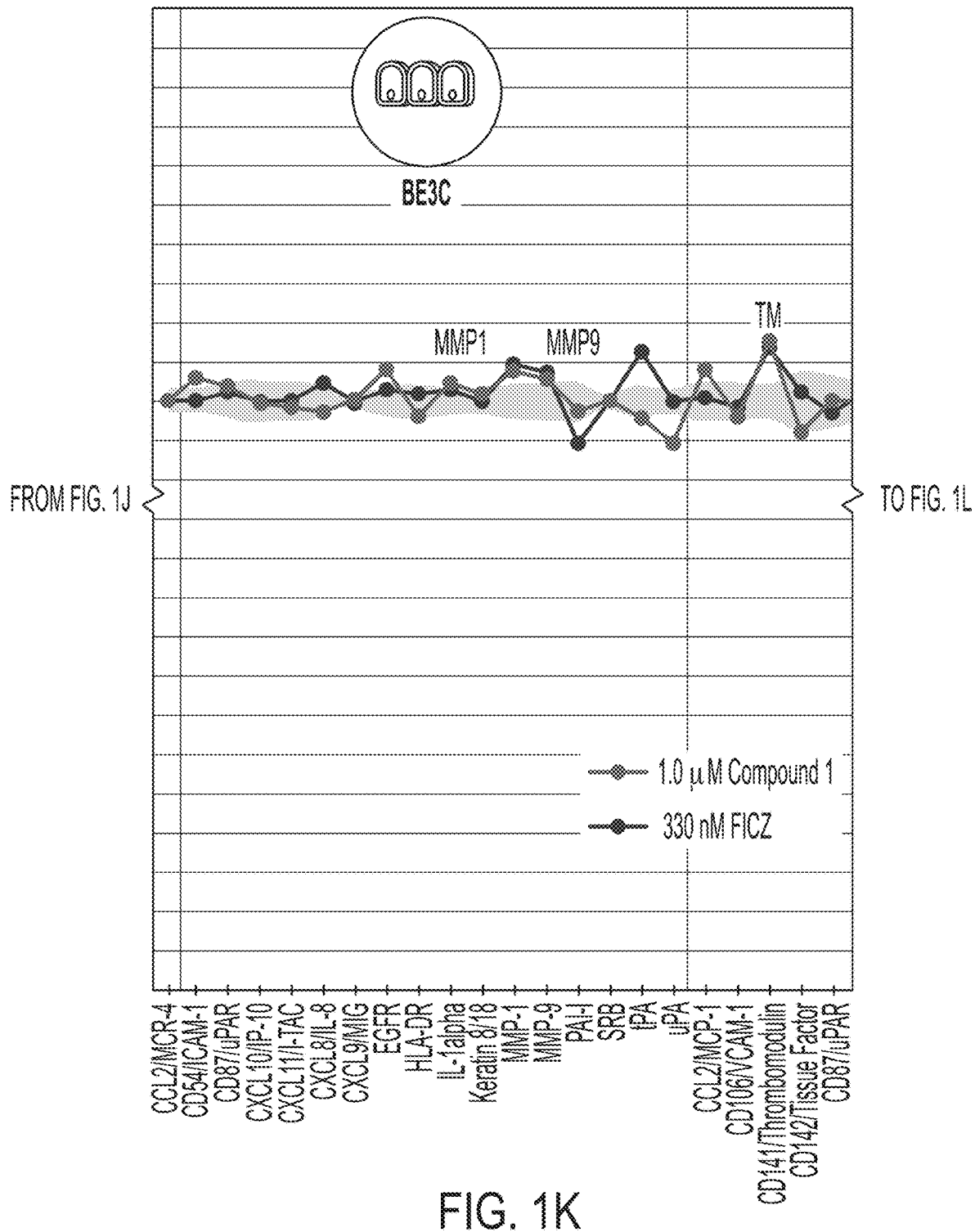
Figure 1L:
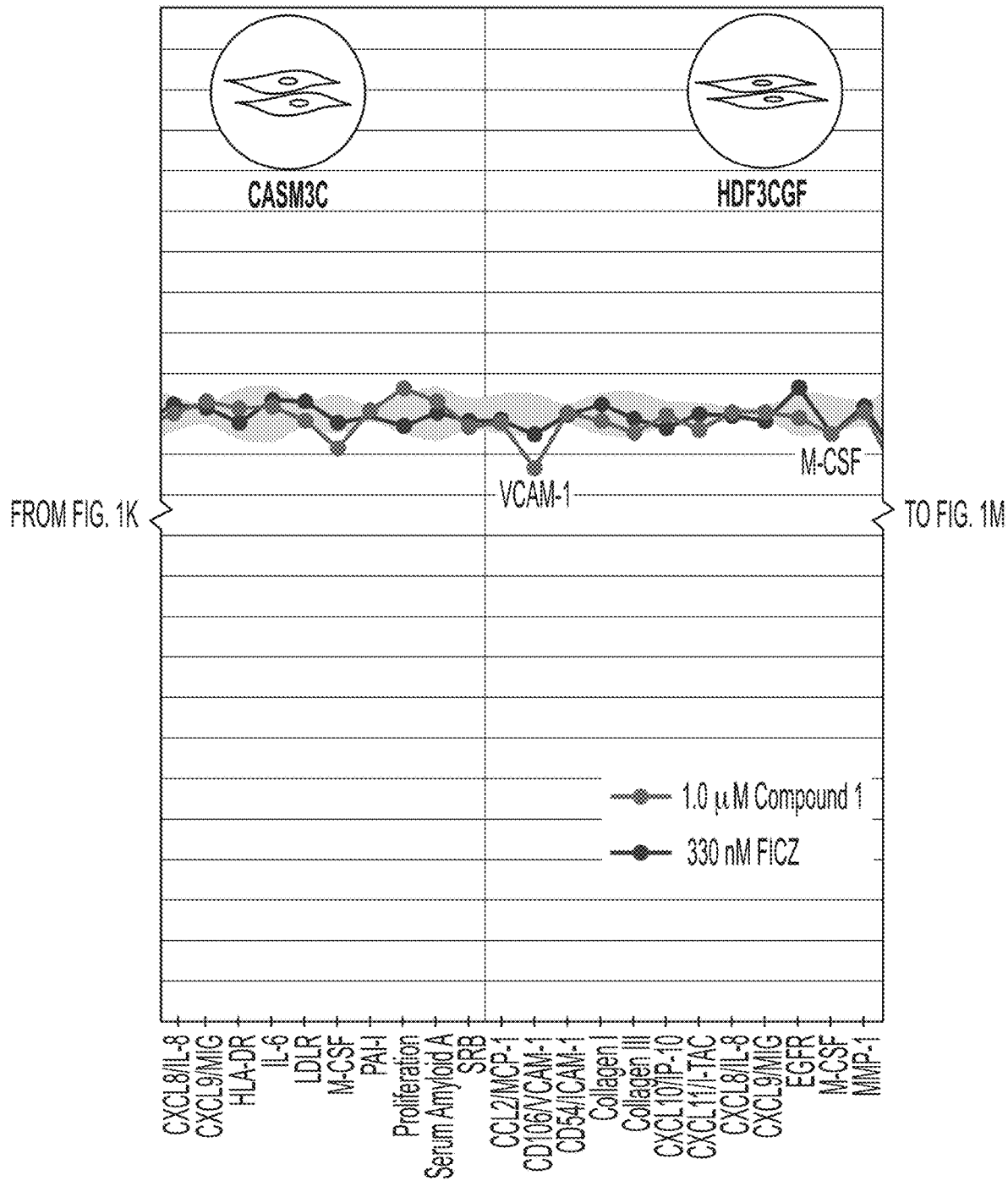
Figure 1M:
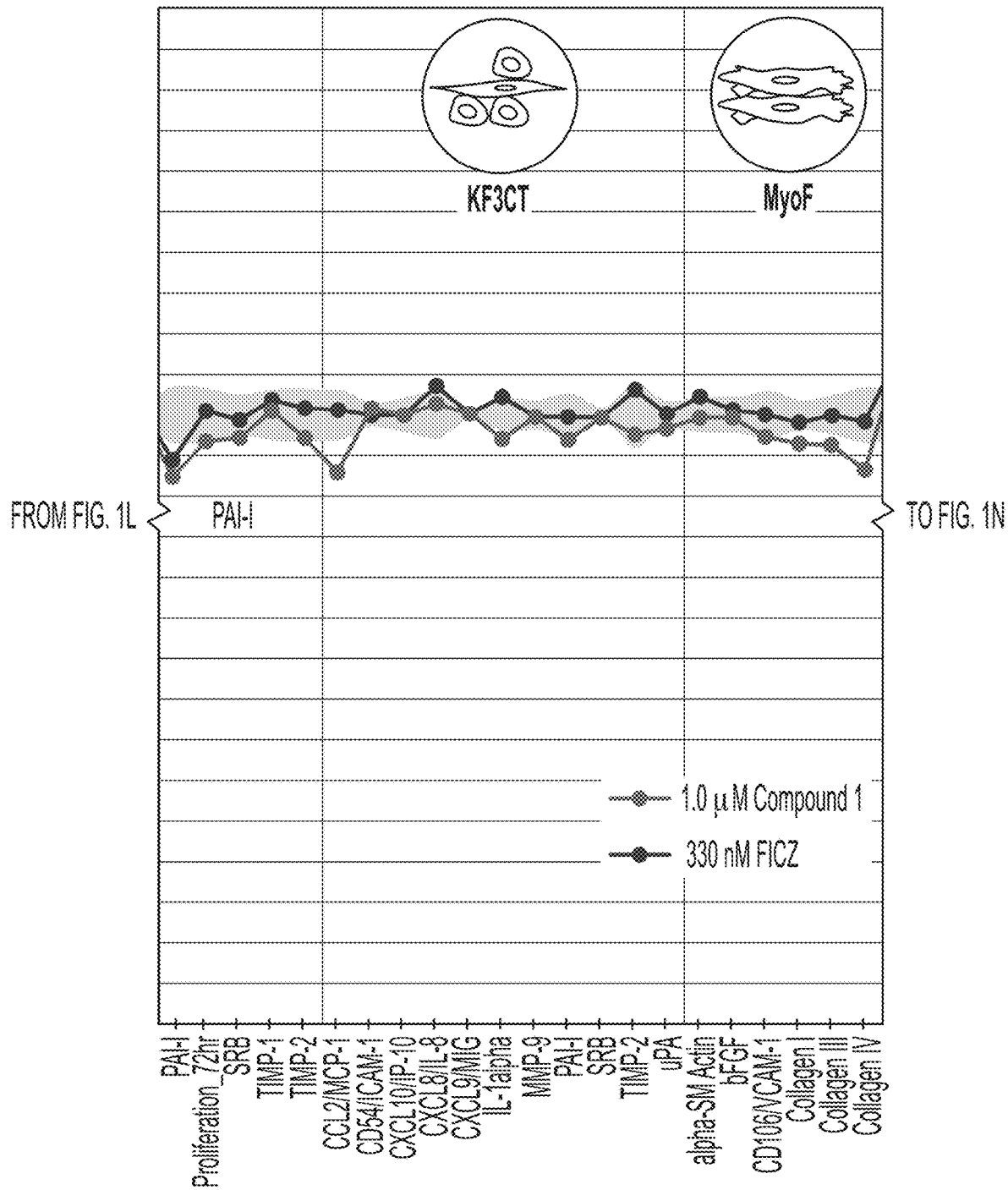
Figure 1N:
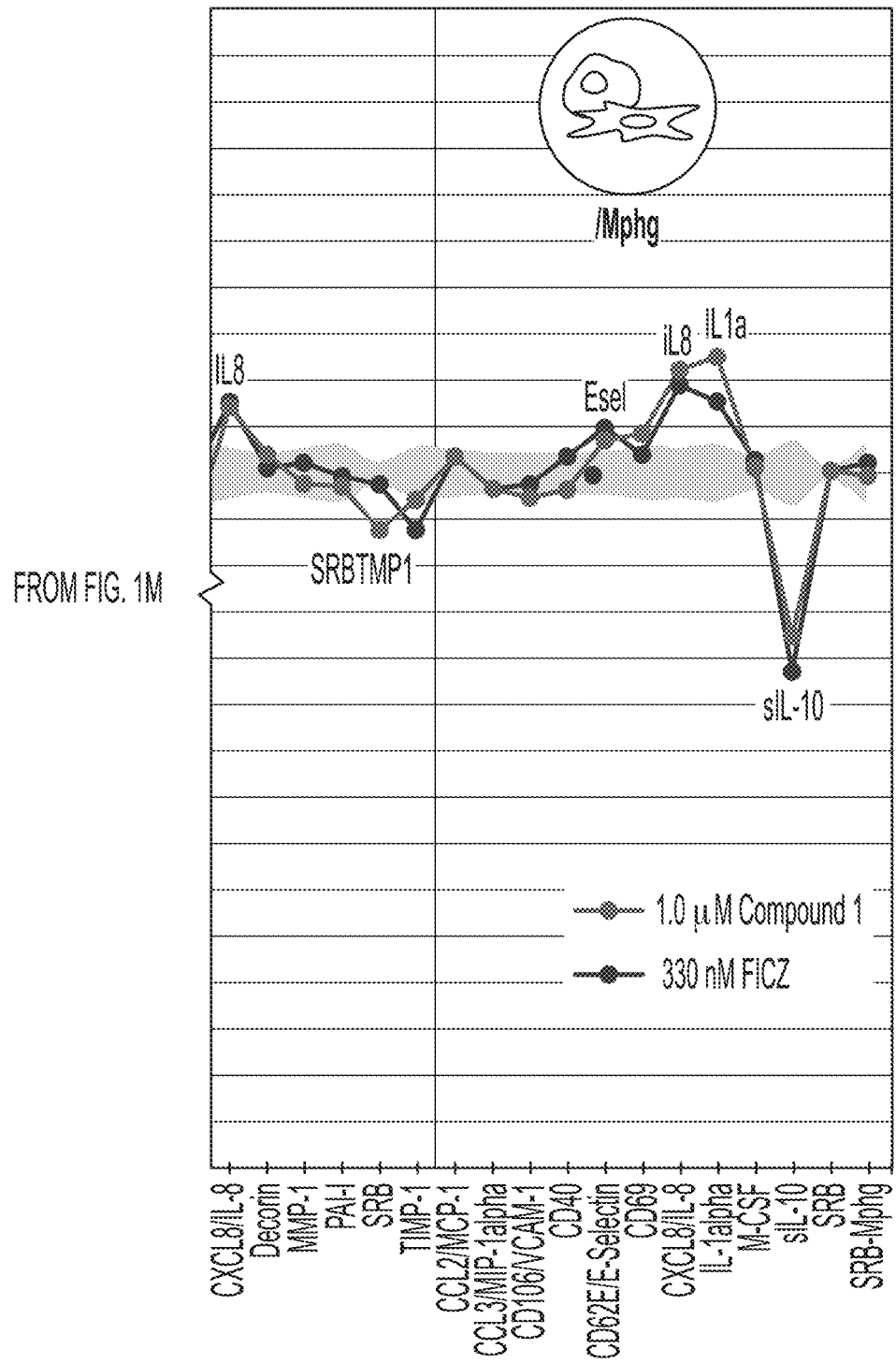
Figure 1O:
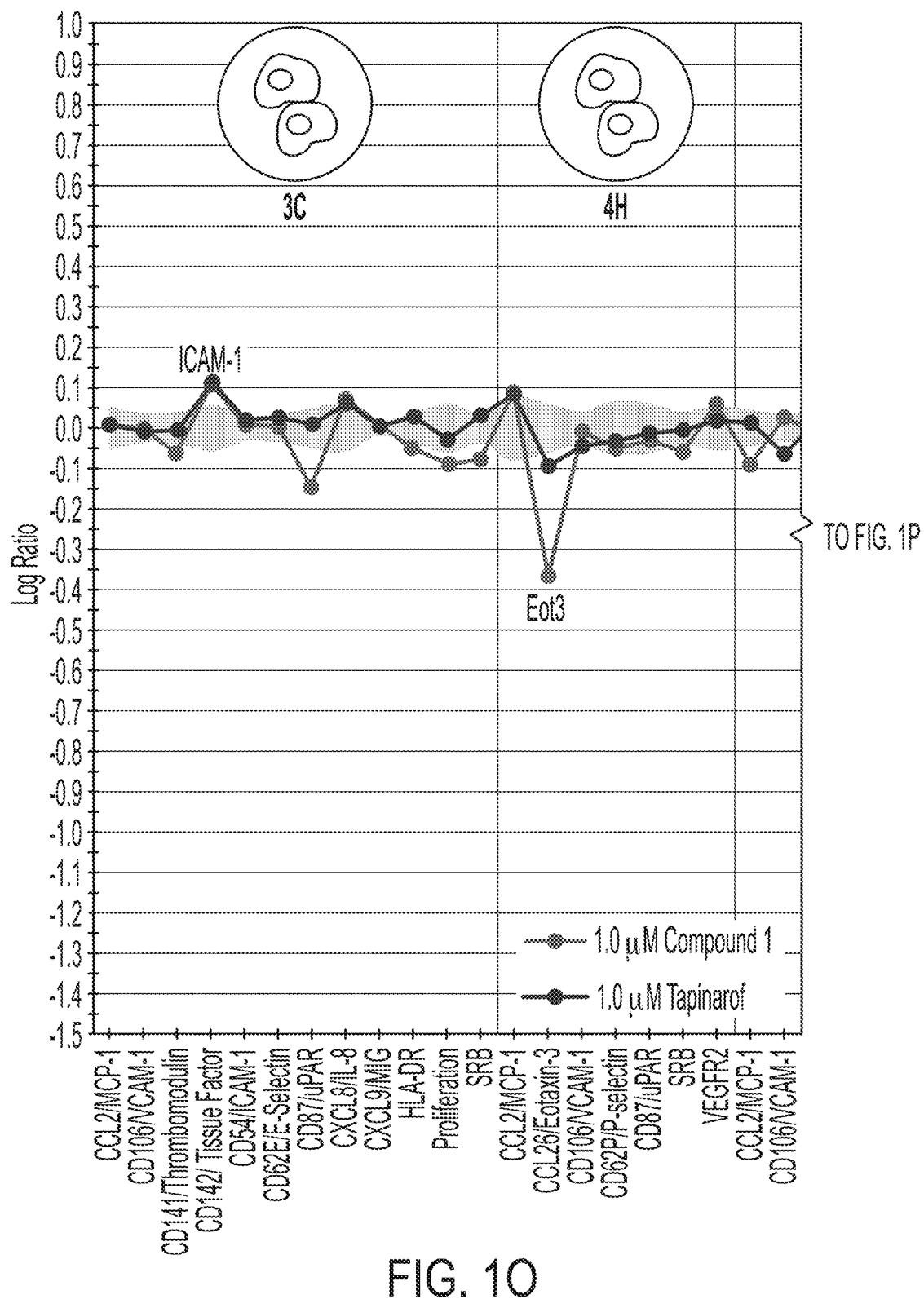
Figure 1P:
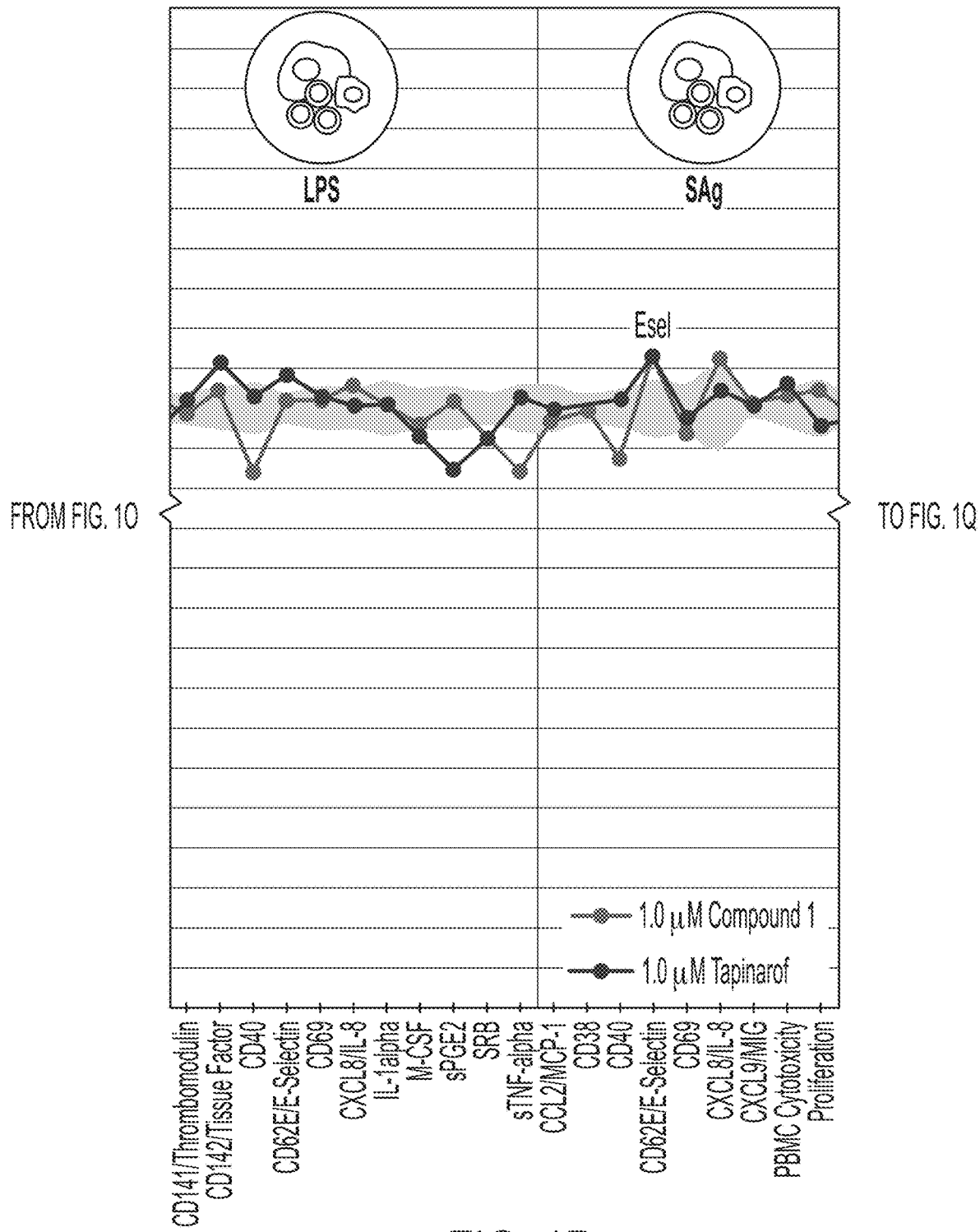
Figure 1Q:
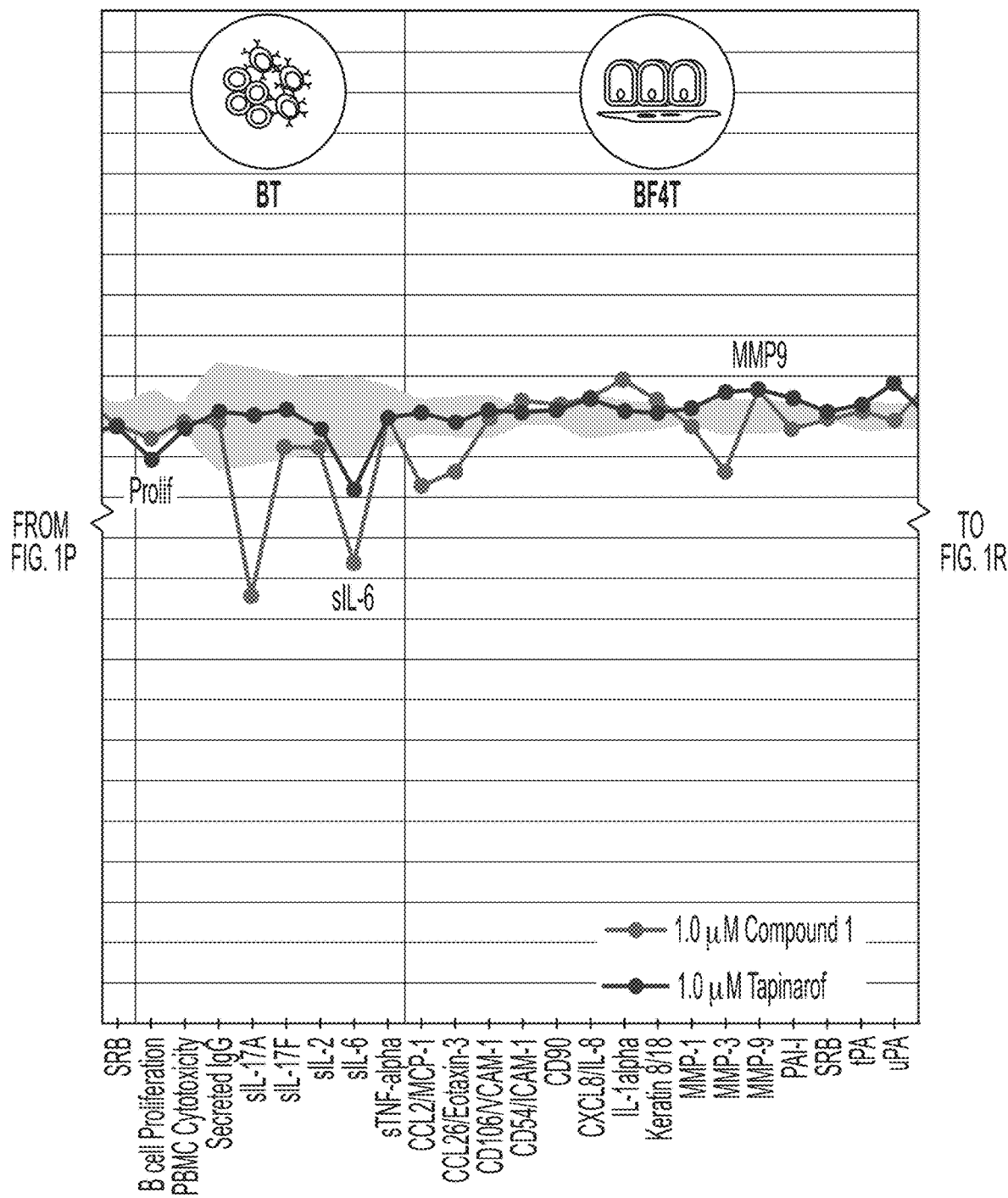
Figure 1R:
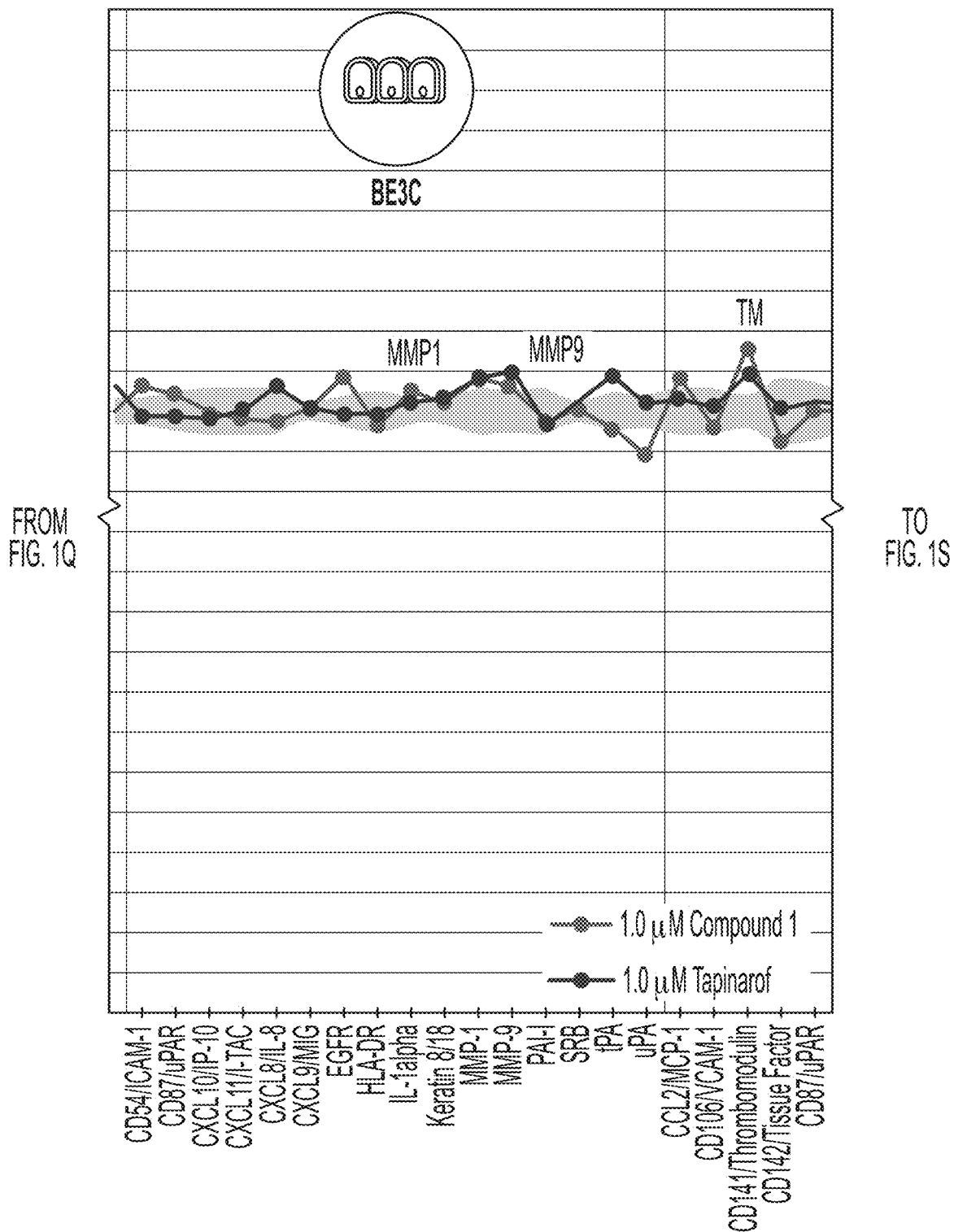
Figure 1S:
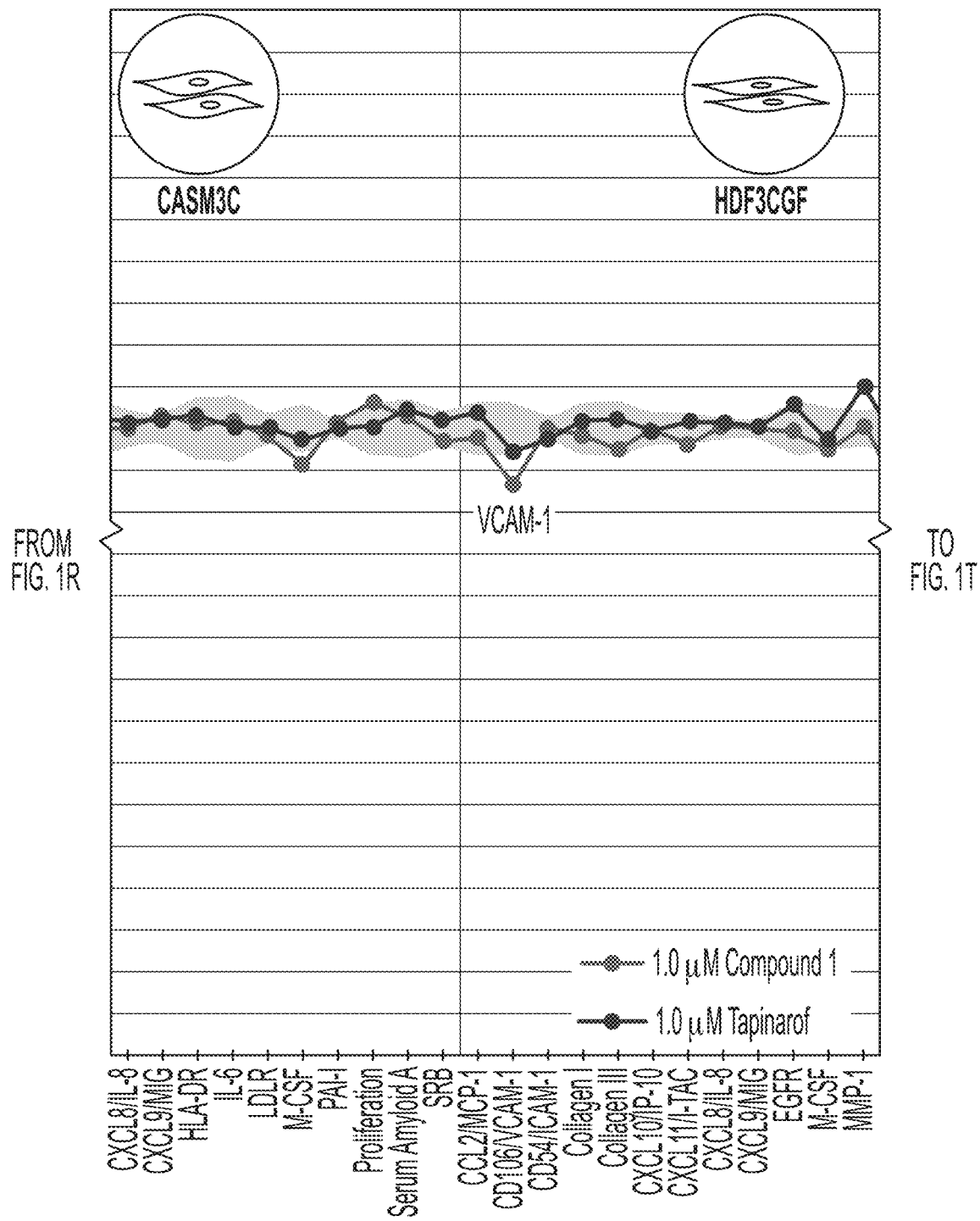
Figure 1T:
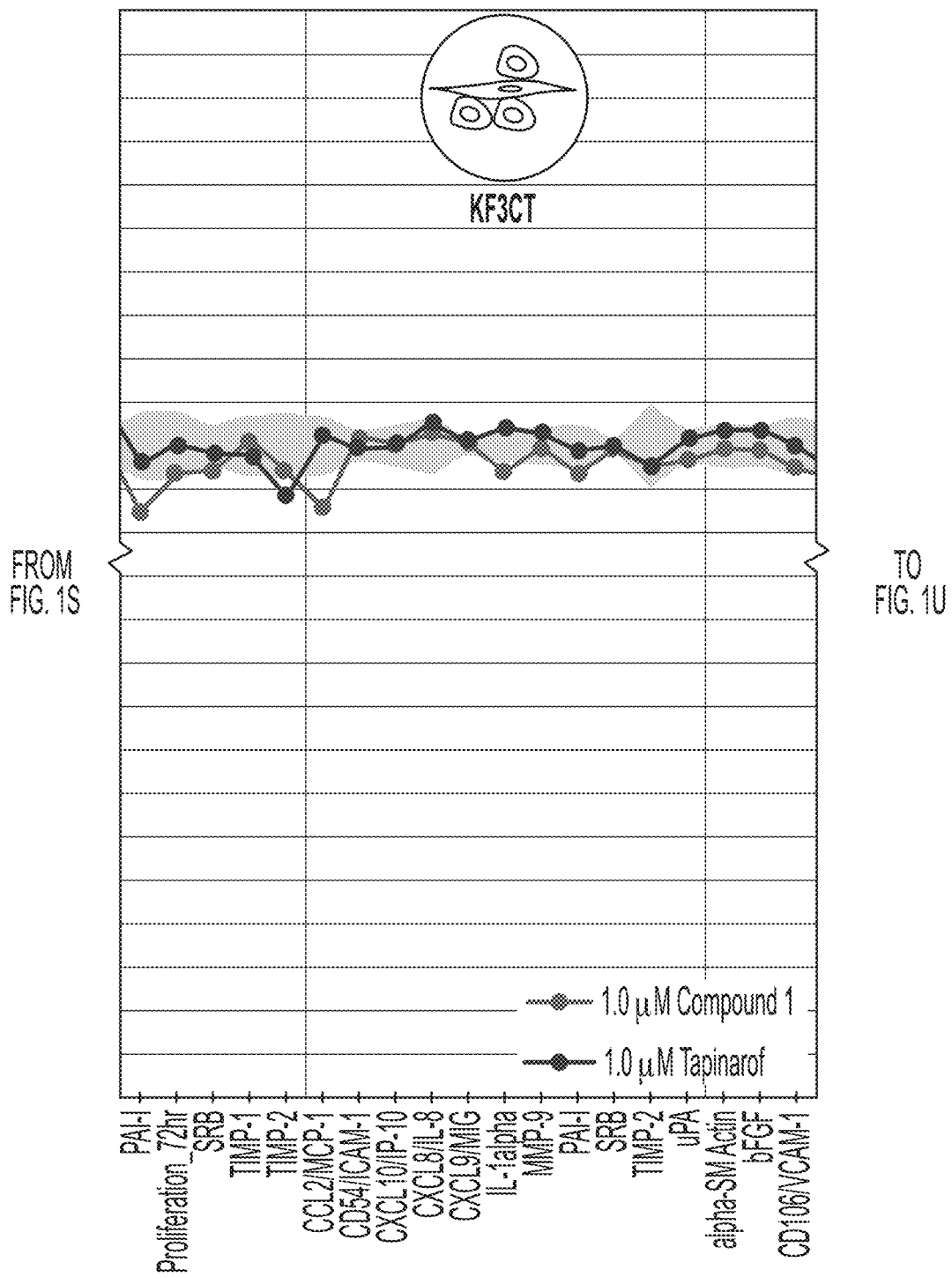
Figure 1U:
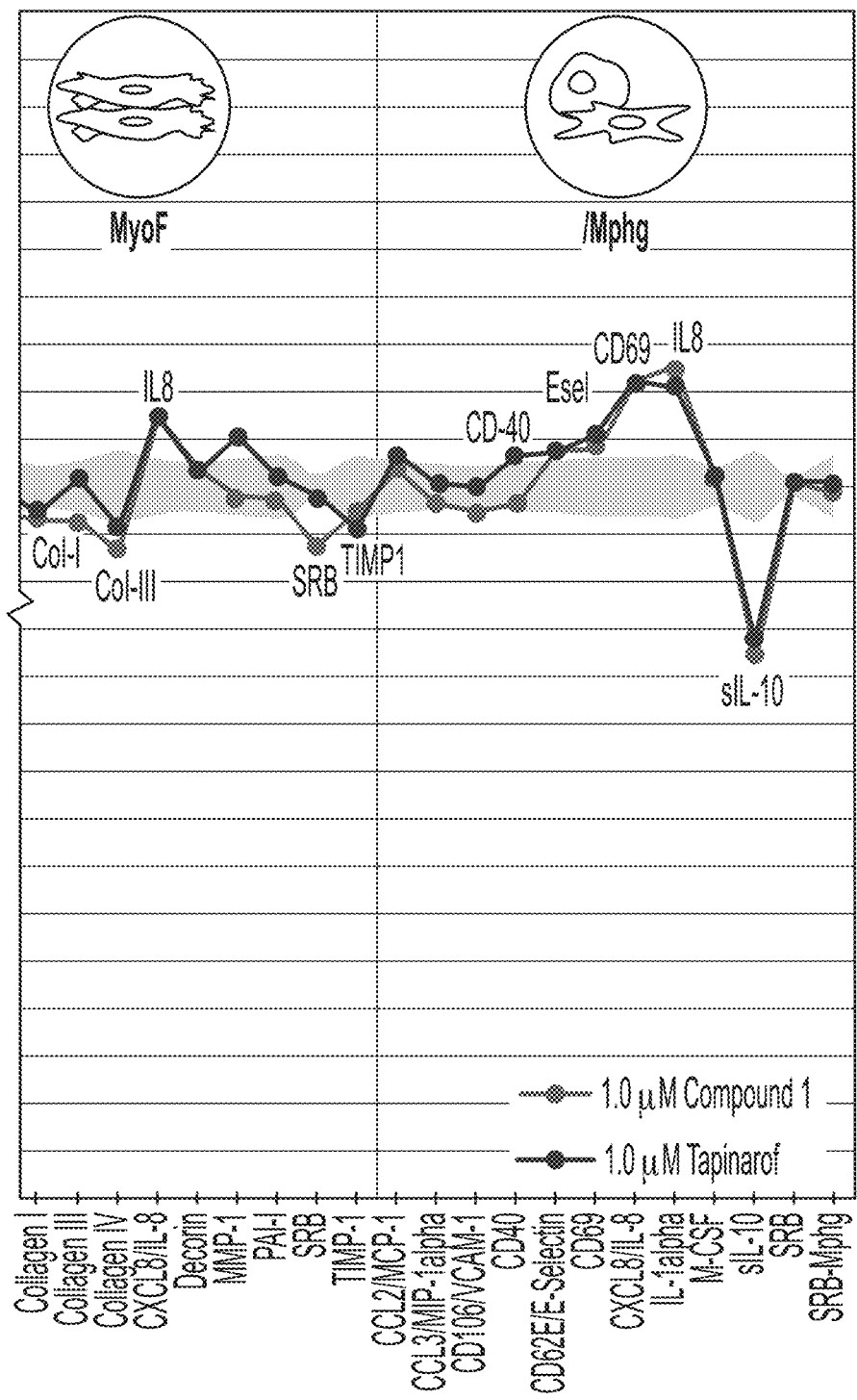

The aryl hydrocarbon receptor (AhR), a member of the bHLH-PAS family of transcription factors, is a cytosolic ligand-activated transcription factor that senses diverse endogenous and exogenous molecules mediating multiple biological activities It is best known for mediating the toxic effects of environmental contaminants such as TCDD (dioxin) and a range of other xenobiotic substances. Recent evidence points to AhR as a highly-conserved pathway that can modulate inflammatory responses, thus the AhR pathway could be an important target for treating inflammatory diseases.

There is a wide expression of AhR in several cell types of the skin, including keratinocytes, fibroblasts, melanocytes, and skin immune cells. In keratinocytes, AhR signaling controls the expression of epidermal differentiation genes, such as filaggrin, loricrin, and hornerin, thus promoting skin barrier formation. Additionally, it has been shown that AhR plays a critical role as a regulator of both innate and adaptive immune responses by impacting the balance of Th17 and Treg T cells. Th17-associated cytokines, including IL-17, contribute to the immunopathogenesis of inflammatory skin diseases such as psoriasis. Therefore, attention has recently been drawn to AhR as a target for the treatment or prevention of inflammatory skin diseases, concurrently highlighting the need for better topical treatments.

Compounds such as those described herein, that bind and activate the Aryl hydrocarbon Receptor (AhR), provide for a novel class of anti-inflammatory compounds with AhR-dependent cytokine modulation useful for the treatment of inflammatory disease states.

Thus, the beneficial effects of AhR activation provide for new therapeutic interventions in the treatment of inflammatory disease states. The need exists for better topical treatment of skin diseases, and in particular chronic inflammatory skin diseases. Suitably, a compound which binds and activates the Aryl hydrocarbon Receptor (AhR) in multiple cell types, including cells of the human skin, will provide a novel and useful treatment for inflammatory disease states. The present invention thus provides for a novel class of anti-inflammatory compounds with AhR-dependent cytokine modulation for treatment thereof.

Definitions

It should be understood that the terms "a" and "an" as used herein refer to "one or more" of the recited components. It will be clear to one of ordinary skill in the art that the use of the singular includes the plural unless specifically stated otherwise.

The term "about" means within an acceptable range for the particular parameter specified as determined by one of ordinary skill in the art, which will depend, in part, on how the value is measured or determined, i.e., the limitations of the measurement system. For example, "about" can mean a range of 10% of a given value. For example about 55% means 45% to 55%.

As used herein, "acyl" mean an alkyl or aryl group bonded through a carbonyl group —C(O)—. For example, acyl includes a $C_{1-6}$ alkanoyl. Typical acyl groups include acetyl, benzoyl, and the like.

The terms "administering" and "administration" are used herein to mean any method which in sound medical practice delivers the compound or pharmaceutical composition thereof to a patient in such a manner as to provide the desired therapeutic effect. In some embodiments the compound is in a pharmaceutical emulsion composition.

As used herein, the term "alkoxy" refers to an —O-alkyl group containing a specified number of carbon atoms. For example, $C_{1-6}$ alkoxy means alkoxy group containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy or hexyloxy.

As used herein, "alkyl" refers to a monovalent saturated hydrocarbon chain having the specified number of carbon member atoms. For example, $C_{1-6}$ alkyl refers to an alkyl group having from 1 to 6 carbon member atoms. Alkyl groups may be straight or branched. Representative branched alkyl groups have one, two, or three branches. Alkyl includes methyl, ethyl, propyl, (n-propyl and isopropyl), butyl (n-butyl, isobutyl, s-butyl, and t-butyl), and n-pentyl, and the like.

The term "alkylene" means a linker which is a straight or branched carbon chain having 1 to 6 carbon atoms and having two bonding sites. Examples of $C_{1-6}$ alkylene linker groups include but are not limited to —CH$_2$—, —CH$_2$CH$_2$—, —CH$_2$CH$_2$CH$_2$CH$_2$—, —CH$_2$CH(CH$_3$)CH$_2$—, and the like.

The term "and/or" as used herein covers both additively and also alternatively the individual elements of a list which are thus linked so that these elements are to be understood as linked selectively with "and" or respectively with "or". Furthermore, the terms used in the singular of course also comprise the plural.

The term "applying" as used herein refers to any method which, in sound medical or cosmetic practice, delivers a topical composition to the subject in such a manner so as to provide a positive effect on a dermatological disorder, condition, or appearance.

As used herein, the term "aryl" refers to substituted or unsubstituted hydrocarbon aromatic rings such as phenyl, naphthyl and the like.

As used herein, the term "arylalkyl" or "araalkyl" refers to an aryl ring such as benzene or naphthalene and a connecting $C_{1-6}$ alkyl moiety, unless otherwise indicated, such as —(CH$_2$)$_n$phenyl wherein n is 1-6.

As used herein, the terms "compound(s) of the invention" or "compound(s) of this invention" mean a compound, as defined herein, in any form, i.e., any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms.

Throughout the application, descriptions of various embodiments use "comprising" language, however in some specific instances, an embodiment can alternatively be described using the language "consisting essentially of" or "consisting of".

The term "dermatologically acceptable excipient or diluent" as used herein refers to any inactive ingredient present in a composition for use in a topical composition described herein.

"Effective amount", "pharmaceutically effective amount" or "therapeutically effective amount" is used herein to refer to an amount of the active ingredient sufficient to have a therapeutic effect upon administration, e.g. that amount which will cause an improvement or change in the condition for which it is administered. Effective amounts will vary with the particular condition being treated, the severity of the condition, the duration of the treatment, the stage of advancement of the condition, the body surface area affected with the clinical condition (for topical administration), and the specific components of the composition. The amount is sufficient to treat a disorder, disease or condition or one or more of its symptoms and/or to prevent the occurrence of the disease or disorder, and can be determined by standard clinical techniques. Appropriate amounts in any given instance will be readily apparent to those skilled in the art or capable of determination by routine experimentation. In some embodiments, compositions of the invention are generally applied in a topical manner to the affected area, i.e. localized application to the skin region where the clinical abnormality is manifest.

As used herein, the term "haloalkyl" or "halo substituted alkyl" refers to a straight or branched saturated hydrocarbon chain containing a specified number of carbon atoms, substituted with halo atoms. For example, halo $C_1$-6 alkyl means a straight or branched alkyl group containing at least 1, and at most 6, carbon atoms, substituted with 1 to 3 halo atoms per carbon atom. Examples of "haloalkyl" as used herein include, but are not limited to, fluoromethyl, difluoromethyl, and trifluoromethyl.

As used herein, the terms "halogen" and "halo" include fluorine, chlorine, bromine and iodine, and fluoro, chloro, bromo, and iodo, respectively.

As used herein, the terms "heteroaryl ring", "heteroaryl moiety", and "heteroaryl" mean a monocyclic five to seven membered unsaturated hydrocarbon ring containing at least one heteroatom selected from oxygen, nitrogen and sulfur. Examples of heteroaryl rings include, but are not limited to, furyl, pyranyl, thienyl, pyrrolyl, oxazolyl, thiazolyl, isoxazolyl, isothiazolyl, imidazolyl, pyrazolyl, oxadiazolyl, oxathiadiazolyl, triazolyl, tetrazolyl, thiadiazolyl, pyridyl, pyridazinyl, pyrimidinyl, pyrazinyl, triazinyl, and uracil. The terms "heteroaryl ring", "heteroaryl moiety", and "heteroaryl" as used herein, also refer to fused aromatic rings comprising at least one heteroatom selected from oxygen, nitrogen and sulfur. Each of the fused rings may contain five or six ring atoms. Examples of fused aromatic rings include, but are not limited to, indolyl, isoindolyl, indazolyl, indolizinyl, azaindolyl, benzoxazolyl, benzimidazolyl, benzothiazolyl, benzofuranyl, benzothiophenyl, quinolyl, isoquinolyl, quinazolinyl, quinoxalinyl, naphthyridinyl, cinnolinyl, purinyl, and phthalazinyl.

As used herein, the term "heteroarylalkyl" means a $C_1$-6 alkyl as defined above, (unless otherwise defined) attached to a heteroaryl moiety as also defined herein unless otherwise indicated.

As used herein, the term "heterocyclicalkyl" or "heterocyclylalkyl" means a $C_{1-6}$ alkyl as defined above, (unless otherwise defined) attached to a heterocyclic moiety as also defined herein unless otherwise indicated.

As used herein, the term "heterocyclic" or "heterocyclyl" (on its own or in any combination, such as "heterocyclylalkyl") is used herein to mean a saturated or partially unsaturated 4 to 10 membered ring system in which one or more rings contain one or more heteroatoms selected from the group consisting of N, O, S, or S(O)q, wherein q is 0 or an integer having a value of 1 or 2. Examples include, but not limited to, tetrahydropyrrolyl, tetrahydropyranyl, tetrahydrofuranyl, tetrahydrothiophenyl (including oxidized versions of the sulfur moiety), pyrrolidinyl, piperidinyl, piperazinyl, morpholinyl, thiomorpholinyl (including oxidized versions of the sulfur moiety), or imidazolidinyl.

As used herein in the in vitro skin penetration studies, the term "epidermis" includes the stratum corneum and tissue or layers down to the basement membrane, as isolated by heat separation treatment.

As used herein in the in vitro skin penetration studies with ex vivo human abdominal skin dermatomed at a thickness of 500 microns (+/−100 microns) or 750 (+/−100 microns), the term "epidermis" is the top/superficial layer obtained after a washing/tape striping procedure followed by heat separation, and the term "dermis" is the underlying layer.

As used herein, the term "independently" means that where more than one substituent is selected from a number of possible substituents, those substituents may be the same or different. That is, each substituent is separately selected from the entire group of recited possible substituents.

The terms "modulate" or "modulates" refer to an increase or decrease in the amount, quality or effect of a particular activity.

As used herein, the term "oxo" represents a double-bonded oxygen moiety; for example, if attached directly to a carbon atom it forms a carbonyl moiety (C=O).

As used herein, the term "hydroxy" or "hydroxyl" is intended to mean the radical —OH.

As used herein, the term "sulfinyl" is used herein to mean the oxide S(O) of the corresponding sulfide, the term "thio" refers to the sulfide, and the term "sulfonyl" refers to the fully oxidized $S(O)_2$ moiety.

As used herein, the term "optionally" means that the subsequently described event(s) may or may not occur, and includes both event(s) that occur and event(s) that do not occur.

As used herein, "optionally substituted", unless specifically defined herein shall mean the moiety may be optionally substituted one or more times, such as one to three times, independently with halo, e.g. fluoro, chloro, bromo or iodo; hydroxy; hydroxy substituted $C_{1-3}$ alkyl; $C_{1-3}$ alkoxy, such as methoxy or ethoxy; halo substituted $C_{1-3}$ alkoxy; $S(O)_m$ $C_{1-3}$ alkyl, such as methyl thio, methylsulfinyl or methyl sulfonyl; $NR^{22}R^{23}$, wherein $R^{22}$ and $R^{23}$ are independently selected from H or $C_{1-3}$ alkyl or wherein $R^{22}$ and $R^{23}$ together with the nitrogen to which they are attached form a 5 to 7 membered ring which optionally contains an additional heteroatom selected from O, N, or S; $C_{1-3}$ alkyl;

$C_{3-7}$ cycloalkyl, or $C_{3-7}$ cycloalkyl $C_{1-3}$ alkyl group, such as cyclopropyl methyl; halosubstituted $C_{1-3}$ alkyl, such $CF_2CF_2H$, or $CF_3$; optionally substituted aryl, such as phenyl or optionally substituted aryl $C_{1-3}$ alkyl, such as benzyl or phenethyl, and wherein these aryl containing moieties may also be substituted one to two times by halo; hydroxy; hydroxy substituted $C_{1-3}$ alkyl; $C_{1-3}$ alkoxy; $S(O)_m,C_{1-3}$ alkyl; amino, mono and di-substituted $C_{1-3}$ alkylamino; $C_{1-3}$ alkyl, or $CF_3$. In addition, it will be appreciated by those skilled in the art that the compounds of this invention, depending on further substitution, may exist in other tautomeric forms. All tautomeric forms of the compounds described herein are intended to be encompassed within the scope of the present invention. It is to be understood that any reference to a named compound of this invention is intended to encompass all tautomers of the named compound and any mixtures of tautomers of the named compound.

As used herein, "patients" includes human patients, including adult, teens and children (e.g. pediatric patients). A pediatric patient can include teenagers under the age of 18. A child for purposes herein is under the age of 12.

As used herein, "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio. The terms "pharmaceutically acceptable" and "dermatologically acceptable" mean approvable by a regulatory agency or listed in a Pharmacopeia or other generally recognized guide for use in animals, and more particularly in humans.

The term "pharmaceutically acceptable salt thereof" refers to salts that are safe and effective for use in the patient and possess the desired pharmaceutical activity. Salts encompassed within the term pharmaceutically acceptable salts refer to non-toxic salts of the compounds of this invention. Such salts include compounds wherein the parent compound is modified by making acid or base salts thereof.

As used herein, the term "skin penetration" refers to the diffusion of a compound, preferably a compound of Formula (I) or a pharmaceutically acceptable salt thereof through the stratum corneum and into the epidermis and/or dermis of the skin.

"Substantially free" of a specified component refers to a composition with less than about 1% by weight of the specified component. "Free" of a specified component refers to a composition where the specified component is absent.

As used herein, the term "substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituents, one or more (as appropriate) member atoms within the group may be substituted. In addition, a single member atom within the group may be substituted with more than one substituent as long as such substitution is in accordance with the permitted valence of the atom. Suitable substituents are defined herein for each substituted or optionally substituted group.

The term "topical" delivery or "topical" administration refers to application of a drug-containing formulation to the skin to directly treat cutaneous disorders or the cutaneous manifestations of a disease with the intent of substantially directing the pharmacological effect of the drug to the surface of the skin or within the skin. The term "topical" delivery also includes dermal, inhaled and ocular/otic administration. "Topical" administration also refers to application to and diffusion through the stratum corneum, including but not limited to application to psoriatic lesions and broken skin.

The term "treating" or "treatment" as used herein refers to administration of a compound or agent to a subject who has a disorder or is at risk of developing the disorder with the purpose to cure, alleviate, relieve, remedy, delay the onset of, prevent, or ameliorate the disorder, the symptom of the disorder, the disease state secondary to the disorder, or the predisposition toward the disorder. Treatment need not mean that the condition or disorder is totally cured. A useful pharmaceutical composition, e.g. a pharmaceutical emulsion composition, herein need only to reduce the severity of the condition or disorder, reduce the severity of symptoms associated therewith, provide improvement to a patient's quality of life, or delay, prevent or inhibit the onset of the condition or disorder. A treatment need not be effective in every member of a population, e.g. a population of patients with atopic dermatitis, to have clinical utility, as is recognized in the medical and pharmaceutical arts.

Concentrations, amounts, solubilities, and other numerical data may be presented herein in a range format. It is to be understood that such range format is used merely for convenience and brevity and should be interpreted flexibly to include not only the numerical values explicitly recited as the limit of the range, but also to include all the individual numerical values or sub-ranges encompassed within that range as if each numerical value and sub-range is explicitly recited. All numbers expressing quantities, percentages or proportions, and other numerical values used in the specification, are to be understood as being modified in all instances by the term "about".

For example, a concentration range of 0.1 to 5 ng/ml should be interpreted to include not only the explicitly recited concentration limits of 0.1 ng/ml and 5 ng/ml but also to include individual concentrations such as 0.2 ng/ml, 0.8 ng/ml, 1.0 ng/ml 2.2 ng/ml, 3.6 ng/mol, and sub-ranges such as 0.3-2.5 ng/ml, 1.8-3.2 ng/ml, etc. This interpretation should apply regardless of the breadth of the range or the characteristic being described.

Any concentration range, percentage range or ratio range recited herein is to be understood to include concentrations, percentages or ratios of any integer within that range and fractions thereof, such as one tenth and one hundredth of an integer, unless otherwise indicated.

Other terms used herein are intended to be defined by their well-known meanings in the art.

The alternative definitions for the various groups and substituent groups of Formula (I), Formula (Ia) and Formula (II) provided throughout the specification are intended to particularly describe each compound species disclosed herein, individually, as well as groups of one or more compound species. The scope of this invention includes any combination of these group and substituent group definitions.

Compounds

In some embodiments, the present disclosure describes a compound of Formula (I):

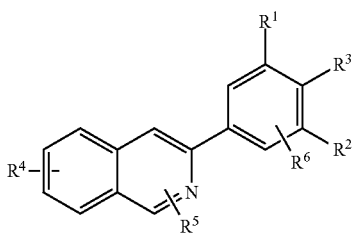
(I)

or a salt, solvate or hydrate thereof.

Each of substituents $R^1$ and $R^2$ of Formula (I) is independently selected from the group consisting of OH, $OR^7$, and H, provided that at least one of $R^1$ and $R^2$ is OH or $OR^7$.

Substituent $R^7$ of Formula (I) is independently selected from the group consisting of optionally substituted $C_{1-6}$ alkyl, optionally substituted $C_{3-6}$ cycloalkyl, optionally substituted aryl, optionally substituted aryl $C_{1-6}$ alkyl and acyl.

Substituent $R^3$ of Formula (I) is selected from the group consisting of optionally substituted $C_{1-6}$ alkyl, optionally substituted $C_{2-6}$ alkenyl, optionally substituted $C_{2-6}$ alkynyl, optionally substituted aryl, optionally substituted aryl $C_{1-6}$ alkyl, optionally substituted $C_{3-6}$ cycloalkyl, optionally substituted $C_{4-6}$ cycloalkenyl, halo, cyano, $-C(O)OR^8$, $-NR^9R^{10}$, $-S(O)_2NR^9R^{10}$, $-C(O)R^{11}$, $-OR^{12}$, $-S(O)_n R^{13}$, and optionally substituted heterocyclic ring.

The substituent $R^8$ of Formula (I) is independently selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl;

Each of $R^9$ and $R^{10}$ of Formula (I) is independently selected from the group consisting of H, optionally substituted $C_{1-6}$ alkyl, optionally substituted $C_{3-6}$ cycloalkyl, optionally substituted aryl, and optionally substituted aryl $C_1$-6 alkyl. Alternatively, substituents $R^9$ and $R^{10}$ together with the nitrogen atom to which they are attached, form a 5-7 membered cyclic saturated or unsaturated ring.

Substituent $R^{11}$ of Formula (I) is independently selected from the group consisting of hydrogen, optionally substituted $C_{1-6}$ alkyl, optionally substituted $C_{2-6}$ alkenyl, optionally substituted $C_{2-6}$ alkynyl, optionally substituted aryl, optionally substituted aryl $C_{1-6}$ alkyl, optionally substituted $C_{3-6}$ cycloalkyl, $-NR^9R^{10}$, and $-OR^{12}$.

Each of substituents $R^{12}$ and $R^{13}$ of Formula (I) is independently selected from the group consisting of H, optionally substituted alkyl, optionally substituted alkenyl, optionally substituted alkynyl, optionally substituted aryl, optionally substituted aryl $C_1$-6 alkyl, and optionally substituted $C_{3-6}$ cycloalkyl.

Substituent $R^6$ of Formula (I) is selected from the group consisting of H, halo, hydroxyl, alkoxy, optionally substituted $C_{1-6}$ alkyl, halogenated alkyl, optionally substituted $C_{2-6}$ alkenyl, optionally substituted $C_{2-6}$ alkynyl, and optionally substituted aryl $C_1$-6 alkyl.

Subscript n of Formula (I) is an integer having a value of 0, 1 or 2.

Subscript s of Formula (I) is an integer having a value of 0, 1 or 2.

Subscript t of Formula (I) is an integer having a value of 0 to 6.

The substituent $R^5$ of Formula (I) is selected from the group consisting of H, halo, optionally substituted $C_{1-6}$ alkyl, $-C(O)OR^{14}$, $-C(O)NR^{15}R^{16}$, optionally substituted aryl, and optionally substituted $-C_{1-6}$ alkylaryl.

Substituent $R^{14}$ of Formula (I) is selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl.

Each of substituents $R^{15}$ and $R^{16}$ of Formula (I) is independently selected from the group consisting of H, optionally substituted $C_{1-6}$ alkyl, optionally substituted $C_{3-6}$ cycloalkyl, optionally substituted aryl, optionally substituted aryl $C_{1-6}$ alkyl, and optionally substituted $C_{3-6}$ cycloalkyl. Alternatively, $R^{15}$ and $R^{16}$ together with the nitrogen to which they are attached, forms a 5-7 membered cyclic saturated or unsaturated ring.

Substituent $R^4$ of Formula (I) is selected from the group consisting of H, halo, cyano, optionally substituted $C_{1-6}$ alkyl, optionally substituted $C_{2-6}$ alkenyl, optionally substituted $C_{2-6}$ alkynyl, optionally substituted aryl, optionally substituted aryl $C_{1-6}$ alkyl, optionally substituted $C_{3-6}$ cycloalkyl, $-(CR^{18}R^{19})_t COOR^8$, $-(CR^{18}R^{19})_t OC(O)R^8$; $-(CR^{18}R^{19})_t NR^9R^{10}$, $-(CR^{18}R^{19})_t C(O)NR^9R^{10}$, $-(CR^{18}R^{19})_t NR^9C(O)R^8$, $-(CR^{18}R^{19})_t S(O)_2NR^9R^{10}$, $-(CR^{18}R^{19})_t COR^{11}$, $-(CR^{18}R^{19})_t CH(O)$, $-(CR^{18}R^{19})_t OR^{12}$, $-(CR^{18}R^{19})_t S(O)_s R^{13}$; optionally substituted heterocyclic and optionally substituted heterocyclic$C_{1-6}$ alkyl.

Each of substituent $R^{18}$ and $R^{19}$ of Formula (I) is independently selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl.

In some embodiments, the salt is a pharmaceutically acceptable salt.

In some embodiments each of $R^1$ and $R^2$ is independently OH. In some embodiments, one of $R^1$ and $R^2$ is OH and the other is H. In some embodiments, one of $R^1$ and $R^2$ is OH and the other is $OR^7$ and in some embodiments both $R^1$ and $R^2$ are $OR^7$ wherein each $R^7$ is independently selected from the group consisting of optionally substituted $C_{1-6}$ alkyl, optionally substituted $C_{3-6}$ cycloalkyl, optionally substituted aryl, optionally substituted aryl $C_1$-6 alkyl and acyl. In some embodiments, $R^7$ is optionally substituted $C_1$-4 alkyl. In some embodiments, $R^7$ is methyl or ethyl. In other embodiments, $R^7$ is optionally substituted $C_1$-4 alkyl substituted with $NR^{22}R^{23}$. In some embodiments, each of $R^{22}$ and $R^{23}$ is independently selected from the group consisting of H and $C_{1-3}$ alkyl, such as $-(CH_2)_3NH_2$. In some embodiments each of $R^1$ and $R^2$ is methoxy. In some embodiments $R^1$ is OH and $R^2$ is $OR^7$, wherein $R^7$ is a substituted $C_{1-6}$ alkyl. In some embodiments $R^1$ is OH and $R^2$ is $OR^7$, wherein $R^7$ is $C_1$-6 alkyl substituted with $NR^{22}R^{23}$. In some embodiments $R^1$ is OH and $R^2$ is $-O(CH_2)_3NH_2$.

When $R^7$ is an optionally substituted moiety, the moiety being substituted may be optionally substituted one or more times, such as one to three times, independently with halo; hydroxyl; hydroxy substituted $-C_{1-3}$ alkyl; $C_{1-3}$ alkoxy; halosubstituted $C_{1-3}$ alkoxy; $-S(O)_m C_{1-3}$, wherein m is an integer having a value of 0, 1 or 2; $-NR^{22}R^{23}$, wherein $R^{22}$ and $R^{23}$ are independently selected from H or a $C_{1-3}$ alkyl or wherein $R^{22}$ and $R^{23}$ together with the nitrogen to which they are attached form a 5 to 7 membered ring which optionally contains an additional heteroatom selected from O, N, or S; $C_{3-7}$ cycloalkyl; halosubstituted $C_{1-3}$ alkyl, such as $CF_2CF_2H$, or $CF_3$; or optionally substituted aryl, wherein the aryl moiety may also be optionally substituted one to two times by halo; hydroxyl; hydroxy substituted $-C_{1-3}$ alkyl; $C_{1-3}$ alkoxy; $-S(O)_m C_{1-3}$ alkyl, wherein m is an integer having a value of 0, 1 or 2; amino; mono and di-substituted $C_{1-3}$ alkylamino; $C_{1-3}$ alkyl; or $CF_3$.

In some embodiments $R^7$ is optionally substituted $C_{1-6}$ alkyl. In some embodiments $R^7$ is $C_1$-6 alkyl substituted with $NR^{22}R^{23}$. In some embodiments $R^7$ is $C_1$-6 alkyl substituted with $NH_2$. In some embodiments $R^7$ is —$(CH_2)_3$ $NH_2$.

In some embodiments, when $R^3$ is an optionally substituted moiety, the moiety may be substituted independently one or more times, such as one to three times. In some embodiments, the moieties may be optionally substituted independently one to three times with halo, hydroxy, $C_{1-3}$ alkoxy, $C_{1-3}$ alkyl, aryl or arylalkyl.

In some embodiments $R^3$ is selected from the group consisting of optionally substituted $C_{3-6}$ alkyl and optionally substituted $C_{3-6}$ cycloalkyl. In some embodiments, the $C_{3-6}$ alkyl is isopropyl, n-propyl, n-butyl, t-butyl, sec-butyl, n-pentyl, isopentyl, 2-methylbutyl, n-hexyl, and the like. In some embodiments, the alkyl is isopropyl or t-butyl. In some embodiments, the $C_{3-6}$ alkyl is isopropyl. In some embodiments, the $C_{3-6}$ cycloalkyl is a cyclopropyl, cyclopentyl or cyclohexyl. In some embodiments, the $C_{3-6}$ cycloalkyl is cyclopentyl.

In some embodiments $R^3$ is a heterocyclic ring.

In some embodiments $R^3$ is isopropyl.

In some embodiments, $R^6$ is selected from the group consisting of H, halo, hydroxyl, $C_{1-3}$ alkoxy, optionally substituted $C_{1-6}$ alkyl, halogenated alkyl, optionally substituted $C_{2-6}$ alkenyl, optionally substituted $C_{2-6}$ alkynyl, and optionally substituted aryl $C_{1-6}$ alkyl. In some embodiments $R^6$ is selected from the group consisting of H, halo, hydroxyl, $C_{1-3}$ alkoxy, optionally substituted $C_{1-3}$ alkyl, and halogenated alkyl. In some embodiments, $R^6$ is selected from the group consisting of H and halo. In some embodiments, $R^6$ is selected from the group consisting of H and bromo. In some embodiments, $R^6$ is H.

In some embodiments $R^5$ is selected from the group consisting of H, halo, optionally substituted —$C_{1-6}$ alkyl, —$C(O)OR^{14}$, —$C(O)NR^{15}R^{16}$ aryl and —$C_{1-6}$ alkylaryl. In some embodiments, $R^5$ is selected from the group consisting of H, halo, optionally substituted $C_{1-6}$ alkyl, $C(O)OR^{14}$, and $C(O)NR^{15}R^{16}$. In some embodiments, $R^5$ is selected from the group consisting of H, halo, optionally substituted $C_{1-6}$ alkyl, and $C(O)OR^{14}$. In some embodiment, $R^5$ is selected from the group consisting of H and optionally substituted $C_{1-6}$ alkyl. In some embodiments, $R^5$ is selected from the group consisting of H, $C(O)OR^{14}$, and $C(O)NR^{15}R^{16}$. In some embodiments, $R^5$ is optionally substituted $C_{1-3}$ alkyl. In some embodiments when $R^5$ is an optionally substituted —$C_1$-6 alkyl moiety, the —$C_1$-6 alkyl is optionally substituted one to three times, independently with halo; hydroxyl; $C_{1-3}$ alkoxy; halosubstituted $C_{1-3}$ alkoxy; —$S(O)_mC_{1-3}$ alkyl, wherein m is an integer having a value of 0, 1 or 2; —$NR^{20}R^{21}$, wherein $R^{20}$ and $R^{21}$ are independently selected from the group consisting of H and $C_{1-3}$ alkyl; halo substituted $C_{1-3}$ alkyl, such as $CF_2CF_2H$, or $CF_3$; or aryl. In some embodiments, $R^5$ is H.

In some embodiments, $R^4$ is selected from the group consisting of H, —$(CR^{18}R^{19})_tCOOR^8$, —$(CR^{18}R^{19})_tC(O)NR^9R^{10}$, —$(CR^{18}R^{19})NR^9R^{10}$, optionally substituted $C_1$-6 alkyl, —$(CR^{18}R^{19})_tOR^{12}$ and —$(CR^{18}R^{19})_tS(O)_rR^{13}$. In some embodiments, $R^4$ is selected from the group consisting of H, —$(CR^{18}R^{19})_tCOOR^8$, and —$(CR^{18}R^{19})_tC(O)NR^9R^{10}$; wherein t is 0, $R^9$ is H and $R^{10}$ is optionally substituted $C_{1-6}$ alkyl. In some embodiments $R^4$ is selected from the group consisting of H, —COOH, —COOCH$_3$ and —CONH$(CH_2)_2$ NH$_2$. In some embodiments $R^4$ is H.

In some embodiments, t is an integer having a value of 0, 1, 2, or 3. In some embodiments, t is 0.

In some embodiments, each of $R^9$ and $R^{10}$ is independently selected from the group consisting of H and optionally substituted $C_{1-6}$ alkyl.

In some embodiments, $R^{11}$ is selected from the group consisting of H, and optionally substituted $C_{1-6}$ alkyl.

In some embodiments, each of $R^{12}$ and $R^{13}$ is independently selected from the group consisting of H and optionally substituted alkyl.

In some embodiments, n is 0 or 2. In some embodiments, n is 0. In some embodiments, n is 2.

In some embodiments, each of $R^{18}$ and $R^{19}$ is independently selected from the group consisting of H and optionally substituted $C_{1-6}$ alkyl.

Some embodiments describe a compound of Formula (I) wherein:

$R^1$ is selected from the group consisting of OH and $OR^7$, wherein $R^7$ is optionally substituted $C_{1-6}$ alkyl;

$R^2$ is selected from the group consisting of OH and $OR^7$, wherein $R^7$ is optionally substituted $C_{1-6}$ alkyl;

$R^3$ is optionally substituted $C_{1-6}$ alkyl;

$R^4$ is selected from the group consisting of H, —$(CR^{18}R^{19})_tCOOR^8$, —$(CR^{18}R^{19})_tC(O)NR^9R^{10}$; wherein t is 0, $R^8$ is selected from H and optionally substituted $C_{1-6}$ alkyl, $R^9$ is H and $R^{10}$ is optionally substituted $C_{1-6}$ alkyl;

$R^5$ is H; and $R^6$ is H or halo.

Some embodiments describe a compound of Formula (I) wherein:

$R^1$ is selected from the group consisting of OH and $OR^7$, wherein $R^7$ is alkyl;

$R^2$ is selected from the group consisting of OH and $OR^7$, wherein $R^7$ is $C_1$-6 alkyl substituted with $NR^{22}R^{23}$; wherein $R^{22}$ and $R^{23}$ are independently selected from the group consisting of H and $C_{1-3}$ alkyl;

$R^3$ is optionally substituted $C_{1-6}$ alkyl;

$R^4$ is selected from the group consisting of H, —COOH, —COOCH$_3$, and —$C(O)NR^9R^{10}$; wherein $R^9$ is H; and $R^{10}$ is selected from the group consisting of amino substituted $C_{1-6}$ alkyl and —$(CH_2)_2NHC(O)$O-t-butyl;

$R^5$ is H; and $R^6$ is selected from the group consisting of H and halo.

Some embodiments describe a compound of Formula (I) wherein:

$R^1$ is selected from the group consisting of OH and —OCH$_3$;

$R^2$ is selected from the group consisting of OH, —OCH$_3$ and —O—$(CH_2)_3NH_2$;

$R^3$ is $C_1$—$_6$ alkyl;

$R^4$ is selected from the group consisting of H, —COOH, —COOCH$_3$, —$C(O)NH(CH_2)_2NH_2$; and —$C(O)NH(CH_2)_2$NHC(O)O-t-butyl;

$R^5$ is H; and $R^6$ is selected from the group consisting of H and bromo.

Some embodiments describe a compound of Formula (I) wherein:

$R^1$ is selected from the group consisting of OH and —OCH$_3$;

$R^2$ is selected from the group consisting of OH, —OCH$_3$ and —O—$(CH_2)_3NH_2$;

$R^3$ is isopropyl;

$R^4$ is selected from the group consisting of H, —COOH, —COOCH$_3$, —$C(O)(CH_2)_2NH_2$; and —$C(O)NH(CH_2)_2$NHC(O)O-t-butyl;

$R^5$ is H; and $R^6$ is is selected from the group consisting of H and bromo.

In one embodiment, the present disclosure describes a compound of Formula (Ia):

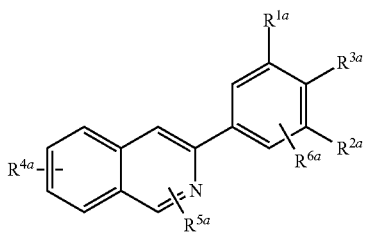

or a salt, solvate or hydrate thereof.

Each of substituents $R^{1a}$ and $R^{2a}$ of Formula (Ia) is independently selected from the group consisting of OH, $OR^{7a}$, and H, provided that at least one of $R^{1a}$ and $R^{2a}$ is OH or $OR^{7a}$.

Substituent $R^{7a}$ of Formula (Ia) is selected from the group consisting of optionally substituted $C_{1-6}$ alkyl, optionally substituted $C_{3-6}$ cycloalkyl, optionally substituted aryl, optionally substituted aryl $C_{1-6}$ alkyl and acyl.

Substituent $R^{3a}$ of Formula (Ia) is selected from the group consisting of optionally substituted $C_{1-6}$ alkyl, optionally substituted $C_{2-6}$ alkenyl, optionally substituted $C_{2-6}$ alkynyl, optionally substituted aryl, optionally substituted aryl $C_{1-6}$ alkyl, optionally substituted $C_{3-6}$ cycloalkyl, optionally substituted $C_{4-6}$ cycloalkenyl, halo, and optionally substituted heterocyclic ring.

Substituent $R^{6a}$ of Formula (Ia) is selected from the group consisting of H, halo, hydroxyl, alkoxy, optionally substituted $C_{1-6}$ alkyl, halogenated alkyl, optionally substituted $C_{2-6}$ alkenyl, optionally substituted $C_{2-6}$ alkynyl, and optionally substituted aryl $C_{1-6}$ alkyl.

The substituent $R^{5a}$ of Formula (Ia) is selected from the group consisting of H, halo, optionally substituted $C_{1-6}$ alkyl, $—C(O)OR^{14a}$, $—C(O)NR^{15a}R^{16a}$, optionally substituted aryl, and optionally substituted $—C_{1-6}$ alkylaryl.

Substituent $R^{14a}$ of Formula (Ia) is independently selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl.

Each of substituents $R^{15a}$ and $R^{16a}$ of Formula (Ia) is independently selected from the group consisting of H, optionally substituted $C_{1-6}$ alkyl, optionally substituted $C_{3-6}$ cycloalkyl, optionally substituted aryl, optionally substituted aryl $C_{1-6}$ alkyl, and optionally substituted $C_{3-6}$ cycloalkyl. Alternatively, $R^{15a}$ and $R^{16a}$ together with the nitrogen to which they are attached, forms a 5-7 membered cyclic saturated or unsaturated ring.

Subscript s' of Formula (Ia) is an integer having a value of 0, 1 or 2.

Subscript t' of Formula (Ia) is an integer having a value of 0 to 6.

Substituent $R^{4a}$ of Formula (Ia) is selected from the group consisting of H, halo, cyano, optionally substituted $C_{1-6}$ alkyl, optionally substituted $C_{2-6}$ alkenyl, optionally substituted $C_{2-6}$ alkynyl, optionally substituted aryl, optionally substituted aryl $C_{1-6}$ alkyl, optionally substituted $C_{3-6}$ cycloalkyl, $—(CR^{18a}R^{19a})_tCOOR^{8a}$, $—(CR^{18a}R^{19a})_tOC(O)R^{8a}$; $—(CR^{18a}R^{19a})_tNR9R10$, $—(CR^{18a}R^{19a})_tC(O)NR^{9a}R^{10a}$, $—(CR^{18a}R^{19a})_tNR^{9a}C(O)R^{8a}$, $—(CR^{18a}R^{19a})_tS(O)_sNR^{9a}R^{10a}$, $—(CR^{18a}R^{19a})_tCOR^{11a}$, $—(CR^{18a}R^{19a})_t$ CH(O), $—(CR^{18a}R^{19a})_tOR^{12a}$, $—(CR^{18a}R^{19a})_tS(O)_s.R^{13a}$; optionally substituted heterocyclic and optionally substituted heterocyclic$C_{1-6}$ alkyl.

Each of substituent $R^{18a}$ and $R^{19a}$ of Formula (Ia) is independently selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl.

The substituent $R^{8a}$ of Formula (Ia) is independently selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl.

Each of substituents $R^{9a}$ and $R^{10a}$ of Formula (Ia) is independently selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl. Alternatively, substituents $R^{9a}$ and $R^{10a}$ together with the nitrogen atom to which they are attached, form a 5-7 membered cyclic saturated or unsaturated ring.

Substituent $R^{11a}$ of Formula (Ia) is independently selected from the group consisting of hydrogen, optionally substituted $C_{1-6}$ alkyl, optionally substituted $C_{2-6}$ alkenyl, optionally substituted $C_{2-6}$ alkynyl, optionally substituted aryl, optionally substituted aryl $C_{1-6}$ alkyl, optionally substituted $C_{3-6}$ cycloalkyl, $—NR^{9a}R^{10a}$, and $—OR^{12a}$.

Each of substituents $R^{12a}$ and $R^{13a}$ of Formula (Ia) is independently selected from the group consisting of H, optionally substituted alkyl, optionally substituted alkenyl, optionally substituted alkynyl, optionally substituted aryl, optionally substituted aryl $C_{1-6}$ alkyl, and optionally substituted $C_{3-6}$ cycloalkyl.

In some embodiments, the salt of Formula (Ia) is a pharmaceutically acceptable salt.

In some embodiments, each of $R^{1a}$ and $R^{2a}$ a is independently OH. In some embodiments, one of $R^{1a}$ and $R^{2a}$ is OH and the other is H. In some embodiments, one of $R^{1a}$ and $R^{2a}$ is OH and the other is $OR^{7a}$ and in some embodiments each of $R^{1a}$ and $R^{2a}$ is independently $OR^{7a}$, wherein each $R^{7a}$ is independently selected from the group consisting of optionally substituted $C_{1-6}$ alkyl, optionally substituted $C_{3-6}$ cycloalkyl, optionally substituted aryl, optionally substituted aryl $C_{1-6}$ alkyl and acyl. In some embodiments, $R^{7a}$ is an optionally substituted $C_{1-4}$ alkyl. In some embodiments, $R^{7a}$ is methyl or ethyl.

In some embodiments, $R^{3a}$ is selected from the group consisting of optionally substituted $C_{1-6}$ alkyl, and optionally substituted $C_{3-6}$ cycloalkyl. In some embodiments, $R^{3a}$ is optionally substituted $C_{3-6}$ alkyl. In some embodiment, $R^{3a}$ is isopropyl. In some embodiments, $R^{3a}$ is optionally substituted $C_{3-6}$ cycloalkyl. In some embodiments, the cycloalkyl is cyclopentyl.

In some embodiments, $R^{3a}$ is selected from the group consisting of optionally substituted $C_{3-6}$ alkyl, and optionally substituted $C_{3-6}$ cycloalkyl; and $R^{1a}$ and $R^{2a}$ are each independently OH. In some embodiments, $R^{3a}$ is selected from the group consisting of optionally substituted $C_{3-6}$ alkyl, and optionally substituted $C_{3-6}$ cycloalkyl; and each of $R^{1a}$ and $R^{2a}$ is independently selected from the group consisting of OH, $OR^{7a}$, and H, provided that at least one of $R^{1a}$ and $R^{2a}$ is OH or $OR^{7a}$. In another embodiment, $R^{3a}$ is selected from the group consisting of optionally substituted $C_{3-6}$ alkyl and optionally substituted $C_{3-6}$ cycloalkyl; and one of $R^{1a}$ and $R^{2a}$ is OH and the other is H.

In some embodiments, each of $R^{4a}$ and $R^{5a}$ is independently selected from H and halo.

In some embodiments, $R^{4a}$ is H, and $R^{5a}$ is selected from the group consisting of H, halo, optionally substituted $C_{1-6}$ alkyl, $C(O)OR^{14a}$, and $C(O)NR^{15a}R^{16a}$. In some embodiments, $R^{5a}$ is H, and $R^{4a}$ is selected from the group consisting of H, halo, optionally substituted $C_{1-6}$ alkyl, $C(O)OR^{14a}$, and $C(O)NR^{15a}R^{16a}$.

In some embodiments, $R^{3a}$ is selected from the group consisting of optionally substituted $C_{3-6}$ alkyl and optionally substituted $C_{3-6}$ cycloalkyl; both $R^{1a}$ and $R^{2a}$ are OH, and each of $R^{4a}$ and $R^{5a}$ independently selected from H and halo.

In some embodiments, $R^{3a}$ is an optionally substituted $C_{3-6}$ alkyl, each of $R^{1a}$ and $R^{2a}$ is OH, and each of $R^{4a}$ and $R^{5a}$ is independently H or halo.

In some embodiments, $R^{6a}$ is independently selected from the group consisting of H, halo, hydroxyl, $C_{1-6}$ alkoxy, optionally substituted $C_{1-6}$ alkyl, halogenated alkyl, optionally substituted $C_{2-6}$ alkenyl, optionally substituted $C_{2-6}$ alkynyl, and optionally substituted aryl $C_{1-6}$ alkyl. In some embodiments, $R^{6a}$ is selected from the group consisting of H, halo, hydroxyl, $C_{1-3}$ alkoxy, optionally substituted $C_{1-3}$ alkyl, and halogenated alkyl. In some embodiments, $R^{6a}$ is selected from the group consisting of H and halo. In some embodiments, $R^{6a}$ is H.

In some embodiments, $R^{6a}$ is selected from the group consisting of H and halo; $R^{3a}$ is an optionally substituted $C_{3-6}$ alkyl, each of $R^{1a}$ and $R^{2a}$ is OH, and each of $R^{4a}$ and $R^{5a}$ is independently selected from the group consisting of H and halo In some embodiments, t is 0. In some embodiments, t is 0, 1, 2, or 3.

Some embodiments of the invention are directed to a compound of selected from the group consisting of:

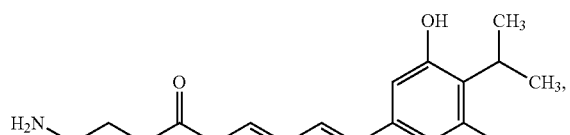

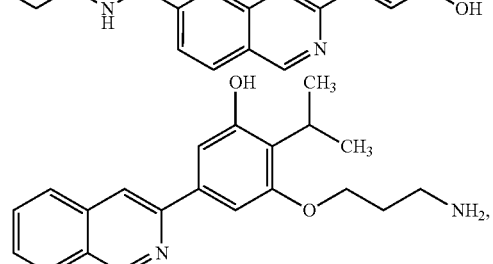

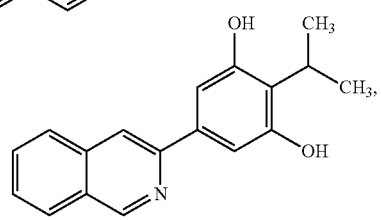

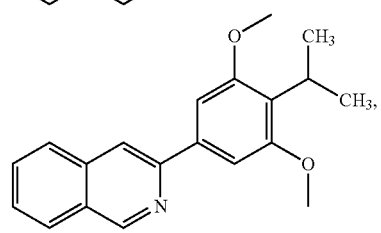

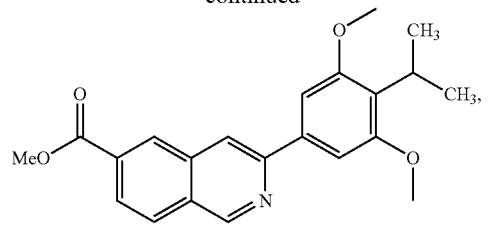

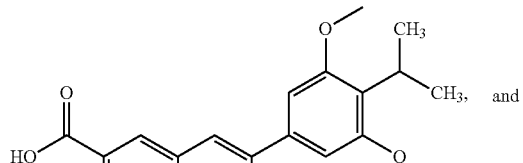

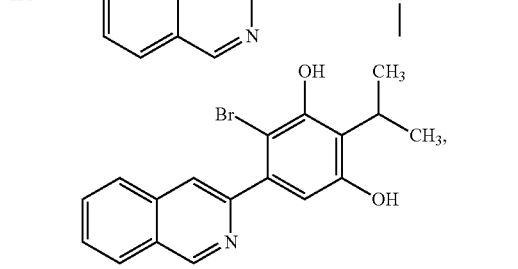

or a salt, solvate or hydrate thereof.

Some embodiments of the invention are directed to 2-isopropyl-5-(isoquinolin-3-yl)benzene-1,3-diol:

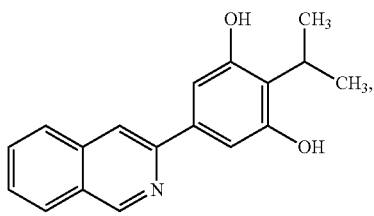 [SMILES: CC(C)c1c(O)cc(-c2cc3ccccc3cn2)cc1O]

or a pharmaceutically acceptable salt, solvate or hydrate thereof.

In some embodiments the 2-isopropyl-5-(isoquinolin-3-yl)benzene-1,3-diol, is a solid. In some embodiments the solid is a crystalline solid. In some embodiments the solid is an amorphous solid. In some embodiments the 2-isopropyl-5-(isoquinolin-3-yl)benzene-1,3-diol is a non-solvated crystal. Some embodiments describe isolated 2-isopropyl-5-(isoquinolin-3-yl)benzene-1,3-diol. In some embodiments the 2-isopropyl-5-(isoquinolin-3-yl)benzene-1,3-diol is a hydrate. In some embodiments the 2-isopropyl-5-(isoquinolin-3-yl)benzene-1,3-diol is an organic solvate. Some embodiments describe isolated 2-isopropyl-5-(isoquinolin-3-yl)benzene-1,3-diol organic solvate. Some embodiments describe 2-isopropyl-5-(isoquinolin-3-yl)benzene-1,3-diol acetonitrile/water solvate. Some embodiments describe 2-isopropyl-5-(isoquinolin-3-yl)benzene-1,3-diol acetone solvate. Some embodiments describe 2-isopropyl-5-(isoquinolin-3-yl)benzene-1,3-diol N,N-dimethylformamide solvate. Some embodiments describe 2-isopropyl-5-(isoquinolin-3-yl)benzene-1,3-diol 1,4-dioxane/water solvate. Some embodiments describe 2-isopropyl-5-(isoquinolin-3-yl)benzene-1,3-diol butanone solvate. Some embodiments describe 2-isopropyl-5-(isoquinolin-3-yl)benzene-1,3-diol tetrahydrofuran/water solvate. Some embodiments describe 2-isopropyl-5-(isoquinolin-3-yl)benzene-1,3-diol ethylacetate solvate. Some embodiments describe 2-isopropyl-5-(isoquinolin-3-yl)benzene-1,3-diol dimethylcarbonate solvate. Some embodiments describe 2-isopropyl-5-(isoquinolin-3-yl)benzene-1,3-diol dimethylsulfoxide solvate. Some embodiments describe 2-isopropyl-5-(isoquinolin-3-yl)benzene-1,3-diol 1-butanol solvate. Some embodiments describe 2-isopropyl-5-(isoquinolin-3-yl)benzene-1,3-diol tetrahydrofuran solvate. Some embodiments describe 2-isopropyl-5-(isoquinolin-3-yl)benzene-1,3-diol methyl t-butyl ether solvate.

The invention also includes various isomers of a compound according to any embodiment described herein, and mixtures thereof. Isomers are compounds that have the same composition and molecular weight but differ in physical and/or chemical properties. The structural difference may be in constitution (geometric isomers) or in the ability to rotate the plane of polarized light (stereoisomers). A compound according to any embodiment described herein, may contain one or more asymmetric centers, also referred to as chiral centers, and may, therefore, exist as individual enantiomers, diastereomers, or other stereoisomeric forms, or as mixtures thereof. All such isomeric forms are included within the present invention, including mixtures thereof. Chiral centers may also be present in a substituent such as an alkyl group. Where the stereochemistry of a chiral center present in a formula, or in any chemical structure illustrated herein, is not specified the structure is intended to encompass any stereoisomer and all mixtures thereof. Thus, a compound according to any embodiment described herein, containing one or more chiral centers may be used as racemic mixtures, enantiomerically enriched mixtures, or as enantiomerically pure individual stereoisomers. A mixture containing unequal portions of the enantiomers is described as having an "enantiomeric excess" (ee) of either the R or S compound. The excess of one enantiomer in a mixture is often described with a % enantiomeric excess. The ratio of enantiomers can also be defined by "optical purity" wherein the degree at which the mixture of enantiomers rotates plane polarized light is compared to the individual optically pure R and S compounds. The compounds can also be a substantially pure (+) or (−) enantiomer of the compounds described herein. In some embodiments, a composition can include a substantially pure enantiomer of a compound according to any embodiment described herein, that is at least 90%, 91%, 92%, 93%, 94%, 95%, 96%, 97%, 98%, or 99% of one enantiomer. In certain embodiments, a composition may include a substantially pure enantiomer of a compound according to any embodiment described herein, that is at least 99.5% of one enantiomer.

Individual stereoisomers of a compound according to any embodiment described herein, which contain one or more asymmetric centers may be resolved by methods known to those skilled in the art. For example, such resolution may be carried out (1) by formation of diastereoisomeric salts, complexes or other derivatives; (2) by selective reaction with a stereoisomer specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation. Further embodiments include prodrugs of a compound according to any embodiment described herein, i.e. compounds which release an active compound according to any of the embodiments described herein, in vivo when administered to a mammalian subject. A prodrug is a pharmacologically active or more typically an inactive compound that is converted into a pharmacologically active agent by a metabolic transformation. Prodrugs of a compound according to any embodiment described herein, are prepared by modifying functional groups present in the compound in such a way that the modifications may be cleaved in vivo to release the parent compound. In vivo, a prodrug readily undergoes chemical changes under physiological conditions (e.g. are hydrolyzed or acted on by naturally occurring enzyme(s)) resulting in liberation of the pharmacologically active agent. Prodrugs include compounds according to any embodiment described herein, wherein a hydroxyl, amino, or carboxy group is bonded to any group that may be cleaved in vivo to regenerate the free hydroxyl, amino or carboxy group, respectively. Examples of prodrugs include, but are not limited to esters (e.g., acetate, formate, and benzoate derivatives) of compounds according to any embodiment described herein, or any other derivative which upon being brought to the physiological pH or through enzyme action is converted to the active parent drug. Conventional procedures for the selection and preparation of suitable prodrug derivatives are described in the art.

Certain of the compounds of the invention may form salts with one or more equivalents of an acid (if the compound contains a basic moiety) or a base (if the compound contains an acidic moiety). The present invention includes within its scope all possible stoichiometric and non-stoichiometric salt forms.

When a compound of the invention contains a basic moiety, a desired salt form may be prepared by any suitable method known in the art, including treatment of the free base with an inorganic acid, such as hydrochloric acid, hydrobromic acid, sulfuric acid, nitric acid, phosphoric acid, and the like; or with an organic acid, such as acetic acid, trifluoroacetic acid, maleic acid, succinic acid, mandelic acid, fumaric acid, malonic acid, pyruvic acid, oxalic acid, glycolic acid, salicylic acid, and the like; or with a pyranosidyl acid, such as glucuronic acid or galacturonic acid; or with an alpha-hydroxy acid, such as citric acid or tartaric acid; or with an amino acid, such as aspartic acid or glutamic acid; or with an aromatic acid, such as benzoic acid or cinnamic acid; or with a sulfonic acid, such as p-toluenesulfonic acid, methanesulfonic acid, ethanesulfonic acid or the like.

Suitable addition salts are formed from acids which form non-toxic salts and examples include acetate, p-aminobenzoate, ascorbate, aspartate, benzenesulfonate, benzoate, bicarbonate, bismethylenesalicylate, bisulfate, bitartrate, borate, calcium edetate, camsylate, carbonate, clavulanate, citrate, cyclohexylsulfamate, edetate, edisylate, estolate, esylate, ethanedisulfonate, ethanesulfonate, formate, fumarate, gluceptate, gluconate, glutamate, glycollate, glycollylarsanilate, hexylresorcinate, hydrobromide, hydrochloride, dihydrochloride, hydrofumarate, hydrogen phosphate, hydroiodide, hydromaleate, hydrosuccinate, hydroxynaphthoate, isethionate, itaconate, lactate, lactobionate, laurate, malate, maleate, mandelate, mesylate, methylsulfate, monopotassium maleate, mucate, napsylate, nitrate, N-methylglucamine, oxalate, oxaloacetate, pamoate (embonate), palmate, palmitate, pantothenate, phosphate/diphosphate, pyruvate, polygalacturonate, propionate, saccharate, salicylate, stearate, subacetate, succinate, sulfate, tannate, tartrate, teoclate, tosylate, triethiodide, trifluoroacetate and valerate.

Other exemplary acid addition salts include pyrosulfate, sulfite, bisulfite, decanoate, caprylate, acrylate, isobutyrate, caproate, heptanoate, propiolate, oxalate, malonate, suberate, sebacate, butyne-1,4-dioate, hexyne-1,6-dioate, chlorobenzoate, methylbenzoate, dinitrobenzoate, hydroxybenzoate, methoxybenzoate, phthalate, phenylacetate, phenylpropionate, phenylbutrate, lactate, Thydroxybutyrate, mandelate, and sulfonates, such as xylenesulfonate, propanesulfonate, naphthalene-1-sulfonate and naphthalene-2-sulfonate.

If an inventive basic compound is isolated as a salt, the corresponding free base form of that compound may be prepared by any suitable method known to the art, including treatment of the salt with an inorganic or organic base, suitably an inorganic or organic base having a higher $pK_a$ than the free base form of the compound.

When a compound of the invention contains an acidic moiety, a desired salt may be prepared by any suitable method known to the art, including treatment of the free acid with an inorganic or organic base, such as an amine (primary, secondary, or tertiary), an alkali metal or alkaline earth metal hydroxide, or the like. Illustrative examples of suitable salts include celitec salts derived from amino acids such as glycine and arginine, ammonia; primary, secondary, and tertiary amines, and cyclic amines, such as N-methyl-D-glucamine, diethylamine, isopropylamine, trimethylamine, ethylene diamine, dicyclohexylamine, ethanolamine, piperidine, morpholine, and piperazine; as well as inorganic salts derived from sodium, calcium, potassium, magnesium, manganese, iron, copper, zinc, aluminum, and lithium.

Those compounds of the invention having both a basic and acidic moiety may be in the form of zwitterions, acid-addition salt of the basic moiety or base salts of the acidic moiety.

Because of their potential use in medicine, the salts of the compounds of the invention are preferably pharmaceutically acceptable salts. Suitable pharmaceutically acceptable salts are known to those of skill in the art.

These pharmaceutically acceptable salts may be prepared in situ during the final isolation and purification of the compound, or by separately treating the purified compound in its free acid or free base form with a suitable base or acid, respectively.

In certain embodiments, compounds of the invention may contain an acidic functional group and are, therefore, capable of forming pharmaceutically acceptable base addition salts by treatment with a suitable base. Examples of such bases include, but are not limited to, a) hydroxides, carbonates, and bicarbonates of sodium, potassium, lithium, calcium, magnesium, aluminum, and zinc; and b) primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds of the invention may contain a basic functional group and are therefore capable of forming pharmaceutically acceptable acid addition salts by treatment with a suitable acid. Suitable acids include pharmaceutically acceptable inorganic acids and organic acids. Representative pharmaceutically acceptable acids include hydrogen chloride, hydrogen bromide, nitric acid, sulfuric acid, sulfonic acid, phosphoric acid, acetic acid, hydroxyacetic acid, phenylacetic acid, propionic acid, butyric acid, valeric acid, maleic acid, acrylic acid, fumaric acid, succinic acid, malic acid, malonic acid, tartaric acid, citric acid, salicylic acid, benzoic acid, tannic acid, formic acid, stearic acid, lactic acid, ascorbic acid, methylsulfonic acid, p-toluenesulfonic acid, oleic acid, lauric acid, and the like.

This invention also provides for the conversion of one pharmaceutically acceptable salt of a compound of the invention into another pharmaceutically acceptable salt of a compound of this invention.

A compound according to any embodiment described herein, may exist in solid or liquid form. In the solid state, it may exist in crystalline or non-crystalline form, or as a mixture thereof. The skilled artisan will appreciate that pharmaceutically acceptable solvates may be formed from crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

For solvates of a compound according to any embodiment described herein, including solvates of salts of a compound according to any embodiment described herein, that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that a compound according to any embodiment described herein that exists in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The subject invention also includes isotopically-labelled compounds, which are identical to those recited in compounds of the invention and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts, solvates or hydrates thereof, include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds according to any embodiment described herein and pharmaceutically acceptable salts, solvates or hydrates of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), and are also useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds according to any embodiment described herein, can generally be prepared by carrying out the procedures disclosed in the Schemes and/or in the Examples below, by substituting a readily available isotopically labeled reagent for a non-isotopically labeled reagent.

The invention also embraces isolated compounds. An isolated compound refers to a compound which represents at least 10%, preferably at least 20%, more preferably at least 50% and most preferably at least 80% of the compound present in the mixture.

Because the compounds according to any embodiment described herein are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). In some embodiments, a compound according to any embodiment described herein is at least 90%, at least 91%, at least 92%, at least 93%, at least 94%, at least 95%, at least 96%, at least 97%, at least 98%, or at least 99% pure. Impure preparations of the compounds may be used for preparing the more pure forms used in the pharmaceutical compositions.

Pharmaceutical Compositions

Some embodiments describe a pharmaceutical composition comprising: a compound according to any embodiment described herein, a pharmaceutically acceptable salt thereof, a solvate thereof, or a hydrate thereof; and a pharmaceutically acceptable carrier or diluent. The pharmaceutical compositions can be prepared in a manner well known in the pharmaceutical arts, and can be administered by a variety of routes, depending upon whether local or systemic treatment is desired and upon the area to be treated.

While it is possible that a compound as described in any embodiment herein, may be administered as the bulk substance, it is preferable to present the compound in a pharmaceutical formulation, e.g., wherein the active agent is in an admixture with a pharmaceutically acceptable carrier selected with regard to the intended route of administration and standard pharmaceutical practice.

In particular, the disclosure provides a pharmaceutical composition comprising a therapeutically effective amount of at least one compound according to any embodiment described herein, and optionally, a pharmaceutically acceptable carrier.

Some embodiments describe a pharmaceutical composition comprising 2-Isopropyl-5-(isoquinolin-3-yl)benzene-1, 3-diol:

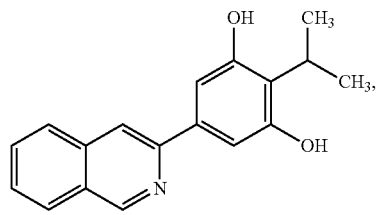 [SMILES: CC(C)c1c(O)cc(-c2cc3ccccc3cn2)cc1O]

or a pharmaceutically acceptable salt, solvate or hydrate thereof and a pharmaceutically acceptable carrier or diluent.

Some embodiments describe a pharmaceutical composition comprising N-(2-aminoethyl)-3-[3,5-dihydroxy-4-(propan-2-yl)phenyl]isoquinoline-6-carboxamide:

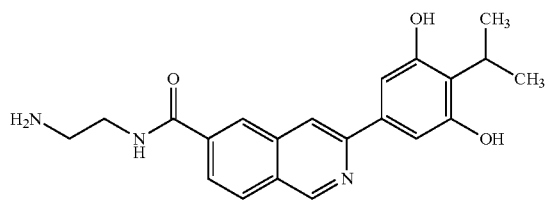 [SMILES: CC(C)c1c(O)cc(-c2cc3cc(C(=O)NCCN)ccc3cn2)cc1O]

or a pharmaceutically acceptable salt, solvate or hydrate thereof and a pharmaceutically acceptable carrier or diluent.

Some embodiments describe a pharmaceutical composition comprising 3-(3-aminopropoxy)-5-(isoquinolin-3-yl)-2-(propan-2-yl)phenol:

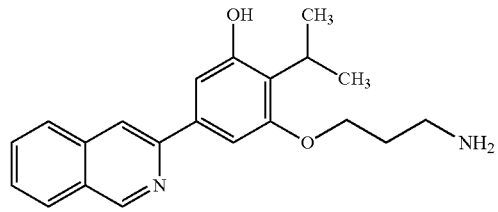 [SMILES: CC(C)c1c(O)cc(-c2cc3ccccc3cn2)cc1OCCCN]

or a pharmaceutically acceptable salt, solvate or hydrate thereof and a pharmaceutically acceptable carrier or diluent. In one embodiment, the salt is trifluroacetic acid salt:

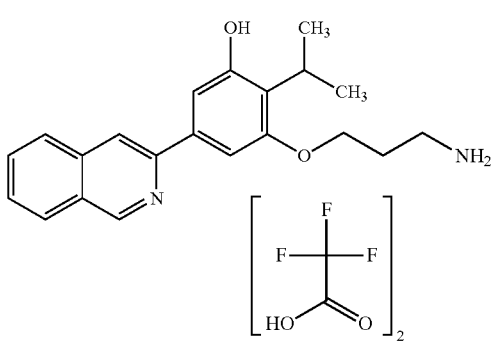

Methods of Treatment

Vitiligo is a depigmentation disorder resulting from selective destruction of melanocytes. In melanocytes, AhR links solar UVB radiation to skin pigmentation. A decreased risk of vitiligo associated with a specific variant of the AhR gene has been described, and, in further work, these authors found an AhR variant promoted Ahr transcriptional activity, facilitating its interaction with the SP1 transcripion factor, resulting in increased AhR expression and IL-10 production in humans (.

AhR-activating ligands have been shown to reduce inflammation in the lesional skin of patients with psoriasis and AhR antagonists exacerbated this disease. AhR signaling via FICZ reduce the inflammation in imiquimod-induced mouse models and AhR-deficient mice showed exacerbation of the disease compared to WT controls. It should also be noted that keratinocytes were implicated to be involved in the inflammatory response.

Activation of the AhR pathway has also been shown to result in inflammatory skin lesions, such as atopic dermatitis, and exacerbation of inflammatory diseases, after exposure to occupation or environmental xenobiotics. An AhR agonist, coal tar, was shown to completely restore expression of major skin barrier proteins.

Early dry age-related macular degeneration (AMD) is the leading cause of vision loss in the elderly. AhR activity and protein in human retinal pigment epithelial cells decrease with age and AhR(−/−) mice exhibit decreased visual function and develop dry AMD-like pathology. Another group also showed that Ahr(−/−) mice exhibited subretinal accumulation of microglia and focal retinal pigment epithelial cell atrophy, which is a phenotype observed in AMD.

The Malek lab has found that AhR is also implicated in wet AMD. They showed that in experimentally induced choroidal neovascular lesions in AhR(−/−) mice, there were lesions that displayed a higher number of ionized calcium-binding adaptor molecule 1-positive (Iba1(+)) microglial cells and a greater amount of collagen type IV deposition, all events also seen in human wet AMD.

There are many other potential indications where AhR agonism, or antagonism, may have an effect on disease severity or progression. There is also mounting evidence that targeting AhR in other disease conditions may be beneficial, such as for treatment of inflammation of the gut as in Irritable bowel disease (IBD), colitis and Crone's disease. AhR has also been shown to play an important role in protecting lungs from allergen-induced inflammation by modulating MSC recruitment and their immune-suppressive activity.

Atopic dermatitis (AD) is an intensely pruritic, chronic, relapsing, inflammatory skin disease. The cause of atopic dermatitis is multifactorial, with genetic and environmental factors, deficient skin barrier function, and an impaired immune response being the most predominant factors. The impaired immune response is characterized by activation of T-helper type 2 (Th2) cells with an increase in IgE production; there is also an over-expression of eotaxin-3, IL-2, IL-5, and IL-13 in skin lesions. The inflammatory component of atopic dermatitis is also thought to be mediated primarily by the Th2 type T cell activation pathway, although in chronic atopic dermatitis skin lesions, a shift towards a T-helper type 1 (Th1) driven pathway has been described. Atopic dermatitis often occurs in families with other atopic conditions, supporting the hypothesis that it may be genetically linked.

Skin barrier dysfunction is one of the critical factors in the pathogenesis of atopic dermatitis. The characteristic signs and symptoms of atopic dermatitis include sensations of pruritus and burning, lichenification, and xerosis, with erythematous papules and plaques, vesiculation, exudation and crusting, erosion, and scaling. Atopic dermatitis often has a major impact on quality of life, because of both the stigma associated with having a visible skin lesion and the intense and constant itching that leads to sleep deprivation.

To date, there is no curative therapy for atopic dermatitis. Stabilizing the disease and reducing the number and severity of flares are the primary goals of treatment for both pediatric and adult patients. Patients require treatment of acute flares and, in persistent cases, long-term maintenance therapy. Topical therapies are directed at skin inflammation and are a key factor in disease management, as is symptomatic relief of itching in atopic dermatitis. Although multiple topical treatment options are available, there remains a need for a topical treatment that combines a high level of efficacy with an acceptable adult and pediatric safety profile that permits application to a large body surface area without restrictions on duration of treatment. Topical corticosteroids (TCSs) are typically the standard of care for acute flares of atopic dermatitis. However, TCSs are not generally suitable for long-term use due to the potential for local and systemic adverse events (e.g., skin atrophy and increased risk of systemic exposure). Current treatment options for atopic dermatitis in children are especially limited, given the safety concerns of long-term use (>2-4 weeks) or application to sensitive areas such as the face or intertriginous regions.

Without wishing to be bound by any theory, compounds according to embodiments described herein, are believed to have a different mechanism of action than topical corticosteroids (TCSs) and topical calcineurin inhibitors (TCIs), and are expected to have an improved safety profile with efficacy superior to TCIs. The compounds of embodiments described herein, would provide benefit to children who: are not adequately responsive to TCS; are intolerant to TCS; or are not indicated for TCS (e.g., due to lesion location or treatment duration). Having an effective option for a safe topical treatment may delay the transition to systemic therapies, limiting significant risks associated with treatment as well as costs to the patient.

Psoriasis vulgaris is a chronic autoimmune inflammatory skin disorder that results from an interaction of genetic, environmental and systemic factors and affects 2-3% of the Caucasian population. Immune system dysregulation is implicated in disease pathogenesis and includes aberrant cellular infiltrates, production of inflammatory mediators, and keratinization. At the crux of this process are the Th17-type cytokines (IL-17A, IL-17F and IL-22) which (i) drive keratinocyte hyperproliferation and chemokine production, and (ii) perpetuate further leukocyte recruitment.

Compounds according to embodiments described herein may be used be used for the treatment of mild to moderate psoriasis. Although there have been numerous new biological treatment options for severe psoriasis, there has been limited recent innovation in treatment options for patients with mild to moderate disease. Treatment with TCSs carry significant contraindications (long-term use and use in sensitive areas), thus a safe and effective topical treatment would be a tremendous advantage for mild to moderate psoriasis patients.

The present invention thus provides methods for the treatment of disorders associated with the abovementioned diseases or disorders, comprising the step of administering to a subject in need thereof at least one compound, as described in any embodiment herein, in an amount effective therefore.

In some embodiments, the disclosure provides methods of preventing or treating a condition associated with an AhR imbalance.

In some embodiments, the disclosure provides methods of treating or preventing an AhR mediated disease in a subject in need thereof, comprising administering to said subject an effective amount of a compound according to any embodiment described herein, or pharmaceutically acceptable salt, solvate or hydrate thereof; or a pharmaceutical composition according to any embodiment described herein. In some embodiments the compound is a compound of Formula (I) or Formula (Ia) or a pharmaceutically acceptable salt, solvate or hydrate thereof. In some embodiments the compound is a compound of Formula (I) or Formula (Ia), or a pharmaceutically acceptable salt, solvate or hydrate thereof in combination with another therapeutic agent. In some embodiments the compound is 2-isopropyl-5-(isoquinolin-3-yl)benzene-1,3-diol, or a pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof in combination with another therapeutic agent.

Some embodiments describe a method for treating or preventing disorders such as: clinical transplants (such as organ transplant, acute transplant or heterograft or homograft (such as is employed in burn treatment) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; IBD, including ulcerative colitis and Crohn's disease; lupus (systemic lupus erythematosis); graft vs. host disease; T-cell mediated hypersensitivity diseases, including contact hypersensitivity, eczema, delayed-type hypersensitivity, and gluten-sensitive enteropathy (Celiac disease); psoriasis; contact dermatitis (including that due to poison ivy); Hashimoto's thyroiditis; Sjogren's syndrome; autoimmune hyperthyroidism, such as Graves' Disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis, serum sickness; uticaria; allergic diseases such as respiratory allergies (asthma, hay fever, allergic rhinitis) or skin allergies; scleracierma; mycosis fungoides; acute inflammatory responses (such as acute respiratory distress syndrome and ishchemia/reperfusion injury); dermatomyositis; alopecia greata; chronic actinic dermatitis; eczema; Behcet's disease; Pustulosis palmoplanteris; Pyoderma gangrenum; Sezary's syndrome; atopic dermatitis; systemic sclerosis; and morphea; comprising administering an effective amount of a compound according to any embodiment described herein, or pharmaceutically acceptable salt thereof, or a pharmaceutical composition, according to any embodiment described herein.

Some embodiments describe a method for treating or preventing an allergic disease or disorder, an inflammatory disease or disorder or an autoimmune disease or disorder in a subject in need thereof, comprising administering to said subject an effective amount of a compound according to any embodiment described herein, or pharmaceutically acceptable salt, solvate or hydrate thereof. In some embodiments the compound is a compound of Formula (I) or Formula (Ia) or a pharmaceutically acceptable salt, solvate or hydrate thereof. In some embodiments the compound is a compound of Formula (I) or Formula (Ia) or pharmaceutically acceptable salt, solvate or hydrate thereof in combination with another therapeutic agent. In some embodiments the compound is 2-isopropyl-5-(isoquinolin-3-yl)benzene-1,3-diol, or a pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof in combination with another therapeutic agent.

Some embodiments describe a method for treating or preventing an inflammatory disease or disorder in a subject in need thereof, comprising administering to said subject an effective amount of a compound or pharmaceutical composition according to any embodiment described herein, or pharmaceutically acceptable salt, solvate or hydrate thereof. In some embodiments the compound is a compound of Formula (I) or Formula (Ia) or a pharmaceutically acceptable salt, solvate or hydrate thereof. In some embodiments the compound is a compound of Formula (I) or Formula (Ia) or pharmaceutically acceptable salt, solvate or hydrate thereof in combination with another therapeutic agent. In some embodiments the compound is 2-isopropyl-5-(isoquinolin-3-yl)benzene-1,3-diol, or a pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof in combination with another therapeutic agent.

In some embodiments the inflammatory disease or disorder is an inflammatory skin disease or disorder. In some embodiments the inflammatory skin disease or disorder is a chronic inflammatory skin disease or disorder, acne, psoriasis, rosacea or aging skin. In some embodiments the chronic inflammatory skin disease is dermatitis, e.g. atopic dermatitis, contact dermatitis, eszematous dermatitis, or seborrheic dermatitis.

In some embodiments, the inflammatory disease or disorder is selected from the group consisting of psoriasis, atopic dermatitis, contact dermatitis, eczematous dermatitis, or seborrhoic dermatitis and acne. In some embodiments, the inflammatory disease or disorder is selected from the group consisting of psoriasis, atopic dermatitis, and acne. In some embodiments, the inflammatory disease or disorder is psoriasis. In some embodiments, the inflammatory disease or disorder is atopic dermatitis. In some embodiments, the inflammatory disease or disorder is acne.

Some embodiments describe a method for treating or preventing a dermatological condition or disorder in a subject in need thereof, comprising administering to said subject an effective amount of a compound or pharmaceutical composition according to any embodiment described herein, or pharmaceutically acceptable salt, solvate or hydrate thereof. In some embodiments the compound is a compound of Formula (I) or Formula (Ia) or a pharmaceutically acceptable salt, solvate or hydrate thereof. In some embodiments the compound is a compound of Formula (I) or Formula (Ia) or pharmaceutically acceptable salt, solvate or hydrate thereof in combination with another therapeutic agent. In some embodiments the compound is 2-isopropyl-5-(isoquinolin-3-yl)benzene-1,3-diol, or a pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof in combination with another therapeutic agent.

In some embodiments the dermatological condition or disorder is a skin disease. In some embodiments the skin disease is selected from 1) a skin disorder of persistent inflammation, cell kinetics, and differentiation (e.g., psoriasis, psoriatic arthritis, exfoliative dermatitis, pityriasis rosea, lichen planus, lichen nitidus, or porokeratosis); 2) a skin disorder of epidermal cohesion, vesicular and bullous disorders (e.g., pemphigus, bulluous pemphigoi, epidermamolysis bullosa acquisita, or pustular eruptions of the palms or soles); 3) a skin disorder of epidermal appendages and related disorders (e.g., hair disorders, nails, rosacea, perioral dermatitis, or follicular syndromes); 4) a skin disorder such as an epidermal and appendageal tumors (e.g., squamous cell carcinoma, basal cell carcinoma, keratoacanthoma, benign epithelial tumors, or merkel cell carcinoma); 5) a disorder of melanocytes (e.g., pigmentary disorders, albinism, hypomelanoses and hypermelanoses, melanocytic nevi, or melanoma); 6) a skin disorder of inflammatory and neoplastic disorders of the dermis (e.g., erythema elavatum diutinum, eosinophils, granuloma facilae, pyoderma gangrenosum, malignant atrophic papulosis, fibrous lesions of dermis and soft tissue, or Kaposi sarcoma); 7) a disorder of the subcutaneous tissue (e.g., panninculitis or lipodystrophy); 8) a skin disorder involving cutaneous changes of altered reactivity (e.g., urticaria, angiodererma, graft-vs-host, allergic contact dermatitis, autosensitization dermatitis, atopic dermatitis, or seborrheic dermatitis); 9) a skin change due to mechanical and physical factors (e.g., thermal injury, radiation dermatitis, corns, or calluses); 10) photodamage (e.g., acute and chronic UV radiation, or photosensitization); or 11) a skin disorder due to microbial agents (e.g., leprosy, lyme borreliosis, onychomycosis, tinea pedra, rubella, measles, herpes simplex, Epstein-Barr virus (EBV), Human papillomavirus (HPV, e.g., HPV6 & 7), warts, or prions).

Some embodiments describe a method for treating or preventing a radiation dermatitis in a subject in need thereof, comprising administering to said subject an effective amount of a compound or pharmaceutical composition according to any embodiment described herein, or pharmaceutically acceptable salt, solvate or hydrate thereof. In some embodiments the compound is a compound of Formula (I) or Formula (Ia) or a pharmaceutically acceptable salt, solvate or hydrate thereof. In some embodiments the compound is a compound of Formula (I) or Formula (Ia) or pharmaceutically acceptable salt, solvate or hydrate thereof in combination with another therapeutic agent. In some embodiments the compound is 2-isopropyl-5-(isoquinolin-3-yl)benzene-1,3-diol, or a pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof in combination with another therapeutic agent. In some embodiments the radiation dermatitis is chronic raditation dermatitis. In some embodiments the radiation dermatitis is acute raditation dermatitis. In some embodiments the radiation dermatitis is acute erythema, sale, desquamation, fibrosis, telangiectasias and skin atrophy or combinations thereof. In some embodiments the radiation dermatitis is acute erythema, sale, or desquamation, or combinations thereof. In some embodiments the radiation dermatitis is fibrosis, telangiectasias and skin atrophy or combinations thereof.

Some embodiments describe a method for treating or preventing an inflammatory mucosal conditions in a subject in need thereof, comprising administering to said subject an effective amount of a compound or pharmaceutical composition according to any embodiment described herein, or pharmaceutically acceptable salt, solvate or hydrate thereof. In some embodiments the compound is a compound of Formula (I) or Formula (Ia) or a pharmaceutically acceptable salt, solvate or hydrate thereof. In some embodiments the compound is a compound of Formula (I) or Formula (Ia) or pharmaceutically acceptable salt, solvate or hydrate thereof in combination with another therapeutic agent. In some embodiments the compound is 2-isopropyl-5-(isoquinolin-3-yl)benzene-1,3-diol, or a pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof in combination with another therapeutic agent. In some embodiments the inflammatory mucosal condition is induced by cancer radiation or chemotherapy treatment. In some embodiments the inflammatory mucosal condition is oral mucositis, lichen planus, pemphigus vulgaris. In some embodiments the inflammatory mucosal condition is an oral mucositis such as oral lichen planus, erythema multiforme, mucous membrane pemphigoid, pemphigus vulgaris, epidermolysis bullosa aquisita. In some embodiments the oral mucositis is induced by cancer radiation or chemotherapy treatment. In some embodiments the oral mucositis is induced by head and/or neck cancer radiation or chemotherapy treatment. In some embodiments the oral mucositis is induced by head and/or neck cancer radiation treatment.

Some embodiments describe a method of treating atopic dermatitis in a subject in need thereof, comprising administering to the subject, a therapeutically effective amount of a compound of the formula

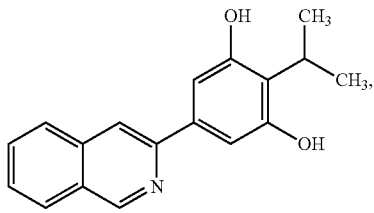 [SMILES: CC(C)c1c(O)cc(-c2cc3ccccc3cn2)cc1O]

or a pharmaceutically acceptable salt, solvate or hydrate thereof or a pharmaceutical composition thereof.

Some embodiments describe a method of treating psoriasis in a subject in need thereof, comprising administering to the subject, a therapeutically effective amount of 2-isopropyl-5-(isoquinolin-3-yl)benzene-1,3-diol:

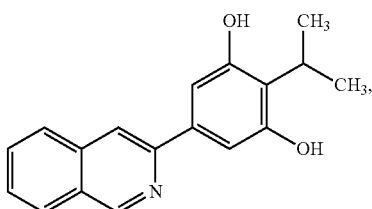

or a pharmaceutically acceptable salt, solvate or hydrate thereof or a pharmaceutical composition thereof.

Some embodiments describe a method of treating atopic dermatitis in a subject in need thereof, comprising administering to the subject, 2-isopropyl-5-(isoquinolin-3-yl)benzene-1,3-diol:

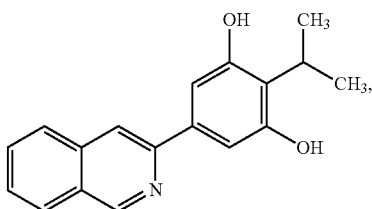

or a pharmaceutically acceptable salt, solvate or hydrate thereof or a pharmaceutical composition thereof.

Some embodiments describe a method of treating atopic dermatitis or psoriasis, in a subject in need thereof, comprising administering to the subject, a topical cream comprising a therapeutically effective amount of 2-isopropyl-5-(isoquinolin-3-yl)benzene-1,3-diol, or a pharmaceutically acceptable salt, solvate or hydrate thereof.

Some embodiments describe a method of treating atopic dermatitis or psoriasis, in a subject in need thereof, comprising administering to the subject, a topical gel comprising a therapeutically effective amount of 2-isopropyl-5-(isoquinolin-3-yl)benzene-1,3-diol, or a pharmaceutically acceptable salt, solvate or hydrate thereof.

Some embodiments describe a method of treating atopic dermatitis or psoriasis, in a subject in need thereof, comprising administering to the subject, a topical lotion comprising a therapeutically effective amount of 2-isopropyl-5-(isoquinolin-3-yl)benzene-1,3-diol, or a pharmaceutically acceptable salt, solvate or hydrate thereof.

In some embodiments, the compound is an agonist of the AhR ligand. In some embodiments, the compound is an antagonist of the AhR ligand.

A compound according to any embodiment described herein may be used in a veterinary setting or in a medical setting. It is recognized that the subject or patient may be an animal, a domestic animal, such as a mammal, including horses, cows, pigs, sheep, poultry, fish, cats, dogs and zoo animals. In some embodiment, the subject is an animal.

In some embodiments, the subject is a mammal. In some embodiments, the subject is a human. In some embodiments, the human is an adult, or a pediatric patient. In some embodiments, the human is a pediatric patient. In some embodiments, the pediatric patient is a child. In some embodiments, the pediatric patient is 3 months to 2 years of age and older. In some embodiments, the human is an adult.

Some embodiments describe a compound according to any embodiment described herein, or pharmaceutically acceptable salt, solvate or hydrate thereof, for use in therapy.

In some embodiments the compound is a compound of Formula (I) or Formula (Ia) or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof.

Some embodiments describe a compound according to any embodiment described herein, or pharmaceutically acceptable salt, solvate or hydrate thereof, for use in the treatment or prevention of a condition associated with an AhR imbalance. In some embodiments the compound is a compound of Formula (I) or Formula (Ia), or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof.

Some embodiments describe a compound according to any embodiment described herein, or pharmaceutically acceptable salt, solvate or hydrate thereof, for use in the treatment or prevention of an AhR mediated disease. In some embodiments the compound is a compound of Formula (I) or Formula (Ia), or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof.

Some embodiments describe a compound according to any embodiment described herein, or pharmaceutically acceptable salt, solvate or hydrate thereof, for use in the treatment or prevention of an inflammatory disease or disorder. In some embodiments the compound is a compound of Formula (I) or Formula (Ia), or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof.

Some embodiments describe a compound according to any embodiment described herein, or pharmaceutically acceptable salt, solvate or hydrate thereof, for use in the treatment or prevention of a dermatological condition or disorder. In some embodiments the compound is a compound of Formula (I) or Formula (Ia), or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof.

Some embodiments describe a compound according to any embodiment described herein, or pharmaceutically acceptable salt, solvate or hydrate thereof, for use in the treatment or prevention of psoriasis. In some embodiments the compound is a compound of Formula (I) or Formula (Ia), or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof.

Some embodiments describe a compound according to any embodiment described herein, or pharmaceutically acceptable salt, solvate or hydrate thereof, for use in the treatment or prevention of a atopic dermatitis. In some embodiments the compound is a compound of Formula (I) or Formula (Ia), or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof.

Some embodiments describe use of a compound according to any embodiment described herein, or a pharmaceutically acceptable salt, solvate or hydrate thereof, in the manufacture of a medicament for a condition associated with an AhR imbalance. in a subject in need thereof. In some embodiments the compound is a compound of Formula (I) or Formula (Ia), or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof.

Some embodiments describe use of a compound according to any embodiment described herein, or a pharmaceutically acceptable salt, solvate or hydrate thereof, in the manufacture of a medicament for the treatment of an AhR mediated disease in a subject in need thereof. In some embodiments the compound is a compound of Formula (I) or Formula (Ia), or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof.

Some embodiments describe use of a compound according to any embodiment described herein, or a pharmaceutically acceptable salt, solvate or hydrate thereof, in the manufacture of a medicament for the treatment or prevention of an inflammatory disorder in a subject in need thereof. In some embodiments the compound is a compound of Formula (I) or Formula (Ia), or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof.

Some embodiments describe use of a compound according to any embodiment described herein, or a pharmaceutically acceptable salt, solvate or hydrate thereof, in the manufacture of a medicament for the treatment or prevention of a dermatological condition or disorder in a subject in need thereof. In some embodiments the compound is a compound of Formula (I) or Formula (Ia), or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof. Some embodiments describe use of a compound according to any embodiment described herein, or a pharmaceutically acceptable salt, solvate or hydrate thereof, in the manufacture of a medicament for the treatment or prevention of psoriasis in a subject in need thereof. In some embodiments the compound is a compound of Formula (I) or Formula (Ia), or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof.

Some embodiments describe use of a compound according to any embodiment described herein, or a pharmaceutically acceptable salt, solvate or hydrate thereof, in the manufacture of a medicament for the treatment or prevention of atopic dermatitis in a subject in need thereof. In some embodiments the compound is a compound of Formula (I) or Formula (Ia), or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof.

Some embodiments describe use of a compound according to any embodiment described herein, or pharmaceutically acceptable salt, solvate or hydrate thereof, for the treatment or prevention of a condition associated with AhR imbalance in a subject in need thereof. In some embodiments the compound is a compound of Formula (I) or Formula (Ia), or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof.

Some embodiments describe use of a compound according to any embodiment described herein, or pharmaceutically acceptable salt, solvate or hydrate thereof, for the treatment or prevention of AhR mediated disease. In some embodiments the compound is a compound of Formula (I) or Formula (Ia), or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof.

Some embodiments describe use of a compound according to any embodiment described herein, or pharmaceutically acceptable salt, solvate or hydrate thereof, for the treatment or prevention of an inflammatory disease or disorder. In some embodiments the compound is a compound of Formula (I) or Formula (Ia), or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof.

Some embodiments describe use of a compound according to any embodiment described herein, or pharmaceutically acceptable salt, solvate or hydrate thereof, in the manufacture of a medicament for the treatment or prevention of a dermatological condition or disorder. In some embodiments the compound is a compound of Formula (I) or Formula (Ia), or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof.

Some embodiments describe use of a compound according to any embodiment described herein, or pharmaceutically acceptable salt, solvate or hydrate thereof, in the manufacture of a medicament for the treatment or prevention of psoriasis. In some embodiments the compound is a compound of Formula (I) or Formula (Ia), or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof.

Some embodiments describe use of a compound according to any embodiment described herein, or pharmaceutically acceptable salt, solvate or hydrate thereof, in the manufacture of a medicament for the treatment or prevention of atopic dermatitis. In some embodiments the compound is a compound of Formula (I) or Formula (Ia), or pharmaceutically acceptable salt, solvate or hydrate thereof. In some embodiments the compound is 2-isopropyl-5-(isoquinolin-3-yl)benzene-1,3-diol, or a pharmaceutically acceptable salt, solvate or hydrate thereof.

Combinations

For the pharmaceutical compositions and the methods/uses described herein, a compound of any embodiment described herein, may be administered in combination with one or more other therapies and/or active agents. In some embodiments, the compound of any embodiment described herein is administered in combination with a second agent indicated for the disorders or diseases described herein, either concomitant with, prior to, or after the administration of the second agent. In some embodiments the second agent is in the same formulation as a compound according to any embodiment described herein. In some embodiments, the second agent is in a separate formulation. The second therapeutic agent may be administered by the same route as the compound according to any embodiment described herein, or it may be administered by a different route than the compound according to any embodiment described herein. For example, a compound according to any embodiment described herein may be administered topically and the second agent may be administered topical, orally, intravenously intramuscularly, otic, opthamologicaly, opthalmically, vaginally, rectally, etc. In some embodiments the second agent is administered concomitant with a compound of the invention. In some embodiments the second agent is administered prior to the compound of the invention. In some embodiments the second agent is administered after the compound of the invention.

In other words, a compound according to any embodiment described herein, may be administered together, contemporaneously or sequentially in either order to the site of administration, or to a desired site of action. The order of administration is not deemed necessary. However, if topically administered it may be preferable that the two or more actives are in contact at some point together at the site of administration or desired site of action. Alternatively, it is desirable that the time period for appropriate mode of action of the actives is timed appropriately in the delivery time of the active. If both are present in the same vehicle they provide ease of administration to the patient, and perhaps increased compliance, but it is not required for the invention herein.

When a compound according to any embodiment described herein, is administered in combination with one or more other therapies and/or active agents as described herein, each of the active drug components (i.e. the compound of the present invention and the second agent) is contained in an effective dosage amount.

In some embodiments, the second agent is an agent for treating or preventing a condition associated with an AhR imbalance.

In some embodiments the other agent(s) is useful in the prevention or treatment of allergic disease, inflammatory disease, or autoimmune disease. In some embodiments the agent(s) is antigen immunotherapy agents; anti-histamines; corticosteroids, for example, fluticasone propionate, fluticasone furoate, beclomethasone dipropionate, budesonide, ciclesonide, mometasonefuroate, triamcinolone, and flunisolide; NSAIDs; leukotriene modulators, such as montelukast, zafirlukast, and pranlukast; iNOS inhibitors; tryptase inhibitors; IKK2 inhibitors; p38 inhibitors; Syk inhibitors; protease inhibitors; elastase inhibitors; integrin antagonists, for example, beta-2integrin antagonists; adenosine A2a agonists; mediator release inhibitors, for example, sodium chromoglycate, 5-lipoxygenase inhibitors (zyflo); DP1 antagonists; DP2 antagonists; PI3K delta inhibitors; ITK inhibitors; LP (lysophosphatidic) inhibitors; or FLAP (5-lipoxygenase activating protein) inhibitors, for example, sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate); bronchodilators, for example, muscarinic antagonists and beta-2 agonists; methotrexate, and similar agents; monoclonal antibody therapy agents such as anti-IgE, anti-TNF, anti-IL-5, anti-IL-6, anti-IL-12, anti-IL-1 and similar agents; cytokine receptor therapies, for examples, etanercept and similar agents; and antigen non-specific immunotherapies, for example, interferon or other cytokines/chemokines, chemokine receptor modulators such as CCR3, CCR4 or CXCR2 antagonists, other cytokine/chemokine agonists or antagonists, TLR agonists and similar agents.

In some embodiments the other agent(s) is an agent for aiding transplantation, including cyclosporines, tacrolimus, mycophenolate mofetil, prednisone, azathioprine, sirolimus, daclizumab, basiliximab, or OKT3.

In some embodiments the other agent(s) is an agent for treating diabetes, for example, metformin (biguanides), meglitinides, sulfonylureas, DPP-4 inhibitors, thiazolidinediones, or alpha-glucosidase inhibitors, amylin mimetics, incretin mimetics, or insulin.

In some embodiments the other agent(s) is an antihypertensive such as diuretics, ACE inhibitors, ARBS, calcium channel blockers, and beta blockers.

Accordingly, the disclosure provides, in a further aspect, a pharmaceutical composition comprising at least one compound according to any embodiment described herein, or pharmaceutically acceptable derivative thereof; a second active agent; and, optionally a pharmaceutically acceptable carrier.

When combined in the same formulation it will be appreciated that the two or more compounds must be stable and compatible with each other and the other components of the formulation. When formulated separately they may be provided in any convenient formulation, in such manner as are known for such compounds in the art.

Preservatives, stabilizers, dyes and flavoring agents may be provided in any pharmaceutical composition described herein. Examples of preservatives include sodium benzoate, ascorbic acid and esters of p-hydroxybenzoic acid. Antioxidants and suspending agents may be also used.

With respect to combinations including biologics such as monoclonal antibodies or fragments, suitable excipients will be employed to prevent aggregation and stabilize the antibody or fragment in solution with low endotoxin, generally for parenteral administration, for example, intravenous, administration. For example, see Formulation and Delivery Issues for Monoclonal Antibody Therapeutics, Daugherty et al., in Current Trends in Monoclonal Antibody Development and Manufacturing, Part 4, 2010, Springer, New York pp 103-129.

Routes of Administration and Unit Dosage Forms

Compounds according to any embodiment described herein and pharmaceutical compositions incorporating said compounds may conveniently be administered by any of the routes conventionally used for drug administration, for instance, orally, topically, transdermally, parenterally or by inhalation. The compounds may be administered in conventional dosage forms prepared by combining a compound according to any embodiment described herein with standard pharmaceutical carriers according to conventional procedures. A compound according to any embodiment described herein, may also be administered in conventional dosages in combination with known, second therapeutically active compounds as further described herein. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

A compound according to any embodiment described herein, may be administered topically, that is by non-systemic administration. This includes the application of the compound externally to the epidermis, the buccal cavity, or the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, gels, solutions, ointments, pastes, and drops suitable for administration to the skin, the eye, ear or nose.

Lotions according to the present invention include those suitable for application to the skin, ear, nose or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, gels, ointments or pastes according to the present invention are semi-solid formulations of the active ingredient for external application. They may be made by mixing the active ingredient (i.e., a compound according to any embodiment described herein) in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenyl mercuric nitrate or acetate (0.002%), benzalkonium chloride (0.01%) and chlorhexidine acetate (0.01%). Suitable solvents for the preparation of an oily solution include glycerol, diluted alcohol and propylene glycol.

In some embodiments, a compound according to any embodiment described herein is administered topically in as a cream, gel ointment, paste, drop or lotion. In some embodiments a compound according to any embodiment described herein is administered as a gel or cream. In some embodiments a compound according to any embodiment described herein is administered as a gel. In some embodiments a compound according to any embodiment described herein is administered as a cream.

In some embodiments, the pharmaceutical formulation comprises a compound according to any embodiment described herein, and a pharmaceutically acceptable excipient or diluent and an anti-oxidant, preservative, gelling agent, pH adjusting agent, or stabilizer, or mixtures thereof suitably adapted for topical administration to the skin, eye, or ear of a patient.

In some embodiments the composition is a cream or gel composition and the compound of Formula (I) is 2-isopropyl-5-(isoquinolin-3-yl)benzene-1,3-diol.

In some embodiments the composition is a cream formulation. In some embodiments the composition is cream formulation 1 comprising the following:

| Formulation Component | Composition (% w/w) |
|---|---|
| 2-isopropyl-5-(isoquinolin-3-yl)benzene-1,3-diol | 0-1 |
| Propylene glycol | 15.0 |
| Transcutol P | 10.0 |
| PEG400 | 20.0 |
| Miglyol 810 | 5.0 |
| PEG40 Stearate | 1.0 |
| Glyceryl monostearate | 1.5 |
| Stearic acid | 0.15 |
| Cetostearyl alcohol 50 | 3.0 |
| Benzyl alcohol | 1.0 |
| BHT | 0.1 |
| Water | QS 100 |

QS 100: the amount needed to result in a composition totaling 100%.

It will be understood that when the 2-isopropyl-5-(isoquinolin-3-yl)benzene-1,3-diol in cream formulation 1 is present at a particular concentration (in the range of 0-1%), the formulation may be referred to as X % cream formulation 1. For example, in some embodiments the composition is a cream formulation 1, comprising 1% of 2-isopropyl-5-(isoquinolin-3-yl)benzene-1,3-diol (1% cream formulation 1). Thus, 1% cream formulation 1 comprises:

| Formulation Component | Composition (% w/w) |
|---|---|
| 2-isopropyl-5-(isoquinolin-3-yl)benzene-1,3-diol | 1 |
| Propylene glycol | 15.0 |
| Transcutol P | 10.0 |
| PEG400 | 20.0 |
| Miglyol 810 | 5.0 |
| PEG40 Stearate | 1.0 |
| Glyceryl monostearate | 1.5 |
| Stearic acid | 0.15 |
| Cetostearyl alcohol 50 | 3.0 |
| Benzyl alcohol | 1.0 |
| BHT | 0.1 |
| Water | QS 100 |

In some embodiments the composition is 0.5% cream formulation 1 comprising

| Formulation Component | Composition (% w/w) |
|---|---|
| 2-isopropyl-5-(isoquinolin-3-yl)benzene-1,3-diol | 0.5 |
| Propylene glycol | 15.0 |
| Transcutol P | 10.0 |
| PEG400 | 20.0 |
| Miglyol 810 | 5.0 |
| PEG40 Stearate | 1.0 |
| Glyceryl monostearate | 1.5 |
| Stearic acid | 0.15 |
| Cetostearyl alcohol 50 | 3.0 |
| Benzyl alcohol | 1.0 |

In some embodiments the composition is 0.1% cream formulation 1 comprising

| Formulation Component | Composition (% w/w) |
|---|---|
| 2-isopropyl-5-(isoquinolin-3-yl)benzene-1,3-diol | 0.1 |
| Propylene glycol | 15.0 |
| Transcutol P | 10.0 |
| PEG400 | 20.0 |
| Miglyol 810 | 5.0 |
| PEG40 Stearate | 1.0 |
| Glyceryl monostearate | 1.5 |
| Stearic acid | 0.15 |
| Cetostearyl alcohol 50 | 3.0 |
| Benzyl alcohol | 1.0 |
| BHT | 0.1 |
| Water | QS 100 |

In some embodiments the composition is cream formulation 2 comprising the following:

| Formulation Component | Composition (% w/w) |
|---|---|
| 2-isopropyl-5-(isoquinolin-3-yl)benzene-1,3-diol | 0-1 |
| Propylene glycol | 15.0 |
| Transcutol P | 15.0 |
| PEG400 | 20.0 |
| Miglyol 810 | 5.0 |
| PEG40 Stearate | 1.0 |
| Glyceryl monostearate | 1.5 |
| Stearic acid | 0.15 |
| Cetostearyl alcohol 50 | 3.0 |
| Benzyl alcohol | 1.0 |
| BHT | 0.1 |
| Water | QS 100 |

In some embodiments the composition is cream formulation 3 comprising the following:

| Formulation Component | Composition (% w/w) |
|---|---|
| 2-isopropyl-5-(isoquinolin-3-yl)benzene-1,3-diol | 0-1 |
| Propylene glycol | 35.0 |
| Transcutol P | 15.0 |
| Miglyol 810 | 5.0 |
| Steareth 21 | 5 |
| Steareth 2 | |
| Cetostearyl alcohol 50 | 3.0 |
| Benzyl alcohol | 1.0 |
| BHT | 0.1 |
| Water | QS 100 |

In some embodiments the composition is 1% cream formulation 3 comprising

| Formulation Component | Composition (% w/w) |
|---|---|
| 2-isopropyl-5-(isoquinolin-3-yl)benzene-1,3-diol | 1 |
| Propylene glycol | 35.0 |
| Transcutol P | 15.0 |
| Miglyol 810 | 5.0 |
| Steareth 21 | 5 |
| Steareth 2 | |
| Cetostearyl alcohol 50 | 3.0 |
| Benzyl alcohol | 1.0 |
| BHT | 0.1 |
| Water | QS 100 |

In some embodiments the composition is 0.5% cream formulation 3 comprising

| Formulation Component | Composition (% w/w) |
|---|---|
| 2-isopropyl-5-(isoquinolin-3-yl)benzene-1,3-diol | 0.5 |
| Propylene glycol | 35.0 |
| Transcutol P | 15.0 |
| Miglyol 810 | 5.0 |
| Steareth 21 | 5 |
| Steareth 2 | |
| Cetostearyl alcohol 50 | 3.0 |
| Benzyl alcohol | 1.0 |
| BHT | 0.1 |
| Water | QS 100 |

In some embodiments the composition is cream formulation 4 comprising the following:

| Formulation Component | Composition (% w/w) |
|---|---|
| 2-isopropyl-5-(isoquinolin-3-yl)benzene-1,3-diol | 0-1 |
| Propylene glycol | 15.0 |
| Transcutol P | 25.0 |
| Miglyol 810 | 5.0 |
| Steareth 21 | 5 |
| Steareth 2 | |
| Cetostearyl alcohol 50 | 3.0 |
| Benzyl alcohol | 1.0 |
| BHT | 0.1 |
| Carbomer p980 | 0.25 |
| Triethanolamine | 0.2 |
| Water | QS 100 |

In some embodiments the composition is cream formulation 5 comprising the following:

| Formulation Component | Composition (% w/w) |
|---|---|
| 2-isopropyl-5-(isoquinolin-3-yl)benzene-1,3-diol | 0-1 |
| Propylene glycol | 15.0 |
| Transcutol P | 25.0 |
| Miglyol 810 | 5.0 |
| Steareth 21 | 5 |
| Steareth 2 | |
| Cetostearyl alcohol 50 | 3.0 |
| Benzyl alcohol | 1.0 |
| BHT | 0.1 |
| Xanthan gum | 0.75 |
| Water | QS 100 |

In some embodiments the composition is cream formulation 6 comprising the following:

| Formulation Component | Composition (% w/w) |
| --- | --- |
| 2-isopropyl-5-(isoquinolin-3-yl)benzene-1,3-diol | 0-1 |
| Propylene glycol | 15.0 |
| Transcutol P | 25.0 |
| Miglyol 810 | 5.0 |
| Steareth 21 | 5 |
| Steareth 2 | |
| Cetostearyl alcohol 50 | 3.0 |
| Benzyl alcohol | 1.0 |
| BHT | 0.1 |
| Xanthan gum | 0.15 |
| Water | QS 100 |

In some embodiments the composition is cream formulation 7 comprising the following:

| Formulation Component | Composition (% w/w) |
| --- | --- |
| 2-isopropyl-5-(isoquinolin-3-yl)benzene-1,3-diol | 0-1 |
| Propylene glycol | 15.0 |
| Transcutol P | 25.0 |
| Miglyol 810 | 5.0 |
| Steareth 21 | 5 |
| Steareth 2 | |
| Cetostearyl alcohol 50 | 3.0 |
| Benzyl alcohol | 1.0 |
| BHT | 0.1 |
| Water | QS 100 |

In some embodiments the composition is a gel formulation (gel formulation 1) comprising the following:

| Formulation Component | Composition (% w/w) |
| --- | --- |
| 2-isopropyl-5-(isoquinolin-3-yl)benzene-1,3-diol | 0-1 |
| Propylene glycol | 10.0 |
| Transcutol P | 35.0 |
| Benzyl alcohol | 2.0 |
| BHT | 0.05 |
| Carbomer p980 | 0.5 |
| Trolamine | 0.15 |
| Water | QS 100 |

In some embodiments the composition is a gel formulation (1% gel formulation 1) comprising the following:

| Formulation Component | Composition (% w/w) |
| --- | --- |
| 2-isopropyl-5-(isoquinolin-3-yl)benzene-1,3-diol | 1 |
| Propylene glycol | 10.0 |
| Transcutol P | 35.0 |
| Benzyl alcohol | 2.0 |
| BHT | 0.05 |
| Carbomer p980 | 0.5 |
| Trolamine | 0.15 |
| Water | QS 100 |

In some embodiments the composition is a gel formulation (gel formulation 2) comprising the following:

| Formulation Component | Composition (% w/w) |
| --- | --- |
| 2-isopropyl-5-(isoquinolin-3-yl)benzene-1,3-diol | 0-1 |
| Transcutol P | 35.0 |
| PEG400 | 10.0 |
| Benzyl alcohol | 2.0 |
| BHT | 0.05 |
| Carbomer p980 | 0.5 |
| Trolamine | 0.2 |
| Water | QS 100 |

In some embodiments the composition is a gel formulation (gel formulation 3) comprising the following:

| Formulation Component | Composition (% w/w) |
| --- | --- |
| 2-isopropyl-5-(isoquinolin-3-yl)benzene-1,3-diol | 0-1 |
| Propylene glycol | 20.0 |
| Transcutol P | 25.0 |
| Benzyl alcohol | 2.0 |
| BHT | 0.05 |
| Carbomer p980 | 0.5 |
| Trolamine | 0.15 |
| Water | QS 100 |

In some embodiments the composition is a gel formulation (gel formulation 4) comprising the following:

| Formulation Component | Composition (% w/w) |
| --- | --- |
| 2-isopropyl-5-(isoquinolin-3-yl)benzene-1,3-diol | 0-1 |
| Propylene glycol | 40.0 |
| Transcutol P | 15.0 |
| Benzyl alcohol | 2.0 |
| BHT | 0.05 |
| Carbomer p980 | 0.5 |
| Trolamine | 0.15 |
| Water | QS 100 |

While topical usage is a preferred administration route, a compounds according to any embodiment described herein, may also be administered parenterally, that is by intravenous, intramuscular, subcutaneous, intranasal, intrarectal, intravaginal or intraperitoneal administration. The subcutaneous and intramuscular forms of parenteral administration are generally preferred. Appropriate dosage forms for such administration may be prepared by conventional techniques. A compound according to any embodiment described herein, may also be administered by inhalation, that is by intranasal and oral inhalation administration. Appropriate dosage forms for such administration, such as an aerosol formulation or a metered dose inhaler, may be prepared by conventional techniques.

The dosage of a compound according to any embodiment described herein, as an active ingredient of this invention may be varied so that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize.

In some embodiments, the amount of the compound to be administered can range between about 0.1 and about 100 mg/kg/day. Generally, dosage levels of between 0.1 to 10 mg/kg of body weight daily are administered to the patient, e.g., humans. In some embodiments the therapeutically effective amount is between a lower limit of about 0.1 mg/kg of body weight, about 0.2 mg/kg of body weight, about 0.3 mg/kg of body weight, about 0.4 mg/kg of body weight, about 0.5 mg/kg of body weight, about 0.6 mg/kg of body weight, about 0.7 mg/kg of body weight, about 0.8 mg/kg of body weight, about 0.9 mg/kg of body weight, about 1 mg/kg of body weight, about 5 mg/kg of body weight, about 10 mg/kg of body weight, about 15 mg/kg of body weight, about 20 mg/kg of body weight, about 25 mg/kg of body weight, about 30 mg/kg of body weight, about 35 mg/kg of body weight, about 40 mg/kg of body weight, about 45 mg/kg of body weight, about 50 mg/kg of body weight, 55 mg/kg of body weight, about 60 mg/kg of body weight, about 65 mg/kg of body weight, about 70 mg/kg of body weight, about 75 mg/kg of body weight, about 80 mg/kg of body weight, about 85 mg/kg of body weight, about 80 mg/kg of body weight, about 95 mg/kg of body weight, and about 100 mg/kg of body weight; and an upper limit of 100 mg/kg of body weight, about 95 mg/kg of body weight, about 90 mg/kg of body weight, about 85 mg/kg of body weight, about 80 mg/kg of body weight, about 75 mg/kg of body weight, about 70 mg/kg of body weight, about 65 mg/kg of body weight, about 60 mg/kg of body weight, about 55 mg/kg of body weight 50 mg/kg of body weight, about 45 mg/kg of body weight, about 40 mg/kg of body weight, about 35 mg/kg of body weight, about 30 mg/kg of body weight, about 25 mg/kg of body weight, about 20 mg/kg of body weight, about 15 mg/kg of body weight, about 10 mg/kg of body weight, about 5 mg/kg of body weight, about 1 mg/kg of body weight, about 0.9 mg/kg of body weight, about 0.8 mg/kg of body weight, about 0.7 mg/kg of body weight, about 0.6 mg/kg of body weight, about 0.5 mg/kg of body weight, about 0.4 mg/kg of body weight, about 0.3 mg/kg of body weight, about 0.2 mg/kg of body weight, and about 0.1 mg/kg of body weight per day.

In some embodiments, a compound according to any embodiment described herein is administered to a subject at a total daily dose of about 0.01 to about 1000 mg/day. In some embodiments the total daily dose is about 0.1 to about 100 mg/day. In some embodiments the total daily dose is between a lower limit of about 0.01 mg/day, about 0.05 mg/day, 0.1 mg/day, about 0.5 mg/day, about 1 mg/day, about 10 mg/day, about 20 mg/day, about 30 mg/day, about 40 mg/day, about 50 mg/day, about 60 mg/day, about 70 mg/day, about 80 mg/day, about 90 mg/day, about 100 mg/day, about 110 mg/day, about 120 mg/day, about 130 mg/day, about 140 mg/day, about 150 mg/day, about 160 mg/day, about 170 mg/day, about 180 mg/day, about 190 mg/day, about 200 mg/day, about 210 mg/day, about 220 mg/day, about 230 mg/day, about 240 mg/day, about 250 mg/day, about 260 mg/day, about 270 mg/day, about 280 mg/day, about 290 mg/day, about 300 mg/day, about 310 mg/day, about 320 mg/day, about 330 mg/day, about 340 mg/day, about 350 mg/day, about 360 mg/day, about 370 mg/day, about 380 mg/day, about 390 mg/day, about 400 mg/day, about 410 mg/day, about 420 mg/day, about 430 mg/day, about 440 mg/day, about 450 mg/day, about 460 mg/day, about 470 mg/day, about 480 mg/day, about 490 mg/day, about 500 mg/day, about 510 mg/day, about 520 mg/day, about 530 mg/day, about 540 mg/day, about 550 mg/day, about 560 mg/day, about 570 mg/day, about 580 mg/day, about 590 mg/day, about 600 mg/day, about 610 mg/day, about 620 mg/day, about 630 mg/day, about 640 mg/day, about 650 mg/day, about 660 mg/day, about 670 mg/day, about 680 mg/day, about 690 mg/day, about 700 mg/day, about 710 mg/day, about 720 mg/day, about 730 mg/day, about 740 mg/day, about 750 mg/day, about 760 mg/day, about 770 mg/day, about 780 mg/day, about 790 mg/day, about 800 mg/day, about 810 mg/day, about 820 mg/day, about 830 mg/day, about 840 mg/day, about 850 mg/day, about 860 mg/day, about 870 mg/day, about 880 mg/day, about 890 mg/day, about 900 mg/day, about 910 mg/day, about 920 mg/day, about 930 mg/day, about 940 mg/day, about 950 mg/day, about 960 mg/day, about 970 mg/day, about 980 mg/day, about 990 mg/day, and about 1000 mg/day, and an upper limit of 1000 mg/day, about 990 mg/day, about 980 mg/day, about 970 mg/day, about 960 mg/day, about 950 mg/day, about 940 mg/day, about 930 mg/day, about 920 mg/day, about 910 mg/day, about 900 mg/day, about 890 mg/day, about 880 mg/day, about 870 mg/day, about 860 mg/day, about 850 mg/day, about 840 mg/day, about 830 mg/day, about 820 mg/day, about 810 mg/day, about 800 mg/day, about 790 mg/day, about 780 mg/day, about 770 mg/day, about 760 mg/day, about 750 mg/day, about 740 mg/day, about 730 mg/day, about 720 mg/day, about 710 mg/day, about 700 mg/day, about 690 mg/day, about 680 mg/day, about 670 mg/day, about 660 mg/day, about 650 mg/day, about 640 mg/day, about 630 mg/day, about 620 mg/day, about 610 mg/day, about 600 mg/day, about 590 mg/day, about 580 mg/day, about 570 mg/day, about 560 mg/day, about 550 mg/day, about 540 mg/day, about 530 mg/day, about 520 mg/day, about 510 mg/day, about 500 mg/day, about 490 mg/day, about 480 mg/day, about 470 mg/day, about 460 mg/day, about 450 mg/day, about 440 mg/day, about 430 mg/day, about 420 mg/day, about 410 mg/day, about 400 mg/day, about 390 mg/day, about 380 mg/day, about 370 mg/day, about 360 mg/day, about 350 mg/day, about 340 mg/day, about 330 mg/day, about 320 mg/day, about 310 mg/day, about 300 mg/day, about 290 mg/day, about 280 mg/day, about 270 mg/day, about 260 mg/day, about 250 mg/day, about 240 mg/day, about 230 mg/day, about 220 mg/day, about 210 mg/day, about 200 mg/day, about 190 mg/day, about 180 mg/day, about 170 mg/day, about 160 mg/day, about 150 mg/day, about 140 mg/day, about 130 mg/day, about 120 mg/day, about 110 mg/day, about 100 mg/day, about 90 mg/day, about 80 mg/day, about 70 mg/day, about 60 mg/day, about 50 mg/day, about 40 mg/day, about 30 mg/day, about 10 mg/day, about 1 mg/day, about 0.5 mg/day, about 0.1 mg/day, and about 0.01 mg/day.

It will be understood that the pharmaceutical compositions of the disclosure need not necessarily contain the entire amount of the compound that is effective in treating the disorder, as such effective amounts can be reached by administration of a plurality of divided doses of such pharmaceutical compositions. The compounds may be administered in a single dose per day or on a regimen of multiple doses per day, (e.g. two, three, four, five, or more) of sub-doses per day such that the total daily dose is the same. An effective amount of a salt thereof may be determined as a proportion of the effective amount of the compound of according to any embodiment described herein. Similar dosages should be appropriate for treatment of the other conditions referred herein for treatment. In general, determination of appropriate dosing can be readily arrived at by one skilled in medicine or the pharmaceutical arts.

The active ingredient, i.e., a compound according to any embodiment described herein, may be for topical administration administered from about 0.001% w/w to about 10% w/w of the topical formulation. In some embodiments, a compound according to any embodiment described herein is 0.1% w/w, 0.2% w/w, 0.3% w/w, 0.4% w/w, 0.5% w/w, 0.6% w/w, 0.7% w/w, 0.8% w/w, 0.9% w/w, 1% w/w, 2% w/w, 3% w/w, 4% w/w, 5% w/w, 6% w/w, 7% w/w, 8% w/w, 9% w/w, or 10% w/w of the topical formulation. In some embodiments a compound according to any embodiment described herein is from 1% w/w to 2% w/w of the formulation. The daily topical dosage regimen may be from about 0.1 mg to 150 mg of a compound according to any embodiment described herein, administered one to four times daily. In some embodiments the daily topical dose is 0.1 mg, 0.2 mg, 0.3 mg, 0.4 mg, 0.5 mg, 0.6 mg, 0.7 mg, 0.8 mg, 0.9 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, or 150 mg. Initial dosages can also be estimated from in vivo data, using animal models. Animal models useful for testing the efficacy of compounds to treat or prevent the various diseases described above are well-known in the art. The compounds may be administered once per week, several times per week (for example, every other day), once per day or multiple times per day, depending upon the judgment of the prescribing physician.

It will also be recognized by one of skill in the art that the optimal quantity and spacing of individual dosages of a compound according to any embodiment described herein, or a pharmaceutically acceptable salt, solvate or hydrate thereof will be determined by the nature and extent of the condition being treated, the form, route and site of administration, and the patient being treated, and that such optimums can be determined by conventional techniques. It will also be appreciated by one of skill in the art that the optimal course of treatment, i.e., the number of doses of a compound according to any embodiment described herein or a pharmaceutically acceptable salt, solvate or hydrate thereof, given per day for a defined number of days, can be ascertained by those skilled in the art using conventional course of treatment determination tests.

Process for Preparing the Compound of Formula 8

Some embodiments describe a process for preparing compound of Formula 8

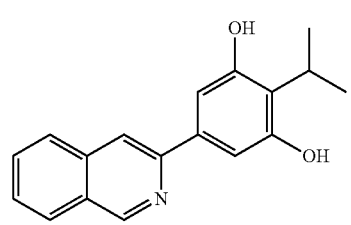

or a pharmaceutically acceptable salt, solvate or hydrate thereof, comprising demethylating a compound of Formula 7

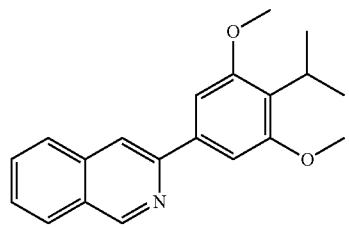

or a pharmaceutically acceptable salt, solvate or hydrate thereof.

In some embodiments the process further comprises coupling a compound of Formula 6

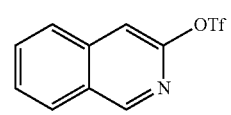

or a pharmaceutically acceptable salt, solvate or hydrate thereof with a compound of Formula 5

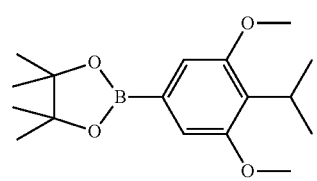

or a pharmaceutically acceptable salt, solvate or hydrate thereof to form the compound of Formula 7.

In some embodiments the process further comprises borylating a compound of Formula 4

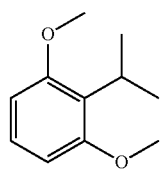

or a pharmaceutically acceptable salt, solvate or hydrate thereof to form the compound of Formula 5.

In some embodiments the process further comprises hydrogenating a compound of Formula 3

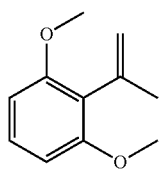

3 or a pharmaceutically acceptable salt, solvate or hydrate thereof to form the compound of Formula 4.

In some embodiments the process further comprises treating a ketone of Formula 2

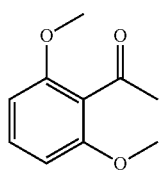

2 or a pharmaceutically acceptable salt, solvate or hydrate thereof with a Grignard reagent, followed by elimination of water under acidic conditions to form the compound of Formula 3.

In some embodiments the process further comprises alkylating 2,6-dihydroxyacetophenone or a pharmaceutically acceptable salt, solvate or hydrate thereof, to form the compound of Formula 2.

In some embodiments the demethylation of the compound of Formula 7 to form the compound of Formula 8 comprises treating the compound of Formula 7 with boron tribromide.

In some embodiments the demethylation of the compound of Formula 7 to form the compound of Formula 8 comprises: a) treating the compound of Formula 7 with boron tribromide to form the compound of Formula 7-1

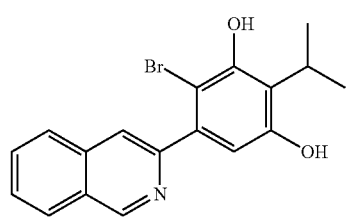

7-1 and b) hydrogenating the compound of Formula 7-1 to form the compound of Formula 8.

In some embodiments the demethylation of the compound of Formula 7 to form the compound of Formula 8 comprises treating the compound of Formula 7 with hydrobromic acid.

Some embodiments describe a process for preparing a compound of Formula

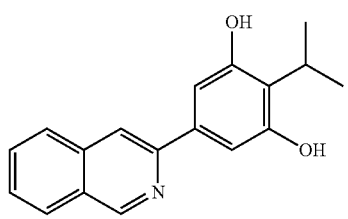

8 comprising:

a) coupling a compound of Formula 6

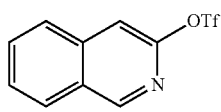

6 or a pharmaceutically acceptable salt, solvate or hydrate thereof with the compound of Formula 5 or a pharmaceutically acceptable salt, solvate or hydrate thereof to form a compound of Formula 7

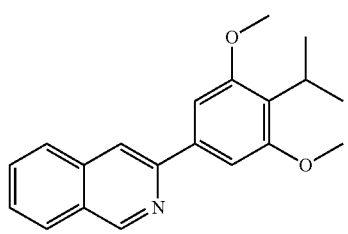

7 or a pharmaceutically acceptable salt, solvate or hydrate thereof; and b) demethylating the compound of Formula 7 to form the compound of Formula 8.

or a pharmaceutically acceptable salt, solvate or hydrate thereof.

In some embodiments the compound of Formula 6

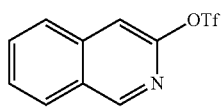

6 or a pharmaceutically acceptable salt, solvate or hydrate thereof according to any process described herein, is prepared by treating isoquinoline-3-ol with a triflating agent.

In some embodiments the compound of Formula 5 or a pharmaceutically acceptable salt, solvate or hydrate thereof, according to any process described herein, is prepared by a process comprising:

a) alkylating 2,6-dihydroxyacetophenone or a pharmaceutically acceptable salt, solvate or hydrate thereof, to form a compound of Formula 2

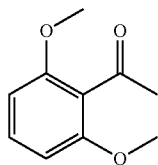

2 or a pharmaceutically acceptable salt, solvate or hydrate thereof;

b) treating the ketone of Formula 2 or a pharmaceutically acceptable salt, solvate or hydrate thereof with a Grignard reagent, followed by elimination of water under acidic conditions to form a compound of Formula 3

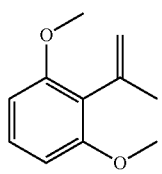

3 or a pharmaceutically acceptable salt, solvate or hydrate thereof;

c) hydrogenating the compound of Formula 3 or a pharmaceutically acceptable salt, solvate or hydrate thereof to form a compound of Formula 4

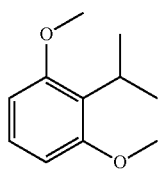

4 or a pharmaceutically acceptable salt, solvate or hydrate thereof; and d) borylating the compound of Formula 4 or a pharmaceutically acceptable salt, solvate or hydrate thereof to form a compound of Formula 5 or a pharmaceutically acceptable salt, solvate or hydrate thereof.

Some embodiments describe a process for preparing a compound of Formula

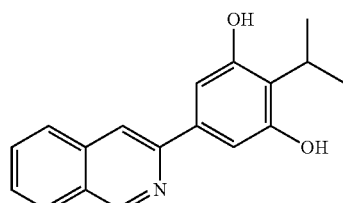

8 or a pharmaceutically acceptable salt, solvate or hydrate thereof, comprising:

a) preparing a compound of Formula 5

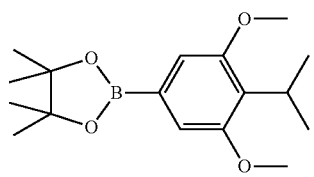

5 or a pharmaceutically acceptable salt, solvate or hydrate thereof, comprising 1) alkylating 2,6-dihydroxyacetophenone or a pharmaceutically acceptable salt, solvate or hydrate thereof, to form a compound of Formula 2

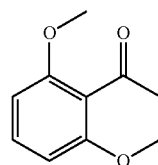

2 or a pharmaceutically acceptable salt, solvate or hydrate thereof;

2) treating the ketone of Formula 2 or a pharmaceutically acceptable salt, solvate or hydrate thereof with a Grignard reagent, followed by elimination of water under acidic conditions to form a compound of Formula 3

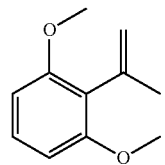

3 or a pharmaceutically acceptable salt, solvate or hydrate thereof;

3) hydrogenating the compound of Formula 3 or a pharmaceutically acceptable salt, solvate or hydrate thereof to form a compound of Formula 4

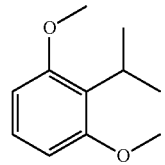

4 or a pharmaceutically acceptable salt, solvate or hydrate thereof; and 4) borylating the compound of Formula 4 or a pharmaceutically acceptable salt, solvate or hydrate thereof to form the compound of Formula 5 or a pharmaceutically acceptable salt, solvate or hydrate thereof;

b) preparing a compound of Formula 6

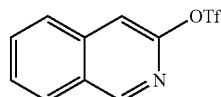

or a pharmaceutically acceptable salt, solvate or hydrate thereof comprising treating isoquinoline-3-ol with a triflating agent; and c) coupling the compound of Formula 6 or a pharmaceutically acceptable salt, solvate or hydrate thereof with the compound of Formula 5 or a pharmaceutically acceptable salt, solvate or hydrate thereof to form a compound of Formula 7

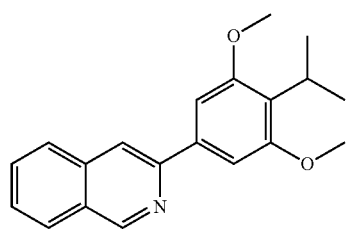

or a pharmaceutically acceptable salt, solvate or hydrate thereof; and d) demethylating the compound of Formula 7 to form the compound of Formula 8.

or a pharmaceutically acceptable salt, solvate or hydrate thereof; wherein steps a and b can be done in either order or simultaneously in different reaction vessels.

In some embodiments according to any process described herein, the process further comprises purifying the compound of Formula 8. In some embodiments the purifying comprises crystallizing the compound of Formula 8.

Appropriate amounts in any given instance will be readily apparent to those skilled in the art or capable of determination by routine experimentation. The compositions are generally applied in topical manner to the affected area, i. e., localized application to the skin region where the clinical abnormality is manifest.

Unless otherwise indicated, all percentages are based on the percent by weight of the final composition prepared, and all totals equal 100% by weight.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various embodiments of the present invention will be illustrated with reference to the following non-limiting examples. The following examples are for illustrative purposes only and are not to be construed as limiting the invention in any manner.

In the experimental descriptions, the following abbreviations may be used:

| Abbreviation | Meaning |
|---|---|
| ACN | Acetonitrile |
| $BBr_3$ | Boron tribromide |
| Brine | saturated aqueous sodium chloride |
| DCM or $CH_2Cl_2$ | methylene chloride |
| DMF | N,N-dimethylformamide |
| DMSO | Dimethylsulfoxide |
| EtOAc | ethyl acetate |
| H or hr | Hour |
| HOAc | Acetic acid |
| HPLC | High performance liquid chromatography |
| L | Liter |
| LC | liquid chromatography |
| LCMS | liquid chromatography-mass spectroscopy |
| MeOH | Methanol |
| MeOD | Tetradeuteromethanol |
| mL | Milliliter |
| MS | mass spectroscopy |
| $Na_2SO_4$ | Sodium sulfate |
| NMR | Nuclear magnetic resonance spectroscopy |
| $PdCl_2$(dppf) | (1,1'-Bis(diphenylphosphino)ferrocene)palladium(II) dichloride |
| SGCC | silica gel column chromatography |
| RT or rt | Room temperature |
| TEA | Triethylamine |
| TFA | trifluoroacetic acid |
| TLC | thin layer chromatography |
| $t_R$ | Retention time |

LCMS Standard Method A
LC Conditions:
The UPLC analysis was conducted on a Waters Acquity BEH C18 2×50 mm 1.7 m column at 50° C.
0.5 uL of sample was injected using a partial loop (with needle overfill) injection mode.
The gradient employed was:
Mobile Phase A: Water+0.20% v/v Formic Acid
Mobile Phase B: Acetonitrile+0.15% v/v Formic Acid
Time % A % B Flow Rate
min 95 5 1 ml/min
1.10 min 1 99 1 ml/min
1.50 min 1 99 1 ml/min
UV detection provided by summed absorbance signal from 210 to 350 nm scanning at 40 Hz.
MS Conditions:
Instrument: Waters Acquity
Serial Number: C07SQD043W
Scan Mode: Alternating Positive/Negative Electrospray
Scan Range: 125-1000 amu
Scan Time: 105 msec
Interscan Delay: 20 msec
Other Information
All equipment supplied by Waters Corp, Milford, Mass.
Quality control samples are run and analyzed minimally once per day
LCMS Standard Method B
Mobile Phase: A:Water (0.01% TFA) B:ACN (0.01% TFA)
Gradient: 5% B increase to 95% B within 1.5 min,
95% B for 1.8 min, back to 5% B within 0.01 min
Flow Rate: 2.0 ml/min
Column: SunFire $C_{18}$, 4.6×50 mm, 3.5 μm
Column Temperature: 50° C.
Detection: UV (280,140 nm) and MS(ESI, Pos mode, 110 to 1000 amu)
LCMS Standard Method C
Mobile Phase: A:Water (10 mM $NH_4HCO_3$) B:ACN
Gradient: 5% B increase to 95% B within 2 min,
95% B for 1.3 min, back to 5% B within 0.01 min
Flow Rate: 1.8 ml/min Column: XBridge C$_{18}$, 4.6×50 mm, 3.5 µm Column Temperature: 40° C.

Detection: UV (280,140 nm) and MS(ESI, Pos mode, 110 to 1000 amu)

Synthetic Examples

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art. In some instances, a substituent may be specifically selected to be reactive under the reaction conditions used. Under these circumstances, the reaction conditions convert the selected substituent into another substituent that is either useful as an intermediate compound or is a desired substituent in a target compound.

The synthesis of the compounds of the general formula as noted in the scheme(s) below and their pharmaceutically acceptable salts, solvates or hydrates thereof may be accomplished as outlined.

Abbreviations are as defined in the Examples section. Starting materials are commercially available or are made from commercially available starting materials using methods known to those skilled in the art. All temperatures are given in degrees centigrade, all solvents are highest available purity and all reactions run under anhydrous conditions in an argon atmosphere unless otherwise indicated.

The compounds herein may be obtained by using synthetic procedures illustrated in the Scheme below or by drawing on the knowledge of a skilled organic chemist. The synthesis provided in this Scheme is applicable for producing compounds of the invention having a variety of different substituent groups employing appropriate precursors, which are suitably protected if needed, to achieve compatibility with the reactions outlined herein. Subsequent deprotection, where needed, affords compounds of the nature generally disclosed. While the scheme is shown with compounds only of Formula (I), it is illustrative of processes that may be used to make the compounds of the invention.

Intermediates (compounds used in the preparation of the compounds of the invention) may also be present as salts, solvates or hydrates. Thus, in reference to intermediates, the phrase "compound(s) of formula (number)" means a compound having that structural formula or a pharmaceutically acceptable salt, solvate or hydrate thereof.

The invention also includes various deuterated forms of the compounds of Formula (I). Each available hydrogen atom attached to a carbon atom may be independently replaced with a deuterium atom. In some embodiments, one or more hydrogen atoms of a compound according to any embodiment described herein, is replaced with a deuterium. A person of ordinary skill in the art will know how to synthesize deuterated forms of the compounds of Formula (I).

As further described herein for the schemes, there is a general formula (I)

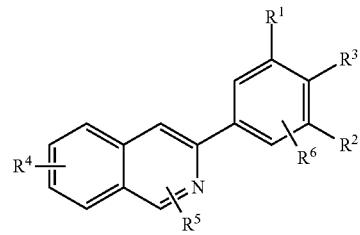

wherein R$^1$-R$^6$ are as defined previously for Formula (I).

General scheme

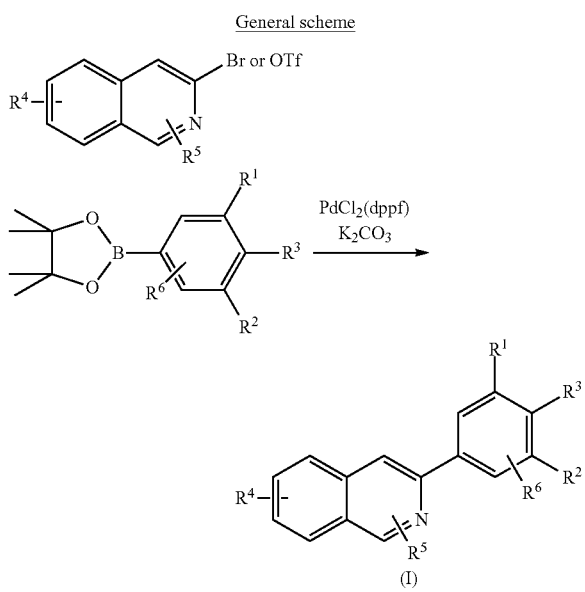

The compounds of Formula (I) may be prepared by a carbon-carbon formation, such as transition metal catalyzed cross-coupling. The reaction may be fulfilled by Suzuki-Miyaura coupling in the presence of a catalyst, such as a Pd(0), Ni(0), Pd(II), or Ni(II) complex with a ligand, including, but not limited to, PdCl$_2$(dppf), Pd(PPh$_3$)$_4$, Pd(OAc)$_2$, Pd$_2$(dba)$_3$, NiCl$_2$(dppf), and NiCl$_2$(PCy$_3$)$_2$, between an organoboronic acid, or boronate ester or potassium trifluoroborate and a halide or a pseudohalide, such as a triflate. Such coupling reaction are carried out in the presence of a mild base, such as K$_2$CO$_3$, and Na$_2$CO$_3$, NaHCO$_3$, Cs$_2$CO$_3$, K$_3$PO$_4$, KF, etc., in a suitable solvent, such as toluene, dioxane, tetrahydrofuran, dimethoxyethane, and dimethylformamide, etc. Selection of suitable bases, ligands, solvents, and reaction conditions, for example, time, temperature, pressure, choice of atmosphere (for example, inert), reaction work up, purification etc. are known to those of skill in the art.

One aspect of the invention is a process for making a compound of Formula (I). The final compounds of Formula (I) may be prepared by de-protection from its precursor if any protecting groups are employed during transformation. Suitable hydroxyl-protecting groups well known to those skilled in the art can be found in Greene (vide supra). One such example of demethylation can be by use of boron tribromide in a suitable organic solvent, such as methylene chloride, at −78° C. to +20° C., preferably about −20° C. to 0° C. for about 0.5-72 hours. The progress of the reaction is monitored by thin layer chromatography or high pressure liquid chromatography. When the reaction is complete, it is quenched slowly with a suitable solvent, such as methyl alcohol at −78° C. to +20° C., preferably −20° C. to 10° C., and continued stirring at room temperature for about 1-4 hours. Adding water afterwards is optional. The excess solvent is removed by distillation. The residue obtained herein is purified by typical chromatography, normal phase or reverse phase, and recrystallization in suitable solvents.

The compounds of Formula (I) may be obtained from a precursor of Formula (I), such as Formula (A) described herein, by hydrogenation in the presence of a suitable catalyst, such as 5 or 10% palladium on carbon, under hydrogen atmosphere at ambient temperature in a suitable organic solvent, such as methanol, ethanol, isopropanol, ethyl acetate, tetrahydrofuran, etc.

General Intermediate 1:
3,5-Diacetoxy-4-isopropylbenzoic Acid

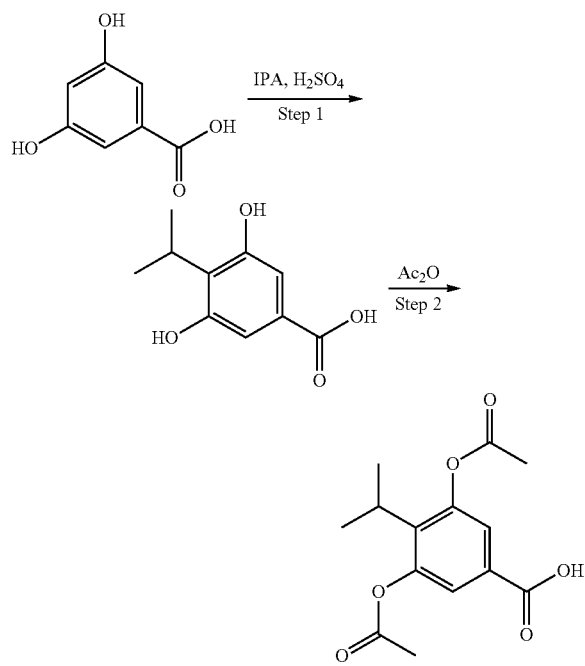

Step 1. 3,5-Dihydroxy-4-isopropylbenzoic Acid Triethylamine Salt 3,5-Dihydroxybenzoic acid (40 g, 0.26 mol, 1.0 equiv.) was charged to 1 L three-neck round bottom flask (RBF) followed by concentrated sulfuric acid (160 mL, 4 volumes) at room temperature. Water (20 mL, 0.5 volumes) was charged to the mixture while stirring. The suspension was heated to 60-65° C., then 2-propanol (25.0 mL, 0.32 mol, 1.25 equiv.) was charged to the reaction drop wise over the period of ~10 minutes. The clear reaction mixture was stirred at 60-65° C. for 4-8 hrs and cooled to room temperature (~20° C.). The reaction mixture was transferred slowly into an aqueous sodium hydroxide solution at 10° C. in a $2^{nd}$ 3 L three-neck round bottom flask (RBF) equipped with overhead stirrer. The aqueous sodium hydroxide solution temperature was maintained in $2^{nd}$ RBF between 10-30° C. The reaction mixture flask was rinsed with water to complete transferring, charged with tert-butyl methyl ether (TBME, 320 mL, 8 volumes), warmed to 20-25° C. and stirred ~30 min. The two layers were separated and the aqueous layer was extracted with TBME (2×160 mL, 4 volumes). Potassium sodium tartrate solution was charged (1N, 160 mL, 4 volumes) to the combined TBME layers and stirred at least for 40 min. at 20-25° C. The two layers were separated, the organic layer was passed through activated carbon Darco G-60, −100 mesh and the carbon cake was washed with TBME. 2-Propanol (90 mL, 2.25 volumes) was charged to the TBME layers, then triethylamine (36.2 mL, 1.0 equiv.) was charged to the mixture (solution of TBME layers+2-propanol) drop-wise over a period of ~15 min at 20-25° C. and stirred at least 2.5 h. The product was isolated by filtration and the cake was rinsed with TBME. The title product was dried in the oven overnight at 40-50° C. Purity by HPLC: 98%.

Step 2. 3,5-Diacetoxy-4-isopropylbenzoic Acid 3,5-Dihydroxy-4-isopropylbenzoic acid triethylamine salt (50.0 g, 0.17 mol, 1.0 equiv.) was charged to a 1 L three-neck round bottom flask (RBF) followed by tert-butyl methyl ether (TBME, 250 mL), and 2-methyl tetrahydrofuran (2Me-THF, 125 mL) at room temperature. Acetic anhydride (38.1 mL, 0.4 mol, 2.4 equiv.) and triethylamine (46.9 mL, 0.34 mol, 2.0 equiv.) were charged to the mixture while stirring. The suspension was heated to 60-65° C. and stirred for 6-20 hrs or until the reaction was deemed complete by 3 min Fast LC. The mixture was cooled to room temperature (~20° C.), and charged with 6N hydrochloric acid (6N HCl, 175 mL) slowly while maintaining the reaction mixture temperature between 20-30° C. and stirred at least 15 min. The two layers were separated, the organic layer was washed with water (100 mL) and evaporated at reduced pressure until ~3.0 volumes were left in the flask. Toluene (200 mL) was added, and evaporated until ~2 volumes were left in the flask. Toluene (75 mL) was added, the mixture was heated to 75-80° C. and stirred at least 30 min. The product suspension was cooled to room temperature (~20° C.), charged with cyclohexane (200 mL) and stirred at least 3 hrs at 15-20° C. The product was isolated by filtration and the cake was rinsed with cyclohexane. The title product was dried in the oven overnight at 40-50° C. $^1$H NMR (400 MHz, DMSO-$d_6$) δ ppm 13.07-13.40 (br. s, 1H), 7.54 (s, 2H), 3.07-3.23 (Sep., 1H), 2.35 (s, 6H), 1.18 (d, J=7 Hz, 6H); Purity by HPLC: 97%.

General Intermediate 2: 2-(4-Isopropyl-3,5-dimethoxyphenyl)-4,4,5,5-tetramethyl-1,3,2-dioxaborolane

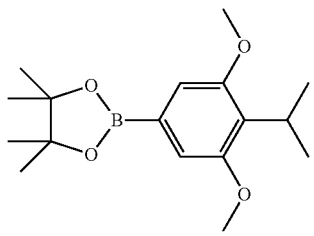

The title compound was prepared according to a method reported in the literature (Xuebin Liao, Levi M. Stanley and John F. Hartwig, J. Am. Chem. Soc. 2011, 133, 2088-2091).

General Intermediate 3:
5-bromo-2-(tert-butyl)phenol

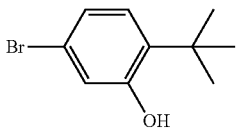

The title compound was prepared by a method reported in the U.S. Pat. No. 5,919,970.

General Intermediate 4:
4-cyclopentyl-3,5-bis(methoxymethoxy)phenyl trifluoromethanesulfonate

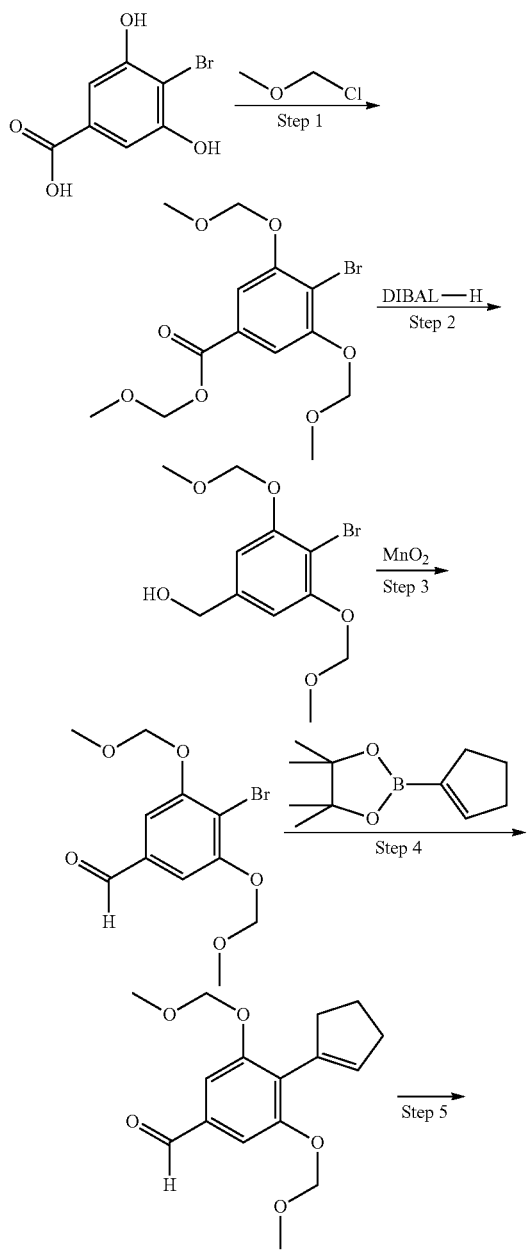

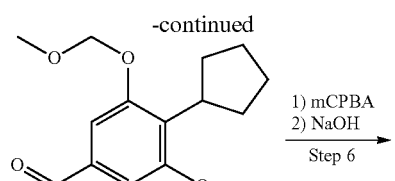

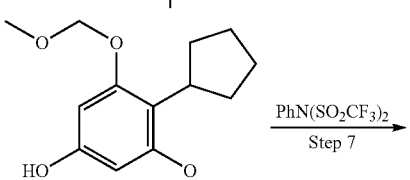

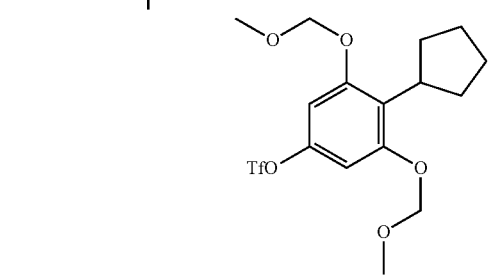

Step 1

To a stirred solution of 4-bromo-3,5-dihydroxybenzoic acid (4.06 g, 17.42 mmol and N,N-diisopropylethylamine (17.65 ml, 101 mmol) in DCM (45.9 mL) at 0° C. was added methoxymethyl chloride (5.96 ml, 78 mmol). The reaction mixture was allowed to warm to rt and stirred for 30 min and then was quenched with saturated aqueous ammonium chloride (40 mL). The organic layer was separated, and the aqueous layer was extracted with dichloromethane (3×40 mL). The combined organic extracts were dried over sodium sulfate, filtered, and concentrated. The residue was purified using a 80 gram Isco brand silica column and eluted with 10-100% EtOAc/Heptane (60 mL/min) to afford the desired compound as a colorless amorphous solid. $^1$H NMR (400 MHz, CHLOROFORM-d) δ ppm 7.54 (s, 2H), 5.50 (s, 2H), 5.33 (s, 4H), 3.57 (s, 3H), 3.55 (s, 6H); LCMS Method A: $t_R$=0.84 min, 92%; MS (ESI): m/z no clear mass.

Step 2

To a stirred solution of methoxymethyl 4-bromo-3,5-bis (methoxymethoxy)benzoate (1.055 g, 2.89 mmol) in dichloromethane (DCM, 20.64 ml) at −78° C. was added DIBAL-H (1M in hexane, 8.67 ml, 8.67 mmol). The reaction mixture was warmed to 0° C., stirred for 30 min and then iteratively quenched with EtOAc (1 mL) and then MeOH (4 mL). Saturated aqueous potassium sodium tartrate (40 mL) was added and the resultant mixture was stirred vigorously overnight. The layers were separated and the aqueous layer was extracted with dichloromethane (3×50 mL). The combined organic extracts were dried over sodium sulfate, filtered, and concentrated. The residue was purified using a 24 gram Isco brand silica column and eluted with 10-100% EtOAc/Heptane (35 mL/min) to yield the desired product as a colorless oil. $^1$H NMR (400 MHz, CHLOROFORM-d) δ ppm 6.87 (s, 2H), 5.28 (s, 4H), 4.66 (s, 2H), 3.54 (s, 6H); LCMS Method A: $t_R$=0.64 min, 94%; MS (ESI): m/z no clear mass.

Step 3

A solution of (4-bromo-3,5-bis(methoxymethoxy)phenyl) methanol (490 mg, 1.595 mmol) and manganese dioxide (1387 mg, 15.95 mmol) in dichloromethane (DCM, 31.908 mL) was stirred at rt for 12 h. The mixture was diluted with diethyl ether, filtered through a pad of CELITE, and washed with diethyl ether. The filtrate was concentrated, yielding the desired compound pure product as a colorless amorphous solid. LCMS Method A: $t_R$=0.78 min, 100%; MS (ESI): m/z 307.35 (M+2)$^+$ Step 4

A sealed tube was charged with 4-bromo-3,5-bis (methoxymethoxy)benzaldehyde (322 mg, 1.055 mmol), 2-(cyclopent-1-en-1-yl)-4,4,5,5-tetramethyl-1,3,2-dioxaborolane (320 μl, 1.583 mmol), 1N sodium bicarbonate (3590 μl), 1,4-dioxane (8974 μl), and tetrakis(triphenylphosphine)palladium(O) (51.7 mg, 0.045 mmol). The reaction mixture was heated at 100° C. overnight, cooled and partitioned between EtOAc and water. The organic phase was separated and the aqueous layer was extracted with EtOAc. The combined organic phases were dried over sodium sulfate, filtered, and concentrated. The residue was purified using a 12 gram Isco brand silica column and eluted with 10-100% EtOAc/Heptane (30 mL/min), yielding the desired product as a bright yellow amorphous solid. $^1$H NMR (400 MHz, CHLOROFORM-d) δ ppm 9.92 (s, 1H), 7.32 (s, 2H), 5.88 (t, J=2 Hz, 1H), 5.22 (s, 4H), 3.50 (s, 6H), 2.66-2.77 (m, 2H), 2.57 (ddd, J=10, 5, 2 Hz, 2H), 2.04 (t, J=7 Hz, 2H); LCMS Method A: $t_R$=0.94 min, 98%; MS (ESI): m/z 293.5 (M+H)$^{30}$ Step 5

4-(Cyclopent-1-en-1-yl)-3,5-bis(methoxymethoxy)benzaldehyde (252 mg, 0.862 mmol) was dissolved in a mixture of methanol (3451 μl) and trimethyl orthoformate (2382 μl, 21.55 mmol) containing a catalytic amount of ammonium chloride (4.61 mg, 0.086 mmol). The mixture was stirred at 65° C. for 2.5 h or until the benzaldehyde had been consumed as measured by NMR. The reaction mixture was cooled to rt and treated dropwise with triethylamine (481 μl, 3.45 mmol). After stirring at rt for 5 min, water (1.5 mL) was added and the mixture was diluted with diethyl ether (1.5 mL). The organic phase was separated and the aqueous phase was extracted with diethyl ether (3×10 mL). The organic phase was washed with water (10 mL), dried over sodium sulfate, filtered, and concentrated. The residue was dissolved in ethanol (3451 μl) and stirred under hydrogen atmosphere (40 psi) in the presence of 10% palladium on carbon (22.93 mg, 0.216 mmol) for 17.5 h. LCMS revealed, ~28% conversion to the desired product and ~59% residual stating material. Additional palladium on carbon (22.93 mg, 0.216 mmol) was added and the reaction was re-subjected to hydrogen atmosphere (40 psi) for an additional 6.5 h (24 h total). The reaction mixture was filtered and evaporated. The crude residue was dissolved in a 1:1 mixture of tetrahydrofuran (THF, 2.374 ml) and 2N H$_2$SO$_4$ (2.374 ml) and stirred at rt for 2 h. The mixture was diluted with EtOAc (1.5 mL) and water (1.5 mL), and the organic phase was separated. The aqueous phase was extracted with EtOAc (3×10 mL) and the organic phase was washed with water (10 mL), saturated aqueous sodium bicarbonate (10 mL), dried over sodium sulfate, filtered, and concentrated. The residue was purified using a 12 gram Isco brand silica column and was eluted with 0-100% EtOAc/Heptane (30 mL/min), yielding the desired product as a colorless amorphous solid. $^1$H NMR (400 MHz, CHLOROFORM-d) δ ppm 9.89 (s, 1H), 7.30 (s, 2H), 5.26 (s, 4H), 3.77 (m, 1H), 3.52 (s, 6H), 1.79-2.04 (m, 6H), 1.63-1.76 (m, 2H); LCMS Method A: $t_R$=1.01 min, 92%; MS (ESI): m/z 295.5 (M+H)$^{30}$ Step 6

A solution of 4-cyclopentyl-3,5-bis(methoxymethoxy) benzaldehyde (100 mg, 0.340 mmol) in anhydrous dichloromethane (833 uL) was slowly added to mCPBA (64.5 mg, 0.374 mmol) in anhydrous dichloromethane (DCM, 3.331 mL). The reaction mixture was warmed to rt, then refluxed for 12 h. After cooling to rt, the solution was extracted with DCM (3×10 mL). The combined organic layer was washed with saturated aqueous sodium bicarbonate solution, and 10% aqueous sodium thiosulfate (10 mL), dried over sodium sulfate, filtered, and concentrated.

The residue was re-dissolved in methanol (0.67 ml) and stirred with 10% aqueous sodium hydroxide (0.679 ml, 16.99 mmol) for 3 h at rt. The pH was adjusted to 2 with 1N HCl and the solution was extracted with dichloromethane (3×10 mL). The combined organic layer was dried over sodium sulfate, filtered, and concentrated. The residue was purified using a 4 gram Isco brand silica column and eluted with 0-100% EtOAc/Heptane (18 mL/min), yielding the desired compound as a yellow amorphous solid. $^1$H NMR (400 MHz, CHLOROFORM-d) δ ppm 6.35 (s, 2H), 5.15 (s, 4H), 4.63 (s, 1H), 3.59 (m, 1H), 3.50 (s, 6H), 1.72-1.98 (m, 6H), 1.61-1.72 (m, 2H); LCMS Method A: $t_R$=0.89 min, 95%; MS (ESI): m/z 283.5 (M+H)$^{30}$ Step 7

To a solution of 4-cyclopentyl-3,5-bis(methoxymethoxy) phenol (25.1 mg, 0.089 mmol) in N,N-Dimethylformamide (DMF, 323 μl) was added triethylamine (24.78 μl, 0.178 mmol) and 1,1,1-trifluoro-N-phenyl-N-((trifluoromethyl) sulfonyl)methanesulfonamide (47.6 mg, 0.133 mmol). The mixture was stirred at rt for 1 h. After 1 h, the progress of the reaction was analyzed by LCMS, revealing full consumption of starting material and conversion to product. Next, the reaction mixture was concentrated and the crude product was diluted with Et$_2$O (2.5 mL), washed with water (3×5 mL) and saturated aqueous sodium chloride (5 mL), dried over sodium sulfate, filtered, and concentrated. The residue was purified using a 4 gram ISCO silica gel column (eluted with 5-100% EtOAc/Heptane), yielding the desired product as a colorless oil. $^1$H NMR (400 MHz, CHLOROFORM-d) δ ppm 6.75 (s, 2H), 5.18 (s, 4H), 3.66 (m, 1H), 3.50 (s, 6H), 1.76-1.98 (m, 6H), 1.63-1.75 (m, 2H); LCMS Method A: $t_R$=1.18 min, 100%; MS (ESI): m/z 413.4 (M−H)$^−$

Example 1A
2-Isopropyl-5-(isoquinolin-3-yl)benzene-1,3-diol
Method A

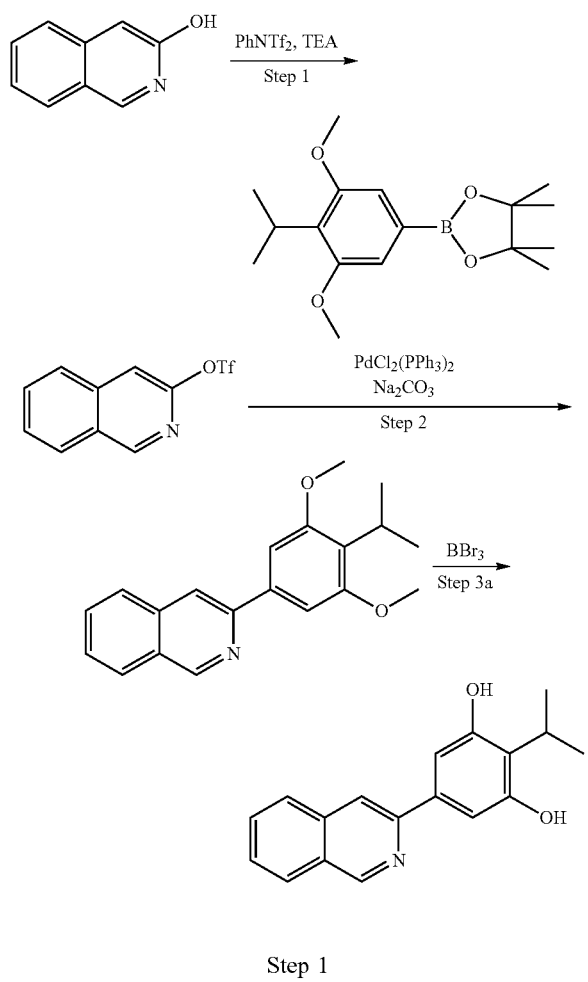

Step 1

To a solution of isoquinolin-3-ol (300 mg, 2.067 mmol) and 1,1,1-trifluoro-N-phenyl-N-((trifluoromethyl)sulfonyl)methanesulfonamide (923 mg, 2.58 mmol) in DCM (20 mL) was added TEA (0.864 mL, 6.20 mmol). The mixture was stirred at room temperature for 2 hrs, diluted with water (25 mL) and extracted with DCM (30 mL×2). The DCM solution was combined, washed with brine, dried, and concentrated. The crude material was purified by preparative TLC (eluted with petroleum ether/ethyl acetate=50/1) to afford isoquinolin-3-yl trifluoromethanesulfonate (350 mg, 1.136 mmol, 55.0% yield) as a colorless liquid. LCMS Method A: $t_R$=1.77 min, 100%; MS: m/z 277.8 (M+H)$^+$

Step 2

In a nitrogen atmosphere, into a mixture of isoquinolin-3-yl trifluoromethanesulfonate (100 mg, 0.361 mmol) and 2-(4-isopropyl-3,5-dimethoxyphenyl)-4,4,5,5-tetramethyl-1,3,2-dioxaborolane (133 mg, 0.433 mmol) in toluene (2 mL) and water (0.500 mL) was added Na$_2$CO$_3$ (76 mg, 0.721 mmol). The reaction mixture was stirred at 80° C. for 5 h, cooled and purified by a reverse phase chromatography (CombiFlash 50 g reverse phase C$_{18}$ column; gradient 20-50% MeOH in water with 0.01% TFA over 30 min). The fractions were combined and concentrated. The residue was re-crystallized in water, and dried by lyophilization to afford 3-(4-isopropyl-3,5-dimethoxyphenyl)isoquinoline (90 mg, 0.190 mmol, 52.8% yield) as a white solid. LCMS Method A: $t_R$=1.81 min, 61%; MS: m/z 307.9 (M+H)$^+$

Step 3a Method A

To a solution of 3-(4-isopropyl-3,5-dimethoxyphenyl)isoquinoline (90 mg, 0.293 mmol) in dichloromethane (DCM, 2 mL) was added BBr$_3$ (0.138 mL, 1.464 mmol) at 0° C. The reaction mixture was stirred at 0° C. for 1 h and purified by reverse phase chromatography (CombiFlash 50 g reverse phase C$_{18}$ column; loaded using MeOH; eluted with 20-50% MeOH/Water with 10 mM TFA over 30 mins). The appropriate fractions containing product were combined, re-crystallized in water, and dried by lyophilization to afford the title compound, 2-isopropyl-5-(isoquinolin-3-yl)benzene-1,3-diol (80 mg, 0.272 mmol, 93% yield), as a yellow solid. $^1$H NMR (400 MHz, MeOD) δ 9.65 (s, 1H), 8.48 (s, 1H), 8.44 (d, 1H), 8.26 (d, 1H), 8.16 (t, 1H), 7.96 (t, 1H), 6.83 (s, 2H), 3.63 (sep., 1H), 1.37 (d, 6H); LCMS Method A: $t_R$=1.79 min, 100%; MS: m/z 280.2 (M+H)$^+$

Step 3b Method B

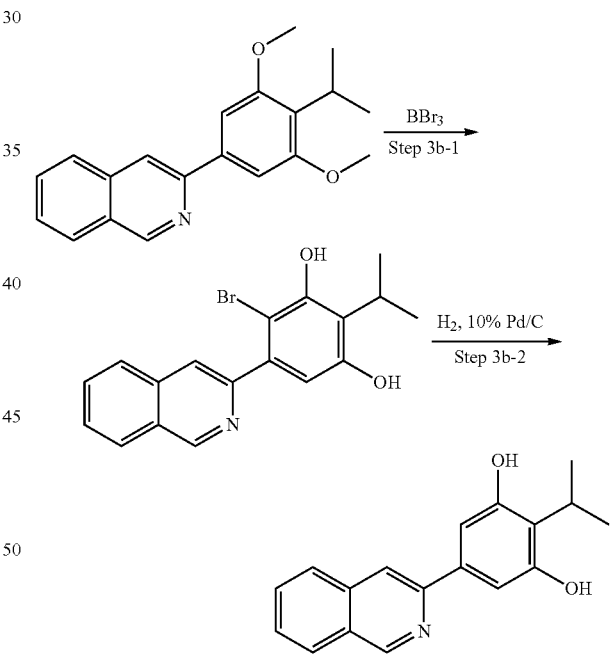

Step 3b-1

To a solution of 3-(4-isopropyl-3,5-dimethoxyphenyl)isoquinoline (3.8 g, 12.36 mmol) in dichloromethane (DCM, 2 mL) was add BBr$_3$ (5.84 mL, 61.8 mmol). The reaction mixture was stirred at 0° C. for 1 h. The solution was concentrated in vacuo, diluted with saturated NaHCO$_3$ and extracted with ethyl acetate. The organic was washed with brine, dried over NaSO$_4$ and concentrated to give the desired compound that was used without further purification. LCMS Method B: $t_R$=1.88 min, 53%; MS (ESI): m/z 359.5 (M+2)$^+$ Step 3b-2

To a solution of 4-bromo-2-isopropyl-5-(isoquinolin-3-yl)benzene-1,3-diol (3.4 g, 9.49 mmol) in methanol (30 mL) was added 10% Pd/C (400 mg). The mixture was stirred at room temperature under $H_2$ atmosphere for 1 h. The reaction mixture was filtered, and concentrated in vacuo to give 2.7 g of the crude product that was purified by reverse phase chromatography (C18 column; mobile phase, A: 10 mM TFA aqueous solution; B: MeOH; gradient: 10 min, 9-71% B) to afford 2-isopropyl-5-(isoquinolin-3-yl)benzene-1,3-diol) as a gray solid. $^1$H NMR (500 MHz, MeOD) δ 9.26 (s, 1H), 8.10 (d, 1H), 8.06 (s, 1H), 7.96 (d, 1H), 7.79 (t, 1H), 7.66 (t, 1H), 6.97 (s, 2H), 3.59 (sep., 1H), 1.37 (d, 6H); LCMS Method B: $t_R$=2.08 min, 98.4%; MS (ESI): m/z 280.0 (M+H)$^+$ Example 1B
2-Isopropyl-5-(isoquinolin-3-yl)benzene-1,3-diol
Method B Stage 0

Isoquinolin-3-yl trifluoromethanesulfonate

DCM (6 vol) was charged into the reactor followed by addition of isoquinolin-3-ol (1.0 eq), $Et_3N$ (1.45 eq) and N-benzyl-bis-trifluoromethanesulphonimide (1.1 eq.). The reaction mixture was stirred at 20-35° C. for 2-3 h. After completion, water (10 vol) was charged into the reaction mixture and stirred for 15 min. The organic and aqueous layers were separated. The organic layer was washed with water (10 vol). The organic and aqueous layers were separated, and the organic layer was dried over $Na_2SO_4$. The organic layer was then filtered to remove the $Na_2SO_4$ and concentrated under reduced pressure at 35-40° C. to afford the crude as a black liquid. The crude was charged into the reactor. Ethyl acetate (6.0 vol), followed by charcoal (0.1 w/w) were added. The contents were heated to 55-60° C. for 30 min, and then cooled to 20-35° C. The contents were filtered through Celite and washed with ethyl acetate (5 vol). The combined organic layer was concentrated under reduced pressure at 40-45° C. to afford a dark brown liquid. The dark

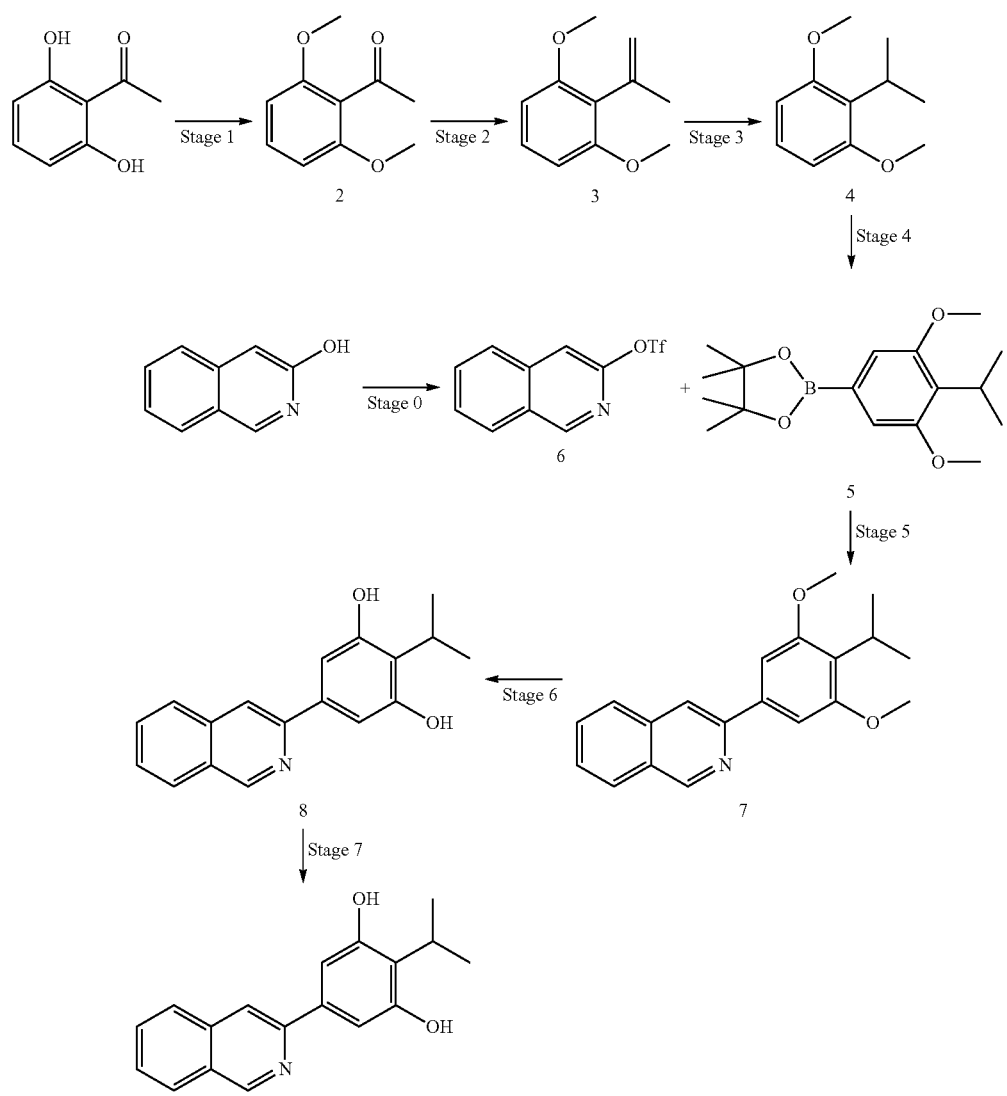

brown liquid was charged into the reactor followed by the addition of heptane (20 vol), and the contents were heated to 60-65° C. for 1 h. The contents were filtered at 60-65° C. through a layer of celite (lot-2), and washed with heptane (5 vol). The combined heptane layers were concentrated under reduced pressure at 40-45° C. to afford the desired product Compound 6 as a light yellow liquid which becomes solid at 2-8° C.

Stage 1

1-(2,6-dimethoxyphenyl)ethanone 2,6-Dihydroxy acetophenone (1.0 eq) and potassium carbonate (5.0 eq) were taken up in acetone (14 vol) at 20-35° C. Dimethyl sulphate (2.5 eq) was added to the contents while at the same temperature. The contents were heated to 60-65° C. (reflux) for 2-3 h, and monitored by IPC-HPLC. The reaction mixture was cooled to 20-35° C., the salts filtered off and rinsed with acetone (5 vol). The combined organic layer was concentrated under reduced pressure to yield the crude liquid product. Water (30 vol) was added to the crude material and the mixture was stirred for 1 h at 20-35° C. The resulting solid was filtered off and washed with water (5 vol), and the wet cake was transferred into a round bottom flask. Saturated $NaHCO_3$ (10 vol) was added and the contents stirred for 1 h. The contents were filtered to remove the solids, and the solids were rinsed with water (lot-3, 5 vol) to afford the product Compound 2 as an off-white solid. The solid was then dried at 40-45° C. until the KF reading showed <1%.

Stage 2

1,3-dimethoxy-2-(prop-1-en-2-yl)benzene

MeMgBr (1.4 M, 1.5 eq) was added to a round bottom flask under nitrogen at 20-35° C. The contents were cooled to 0-10° C. A solution of Compound 2 (1.0 eq) dissolved in THF (10 vol) was then added to the cooled Grignard solution while the temperature was maintained at 0-10° C. The reaction mixture was warmed to room temperature and stirred for 2 h. After 2 h, the reaction mixture was cooled to 0-10° C. A solution of 4 N HCl was added, and the contents allowed to warm to room temperature and stirred for another 2 h. Following this, ethyl acetate (7 vol) was added and the contents were stirred for 30 min. The layers were allowed to separate, and the aqueous layer was extracted with ethyl acetate (3.5 vol). The organic fractions were combined and washed with water (10 vol). The layers were allowed to separate, the aqueous layer was discarded, and the organic layer was again washed with water (10 vol). The layers were allowed to separate, the aqueous layer was discarded, and the organic layer was washed with sat. $NaHCO_3$ (10 vol). The layers were again allowed to separate, the sat. $NaHCO_3$ layer was discarded, and the organic layer was washed a final time with water (10 vol). The organic layer was dried over $Na_2SO_4$. Following drying, the sodium sulfate was filtered off and the solvent was removed under reduced pressure at 40-45° C. to afford 1,3-dimethoxy-2-(prop-1-en-2-yl)benzene Compound 3 as a crude liquid which was used as is in the next stage.

Stage 3

2-isopropyl-1,3-dimethoxybenzene

Ethyl acetate (10 vol) was charged to the reactor followed by 1,3-dimethoxy-2-(prop-1-en-2-yl)benzene (1.0 eq) and the contents were stirred at 25-35° C. until it became a clear solution. 10% Pd/C (0.1 w/w) was added to the reactor and the contents were purged under vacuum before being placed under $H_2$. The contents were then stirred at 25-35° C. for 4 h. Following this, the reaction mixture was filtered through Celite and washed with ethyl acetate (5 vol). The combined organic fractions were reduced in volume under vacuum at 40-45° C. to afford 2-isopropyl-1,3-dimethoxybenzene Compound 4 as a crude liquid which was used as is in the next stage.

Stage 4

2-(4-isopropyl-3,5-dimethoxyphenyl)-4,4,5,5-tetramethyl-1,3,2-dioxaborolane

THF (7 vol) was charged into the reactor and degassed with N2 for 30 min. The iridium catalyst (0.0081 eq), catalyst ligand (0.017 eq), bis-pinacolatodiboron (1.0 eq) and 2-isopropyl-1,3-dimethoxybenzene (1.0 eq) were added in order to the reactor. The reaction mixture was refluxed at 80° C. for 60 h. The contents were filtered through Celite (0.5 w/w) and washed with ethyl acetate (2.5 vol). The combined organic layer was reduced in volume under vacuum at 40-45° C. to afford the crude product as a thick black syrup, which was crystallized from hexanes (5 vol) to give 2-(4-isopropyl-3,5-dimethoxyphenyl)-4,4,5,5-tetramethyl-1,3,2-dioxaborolane Compound 5 as a light brown solid.

Stage 5

3-(4-isopropyl-3,5-dimethoxyphenyl)isoquinoline 1,4-Dioxane (8 vol) and water (2 vol) was charged into the reactor and degassed for 20 min. Compound 6 (1.3 eq) was charged into the reactor and degassed for 10 min. 2-(4-Isopropyl-3,5-dimethoxyphenyl)-4,4,5,5-tetramethyl-1,3,2-dioxaborolane (Compound 5, Stage 4 product, 1.0 eq) was added and the contents were degassed for another 10 min, followed by the addition of the palladium catalyst (0.1 eq). The contents were degassed for an additional 15 min, and then heated to 85-89° C. for 3 h. The reaction mixture was cooled to 20-35° C., and water (20 vol) was charged into the reactor, and the contents stirred for 1-2 h. The contents were filtered through a Buchner funnel, and washed with water (5 vol) resulting in a crude black solid. The solid was taken up in ethyl acetate (10 vol) and charged into the reactor. Charcoal (0.5 w/w) was charged to the reactor, and the contents were then heated to 60-70° C. for 1 h. The contents were cooled to 20-35° C., and filtered through Celite, and the solids washed with ethyl acetate (2.5 vol). The combined organic layer were concentrated under reduced pressure at 40-45° C. to give a viscous liquid. Heptane (1.0 vol) was added to the liquid and distilled. Heptane (0.5 vol) was added and distilled again to afford 3-(4-isopropyl-3,5-dimethoxyphenyl)isoquinoline Compound 7 as a brown solid.

Stage 6

2-isopropyl-5-(isoquinolin-3-yl)benzene-1,3-diol

2-Isopropyl-5-(isoquinolin-3-yl)benzene-1,3-diol Compound 7 (1.0 eq) was charged into the reactor and 33% HBr in acetic acid (15 vol) was added at 20-35° C. The contents were heated to 95-100° C. for 24 h. The contents were then transferred into a second reactor containing water (25 vol), and stirred at 20-35° C. for 2 h. The salt which had formed was filtered through a Buchner funnel and rinsed with water (5 vol). The wet salt cake was added into the reactor. Ethyl acetate (10 vol) was added to the reactor, followed by sat. NaHCO$_3$ soln. (10 vol). The contents were stirred at 20-35° C. for 30 min. Stirring was stopped and the layers were allowed to separate. The aqueous layer was decanted off, and the organic layer was washed with water (10 vol). The phases were allowed to separate, the aqueous layer was drawn off, and the organic layer was dried over Na$_2$SO$_4$. The sodium sulfate was filtered off and rinsed with ethyl acetate (5 vol). The combined organic layer was reduced in volume under vacuum at 40-45° C. to afford the crude free base as a dark black solid. The crude free base was charged into the reactor, followed by ethyl acetate (6.7 vol), silica (1.0 w/w) and lastly charcoal (1.0 w/w) at 20-35° C. The contents were heated to 60-70° C. for 1 h, and then cooled 20-35° C. The contents were filtered through Celite (0.5 w/w), and washed with ethyl acetate (3.35 vol). The combined organic layer was reduced in volume by distillation to afford a gummy solid. Heptane (1.34 vol) was charged to the reactor, and the contents again distilled down. Heptane (1.34 vol) was again charged to the reactor, and the contents distilled down to afford a light brown solid. 1,4-Dioxane (10 vol), silica (1.0 w/w) and charcoal (1.0 w/w; Noret CGP) were charged to the reactor at 20-35° C. The contents were heated to 60-70° C. for 1 h., and then cooled to 20-35° C. The contents were filtered through Celite (0.5 w/w) and washed with 1,4-dioxane (lot-2, 3×5 vol). The combined organic layers were reduced under vacuum at 40-45° C. to afford 2-isopropyl-5-(isoquinolin-3-yl)benzene-1,3-diol, compound of Formula 8 as an off-white solid.

Stage 7

2-isopropyl-5-(isoquinolin-3-yl)benzene-1,3-diol 2-isopropyl-5-(isoquinolin-3-yl)benzene-1,3-diol, compound of Formula 8 was charged into the reactor, followed by isopropyl alcohol at 20-35° C. The heterogeneous mixture was heated to 65-70° C. until it becomes a clear solution, then heptane was added (16 vol) slowly over a period of 20-30 min at 65-70° C. The reaction mixture was maintained at 65-70° C. for 1 h, then cooled to 0-5° C. and held for 1 h. The solid was filtered off at 20-35° C. and washed with heptane (2 vol) which afforded 2-isopropyl-5-(isoquinolin-3-yl)benzene-1,3-diol, as an off-white solid.

Example 2 3-(3-Aminopropoxy)-2-isopropyl-5-(isoquinolin-3-yl)phenol, bis-trifluoroacetic Acid Salt Into a solution of 2-isopropyl-5-(isoquinolin-3-yl)benzene-1,3-diol (185 mg, 0.662 mmol) in N,N-Dimethylformamide (DMF, 4 mL) was added 60% sodium hydride oil dispersion (35 mg, 0.875 mmol) at room temperature with magenetic stirring. After hydrogen evolution ceased, tert-butyl (3-bromopropyl)carbamate (178 mg, 0.748 mmol) was added. The resultant mixture was heated at 50° C. overnight. LCMS revealed a mixture of the starting material, mono-alkylated and di-alkylated product (nearly 1:1:1). The mixture was cooled, quenched with water (25 mL) and filtered to collect a greenish gray solid. The crude material was dissolved in MeOH and purified by Gilson prep-HPLC [Luna acidic on an Agilent Eclipse plus C18 column (5 µm, 30×50 mm), gradient 30-60% acetonitrile/water with 0.1% TFA, 47 mL/min flow rate, 14 min run time, fractions collected from 3.5 min to 4.2 min]. The residue with m/z=437.5 (M+1)$^+$ on LCMS from evaporation of the corresponding fractions was dissolved in DCM (5 mL) and treated with TFA (1 mL) at rt overnight. The reaction mixture was concentrated to dryness under reduced pressure to afford the desired compound as a yellow amorphous solid. $^1$H NMR (400 MHz, METHANOL-d$_4$) δppm 9.76 (s, 1H), 8.61 (s, 1H), 8.48 (d, J=8 Hz, 1H), 8.29 (d, J=8 Hz, 1H), 8.19 (t, J=7 Hz, 1H), 7.97 (t, J=7 Hz, 1H), 6.98-7.11 (m, 2H), 4.26 (t, J=6 Hz, 2H), 3.69 (dt, J=14, 7 Hz, 1H), 3.24 (t, J=8 Hz, 2H), 2.18-2.35 (m, 2H), 1.37 (d, J=7 Hz, 6H); LC/MS: m/z=337.3 (M+1)$^+$, t$_R$=0.52 min, 100%.

Example 3 N-(2-Aminoethyl)-3-(3,5-dihydroxy-4-isopropylphenyl)isoquinoline-6-carboxamide

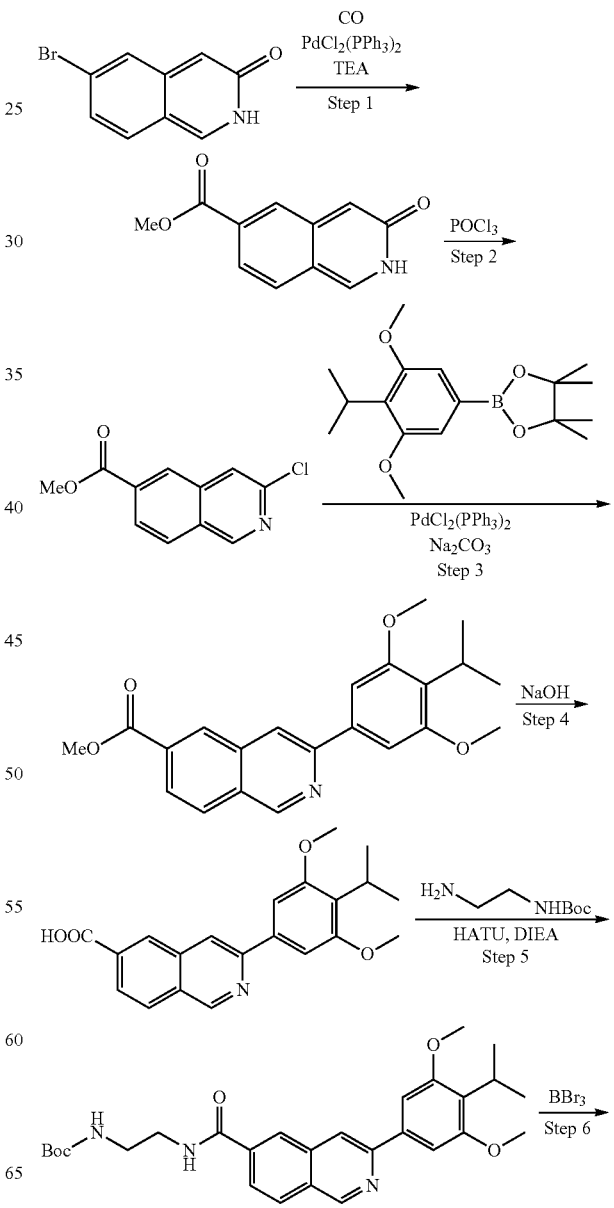

-continued

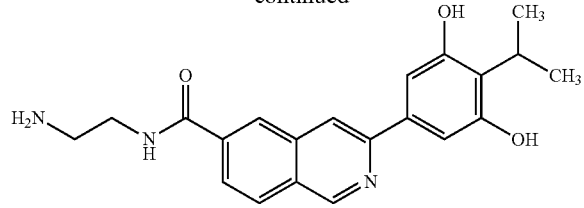

Step 1

A mixture of 6-bromoisoquinolin-3(2H)-one (5 g, 22.32 mmol), PdCl$_2$(dppf) (1.633 g, 2.232 mmol) and Et$_3$N (6.22 mL, 44.6 mmol) in methanol (10 mL) was placed in a pressure vessel. The vessel was purged with nitrogen three times, charged with 300 kPa of carbon monoxide and heated at 100° C. for 20 h. The reaction mixture was cooled and concentrated to give crude methyl 3-oxo-2,3-dihydroisoquinoline-6-carboxylate as a yellow solid that was used at the next step directly. LCMS: m/z=204.0, $t_R$=1.19 min.

Step 2

A solution of methyl 3-oxo-2,3-dihydroisoquinoline-6-carboxylate (1 g, 2.461 mmol) and pyridine (0.389 g, 4.92 mmol) in POCl$_3$ (5 mL) in a sealed tube was stirred at 160° C. for 16 h. The mixture was cooled and poured into ice-water (20 mL). The solid was filtered and dissolved in ethyl acetate (30 mL). The filtrate was extracted with ethyl acetate (10 mL×3). The combined organic phase was washed with water/brine, dried over Na$_2$SO$_4$ and concentrated in vacuo. The residue was purified by column chromatography on silica gel (30 g) with petroleum ether/dichloromethane/methanol (1/1/0.05) to yield methyl 3-chloroisoquinoline-6-carboxylate (130 mg, 0.557 mmol, 22.64% yield) as a yellow solid. $^1$H NMR (400 MHz, DMSO-d6) δ ppm=9.34 (s, 1H), 8.67 (s, 1H), 8.30 (d, J=12.0, 2H), 8.14 (d, J=8.8, 1H), 3.96 (s, 3H); LCMS: m/z=221.9, $t_R$=1.57 min.

Step 3

A mixture of methyl 3-chloroisoquinoline-6-carboxylate (100 mg, 0.451 mmol), 2-(4-isopropyl-3,5-dimethoxyphenyl)-4,4,5,5-tetramethyl-1,3,2-dioxaborolane (145 mg, 0.474 mmol), Na$_2$CO$_3$ (143 mg, 1.354 mmol), and PdCl$_2$(dppf) (33.0 mg, 0.045 mmol) in 1,4-dioxane (10 mL) and water (1.0 mL) was stirred under nitrogen at 100° C. for 16 h. The solvents were removed under reduced pressure. LCMS: m/z=365.9 (M+1)$^+$, $t_R$=1.94 min, 80%. The crude product (150 mg) was used at the next step directly.

Step 4

A mixture of methyl 3-(4-isopropyl-3,5-dimethoxyphenyl)isoquinoline-6-carboxylate (150 mg, 0.410 mmol) and NaOH (49.3 mg, 1.231 mmol) in THF (4 mL) and water (4.00 mL) was stirred under nitrogen at rt for 16 hr then diluted with water (10 mL). The mixture was washed with ethyl acetate (15 mL×3), adjusted to pH 1-2 with 1N HCl and extracted with ethyl acetate (15 mL×3). The combined organic phase was washed with brine, dried over Na$_2$SO$_4$ and concentrated in vacuo to afford 3-(4-isopropyl-3,5-dimethoxyphenyl)isoquinoline-6-carboxylic acid (100 mg) as a pale yellow solid. The crude product was used at the next step. LCMS: m/z=351.9 (M+1)$^+$, $t_R$=1.72 min, 82%.

Step 5

A solution of 3-(4-isopropyl-3,5-dimethoxyphenyl)isoquinoline-6-carboxylic acid (100 mg, 0.285 mmol), HATU (162 mg, 0.427 mmol) and DIEA (0.149 mL, 0.854 mmol) in N,N-Dimethylformamide (DMF, 5 mL) was stirred under nitrogen at rt for 1 hr. Tert-Butyl (2-aminoethyl)carbamate (54.7 mg, 0.341 mmol) was added. The reaction mixture was stirred at 25° C. for 12 h, quenched with ice water (10 mL) and extracted with ethyl acetate (15 mL×5). The combined organic phase was washed with water/brine, dried over Na$_2$SO$_4$ and concentrated in vacuo. The residue was purified by preparative HPLC (Gemini C18 150×21.2 mm, Sum, one injections mobile phase: ACN-H$_2$O, gradient: 10-60%) to afford tert-butyl (2-(3-(4-isopropyl-3,5-dimethoxyphenyl)isoquinoline-6-carboxamido)ethyl)carbamate (70 mg, 0.135 mmol, 47.3% yield) as a pale yellow solid. $^1$H NMR (400 MHz, DMSO-d6) δ ppm=9.47 (s, 1H), 8.79 (t, 1H), 8.56 (s, 1H), 8.53 (s, 1H), 8.22 (d, J=8.8, 1H), 8.04 (d, J=8.4, 1H), 7.49 (s, 2H), 6.98 (t, 1H), 3.91 (s, 6H), 3.64-3.57 (m, 1H), 3.37 (dd, 2H), 3.17 (d, J=5.6, 2H), 1.39 (s, 9H), 1.28 (d, J=7.2, 6H); LCMS: m/z=493.8 (M+1)$^+$, $t_R$=1.77 min, 95%.

Step 6

To a solution of tert-butyl (2-(3-(4-isopropyl-3,5-dimethoxyphenyl)isoquinoline-6-carboxamido)ethyl)carbamate (60 mg, 0.122 mmol) in DCM (10 mL) stirred in nitrogen atmosphere at −30° C. was added BBr$_3$ (0.575 mL, 6.08 mmol). The reaction mixture was stirred at 25° C. for 3 h, poured onto ice, neutralized with NaOH (1N) until pH=7, and extracted with EtOAc (10 mL×5). The combined organic extract was washed with brine, dried over Na$_2$SO$_4$, and concentrated. The light yellow residue was purified by preparative HPLC (Gemini C18 150×21.2 mm Sum, mobile phase: ACN-H$_2$O with 0.1% TFA, gradient: 10-30%) to afford N-(2-aminoethyl)-3-(3,5-dihydroxy-4-isopropylphenyl)isoquinoline-6-carboxamide (30 mg, 0.080 mmol, 66.2% yield) as a yellow solid. $^1$H NMR (400 MHz, DMSO) δ ppm 9.42 (s, 1H), 9.26 (s, 1H), 8.56 (s, 1H), 8.41 (s, 2H), 8.20 (d, J=8.4, 1H), 8.11 (s, 1H), 8.05 (d, J=8.4, 1H), 7.15 (s, 2H), 4.20 (brs, 2H), 3.54-3.47 (m, 3H), 3.00 (s, 2H), 1.29 (d, J=6.8, 6H); LCMS: m/z=365.9 (M+1)$^+$, $t_R$=1.200 min, 98.7%.

Example 4: Crystal Form Screen of 2-Isopropyl-5-(isoquinolin-3-yl)benzene-1,3-diol A crystal form screen was performed on 2-Isopropyl-5-(isoquinolin-3-yl)benzene-1,3-diol. The screen consisted of ~160 experiments using 60 solvent systems, and identified 16 various crystal forms including: a non-solvated form (Group A); two hydrate forms (Groups M and H); 8 stable organic solvates; and 5 putative organic solvates that were unstable and converted to other forms at ambient conditions.

Of the ~160 total experiments, 83 of these experiments yielded solids for analysis. Of those, 39 experiments yielded the non-solvate group A form (also known as form 2); 22 yielded amorphous material; only 5 yielded a hydrate (3 group H, 2 group M); and the remaining 17 resulted in one of the remaining 13 observed forms. These results are shown visually in Tables 1 and 2 below.

TABLES 1

Products of Slurry-Ripening, Cooling, and Evaporation Crystallization

| | | Form | | |
|---|---|---|---|---|
| # | Solvent (v/v) | Slurry-Ripening | Cooling | Evaporation |
| 1 | Water | A3 | NS | amorphous |
| 2 | MeOH/Toluene (1:9) | NS | NS | A |
| 3 | 2-methoxyethanol/i-propyl ether (1:9) | NS | NS | A[1] |
| 4 | 1-propanol/diethyl ether (1:8) | NS | NS | A |
| 5 | Nitromethane/i-propyl ether (5:90) | A | NS | amorphous[1] |
| 6 | MeCN | B | B | B[1] |
| 7 | DMSO/diethyl ether (1:9) | NS | NS | amorphous[1] |
| 8 | Acetone/heptane (1:9) | C | C | NS |
| 9 | 2-butanone/cyclohexane (1:9) | A3 | F | F |
| 10 | DCM | A3 | NS | A[1] |
| 11 | Methylacetate/cyclohexane (1:9) | A3 | NS | amorphous[1] |
| 12 | MIBK/toluene (3:7) | A3 | NS | amorphous[1] |
| 13 | Chloroform | A | NS | A[1] |
| 14 | EtOAc/heptane (1:9) | A3 | NS | A |
| 15 | Chlorobenzene | A3 | NS | amorphous[1] |
| 16 | Tetrahydrofuran/heptane (1:9) | A3 | NS | NS |
| 17 | 1,4-dioxane/i-propyl ether (1:9) | A3 | NS | amorphous[1] |
| 18 | i-propyl ether | A3 | NS | amorphous[1] |
| 19 | Toluene | A3 | NS | NS |
| 20 | Cyclohexane | A3 | NS | NS [2] |
| 21 | heptane | A3 | NS | NS |
| 22 | 1-butanol/toluene (3:7) | NS | NS | L |
| 23 | IPA/i-propyl ether (2:8) | NS | NS | amorphous[1] |
| 24 | Trifluoroethanol/toluene (1:9) | A3 | NS | A |
| 25 | Dimethylcarbonate | A3 | A | J |
| 26 | MTBE | A3 | NS | amorphous[1] |
| 27 | i-propyl acetate/toluene (2:7) | A3 | NS | A[1] |
| 28 | EtOH/Toluene (2:8) | NS | NS | amorphous[1] |
| 29 | 1-methoxy-IPA/heptane (10:95) | NS | NS | amorphous[1] |
| 30 | Cyclohexanone/diethyl ether (5:95) | NS | NS | amorphous[1] |
| 31 | N,N-dimethylformamide/water (2:8) | D | NS | amorphous |
| 32 | 2-methoxy methyl ether/Isopropyl ether (5:5) | NS | NS | amorphous[1] |
| 33 | MeOH/water (95:5) | NS | NS | amorphous[1] |
| 34 | MeCN/water (95:5) | B | B | B[1] |
| 35 | acetone/water (95:5) | NS | NS | amorphous[1] |
| 36 | THF/water (95:5) | NS | NS | D, N |
| 37 | IPA/water (95:5) | NS | NS | amorphous[1] |
| 38 | MeOH/water (2:9) | A3 | NS | |
| 39 | MeCN/water (1:9) | A3 | NS | amorphous |
| 40 | acetone/water (1:9) | A3 | NS | amorphous |
| 41 | THF/water (2:8) | NS | D, N | H |
| 42 | 1,4-dioxane/water (1:9) | E | NS | NS |
| 43 | IPA/water (5:5) | A | NS | H[1] |
| 44 | acetone/water (5:5) | NS | NS | H |
| 45 | dioxane/water (5:5) | NS | NS | E |
| 46 | EtOAc/cyclohexane (1:2) | A3 | NS | A |
| 47 | EtOAc/toluene (1:2) | A | NS | A[1] |
| 48 | MIBK/heptane (1:2) | A3 | NS | amorphous[1] |

TABLES 1-continued

Products of Slurry-Ripening, Cooling, and Evaporation Crystallization

| | | Form | | |
|---|---|---|---|---|
| # | Solvent (v/v) | Slurry-Ripening | Cooling | Evaporation |
| 49 | MeOH | NT | NT | A |
| 50 | EtOAC | NT | NT | I |

[1] discoloration;
[2] not enough solid for analysis;
[3] purified off-white solids
A = non solvate;
B = MeCN/water solvate;
C = acetone solvate;
D = DMF solvate;
E = 1,4-dioxane/water solvate;
F = butanone solvate (putative);
G = THF/water solvate;
H = hydrate;
I = EtOAC solvate(putative);
J = DMC solvate (putative);
K = DMSO solvate(putative);
L = 1-butanol solvate;
M = hydrate (when scaled up);
N = THF solvate;
O = THF solvate (putative);
P = MTBE solvate;
NS = no solid;
NE = no experiment

TABLE 2

Products of Solvent/Antisolvent Crystallization

| # | Solvent | Antisolvent | Group |
|---|---|---|---|
| 1 | MeOH | diethyl ether | NS |
| 2 | MeOH | i-propyl ether | NS |
| 3 | MeOH | MTBE | NS |
| 4 | IPA | diethyl ether | amorphous |
| 5 | IPA | i-propyl ether | NS |
| 6 | IPA | MTBE | NS |
| 7 | EtOAC | diethyl ether | NS |
| 8 | EtOAC | MTBE | NS |
| 9 | EtOAC | pentane | A |
| 10 | DMSO | water | K |
| 11 | DMSO | MTBE | NS |
| 12 | DMSO | toluene | NS |

A = non solvate;
K = DMSO solvate(putative);
NS = no solid

Some embodiments describe a process for making a compound of Formula (I) which comprises treating a compound of Formula (A)

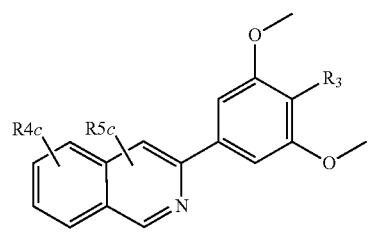

(A)

or a salt thereof;
wherein,
R$^3$ is selected from the group consisting of optionally substituted C$_{1-6}$ alkyl, optionally substituted C$_{2-6}$ alkenyl, optionally substituted $C_{2-6}$ alkynyl, optionally substituted aryl, optionally substituted aryl $C_{1-6}$ alkyl, optionally substituted $C_{3-6}$ cycloalkyl, optionally substituted $C_{4-6}$ cycloalkenyl, halo, cyano, —C(O)OR$^8$, —NR$^9$R$^{10}$, —S(O)$_2$NR$^9$R$^{10}$, —C(O)R$^{11}$, —OR$^{12}$, —S(O)$_n$R$^{13}$, and an optionally substituted heterocyclic ring;

R$^8$ is independently selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl;

each of R$^9$ and R$^{10}$ is independently selected from the group consisting of H, optionally substituted $C_{1-6}$ alkyl, optionally substituted $C_{3-6}$ cycloalkyl, optionally substituted aryl, optionally substituted aryl $C_1$-6 alkyl, or alternatively, R$^9$ and R$^{10}$ together with the nitrogen atom to which they are attached form a 5-7 membered cyclic saturated or unsaturated ring;

R$^{11}$ is independently selected from the group consisting of H, optionally substituted $C_{1-6}$ alkyl, optionally substituted $C_{2-6}$ alkenyl, optionally substituted $C_{2-6}$ alkynyl, optionally substituted aryl, optionally substituted aryl $C_{1-6}$ alkyl, optionally substituted $C_{3-6}$ cycloalkyl, —NR$^9$R$^{10}$, and —OR$^{12}$;

each of R$^{12}$ and R$^{13}$ is independently selected from the group consisting of H, optionally substituted alkyl, optionally substituted alkenyl, optionally substituted alkynyl, optionally substituted aryl, optionally substituted aryl $C_{1-6}$ alkyl, and optionally substituted $C_{3-6}$ cycloalkyl;

R$^6$ is selected from the group consisting of H, halo, hydroxyl, alkoxy, optionally substituted $C_1$-6 alkyl, halogenated alkyl; optionally substituted $C_{2-6}$ alkenyl, optionally substituted $C_{2-6}$ alkynyl, and optionally substituted aryl $C_1$-6 alkyl;

n is an integer having a value of 0, 1 or 2;

s is an integer having a value of 0, 1 or 2;

t is an integer having a value of 0 to 6;

R$^{5c}$ is selected from the group consisting of H, halo, optionally substituted $C_{1-6}$ alkyl, —C(O)OR$^{14}$, —C(O)NR$^{15}$R$^{16}$, aryl and —C$_1$-6 alkylaryl;

R$^{14}$ is independently selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl;

each of R$^{15}$ and R$^{16}$ is independently selected from the group consisting of H, optionally substituted $C_{1-6}$ alkyl, optionally substituted $C_{3-6}$ cycloalkyl, optionally substituted aryl, optionally substituted aryl $C_1$-6 alkyl, and optionally substituted $C_{3-6}$ cycloalkyl; alternatively R$^{15}$ and R$^{16}$ together with the nitrogen to which they are attached, form a 5-7 membered cyclic saturated or unsaturated ring;

R$^{4c}$ is selected from the group consisting of H, halo, cyano, optionally substituted $C_{1-6}$ alkyl, optionally substituted $C_{2-6}$ alkenyl, optionally substituted $C_{2-6}$ alkynyl, optionally substituted aryl, optionally substituted aryl $C_{1-6}$ alkyl, optionally substituted $C_{3-6}$ cycloalkyl, —(CR$^{18}$R$^{19}$)$_t$COOR$^8$, —(CR$^{18}$R$^{19}$)$_t$OC(O)R$^8$, —(CR$^{18}$R$^{19}$)$_t$NR$^9$R$^{10}$, —(CR$^{18}$R$^{19}$)$_t$C(O)NR$^9$R$^{10}$, —(CR$^{18}$R$^{19}$)$_t$NR$^9$C(O)R$^8$, —(CR$^{18}$R$^{19}$)$_t$S(O)$_2$NR$^9$R$^{10}$, —(CR$^{18}$R$^{19}$)$_t$COR$^{11}$, —(CR$^{18}$R$^{19}$)$_t$CH(O), —(CR$^{18}$R$^{19}$)$_t$OR$^{12}$, —(CR$^{18}$R$^{19}$)$_t$S(O)$_s$R$^{13}$, optionally substituted heterocyclic, and optionally substituted heterocyclic $C_1$-6 alkyl; and each of R$^{18}$ and R$^{19}$ is independently selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl;

with boron tribromide dissolved in a suitable organic solvent, such as methylene chloride, with stirring for a sufficient time and temperature, and then adding a suitable alcohol, such as CH$_3$OH to yield a compound of Formula (I), wherein R$^6$ is hydrogen.

Another aspect of the invention is a process for making a compound of Formula (I) which comprises treating a compound of Formula (B)

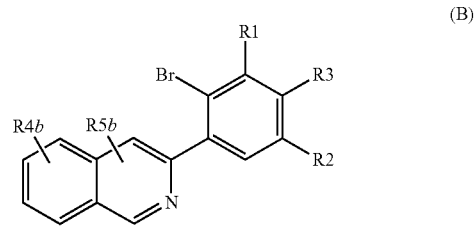

(B)

or a salt thereof;

wherein

R$^3$ is selected from the group consisting of optionally substituted $C_{1-6}$ alkyl, optionally substituted $C_{2-6}$ alkenyl, optionally substituted $C_{2-6}$ alkynyl, optionally substituted aryl, optionally substituted aryl $C_{1-6}$ alkyl, optionally substituted $C_{3-6}$ cycloalkyl, optionally substituted $C_4$-6 cycloalkenyl, halo, cyano, —C(O)OR$^8$, —NR$^9$R$^{10}$, —S(O)$_2$NR$^9$R$^{10}$, —C(O)R$^{11}$, —OR$^{12}$, —S(O)$_n$R$^{13}$, and an optionally substituted heterocyclic ring;

R$^8$ is independently selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl;

each of R$^9$ and R$^{10}$ is independently selected from the group consisting of H, optionally substituted $C_{1-6}$ alkyl, optionally substituted $C_{3-6}$ cycloalkyl, optionally substituted aryl, optionally substituted aryl $C_1$-6 alkyl, or alternatively, R$^9$ and R$^{10}$ together with the nitrogen atom to which they are attached form a 5-7 membered cyclic saturated or unsaturated ring;

R$^{11}$ is independently selected from the group consisting of H, optionally substituted $C_{1-6}$ alkyl, optionally substituted $C_{2-6}$ alkenyl, optionally substituted $C_{2-6}$ alkynyl, optionally substituted aryl, optionally substituted aryl $C_{1-6}$ alkyl, optionally substituted $C_{3-6}$ cycloalkyl, —NR$^9$R$^{10}$, and —OR$^{12}$;

each of R$^{12}$ and R$^{13}$ is independently selected from the group consisting of H, optionally substituted alkyl, optionally substituted alkenyl, optionally substituted alkynyl, optionally substituted aryl, optionally substituted aryl $C_{1-6}$ alkyl, and optionally substituted $C_{3-6}$ cycloalkyl;

n is an integer having a value of 0, 1 or 2;

s is an integer having a value of 0, 1 or 2;

t is an integer having a value of 0 to 6;

R$^{5b}$ is selected from the group consisting of H, halo, optionally substituted $C_{1-6}$ alkyl, —C(O)OR$^{14}$, —C(O)NR$^{15}$R$^{16}$ aryl and —C$_{1-6}$ alkylaryl;

R$^{14}$ is independently selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl;

each of R$^{15}$ and R$^{16}$ is independently selected from the group consisting of H, optionally substituted $C_{1-6}$ alkyl, optionally substituted $C_{3-6}$ cycloalkyl, optionally substituted aryl, optionally substituted aryl $C_1$-6 alkyl, and optionally substituted $C_{3-6}$ cycloalkyl; alternatively R$^{15}$ and R$^{16}$ together with the nitrogen to which they are attached, form a 5-7 membered cyclic saturated or unsaturated ring;

$R^{4b}$ is selected from H, halo, cyano, optionally substituted $C_{1-6}$ alkyl, optionally substituted $C_{2-6}$ alkenyl, optionally substituted $C_{2-6}$ alkynyl, optionally substituted aryl, optionally substituted aryl $C_{1-6}$ alkyl, optionally substituted $C_{3-6}$ cycloalkyl, —$(CR^{18}R^{19})_rCOOR^8$, —$(CR^{18}R^{19})_rOC(O)R^8$, —$(CR^{18}R^{19})_rNR^9R^{10}$, —$(CR^{18}R^{19})_rC(O)NR^9R^{10}$, —$(CR^{18}R^{19})_rNR^9C(O)R^8$, —$(CR^{18}R^{19})_rS(O)_2NR^9R^{10}$, —$(CR^{18}R^{19})_rCOR^{11}$, —$(CR^{18}R^{19})_rCH(O)$, —$(CR^{18}R^{19})_rOR^{12}$, —$(CR^{18}R^{19})_rS(O)_nR^{13}$, optionally substituted heterocyclic, and optionally substituted heterocyclic $C_1$-6 alkyl; and each of $R^{18}$ and $R^{19}$ is independently selected from the group consisting of H, optionally substituted $C_{1-6}$ alkyl, optionally substituted $C_{3-6}$ cycloalkyl, optionally substituted aryl, and optionally substituted aryl $C_{1-6}$ alkyl;

under hydrogenation conditions, such as with 5-10% palladium on carbon, under hydrogen atmosphere at ambient temperature in a suitable organic solvent, such as methanol, ethanol, isopropanol, ethyl acetate, tetrahydrofuran to yield a compound of Formula (I), wherein $R^6$ is hydrogen.

Another aspect of the invention is the novel intermediate compounds of Formula (II)

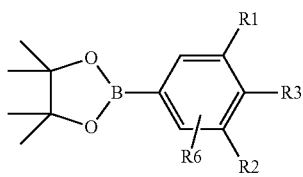

(II)

wherein each of $R^1$ and $R^2$ is independently selected from the group consisting of OH, $OR^7$, and H, provided that at least one of $R^1$ and $R^2$ is —OH or —OW;

$R^7$ is independently selected from the group consisting of optionally substituted $C_{1-6}$ alkyl, optionally substituted $C_{3-6}$ cycloalkyl, optionally substituted aryl, aryl $C_1$-6 alkyl and acyl;

$R^3$ is selected from the group consisting of optionally substituted $C_{1-6}$ alkyl, optionally substituted $C_{2-6}$ alkenyl, optionally substituted $C_{2-6}$ alkynyl, optionally substituted aryl, optionally substituted aryl $C_1$-6 alkyl, optionally substituted $C_{3-6}$ cycloalkyl, optionally substituted $C_{4-6}$ cycloalkenyl, halo, cyano, —$C(O)OR^8$, —$NR^9R^{10}$, —$S(O)_2NR^9R^{10}$, —$C(O)R^{11}$, —$OR^{12}$, —$S(O)_nR^{13}$, and an optionally substituted heterocyclic ring;

$R^8$ is from the group consisting of H, optionally substituted $C_{1-6}$ alkyl, optionally substituted $C_{3-6}$ cycloalkyl, optionally substituted aryl, and optionally substituted aryl $C_1$-6 alkyl;

each of $R^9$ and $R^{10}$ is independently selected from the group consisting of H, optionally substituted $C_{1-6}$ alkyl, optionally substituted $C_{3-6}$ cycloalkyl, optionally substituted aryl, and optionally substituted aryl $C_1$-6 alkyl, or alternatively, $R^9$ and $R^{10}$ together with the nitrogen atom to which they are attached form a 5-7 membered cyclic saturated or unsaturated ring;

$R^{11}$ is independently selected from the group consisting of H, optionally substituted $C_{1-6}$ alkyl, optionally substituted $C_{2-6}$ alkenyl, optionally substituted $C_{2-6}$ alkynyl, optionally substituted aryl, optionally substituted aryl $C_{1-6}$ alkyl, optionally substituted $C_{3-6}$ cycloalkyl, —$NR^9R^{10}$, and —$OR^{12}$;

each of $R^{12}$ and $R^{13}$ is independently selected from the group consisting of H, optionally substituted alkyl, optionally substituted alkenyl, optionally substituted alkynyl, optionally substituted aryl, optionally substituted aryl $C_{1-6}$ alkyl, and optionally substituted $C_{3-6}$ cycloalkyl;

$R^6$ is selected from the group consisting of H, halo, hydroxyl, alkoxy, optionally substituted $C_1$-6 alkyl, halogenated alkyl; optionally substituted $C_{2-6}$ alkenyl, optionally substituted $C_{2-6}$ alkynyl, and optionally substituted aryl $C_1$-6 alkyl;

n is an integer having a value of 0, 1 or 2;

In some embodiment, when $R^3$ of Formula II is an optionally substituted moiety, the moiety may be substituted independently one or more times. In some embodiments when $R^3$ of Formula II is an optionally substituted moiety, the moiety may be substituted independently one to three times. In some embodiments, the moieties may be optionally substituted independently one to three times with halo, hydroxy, $C_{1-3}$ alkoxy, $C_{1-3}$ alkyl, aryl or arylalkyl.

In some embodiment $R^3$ of Formula II is an optionally substituted $C_{3-6}$ alkyl or optionally substituted $C_{3-6}$ cycloalkyl. In some embodiments, the $C_{3-6}$ alkyl is selected from the group consisting of isopropyl, n-propyl, n-butyl, t-butyl, sec-butyl, n-pentyl, isopentyl, 2-methyl butyl, n-hexyl, and the like. In one embodiment, the alkyl is isopropyl group or t-butyl. In another embodiment, the alkyl is isopropyl. In one embodiment, the cycloalkyl is a cyclopropyl, cyclopentyl or cyclohexyl. In another embodiment, the cycloalkyl is a cyclopentyl.

In some embodiments, $R^6$ of Formula II is H.

Biological Data

As stated above, the compounds according to any embodiment described herein are regulators of AhR and are useful in the treatment or prevention of human diseases that exhibit an inflammatory component.

The biological activity of the compounds according to any embodiment described herein can be determined using any suitable assay for determining the activity of a candidate compound as an agonist or antagonist of AhR, as well as using tissue and in vivo models.

The biological activity of the compounds according to any embodiment described herein are demonstrated by the following tests.

Example 5: CYP1A1-bla LS-180 AhR Agonist Assay

LS-180 cells stably transfected with a CYP1A1 promoter-linked beta-lactamase gene reporter construct (termed CYP1A1-bla LS-180 cells) were used to characterize the ability of compounds to activate AhR. In brief, AhR activity was measured using the LiveBLAzer assay kit which utilizes a beta lactamase (bla) reporter gene downstream of CYP1A1 promoter, which metabolizes its substrate to give a fluorescent readout. For the agonist assay, CYP1A1-bla LS-180 cells were treated with increasing concentrations of compound over a 100,000-fold concentration range.

CYP1A1-bla LS-180 cells in exponential growth phase were washed twice with DPBS then seeded into 96-well microplates (50,000 cells/well) and allowed to adhere. Prepared compounds (2× working concentrations in complete media) were then added to the culture wells and cells were incubated for ~20 hrs. The LiveBLAzer FRET B/G β-lactamase substrate was added in the final hour of incubation and resulting blue/green fluorescence was measured using a 96-well microplate reader.

AhR activity was measured as a function of beta-lactamase expression using a fluorescence resonance energy transfer-based readout. TCDD and FICZ were used as controls to validate the system. As expected, CYP1A1-bla LS-180 cells treated with TCDD displayed a conventional dose-response relationship and TCDD exhibited a similar potency (pEcucC$_{50}$=10.34) to that reported by Invitrogen (pEC$_{50}$=9.70). CYP1A1-bla LS-180 cells treated with FICZ also displayed a conventional dose-response relationship and, as predicted from the literature, FICZ exhibited a much lower potency (pEC$_{50}$≤6.82) than TCDD.

For these experiments, compounds of the invention, represented as Examples 1-3, demonstrated a pEC$_{50}$ of ≥6.0 (representing an EC$_{50}$≤1 µM) which is considered a positive response.

Example 6: CYP1A1-bla LS-180 AhR Antagonist Assay

A similar assay was used to evaluate the antagonist capacity of compounds. CYP1A1-bla LS-180 cells in exponential growth phase were washed twice with DPBS then seeded into 96-well microplates (50,000 cells/well) and allowed to adhere. Either FICZ or TCDD was added as an agonist and prepared compounds (2× working concentrations in complete media) were added 2 hours later. Cells were incubated for ~20 hrs, after which compounds were tested for their ability to compete FICZ- or TCDD-induced AhR activation as a means to evaluate potential allosteric or partial agonist activity. The LiveBLAzer FRET B/G β-lactamase substrate was added in the final hour of incubation and resulting blue/green fluorescence was measured using a 96-well microplate reader, as described above.

Compounds of the invention, represented as 2-isopropyl-5-(isoquinolin-3-yl)benzene-1,3-diol, was found to be negative in this assay.

Example 7 CD4+ T Cell IL17 Assay

AhR activation has been shown to modify transcriptional regulation of the immune system and specifically may affect the differentiation of Th17 and Treg cells. Therefore, compounds are evaluated for their ability to reduce IL-17 production from CD4+ T cells stimulated under Th17-skewing conditions. Cryopreserved human CD4+ T cells (AllCells, LLC, Alameda, Calif. and Stemcell Technologies, Inc. Vancouver, Canada) were differentiated to the Th17 subtype by culturing for 5 days in CD3-coated tissue culture plates (2 µg/mL) in Iscove's modified Dulbecco's medium (IMDM) containing 10% HI-FBS, 55 µM 2-mercaptoethanol and soluble anti-CD28 (3 µg/mL) in the presence of a Th17 skewing cocktail, [IL-1β (10 ng/mL), IL-6 (30 ng/mL), TGFβ (0.5 ng/mL), IL-21 (10 ng/mL), IL-23 (10 ng/mL), anti-IFNγ (10 m/mL) and anti-IL-4 (10 m/mL)] in the presence or absence of serially diluted compounds. Secretion of IL-17 from polarized CD4+ T-cells was measured in the culture media using an MSD (Meso Scale Discovery) detection system following 5 day exposure to Th17 polarization reagents with and without compounds.

For these experiments, compounds of the invention all demonstrated a pIC$_{50}$ of ≥6.0 (representing an IC$_{50}$≤1 µM) which is considered a positive response for IL-17 inhibition.

Example 8: IMQ-Mouse Model of In Vivo Anti-Inflammatory Activity

Efficacy of AhR agonist compounds has been observed in mouse models of psoriasis, specifically, the imiquimod (IMQ)-treated mouse model (See Di Meglio et al., (2014) *Immunity*, 40(6): 989-1001, and Smith et al, (2017) *J Invest Dermatol*, 137(10), 2110-2119). The biological activity of compounds of Formula (I) were tested in this mouse model for evidence of anti-inflammatory activity in vivo.

Female BALB/c mice (BALB/cByJRj) were purchased from Janvier (France). Mice are allowed to eat a normal diet A04C from SAFE (France) and drink ad libitum. BALB/c JByRj female mice (8 week-old at study initiation) are treated with imiquimod (IMQ) cream (5%) or vanicream (non-inflammatory inert cream). For three days of pretreatment, and then daily until the end of the study (two hours before each application of IMQ), the same skin area is treated topically with 100 µL of compound. Mice are monitored for changes in clinical symptoms over the course of the study. Affected back skin is examined by histology and qPCR for evidence of compound efficacy.

The biological activity of the compounds of Formula (I), as represented by 2-isopropyl-5-(isoquinolin-3-yl)benzene-1,3-diol, was tested in this mouse model for evidence of anti-inflammatory activity in vivo. Skin histological analysis demonstrated that was able to reduce the epidermis thickening induced by imiquimod. Skin gene expression data revealed IL-17A and IL-17F expression was significantly inhibited by the compound.

Example 9: Mechanism of Compounds of the Invention as AhR Agonist and Similarity to Tapinarof Tapinarof is a first in class topical medicine under development to treat atopic dermatitis and psoriasis. The biological profile of tapinarof differs from other anti-inflammatory and immunomodulatory molecules currently used in the treatment of inflammatory skin diseases, including TCSs, TCIs, vitamin D analogs, and other immunosuppressive agents. All data currently available indicates that tapinarof exerts its pharmacological action in the skin via a novel mechanism involving dual activation of AhR and Nrf2 anti-inflammatory pathways, thereby identifying tapinarof as a therapeutic AhR-modulating agent (TAMA). Tapinarof demonstrated specific inhibition of pro-inflammatory mediators, including interleukin [IL]-6, IL-17A, and eotaxin-3, which may be downstream of AhR pathway activation. In addition, treatment with tapinarof reduces reactive oxygen species (ROS) in chemically redox-stressed keratinocytes, and induces cellular apoptosis in the micromolar range.

A direct mechanistic link between AhR and anti-inflammatory activity has not been fully elucidated, nor has the means to identify a safe TAMA while other compounds might drive AhR-mediated liabilities, been conclusively determined. Therefore, 2-isopropyl-5-(isoquinolin-3-yl)benzene-1,3-diol, was assessed for each of tapinarof's known activities. A summary of this mechanistic work is provided below.

2-isopropyl-5-(isoquinolin-3-yl)benzene-1,3-diol, was evaluated for activity in the primary 'hits' identified in tapinarof's mechanistic studies (Table 3). Indeed, 2-isopropyl-5-(isoquinolin-3-yl)benzene-1,3-diol, exhibited similar potency across each of AhR, Nrf2 and CB2 screening assays, as well as in IL-17A inhibition in CD4+ T cells cultured under Th17-polarizing conditions.

TABLE 3

Primary screen comparison of 2-isopropyl-5-(isoquinolin-3-yl)benzene-1,3-diol, to the clinical lead tapinarof

| Target | Assay Description | tapinarof | 2-isopropyl-5-(isoquinolin-3-yl)benzene-1,3-diol, |
|---|---|---|---|
| AhR | fluorescence-based reporter assay for CYP1A1 gene expression | $pEC_{50} = 7.9$ | $pEC_{50} = 7.8$ |
| Nrf2 | luciferase-based reporter assay for NQO1 gene expression | $pEC_{50} = 7.6$ | $pEC_{50} = 7.0$ |
| CB2 | fluorescence-based agonist assay using genetically modified yeast | $pEC_{50} = 6.8$ | $pEC_{50} = 6.7$ |
| IL-17A | MSD-based readout of secreted IL-17A from Th17-polarized primary human CD4+ peripheral blood T cells | $pIC_{50} = 8.5$ | $pIC_{50} = 8.4$ |

Example 10: BioMAP Profiling of 2-Isopropyl-5-(isoquinolin-3-yl)benzene-1,3-diol 2-isopropyl-5-(isoquinolin-3-yl)benzene-1,3-diol was profiled at multiple doses, 1 µM, 330 nM, 110 nM and 37 nM, using the DiscoveRx BioMAP® Diversity Plus System™ The BioMAP System evaluates 148 biomarkers relevant to multiple inflammatory diseases across 12 different primary human cell culture platforms, and compares the biomarker profile to patterns of biological responses of other compounds, biologics and approved drugs from the BioMAP reference database of >3000 experimental agents. Of the analytes tested 2-isopropyl-5-(isoquinolin-3-yl)benzene-1,3-diol (was found to be anti-proliferative to B cells, led to reductions in various cytokines/chemokines, including M-CSF, sIL-17A, sIL-2, sIL-6, sIL-10, Eot3, sTNFα, MCP-1, VCAM-1, and MIP-1, and increased IL8, IL1α, sPGE$_2$, ICAM-1, and E-selectin (FIGS. 1A-1G). Similar to tapinarof, the endogenous AhR agonist, 6-formylindolo(3,2-b)carbazole (FICZ), was the only compound identified from the BioMAP reference database with a related pattern of biological responses (Pearson correlation, r=0.71; FIGS. 1H-1N). Likewise, marked similarities to tapinarof are noted when the profiles are overlaid (FIGS. 1O-1U). The most striking difference is an observed reduction in sIL-17 by 2-isopropyl-5-(isoquinolin-3-yl)benzene-1,3-diol, that is not seen in tapinarof or FICZ-treated samples.

Figure 2A:
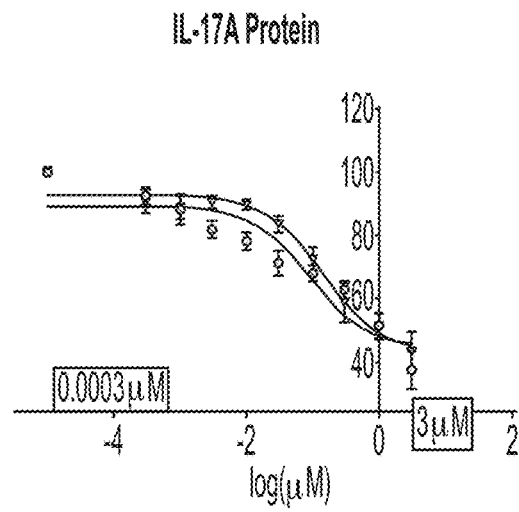
FIGS. 2A to 2C show the effect of 2-isopropyl-5-(isoquinolin-3-yl)benzene-1,3-diol on IL-17A protein secretion in primary human peripheral blood CD4+ T-cells and cell viability in T-cells and keratinocytes.

Example 11: Impact of 2-Isopropyl-5-(isoquinolin-3-yl)benzene-1,3-diol, on Cytokine and Cellular Apoptosis The impact of 2-isopropyl-5-(isoquinolin-3-yl)benzene-1,3-diol treatment on peripheral blood CD4+ T cells cultured under Th17-skewing conditions was evaluated. When applied throughout the culture period, 2-isopropyl-5-(isoquinolin-3-yl)benzene-1,3-diol, reduces IL-17A production in a dose-dependent manner, similar to tapinarof (FIG. 2A).

Figure 2B:
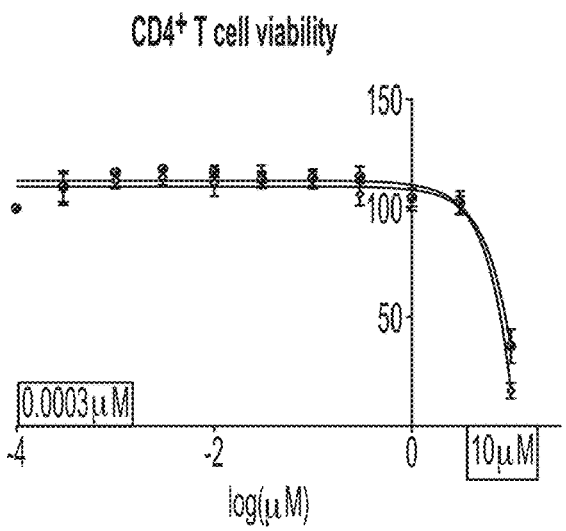
Figure 2C:
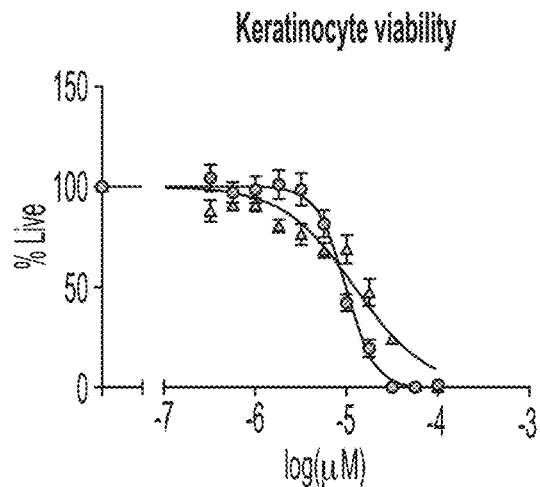

2-isopropyl-5-(isoquinolin-3-yl)benzene-1,3-diol impacts T cell viability with an $IC_{50}$=5.9 µM, and keratinocyte viability with an $IC_{50}$=12.36 µM. These values are similar to that of tapinarof and support the notion that 2-isopropyl-5-(isoquinolin-3-yl)benzene-1,3-diol is a close phenocopy of tapinarof's activity profile (FIG. 2B, FIG. 2C).

Example 12: Inhibition of Reactive Oxygen Species (ROS) by 2-Isopropyl-5-(isoquinolin-3-yl)benzene-1,3-diol Tapinarof was observed to suppress chemically-induced ROS in primary and immortalized (HaCat) keratinocytes, resulting at least in part from intrinsic ROS scavaging properties of the API (Smith et al., 2017, ibid). Importantly, the observed reduction in ROS is a key differentiator between tapinarof and TCDD, a known environmental toxin that leads to increased ROS levels. Therefore, 2-isopropyl-5-(isoquinolin-3-yl)benzene-1,3-diol was tested for its ability to reduce ROS. Using the oxygen radical absorbance capacity (ORAC) test, tapinarof was shown to scavenge peroxinitrite, superoxide anions, singlet oxygen, peroxyl radicals and hydroxyl radicals, all common species of ROS. 2-Isopropyl-5-(isoquinolin-3-yl)benzene-1,3-diol exhibited a similar profile, reducing levels of peroxinitrite, singlet oxygen, peroxyl radicals and hydroxyl radicals (Table 4).

TABLE 4

Oxygen Radical Absorbance Capacity (ORAC), measured in Trolox Equivalent Values (TEV)

| ID | Peroxynitrite | Superoxide anion | Singlet oxygen | Peroxyl radical-hydro | Peroxyl radical-lipo | Hydroxyl-radical | Total ORAC value |
|---|---|---|---|---|---|---|---|
| 2-isopropyl-5-(isoquinolin-3-yl)benzene-1,3-diol | 100 | ND | 2914 | 3267 | 1397 | 759 | 8437 |
| tapinarof | 140 | 11241 | 3581 | 4663 | 2164 | 1067 | 22855 |

Example 13: Demonstration of Biological Activity (Target Engagement) Following Topical Delivery A liquid-air interface skin explant culture with the in situ activation of immunocompetent cells, termed sRICA for skin-Resident Immune Cell Activation model was previously reported (Smith et al., (2016) *PLoS One*, 11(2)). In this assay, specific cytokine profiles of inflammatory skin diseases can be induced, including the Th17-type cytokines, IL17A, IL17F and IL22. Reduction of biomarkers in this assay indicates biological activity of the test compound.

Ex vivo human skin obtained from abdominoplasty surgery was processed to remove fat and dermatomed the tissue to ~750 microns. Dermatomed skin was then cleaned in two serial rinses of 5-10 minutes each in room temperature PBS containing an antibiotic/antimycotic solution.

Skin was treated as aseptic from this point on; all further manipulations were performed in a class II biosafety cabinet. The skin section was cut with disposable single-use biopsy punches to 10 mm diameter round sections, which were then placed in the upper chamber of a 0.4 um PCF membrane transwell (Millicell #PIHP01250) containing 30 ul of a bovine collagen solution (2:1 collagen/corni media). Care was taken to remove any bubbles under the transwell as they would inhibit the permeation of the media into the tissue.

The skin samples were allowed to set on the collagen solution for 30 min at 37° C. in a humidified chamber. After a 30 minute incubation at 37° C., which allows the collagen solution time to set, skin samples on transwells were transferred to 6-well plates (1 sample per well) and the lower chamber filled with 1 mL complete media (Cornification Media) +/−2-isopropyl-5-(isoquinolin-3-yl)benzene-1,3-diol (0 uM, 1 uM, or 10 uM) and allowed to rest overnight (16-18 h) at 37° C.

The next day, media was aspirated from the lower chamber, replaced with 1 mL complete media containing Th17 cocktail (CD3 (1 ug/ml), CD28 (2 ug/ml), anti-IL-4 (1 ug/ml), anti-INFg (1 ug/ml), IL-1b (10 ng/ml), IL-6 (10 ng/ml), TGFb (1 ng/ml), IL-21 (10 ng/ml)) incubated for 24 hours and 48 hours. A total of 3 biological replicates were used for each treatment group.

Cultures were harvested at 24 hrs and 48 hrs post-stimulation. Upon harvest, skin samples were minced with a razor blade and transferred to 1.5 mL RNAse-free tubes with 1 mL RNAlater solution until later analysis by RT-PCR.

RNA Isolation and qRT-PCR

The harvested skin tissue were stored in RNAlater until use. Total RNA was isolated from the tissue with Qiagen's Mini RNA Isolation kit (Cat #74106). Skin tissue were first minced to less than 1×1×1 mm pieces, then added to tube containing 2.8 and 1.4 mm ceramic beads (mixed into one vial). Cells were lysed in 300 uL of RLT buffer supplemented with 1% 2-Beta-Mercapto-Ethanol in Precellys Tissue Homogenizer performed for 4 cycles (6300 rpm 90s) and on ice for 30s between each cycle. Then, 590 µL of water containing 10 µL Proteinase K was added to the lysed cells and incubated at 55° C. for 20 minutes. Samples were then spun down for 3 minutes at 10,000× g and the supernatant was used for RNA isolation using Qiagen's RNeasy mini columns according to manufacturer's protocol. RNA was diluted to a concentration of 23.6 ng/ul (total of 100 ng RNA), and was used as template in a 10 uL PCR volume using Applied Biosciences RNA-to-CT 1 Step kit (AB Catalog #4392938) and the specific TaqMan probes for each gene to be quantified. Applied Biosciences' Master Mix has a ROX dye internal control. A OneStepPlus PCR machine was used for both the RT step and the 40 amplification cycles.

RNA levels of gene of interest's Relative Expression was calculated using the Delta Delta CT formula.

$$\frac{X_{test}}{X_{control}} = 2 \Delta\Delta C_T = 2 \Delta C_{T,control} - \Delta C_{T,test}$$

RNA was isolated from the tissue harvested at 24 hr and 48 hr post stimulation and gene expression was assessed by quantitative PCR. Data and statistical analysis was performed with Microsoft Excel 7 and Prism GraphPad 6.

Figure 3A:
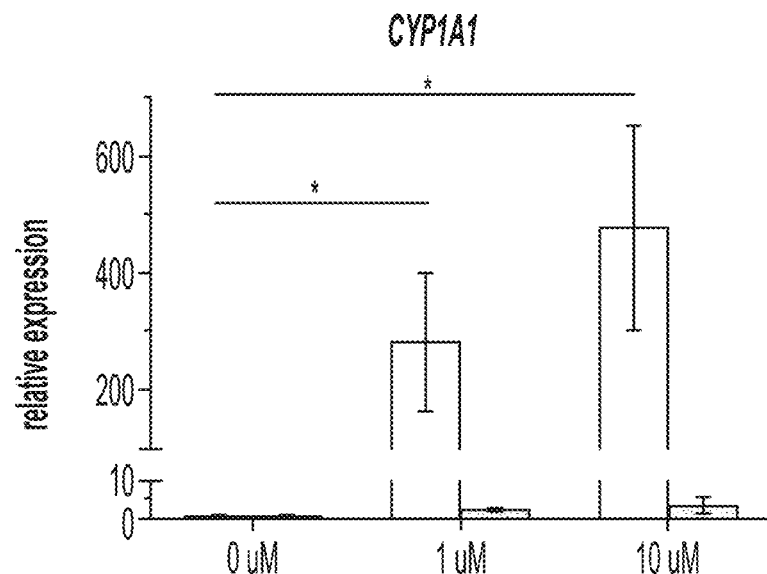
FIGS. 3A-3B show target engagement of 2-isopropyl-5-(isoquinolin-3-yl)benzene-1,3-diol induces AhR target gene, CYP1A1, and reduces IL-17A expression in ex vivo human skin. Skin samples from healthy donors placed in a liquid/air interface culture system and were pre-treated with or without 1 or 10 µM of 2-isopropyl-5-(isoquinolin-3-yl)benzene-1,3-diol (white) or GSK3038548A (grey) for 24 hours then cultured under Th17 polarizing conditions for an additional 24 hours.
Figure 3B:
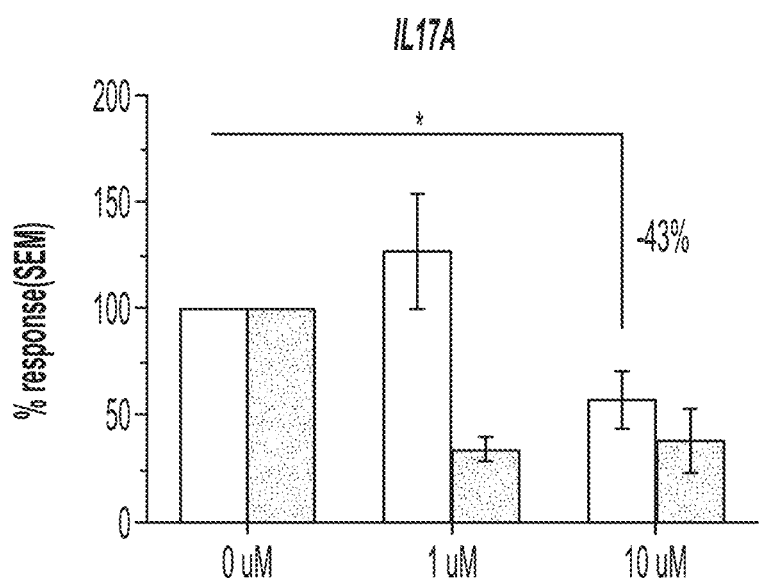

Engagement of the target pathway by 2-isopropyl-5-(isoquinolin-3-yl)benzene-1,3-diol, in this case AhR pathway activation as measured by cyp1a1 gene induction, was confirmed following exposure of skin explants to 1 µM or 10 µM 2-isopropyl-5-(isoquinolin-3-yl)benzene-1,3-diol in the baso-lateral media (FIG. 3A). Next, the impact on inflammatory mediators was assessed, demonstrating that 10 µM of 2-isopropyl-5-(isoquinolin-3-yl)benzene-1,3-diol inhibits IL17A message expression by ~45% (FIG. 3B). In this study, the RORg inverse agonist compound GSK3038548A was used as a positive control for inhibition of Il17a gene expression.

Figure 4:
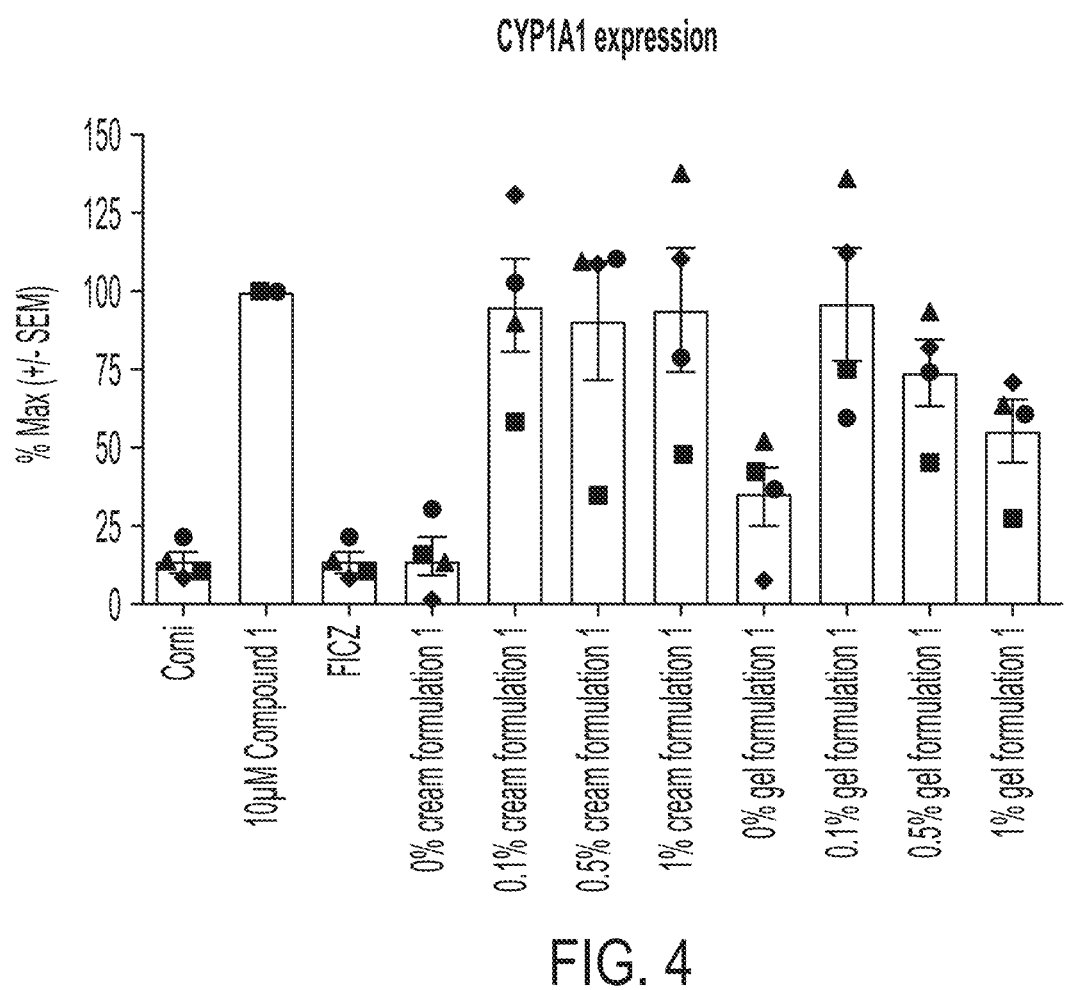
FIG. 4 shows topical target engagement of 2-isopropyl-5-(isoquinolin-3-yl)benzene-1,3-diol in cream formulation 1 and gel formulation 1 at different concentrations. Skin samples from healthy donors placed in a liquid/air interface culture system were treated with or without 10 µM 2-isopropyl-5-(isoquinolin-3-yl)benzene-1,3-diol or 1 µM FICZ in the media or topically applied at the indicated concentrations in formulations for 24 hours. Relative expression of CYP1A1 mRNA transcripts is reported as plots of the mean±SEM of 4 biological replicates from 4 individual donors.

The sRICA model was adapted to the Franz cell apparatus to demonstrate two specific outcomes for topical delivery: (i) that the test compound remains biologically active in its formulation, and (ii) that the test compound can penetrate the skin barrier to reach its dermal target and elicit a biological effect. Topical target engagement of 2-isopropyl-5-(isoquinolin-3-yl)benzene-1,3-diol was assessed in cream formulation 1 and gel formulation 1 at multiple concentrations. Importantly, because these target engagement assays utilize customized Franz cells that clamp the edges of the skin, leakage of topical formulations into the lower chamber of the air-liquid interface culture is prevented. Cyp1a1 gene expression was used as an indicator of AhR pathway activation. As such, no activation of skin resident immune cells under Th17 conditions was performed, as typical for the Th17-sRICA described above. Rather, 12 mm skin sections were clamped between upper (donor) and lower (receiving) chamber of customized Franz cells, then the lower chamber was filled with 2.0 mL complete media ("Corn"), such that the baso-lateral surface was bathed in media and no air bubbles were present. Following a ~2 hour rest period at 37° C., cells were checked again for leakage by simple inversion and then topical formulation (8.4 µl) was applied to the dry stratum cornium using a positive displacement pipette. Franz cells were then placed in a 37° C. humidified incubator for an additional 21 hours. Cyp1a1 levels were assessed, relative to baso-laterally applied 2-isopropyl-5-(isoquinolin-3-yl)benzene-1,3-diol (10 µM) in roughly ½ of each skin section, while the other half was used to determine 2-isopropyl-5-(isoquinolin-3-yl)benzene-1,3-diol concentration. Samples containing at least 0.1% 2-isopropyl-5-(isoquinolin-3-yl)benzene-1,3-diol in the cream formulation 1 exhibited strong cyp1a1 gene induction, with no observable dose dependency (FIG. 4). This data show that the maximum observable biological response is induced with the lowest formulated concentration in this system.

Example 14: In Vivo Efficacy in Mouse Models

Targeting the AhR pathway with systemic FICZ treatment has been demonstrated to positively impact clinical scores of imiquimod (IMQ)-treated mice (Di Meglio et al., (2014)

ibid). Further, tapinarof exhibits anti-inflammatory properties in multiple mouse models, including an ear eczema model, the IMQ mouse model of psoriasis and the DNFB-challenge model, which is a hapten-induced, Th2-dominant challenge model. 2-Isopropyl-5-(isoquinolin-3-yl)benzene-1,3-diol was also tested in two mouse models of inflammation: the IMQ and DNFB mouse models.

IMQ Mouse Model

2-Isopropyl-5-(isoquinolin-3-yl)benzene-1,3-diol was tested in the IMQ mouse model in a preventative manner, with daily topical application of 2-isopropyl-5-(isoquinolin-3-yl)benzene-1,3-diol in a simple ethanolic solution (60% EtOH: 40% $H_2O$). Starting 3 days after first treatment, IMQ cream was applied daily for 4 (StudyA) or 10 days (Study B). Clinical scoring was monitored daily (FIGS. 5A to 5D). At the end of the study, treated skin was evaluated by histology and qPCR for induced cytokine gene expression. 2-Isopropyl-5-(isoquinolin-3-yl)benzene-1,3-diol treatment led to reduced clinical score, reduced epidermal thickening and reduced cytokine gene expression as compared to vehicle-treated mice (N=10 mice per arm, FIGS. 5A to 5D and Table 5).

Study A—

Three groups of ten mice (BALB/cByJRJ Female Mice) were treated as follows: Days −3, −2 −1 (three days before imiquimod application) and days 0, 1, 2, 3 (4 day study): The shaved backs of the mice were treated daily with either vehicle (100 μL of 60% EtOH/40% water) or 2-Isopropyl-5-(isoquinolin-3-yl)benzene-1,3-diol (0.3% in 60% EtOH/40% water). On days 0, 1, 2, 3 a daily topical application of vanicream or 5% imiquimod cream (5% Aldara cream) was applied to the shaved back 2 hours after 2-Isopropyl-5-(isoquinolin-3-yl)benzene-1,3-diol or vehicle application and massaged with a finger until absorbed. On days 0, 1, 2, 3: visual evaluation of the skin and psoriasis clinical score were noted.

Figure 5A:
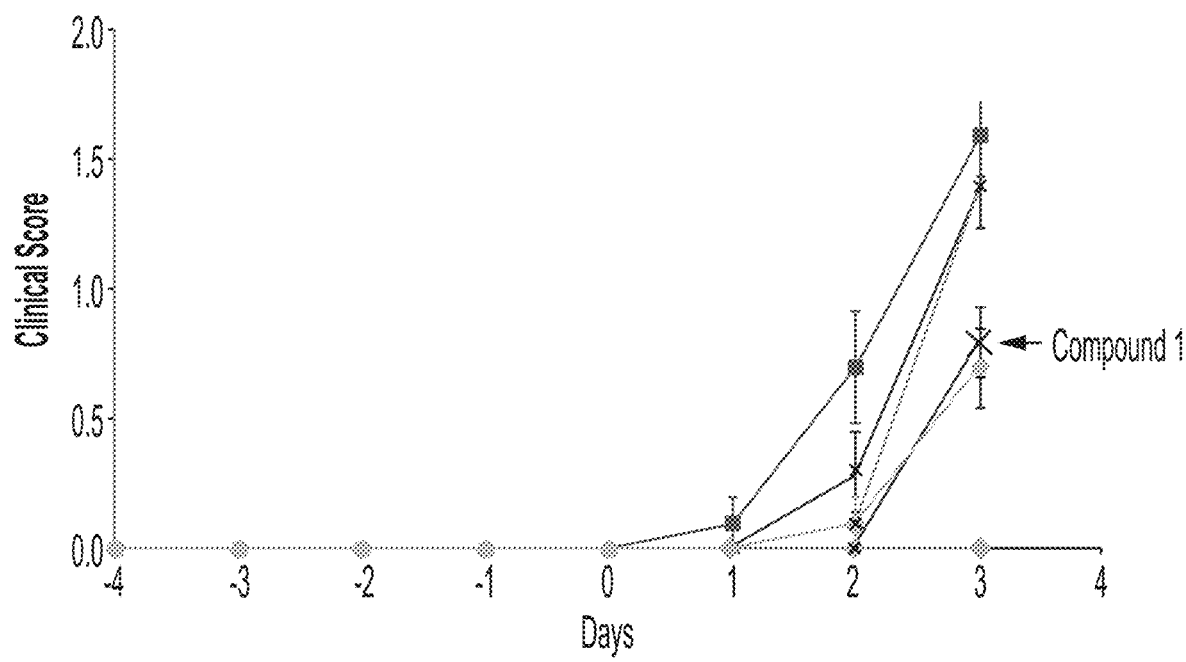
FIGS. 5A to 5F show the effects of 2-isopropyl-5-(isoquinolin-3-yl)benzene-1,3-diol on clinical score and epidermal thickness in the imiquimod mouse model of psoriasis. 2-Isopropyl-5-(isoquinolin-3-yl)benzene-1,3-diol was applied for 3 days prior to IMQ treatment. Then, IMQ and 2-isopropyl-5-(isoquinolin-3-yl)benzene-1,3-diol in 60% ethanolic topical solution was applied to the shaved back sequentially (first IMQ and then 2-isopropyl-5-(isoquinolin-3-yl)benzene-1,3-diol, 1-2 hrs later), for either 4 days at 0.3% (FIGS. 5A to 5B) or 9 days at 0.3% and 0.1% (FIGS. 5C to 5D).

Psoriasis reactions (erythema and plaques) are reported according to a 0-4 scale in ascending order of severity as shown below and results are shown in FIG. 5A.

| Psoriasis score | Grade |
| --- | --- |
| No reaction - Normal | 0 |
| Slight erythema | 1 |
| Moderate to severe erythema and some plaques | 2 |
| Marked erythema and plaques | 3 |
| Very marked erythema and plaques | 4 |

Figure 5B:
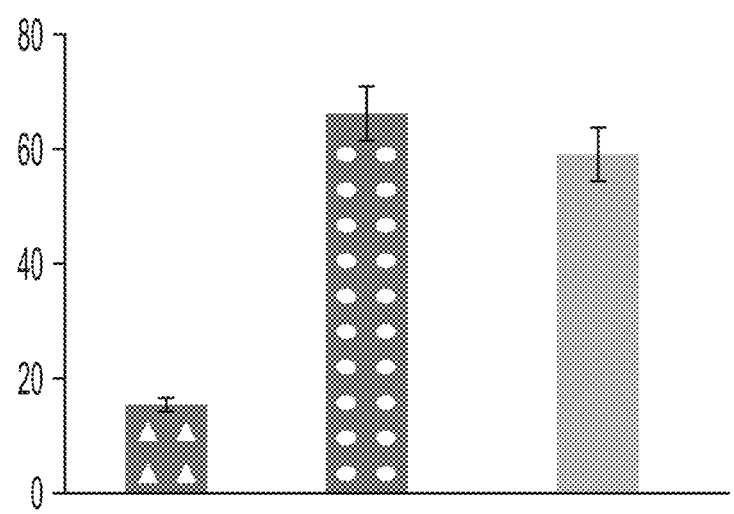

On the last day of treatment, a 6 mm punch of skin in the treated area is collected on a aluminium sheet (to keep the skin flattened) and placed into a tube containing Formalin solution (Neutral Buffered 10% (SIGMA HT501320-9 5 L)) for histological analysis (FIG. 5B).

Study B

Four groups of ten mice (BALB/cByJRJ Female Mice) were treated as follows: Days −3, −2−1 (three days before imiquimod application) and days 0, 1, 2, 3, 5, 6, 7, 8, 9, (10 day study): The shaved backs of the mice were treated daily with either vehicle (100 μL of 60% EtOH/40% water), 2-isopropyl-5-(isoquinolin-3-yl)benzene-1,3-diol (0.1% in 60% EtOH/40% water) or 2-isopropyl-5-(isoquinolin-3-yl)benzene-1,3-diol (0.3% in 60% EtOH/40% water). On days 0, 1, 2, 3, 4, 5, 6, 7, 8, 9 a daily topical application of vanicream or 5% imiquimod cream (5% Aldara cream) was applied to the shaved back 2 hours after 2-isopropyl-5-(isoquinolin-3-yl)benzene-1,3-diol or vehicle application and massaged with a finger until absorbed. On days 0, 1, 2, 3, 4, 5, 6, 7, 8, 9: visual evaluation of the skin and psoriasis clinical score were noted.

Figure 5C:
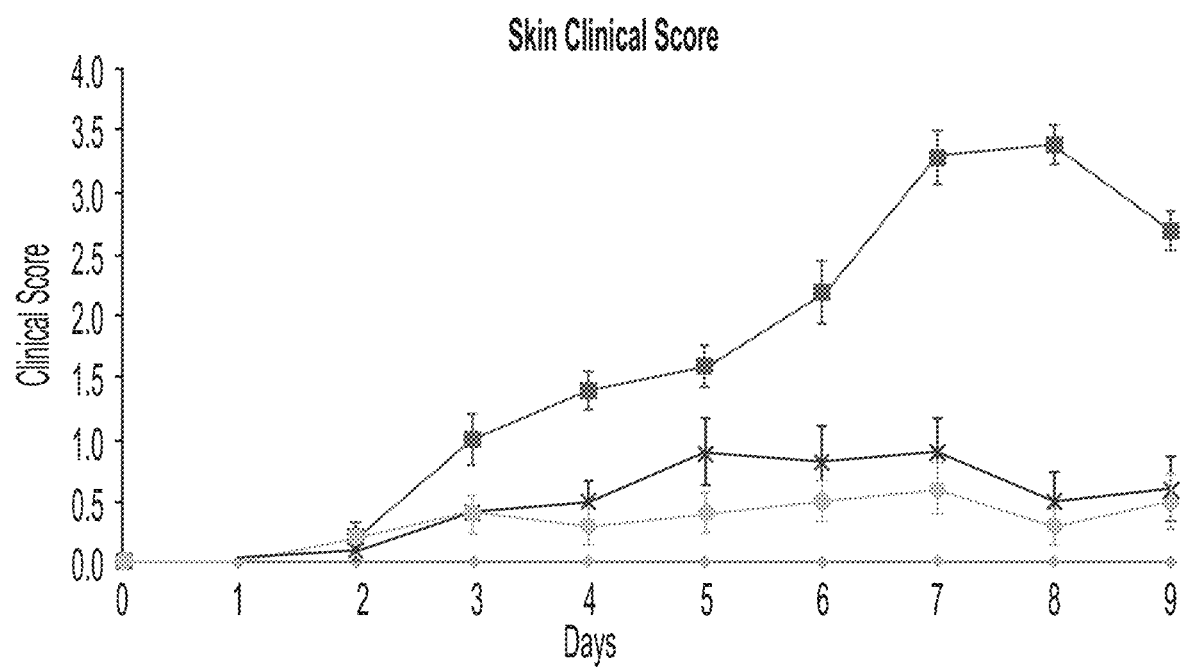

Psoriasis reactions (erythema and plaques) are reported according to a 0-4 scale in ascending order of severity as shown below and results are shown in FIG. 5C.

| Psoriasis score | Grade |
| --- | --- |
| No reaction - Normal | 0 |
| Slight erythema | 1 |
| Moderate to severe erythema and some plaques | 2 |
| Marked erythema and plaques | 3 |
| Very marked erythema and plaques | 4 |

Figure 5D:
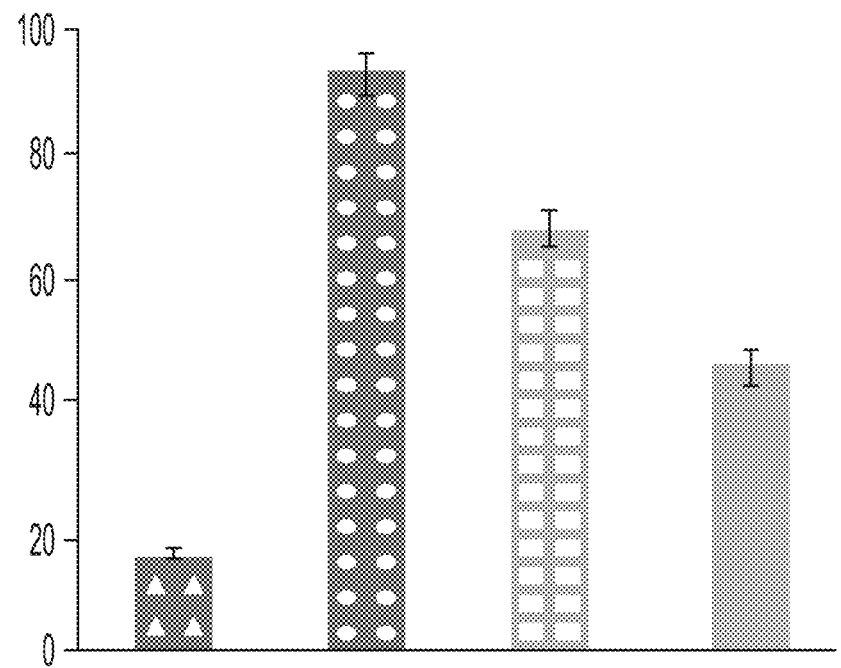
Figure 5E:
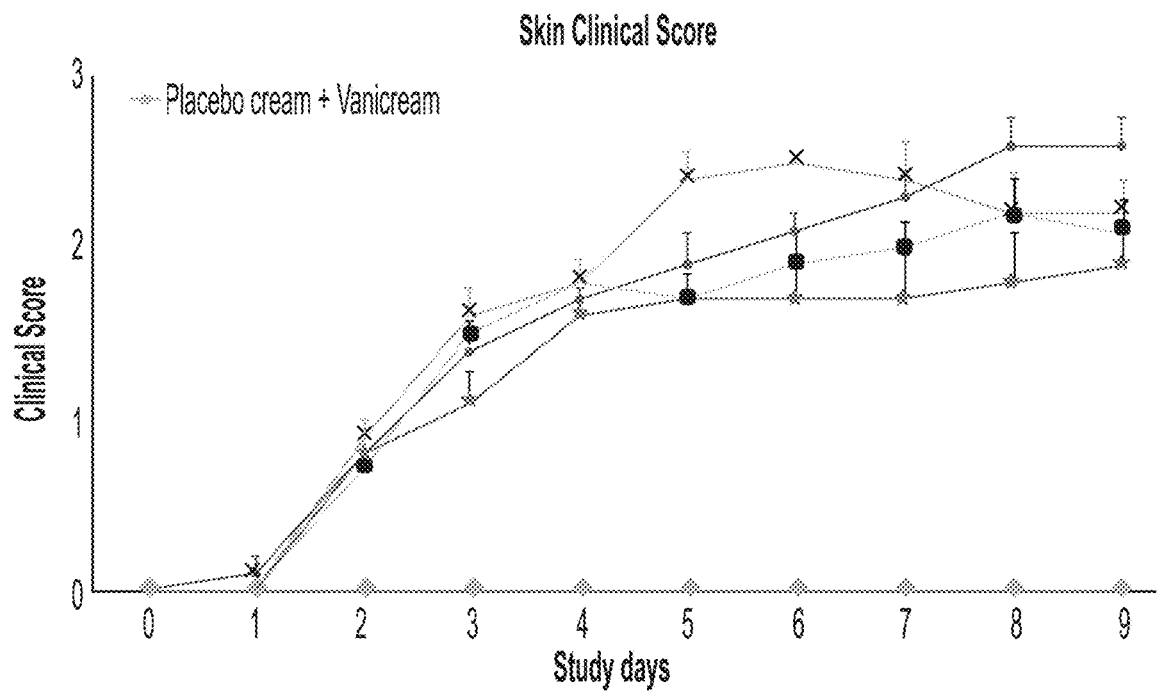
Figure 5F:
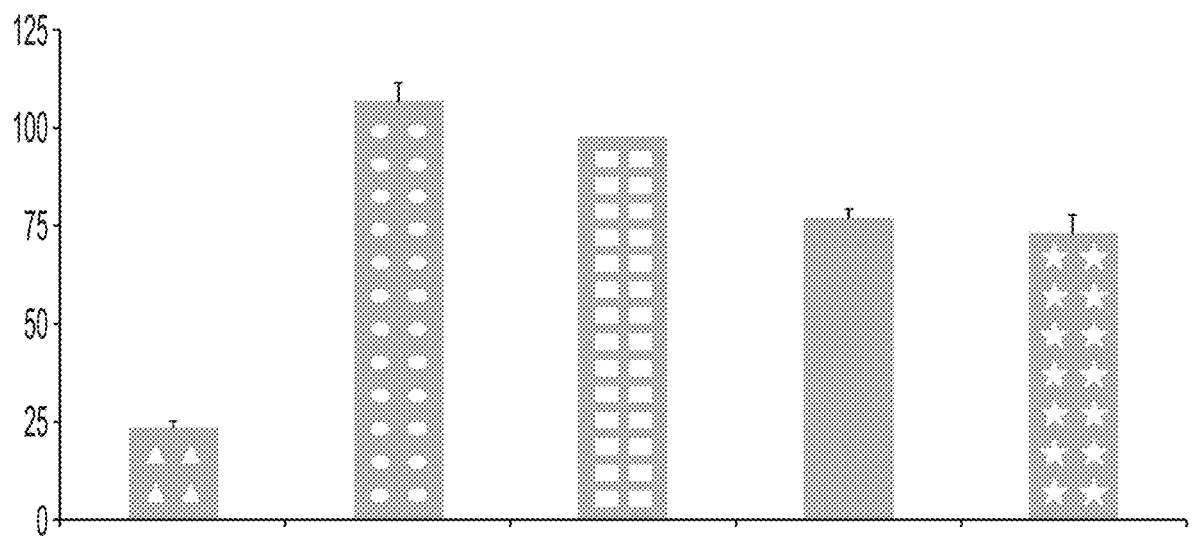

On the last day of treatment, a 6 mm punch of skin in the treated area is collected on a aluminium sheet (to keep the skin flattened) and placed into a tube containing Formalin solution (Neutral Buffered 10% (SIGMA HT501320-9 5 L)) for histological analysis (FIG. 5D).

In a separate study (Study C), 2-isopropyl-5-(isoquinolin-3-yl)benzene-1,3-diol in a cream formulation 1 was re-tested in the IMQ mouse model. In this last study, excessive redness was induced by IMQ in all treatment arms, resulting in no observed change to clinical score with compound treatment. Nonetheless, a reduction in epidermal thickness was observed when 2-isopropyl-5-(isoquinolin-3-yl)benzene-1,3-diol was applied in cream formulation 1 (FIGS. 5A to 5F), as well as significant reductions in IL17A and IL17F levels (>80% at the highest dose tested).

TABLE 5

2-Isopropyl-5-(isoquinolin-3-yl)benzene-1,3-diol reduced IL-17A and IL-17F tissue mRNA expression in the imiquimod mouse model of psoriasis (Study A - corresponding to FIG. 5A, Study B - corresponding to FIG. 5B)

| Study # | Treatment | IL-17% effect vs. IMQ + SEM | IL-17F % effect vs IMQ + SEM |
| --- | --- | --- | --- |
| Study A | Vehicle + IMQ | 100 + 15.055 | 100 + 13.724 |
|  | 2-isopropy1-5-(isoquinolin-3-yl)benzene-1,3-diol (0.3%) + IMQ | 16.27 + 4.816 | 22.21 + 7.418 |
| Study B | Vehicle + IMQ | 100 + 47.848 | 100 + 53.188 |
|  | 2-isopropy1-5-(isoquinolin-3-yl)benzene-1,3-diol (0.1%) + IMQ | 78.48 + 18.771 | 45.23 + 9.519 |
|  | 2-isopropyl-5-(isoquinolin-3-yl)benzene-1,3-diol (0.3%) + IMQ | 79.33 + 22.900 | 60.01 + 12.229 |

DNFB Mouse Model

Figure 6A:
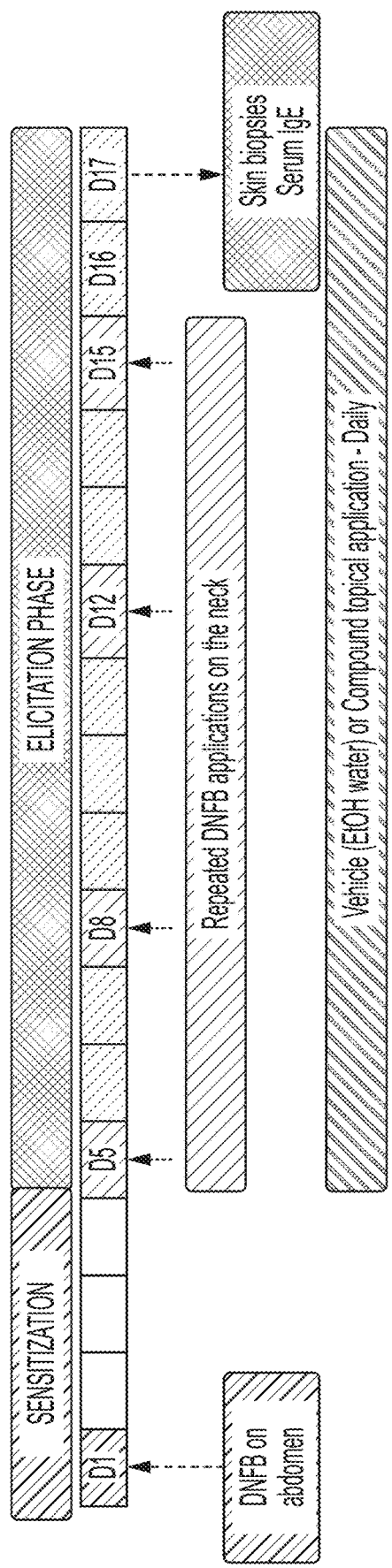
FIGS. 6A to 6E show the effect of 2-isopropyl-5-(isoquinolin-3-yl)benzene-1,3-diol on dermal and epidermal thickness in the DFNB mouse model.
Figure 6B:
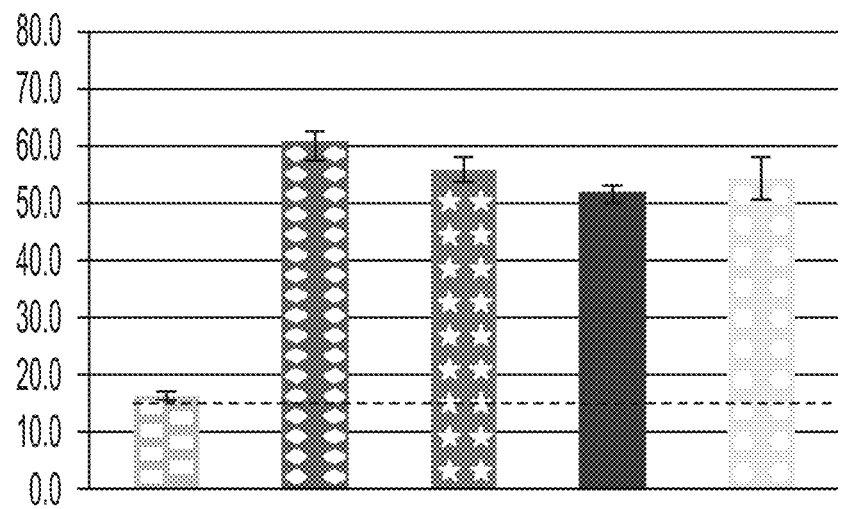
Figure 6C:
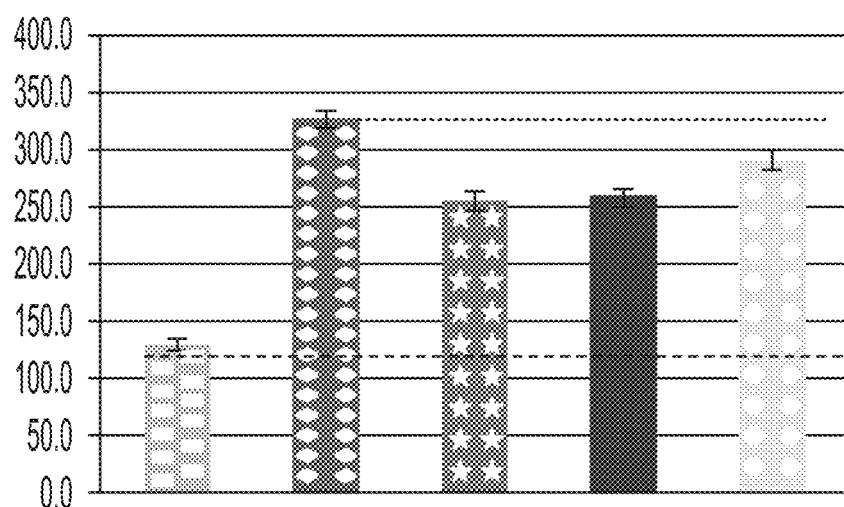
Figure 6D:
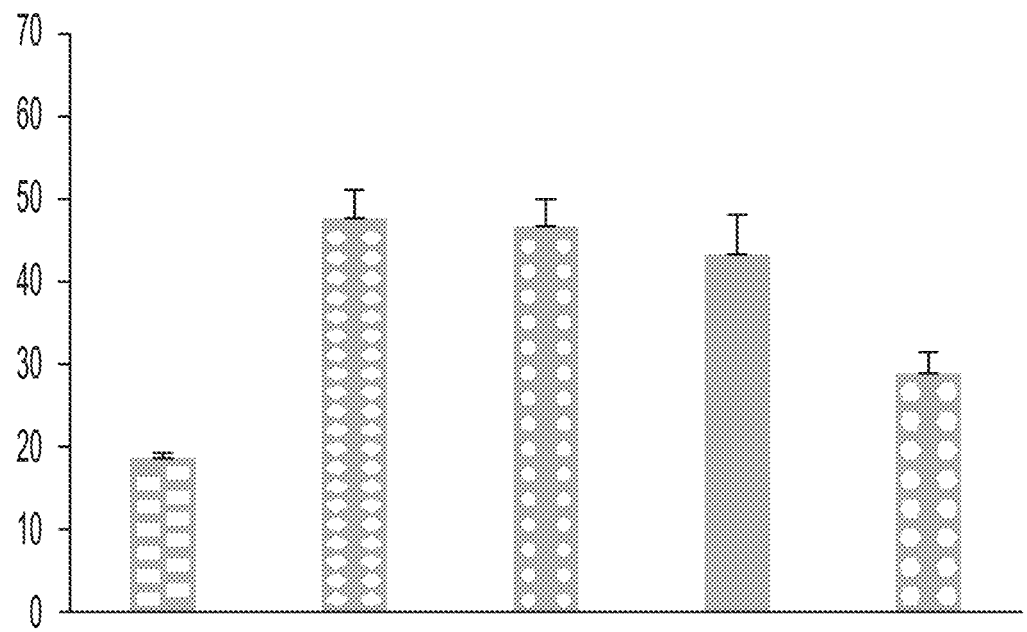
Figure 6E:
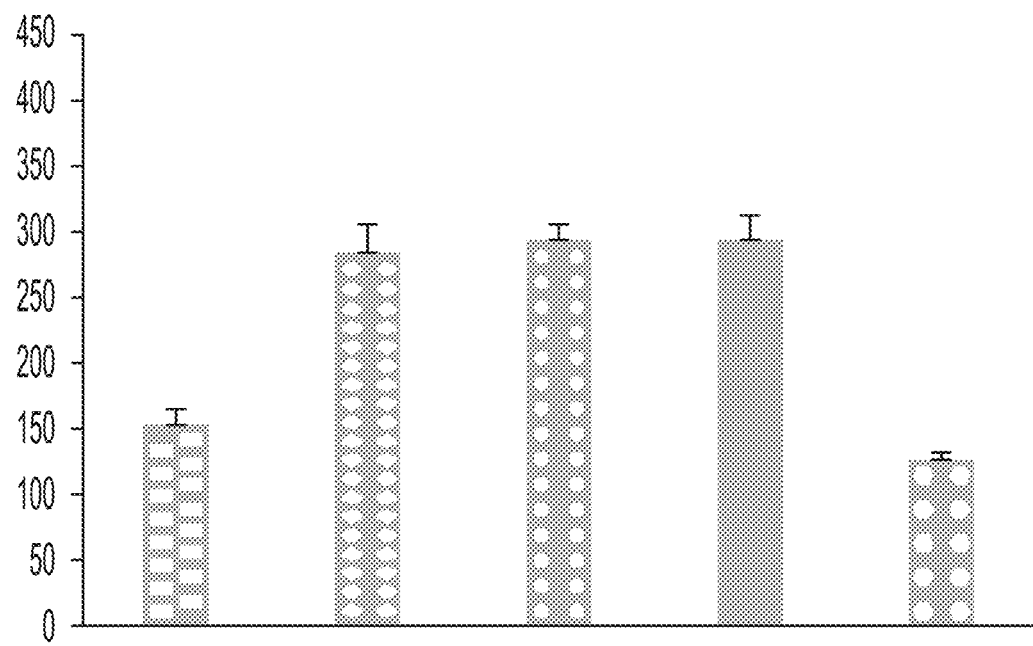

2-Isopropyl-5-(isoquinolin-3-yl)benzene-1,3-diol was next tested in the dinitrofluorobenzene (DNFB) mouse model (See FIGS. 6A to 6E). DNFB is a small chemical hapten that induces a delayed-type hypersensitivity reaction with some similarity to human atopic dermatitis. As with the IMQ challenge studies, 0.3% 2-isopropyl-5-(isoquinolin-3-yl)benzene-1,3-diol was first tested in a simple ethanolic formulation, demonstrating 20% and 34% reductions in epidermal and dermal thickness, respectively, when applied twice daily (FIGS. 6B to 6C). The effect is not observed in a second study where 2-isopropyl-5-(isoquinolin-3-yl)benzene-1,3-diol was formulated in cream formulation 1 and applied only once per day throughout the study (FIGS. 6D to 6E). This may indicate reduced exposure to the compound in the second study, although additional data would be required to understand whether this discrepancy results from different dosing strategies (q.d. vs b.i.d.), limitations of cream formulation 1, or another reason. Nonetheless, taken together with results from the IMQ mouse model, the data indicate that 2-isopropyl-5-(isoquinolin-3-yl)benzene-1,3-diol is anticipated to have broad anti-inflammatory activity that would be beneficial to both atopic dermatitis and psoriasis patients.

Second Study

Healthy female CD1 mice (Crl:CD1 (ICR)) were shaved on the abdomen and the nape of the neck under a 3 to 5% isoflurane anesthesia.

After body weight measurement, animals were allocated to study groups, according to the treatment table below. The study was divided in two arms, separated by 1 week, in order to accommodate for the in life monitoring of scratching monitoring. Half of the animals from each group (6 mice) were allocated in arm 1 and arm 2 respectively.

| Group | # of Animals | Treatment |
|---|---|---|
| 1 | 12 | Acetone/Olive Oil Vehicle (60% EtOH, 40% water) |
| 2 | 12 | DNFB (0.15% in Acetone/Olive Oil) Vehicle (60% EtOH, 40% water) |
| 3 | 12 | DNFB (0.15% in Acetone/Olive Oil) 0% Cream Formulation 1 |
| 4 | 12 | DNFB (0.15% in Acetone/Olive Oil) 0.3% Cream Formulation 1 |
| 5 | 12 | DNFB (0.15% in Acetone/Olive Oil) 0.05% Clobetasol cream |

For each topical treatment, 100 mg of cream or 100 μL of liquid formulation were applied on the mouse nape of the neck skin using a solvent pipette. When creams were used, they were spread with a finger and allowed to penetrate the skin by massage until complete absorption.

On Day 1, a topical application of acetone/olive oil (4:1 vol:vol) or 0.15% DNFB (2,4 Dinitrofluorobenzenzene in acetone/olive oil (4:1 vol:vol) was performed on the shaved abdomen under a volume of 100 μL (sensitization phase). On Days 5, 8, 12 and 15, 100 μL of acetone/olive oil or 0.15% DNFB were applied topically on the shaved nape of the neck skin (elicitation phase). From Days 5 to Day 17, 100 mg of 0.3% cream formulation 1 (group 4), 0% cream formulation 1 (group 3, placebo cream) or 100 mg of 0.05% Clobetasol cream (group 5) were applied once daily on the nape of the neck, 2 hours before the DNFB challenge.

Mice were culled on Day 17 under a 3 to 5% isoflurane anesthesia, 4 hours after the last topical treatment, and 48 hours after the last DNFB or acetone/olive oil challenge. Nape of the neck skin samples were collected for histological analyses in formalin solution, 10% neutral buffered. Epidermal (FIG. 6D) and dermal thickness (FIG. 6E) were measured.

Example 15: In Vitro Human Skin Penetration Evaluation

The in vitro human skin penetration and distribution of 2-isopropyl-5-(isoquinolin-3-yl)benzene-1,3-diol was assessed using a custom-made (ChanneL) flow-through diffusion cell setup and ex vivo human skin (from abdominoplasty surgery) dermatomed at 500±100 μm. The skin distribution (epidermis and dermis) and cumulative amount in the receiving fluid (representative of unbound drug penetrating below 500 μm) over 16 hours was evaluated using a fit-for-purpose LC-MS/MS method with a lower limit of quantification (LLOQ) of 80 pg/mL to determine the dermal delivery profile of the formulation prototypes. The biological target for 2-isopropyl-5-(isoquinolin-3-yl)benzene-1,3-diol was the epidermis/upper dermis, and the formulation ranking focused on the dermis levels due to the low cumulative amounts in the receiving fluid. Epidermis samples may still contain residual drug that did not penetrate the stratum corneum, and therefore were not considered for ranking purposes.

Figure 7:
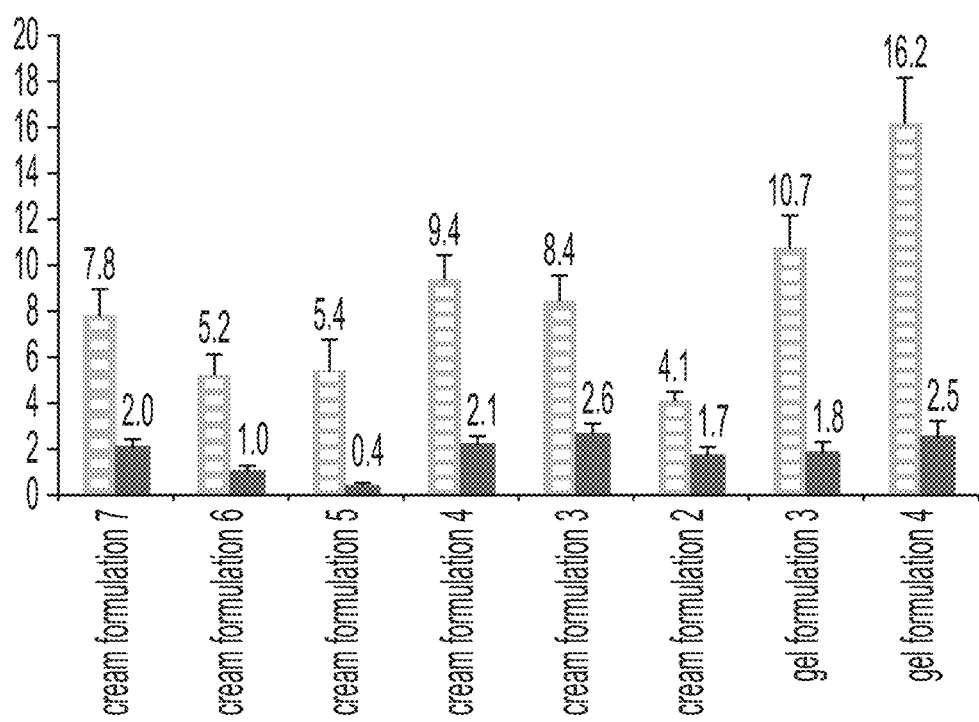
FIG. 7 shows the amount of 2-isopropyl-5-(isoquinolin-3-yl)benzene-1,3-diol in different 1% formulations delivered into the epidermis (square bar of bar set) and dermis (solid bar of bar set) 16 hours post-application. Bars represent the mean amount of 2-isopropyl-5-(isoquinolin-3-yl) benzene-1,3-diol from 15-18 replicates from 3 donors±SEM. Samples were analyzed by UPLC-MS/MS with a LLOQ of 80 pg/mL.
Figure 8:
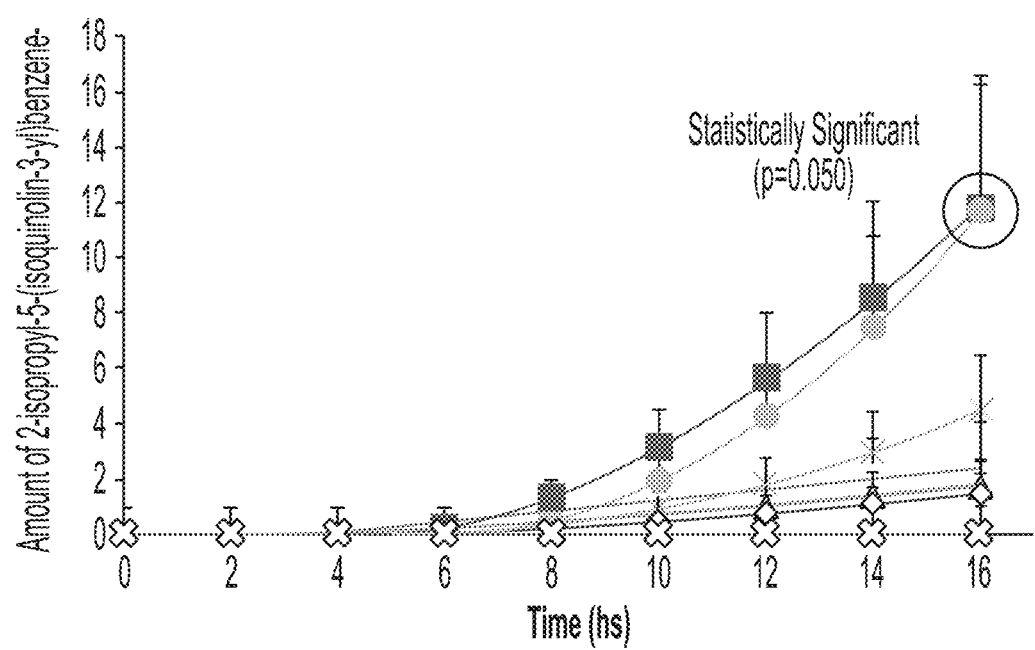
FIG. 8 shows the cumulative amount of 2-isopropyl-5-(isoquinolin-3-yl)benzene-1,3-diol (ng) in the receiving fluid over 16 hours post-application of different formulations. The square represents 1% cream formulation 3; the circle represents 1% gel formulation 4; the asterisk represents 1% gel formulation 3; the single perpendicular line represents 1% cream formulation 4; no symbol (line) represents 1% cream formulation 5; the triangle represents 1% cream formulation 6 the diamond represents 1% cream formulation 7; and the thick X represents 1% cream formulation 2. Lines represent the cumulative mean amount of 2-isopropyl-5-(isoquinolin-3-yl)benzene-1,3-diol from 15-18 replicates from 3 donors±SEM. Samples were analyzed by UPLC-MS/MS with a LLOQ of 80 pg/mL.

During the initial formulation development stage, eight topical formulations (6 creams and 2 gels) loaded with 1.0% 2-isopropyl-5-(isoquinolin-3-yl)benzene-1,3-diol were evaluated in the in vitro human skin penetration assay using three donors. The delivery of 2-isopropyl-5-(isoquinolin-3-yl)benzene-1,3-diol into the epidermis and dermis at 16 hours is shown in FIG. 7. The amounts delivered to the dermis ranged between 0.4 and 2.6 μg, and only low cumulative amounts (less than 20 ng over 16 hours, FIG. 8) were quantified in the receiving fluid.

The statistical significance of the dermis amounts was evaluated using Student's t-test, and presented in a way that formulations not connected by the same letter ("A" to "C") are statistically different (p<0.05, Table 6). The formulations 1% cream formulation 3 and 1% gel formulation 4 delivered higher amounts of drug to the dermis.

TABLE 6

Statistical Evaluation of 2-Isopropyl-5-(isoquinolin-3-yl)benzene-1,3-diol Formulations by Amount Delivered to the Dermis (μg).

| Formulation 2-Isopropyl-5-(isoquinolin-3-yl)benzene-1,3-diol | t-test | | | Dermis amount (pg) | |
|---|---|---|---|---|---|
| | | | | Mean | Standard error of the mean |
| 1% cream formulation 3 | A | | | 2.62 | 0.38 |
| 1% gel formulation 4 | A | | | 2.52 | 0.60 |
| 1% cream formulation 4 | A | B | C | 2.13 | 0.40 |
| 1% cream formulation 7 | A | B | C | 2.03 | 0.38 |
| 1% gel forumlation 3 | A | B | C | 1.78 | 0.52 |
| 1% cream formulation 2 | A | B | C | 1.69 | 0.34 |
| 1% cream formulation 6 | | B | C | 1.04 | 0.20 |
| 1% cream formulation 5 | | | C | 0.36 | 0.06 |

Figure 9:
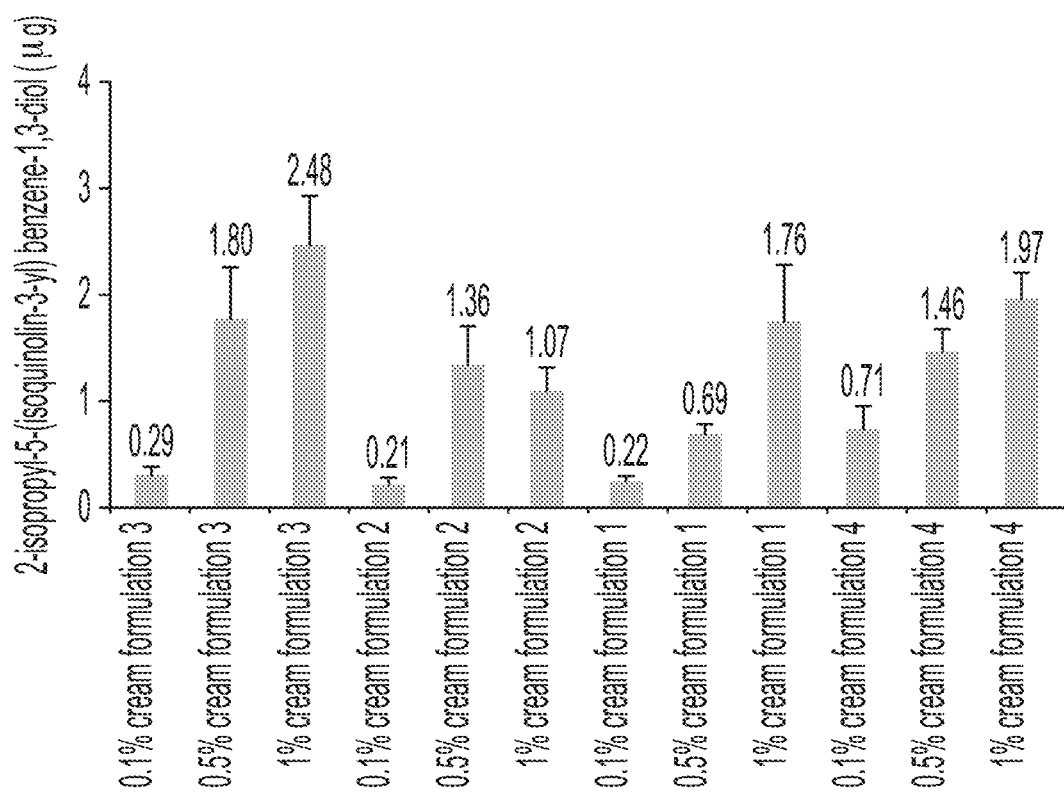
FIG. 9 shows the amount of 2-isopropyl-5-(isoquinolin-3-yl)benzene-1,3-diol delivered into the dermis 16 hours post application of different formulations. Bars represent the mean amount of 2-isopropyl-5-(isoquinolin-3-yl)benzene-1, 3-diol from 13-16 replicates from 3 donors±SEM. Samples were analyzed by UPLC-MS/MS with an LLOQ of 80 pg/mL*.

Additionally, due to improved physical stability, the cream formulation 2 and a similar formulation with lower transcutol P level, cream formulation 1, were also progressed to the dose proportionality study. Based on the dermis amounts shown in FIG. 9, 1% cream formulation 3 and 1% cream formulation 1 yielded the best dose proportionality, with the latter exhibiting comparable delivery to the dermis and improved stability profile.

Figure 10A:
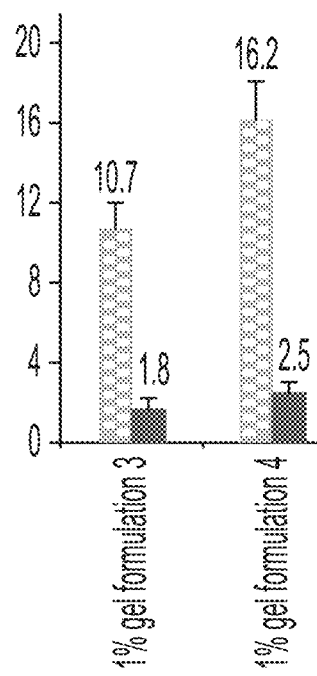
FIGS. 10A to 10B show the amount of 2-isopropyl-5-(isoquinolin-3-yl)benzene-1,3-diol (μg) delivered into the epidermis (square bar of each formulation) and dermis (solid bar of each formulation) 16 hours post application for different gel formulations of 2-isopropyl-5-(isoquinolin-3-yl)benzene-1,3-diol. Bars represent the mean amount of 2-isopropyl-5-(isoquinolin-3-yl)benzene-1,3-diol from 15-18 replicates from 3 donors±SEM (FIG. 10A) and from 7-10 replicates from 1 donor±SEM (FIG. 10B). Samples were analyzed by UPLC-MS/MS with an LLOQ of 80 pg/mL.
Figure 10B:
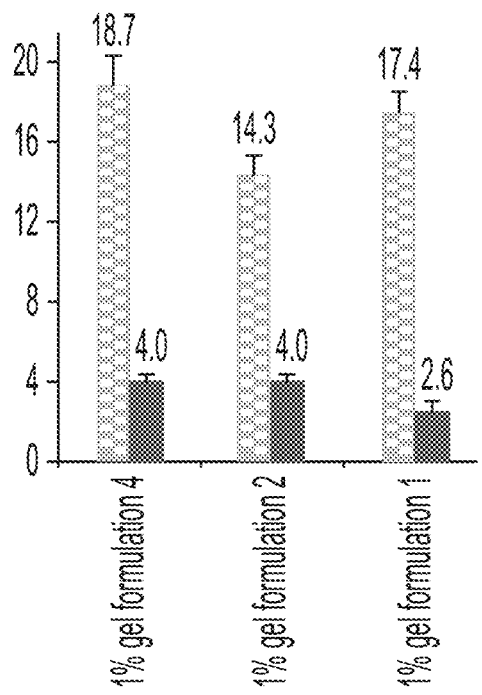
Figure 11:
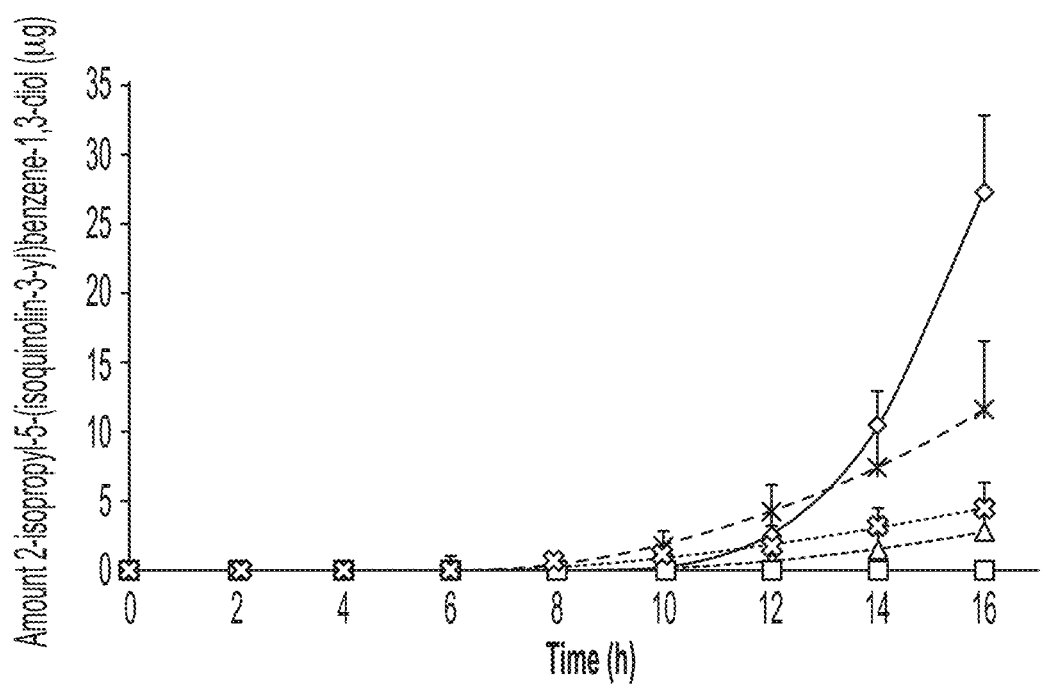
FIG. 11 shows cumulative amount (ng) of 2-isopropyl-5-(isoquinolin-3-yl)benzene-1,3-diol in the receiving fluid over 16 hours post application for different gel formulations. The cumulative amount of 2-isopropyl-5-(isoquinolin-3-yl) benzene-1,3-diol from 15-18 replicates from 3 donors±SEM (N46822-2) is described for gel formulation 4 (diamond), gel formulation 1 (triangle) and gel formulation 2 (square). The cumulative amount of 2-isopropyl-5-(isoquinolin-3-yl) benzene-1,3-diol from 7-10 replicates from 1 donor± is described for gel formulation 4 (asterisk) and gel formulation 3 (broad X). Samples were analyzed by UPLC-MS/MS with an LLOQ of 80 pg/mL.

To further evaluate the potential for a 2-isopropyl-5-(isoquinolin-3-yl)benzene-1,3-diol gel (specifically one with an amount of propylene glycol below 15%), two more formulations (gel formulation 1 and gel formulation 2) were evaluated in the in vitro skin penetration assay. No gel delivered significantly more 2-isopropyl-5-(isoquinolin-3-yl)benzene-1,3-diol to the dermis than any of the other test articles (FIG. 10). Cumulative amounts were measured but not considered in the ranking (FIG. 11).

Matrix-assisted laser desorption ionization imaging mass spectrometry (MALDI IMS) was also used to demonstrate spatial localization of 2-isopropyl-5-(isoquinolin-3-yl)benzene-1,3-diol within the skin layers. The 1% cream formulation 1 was selected for this study, in addition to 0.5% cream formulation 3 and 1% gel formulation 4; these prototypes delivered equivalent amounts of 2-isopropyl-5-(isoquinolin-3-yl)benzene-1,3-diol to the dermis during the dose proportionality study. A single dose of the three formulations was applied to human full-thickness skin and samples were collected at 6 and 24 hours. Following collection and preparation, samples were sent for MALDI. At six hours (Table 7), the amount of 2-isopropyl-5-(isoquinolin-3-yl)benzene-1,3-diol delivered to the level of the dermis is 5.0 to 7.0 fold higher for the 1% gel formulation 4 compared to the 0.5% cream formulation 3 and 1% cream formulation 1; however, after 24 hours this difference was approximately 2.0-fold.

The drug concentrations from the in vitro human skin penetration and the MALDI IMS studies were compared and results presented in Table 7. A few assumptions were made to calculate the concentrations in each compartment using data from the skin penetration assay: (i) the volume of each compartment was calculated using a dosing area of 1 $cm^2$; (ii) the skin thickness for epidermis and dermis was estimated to be 150 μm and 350 μm, respectively, (iii) the drug distribution was assumed to be homogeneous within each compartment, and (iv) the tissue density was assumed to be 1 g/mL. The concentrations did not account for drug fraction bound or unbound.

The concentrations observed in the epidermis for the two creams were on average 2.4-fold higher in the 16 hour in vitro human skin penetration study than at the 6 hour MALDI time point; however, the epidermis amounts delivered by the gel in the 6 hour MALDI study were comparable to those in the in vitro skin penetration assay. At the 24 hour MALDI time point the epidermis amounts for the gel formulation have decreased, making the values from the in vitro skin penetration study 1.5-fold higher in comparison. The creams do not exhibit this behavior, but instead show epidermis amounts increasing from 6 hours to 24 hours, and becoming comparable to the amounts delivered in the in vitro skin penetration study. This difference in behavior suggests a disparity in the formulation delivery kinetics between the gel and cream formulations. A comparison of the dermis values shows that 3.0 to 6.5-fold higher amounts of 2-isopropyl-5-(isoquinolin-3-yl)benzene-1,3-diol were delivered in the in vitro human skin penetration assay (16 hours) than in the MALDI experiment (24 hours). These variations between the concentrations can be attributed to the differences in study protocols used across the two assays, including skin thickness, skin donors and analytical methods.

TABLE 7

Calculated Skin Concentrations (μM and μg/g) in the Epidermis and Dermis Compartments (± SEM, when shown)

| Formulation | In vitro human skin penetration (16 hours, n = 15-18) | | MALDI-IMS (6 hours, n = **) | | MALDI-IMS (24 hours, n = **) | |
|---|---|---|---|---|---|---|
| | Epidermis μM [μg/g] | Dermis μM [μg/g] | Epidermis μM [μg/g] | Dermis μM [μg/g] | Epidermis μM [μg/g] | Dermis μM [μg/g] |
| 1% cream formulation 1 | 1188.4 ± 287.4 [332.0 ± 80.3] | 180.2 ± 52.3 [50.3 ± 14.6] | 442.7 ± 6.1 [123.7 ± 1.7] | 14.0 ± 1.8 [3.9 ± 0.5] | 1448.2 ± 13.6 [404.5 ± 3.8] | 28.3 ± 1.7 [7.9 ± 0.5] |
| 0.5% cream formulation 3 | 1090.0 ± 229.9 [304.5 ± 64.2] | 184.1 ± 47.6 [51.4 ± 13.3] | 533.5 ± 4.8 [149.0 ± 1.3] | 9.7 ± 1.6 [2.7 ± 0.5] | 1024.0 ± 12.6 [286.0 ± 3.5] | 32.7 ± 1.3 [9.1 ± 0.4] |
| 1.0% gel formulation 4 | 4258.0 ± 638.2 [1189.4 ± 178.3] | 201.4 ± 24.2 [56.3 ± 6.8] | 5492.7 ± 64.3 [1534.3 ± 18.0] | 71.9 ± 2.2 [20.1 ± 0.6] | 2768.2 ± 38.8 [773.3 ± 10.8] | 66.8 ± 1.3 [18.7 ± 0.4] |

** Values reported for the MALDI-IMS analysis of ex vivo human skin are the average of 6 skin sections, taken from 2 skin penetration replicates (3 sections per skin replicate), using 1 skin donor Example 16: Absorption, Distribution, Metabolism, and Excretion 2-isopropyl-5-(isoquinolin-3-yl)benzene-1,3-diol showed high binding to plasma proteins and the unbound fraction values at 2 μM were 3.06%, 1.98% and 1.08% in rat, minipig and human, respectively (Table 8). The skin binding of 2-isopropyl-5-(isoquinolin-3-yl)benzene-1,3-diol in whole human skin, epidermis and dermis homogenate was tested at three concentrations (25, 50 and 100 ng/mL, respectively 0.089, 0.179 and 0.358 μM) and showed a mean unbound fraction value of 21.9±0.72%, 51.3±1.1% and 34.1±11.5%. The blood-to-plasma ratios were similar across species (1.22-1.36, Table 9). 2-Isopropyl-5-(isoquinolin-3-yl)benzene-1,3-diol was stable in plasma and blood.

TABLE 8

Binding of 2-Isopropyl-5-(isoquinolin-3-yl)benzene-1,3-diol (2 μM) in Rat, Minipig and Human Plasma Proteins as Determined by Rapid Equilibrium Dialysis (RED) Device

| Species | % Unbound Replicate | | | Mean (% CV) | % Bound | Stability at 4 hrs | Mean % Recovery |
|---|---|---|---|---|---|---|---|
| Rat | 1.37 | 1.44 | 6.36 | 3.06 (93.6) | 96.9 | 94.4 | 104 |
| Minipig | 1.87 | 2.52 | 1.57 | 1.98 (24.6) | 98.0 | 107 | 95.6 |
| Human | 1.06 | 1.05 | 1.13 | 1.08 (3.71) | 98.9 | 101 | 102 |

TABLE 9

The Blood-to-plasma Ratio and Extent of Association of 2-Isopropyl-5-(isoquinolin-3-yl)benzene-1,3-diol (1 μM) with Blood Cells in Rat, Minipig and Human

| Species | Blood-to-plasma Ratio Replicate | | | Mean (% CV) | % Blood Cell Association Replicate | | | Mean (% CV) | Mean % Blood Stability |
|---|---|---|---|---|---|---|---|---|---|
| Rat | 1.31 | 1.29 | 1.46 | 1.36 (6.83) | 58.9 | 58.3 | 63.1 | 60.2 (4.37) | 104 |
| Minipig | 1.21 | 1.25 | 1.19 | 1.22 (2.54) | 55.3 | 56.8 | 54.5 | 55.6 (2.02) | 105 |
| Human | 1.21 | 1.29 | 1.23 | 1.24 (2.95) | 53.9 | 56.4 | 54.6 | 55.0 (2.39) | 107 |

TABLE 11

Detection of GSH Trapped Reactive Metabolites of 2-Isopropyl-5-(isoquinolin-3-yl)benzene-1,3-diol (10 μM) in Liver Microsomes

| Species | P + O + GSH (+323 Da) | P + O + GSH − 2H (+321 Da) | P + GSH (+307 Da) | P + GSH − 2H (+305 Da) |
|---|---|---|---|---|
| Rat | + | + | − | + |
| Human | − | + | − | + |

P = Parent;
O = Oxygen;
GSH = Glutathione 2-isopropyl-5-(isoquinolin-3-yl)benzene-1,3-diol was rapidly metabolized by liver microsomes and/or hepatocytes across species; mouse, rat, minipig, dog, rabbit and human, suggesting high intrinsic in vitro clearance. The intrinsic metabolic clearance in hepatocytes was 2.1 to 11.6-fold greater than the intrinsic clearance in liver microsomes across rat, minipig and human (Table 10), and it correlated well with the in vivo clearance (see below: Animal Pharmacokinetics) measured in rat and minipig pharmacokinetic studies with in vitro-to-in vivo extrapolation (IVIVE) ratios of 0.45 for rat and 0.27 for minipig.

TABLE 10

The Metabolic Stability of 2-Isopropyl-5-(isoquinolin-3-yl)benzene-1,3-diol (0.5 μM) in Liver Microsomes and Hepatocytes in Mouse, Rat, Minipig, Dog, Rabbit and Human

| Species | Liver Weight (g liver/kg) | Liver Microsomes CLint,mic (mL/min/g liver) | Half-life (min) | Scaled CLint,mic (mL/min/kg) | Hepatocytes CLint,hep (mL/min/g liver) | Half-life (min) | Scaled CLint,hep (mL/min/kg) |
|---|---|---|---|---|---|---|---|
| Mouse | 51 | 23.4 | 2.84 | 1194 | 22.3 | 8.39 | 1137 |
| Rat | 36 | 6.21 | 10.3 | 224 | 44.4 | 3.37 | 1597 |
| Minipig | 16.7 | 3.01 | 24.2 | 50.3 | 6.27 | 26.5 | 105 |
| Dog | 32.5 | 1.59 | 32.1 | 51.7 | 7.39 | 31.9 | 240 |
| Rabbit | 30.8 | 11.9 | 6.10 | 367 | 7.80 | 21.3 | 240 |
| Human | 24.5 | 1.35 | 40.9 | 33.1 | 15.7 | 10.4 | 384 |

The in vitro GSH-trapping assay detected reactive metabolites for 2-isopropyl-5-(isoquinolin-3-yl)benzene-1,3-diol following 1 hour incubation in human or rat liver microsomes supplemented with glutathione (GSH) and glutathione ethyl-ester (GSEE, Table 11). These results suggest that there is a potential for 2-isopropyl-5-(isoquinolin-3-yl)benzene-1,3-diol to form reactive metabolites. Despite these findings, 2-isopropyl-5-(isoquinolin-3-yl)benzene-1,3-diol is not expected to pose a safety risk due to the low systemic exposure in vivo following topical administration in rat and minipig (see Animal Pharmacokinetics section below) and estimated low plasma concentration in human (see Estimation of Human Plasma Concentration section below).

Example 17: Animal Pharmacokinetics

Figure 12A:
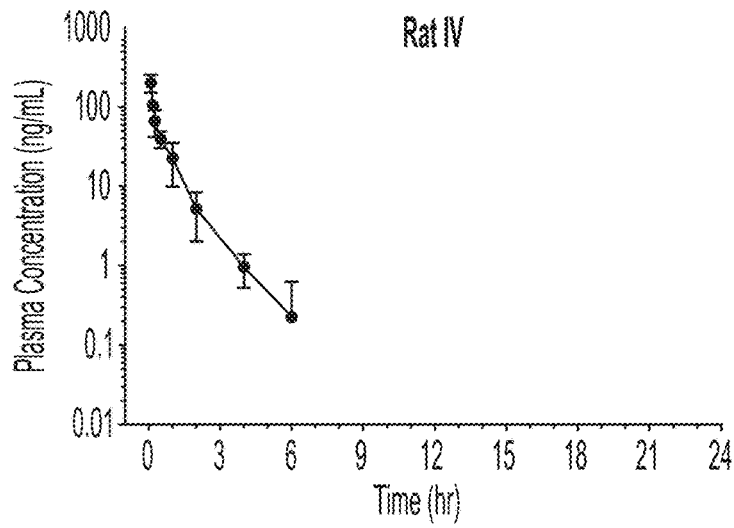
FIGS. 12A to 12C show mean (SD) plasma concentration-time profiles of 2-isopropyl-5-(isoquinolin-3-yl)benzene-1, 3-diol following a single administration in rat.
Figure 12B:
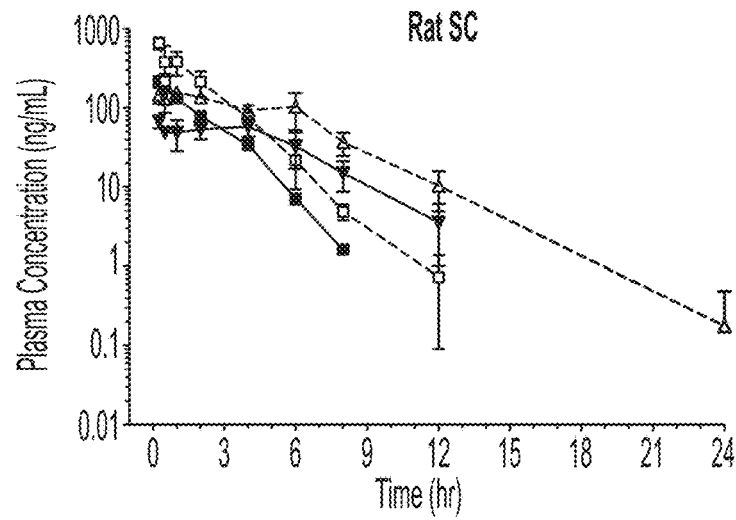
Figure 12C:
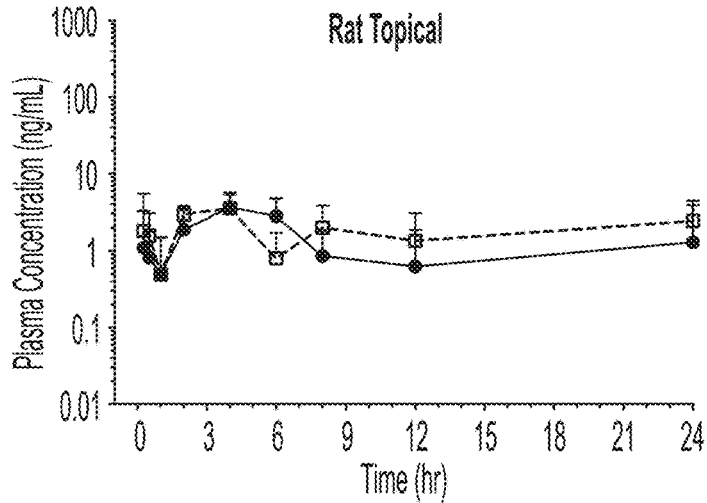

The preclinical pharmacokinetic profiles of 2-isopropyl-5-(isoquinolin-3-yl)benzene-1,3-diol were characterized by high clearance and high volume of distribution with short half-life in rat and minipig (Table 12, FIG. 12). Following subcutaneous administration in rat, the pharmacokinetics of 2-isopropyl-5-(isoquinolin-3-yl)benzene-1,3-diol in plasma were roughly linear between 10 and 25 mg/kg with both 30% Captisol and 30% Cavitron formulations. The 30% Captisol formulation achieved similar (<17%) plasma exposure ($AUC_{24h}$), whereas $C_{max}$ was 3.2 to 4.1 fold higher, compared to the 30% Cavitron formulation (Table 13). Bioavailability was 46.5% and 41.0% for 30% Captisol and 30% Cavitron, respectively. 30% Captisol formulation was selected for the 7-day subcutaneous toxicity study in rat. The bioavailability in minipig following a single 5 mg/kg oral dose with DMSO: Kolliphore HS15: hydroxypropyl-β-cyclodextrin (10:10:80) vehicle was 0.1%, suggesting that the oral route was not suitable for systemic safety assessment in minipig.

TABLE 12

Pharmacokinetics of 2-Isopropyl-5-(isoquinolin-3-yl)benzene-1,3-diol After a Single Intravenous Dose in Rat and Minipig.

| Species | Dose (mg/kg) | $CL_p$ (mL/min/kg) | $V_{ss}$ (L/kg) | $T_{1/2}$ (hr) | $AUC_\infty$ (ng * hr/mL) |
|---|---|---|---|---|---|
| Rat | 1 | 175.2 (±16.4) | 6.0 (±2.6) | 0.69 (±0.17) | 95.7 (±9.3) |
| Minipig | 1 | 21.3 (21.5, 20.8) | 1.5 (1.95, 1.04) | 1.02 (1.4, 0.7) | 783 (766, 800) |

Note:
Mean (±SD), n = 3 for rat and mean (individual) for minipig

TABLE 13

Effect of Dose and Formulation on 2-Isopropyl-5-(isoquinolin-3-yl)benzene-1,3-diol Pharmacokinetics After Subcutaneous Administration in Rat

| Formulation | Dose mg/kg | $C_{max}$ ng/mL | $C_{max}$/Dose ng/mL per mg/kg | $T_{max}$ hour | $AUC_{24\,h}$ ng * hr/mL | $AUC_{24\,h}$/Dose ng * hr/mL per mg/kg | F % |
|---|---|---|---|---|---|---|---|
| 30% Captisol | 10 | 239 (±16.2) | 23.9 (±1.6) | 0.4 (±0.1) | 437 (±28.8) | 43.7 (±2.9) | 45.9 (±2.9) |
|  | 25 | 661 (±111) | 26.4 (±4.4) | 0.25 (±0) | 1123 (±413) | 44.9 (±17) | 47.1 (±17) |
| 30% Cavitron | 10 | 73.9 (±6.6) | 7.4 (±0.66) | 1.8 (±1.9) | 385 (±90) | 38.5 (±9.0) | 41.3 (±10) |
|  | 25 | 162 (±20.4) | 6.5 (±0.82) | 2.4 (±3.1) | 960 (±148) | 38.4 (±5.6) | 40.7 (±5.8) |

Note:
Mean (±SD) n = 3

Following a single 20 mg (of 2-isopropyl-5-(isoquinolin-3-yl)benzene-1,3-diol)/kg topical administration with 10% body surface area (BSA) coverage in rats, 2-isopropyl-5-(isoquinolin-3-yl)benzene-1,3-diol exhibited comparable plasma exposure between 1% cream formulation 1 ($C_{max}$ 3.83 ng/mL and $AUC_{24h}$ 32.1 ng*hr/mL) and 1% gel formulation 1 ($C_{max}$ 5.18 ng/mL and $AUC_{24h}$ 46.0 ng*hr/mL) formulations. Bioavailability was very low; 1.7% for 1% cream formulation 1 and 2.4% for 1% gel formulation 1 (Table 14). Similarly, very low plasma exposure (87% of time points below lower limit of quantification, 50 pg/mL) was observed in minipig following a single 15 mg (of 2-isopropyl-5-(isoquinolin-3-yl)benzene-1,3-diol)/kg topical dose in 1% cream formulation 1 or 1% gel formulation 1 with 10% body surface area coverage, suggesting low systemic safety risk following topical administration.

Figure 13A:
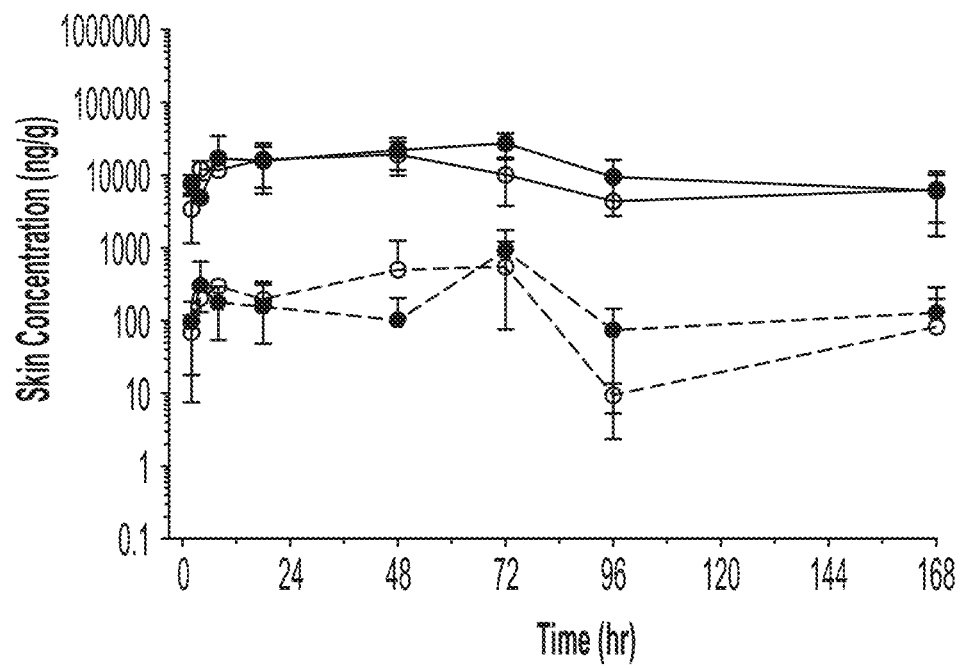
FIGS. 13A to 13B show individual epidermis/upper dermis and dermis concentration-time profiles of 2-isopropyl-5-(isoquinolin-3-yl)benzene-1,3-diol following a single topical dose in minipigs.
Figure 13B:
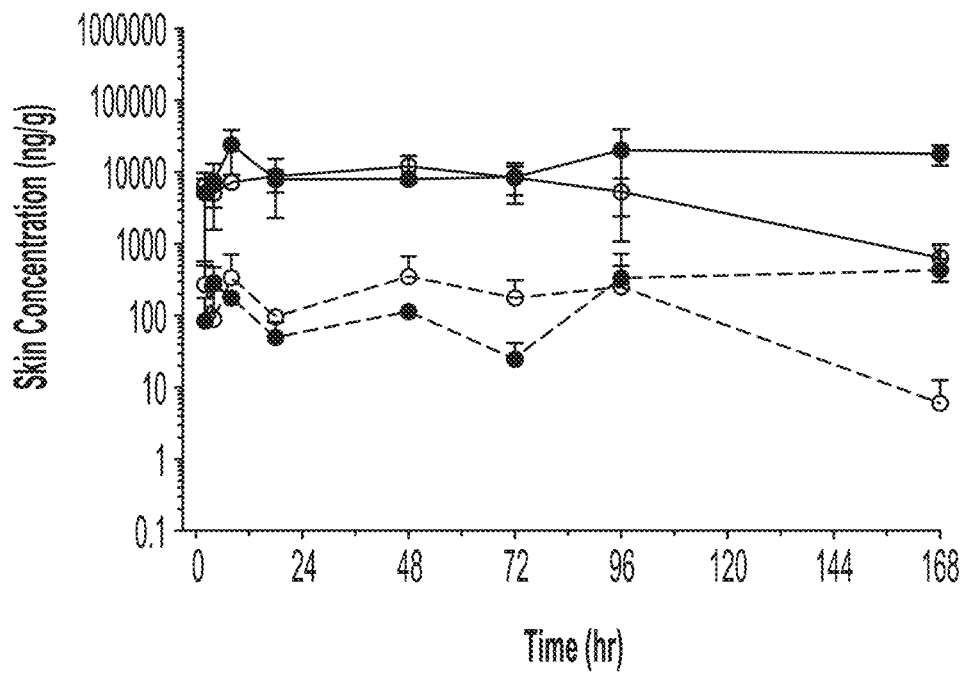
Figure 14A:
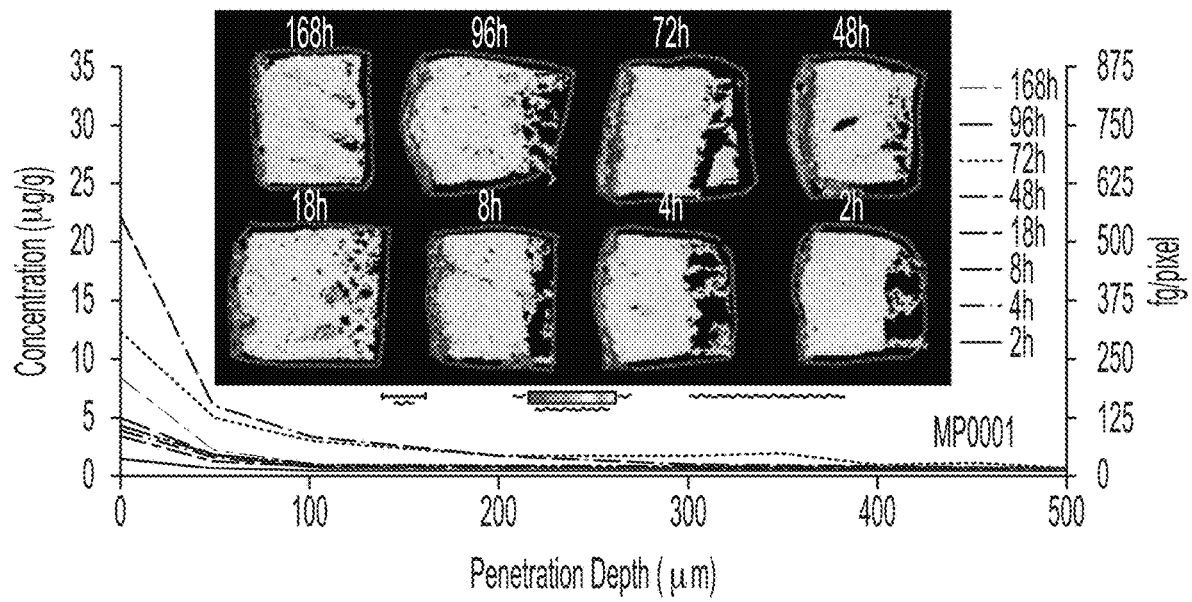
FIGS. 14A-B show depth profiling and skin MALDI IMS at different time points following a single topical dose with: 1% cream formulation 1 (FIG. 14A) and 1% gel formulation 1 (FIG. 14B) in minipig.
Figure 14B:
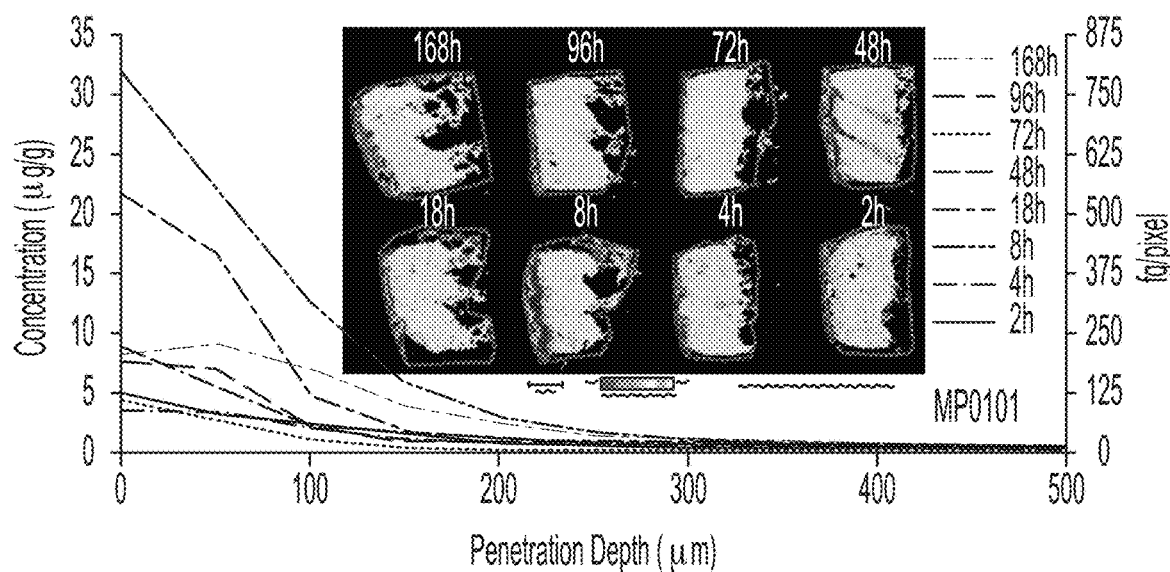

IMS (matrix-assisted laser desorption ionization imaging mass spectrometry) analysis. Higher concentrations of 2-isopropyl-5-(isoquinolin-3-yl)benzene-1,3-diol were noted in the epidermis/upper dermis (0-500 μm) compared to the dermis (500-1500 μm) for both formulations (Table 15, FIG. 13). The 1% cream formulation 1 achieved similar epidermis/upper dermis ($C_{max}$ 23.4 μg/g and $AUC_{168}$ h 2026 μg*hr/mL) and dermis ($C_{max}$ 0.74 μg/g and $AUC_{168}$ h 37.5 μg*hr/mL) exposures compared to that observed for the 1% gel formulation 1: epidermis ($C_{max}$ 18.0 μg/g and $AUC_{168h}$ 1729 μg*hr/mL) and dermis ($C_{max}$ 0.39 μg/g and $AUC_{168h}$ 34.7 μg*hr/mL). Depth profiling by MALDI IMS for one minipig from each group at different time points showed consistency with pharmacokinetic data: the maximum concentration observed in the epidermis (0-100 μm) and upper dermis (100-500 μm) for 1% cream formulation 1 were 9.4 μg/g at 48 hours and 1.37 μg/g at 72 hours; for 1% gel

TABLE 14

Plasma Pharmacokinetics of 2-Isopropyl-5-(Isoquinolin-3-yl)benzene-1,3-diol BSA in Rat

| Formulation | Dose mg/kg | Dose Area cm² | $C_{max}$ ng/mL | $T_{max}$ hour | $AUC_{24\,h}$ ng * hr/mL | $AUC_{24\,h}$/dose ng * hr/mL per mg/kg | F % |
|---|---|---|---|---|---|---|---|
| 1% cream form. 1 | 20 | 40.2 (±0.37) | 3.83 (±1.82) | 4.0 (±1.6) | 32.1 (±37.3) | 1.6 (±1.9) | 1.7 (±1.9) |
| 1% gel form. 1 | 20 | 39.8 (±1.08) | 5.18 (±1.92) | 2.6 (±1.8) | 46.0 (±14.7) | 2.3 (±0.7) | 2.4 (±0.7) |

Note:
Mean (±SD) n = 4

Skin pharmacokinetics of 2-isopropyl-5-(isoquinolin-3-yl)benzene-1,3-diol was investigated in Gottingen minipig for 7 days following a single topical administration of 1% cream formulation 1 or 1% gel formulation 1. The formulations were administered at a dose rate of 1 g of formulation/44 cm², and skin biopsies were collected at different time points up to 168 hours for pharmacokinetics (tissue homogenate levels in epidermis and dermis) and MALDI formulation 1 these were respectively 21.8 μg/g and 1.66 μg/g at 8 hours (Table 16). Some of the MALDI images for 1% cream formulation 1 (e.g. 8 hours) and 1% gel formulation 1 (e.g. 48 hours) also showed drug penetration via the hair follicles, suggesting that the skin appendage route may contribute to systemic exposure (FIG. 12). MALDI IMS signal dropped to below the limit of detection (approximately 500 ng/g) by around 500 μm depth.

TABLE 15

Skin Pharmacokinetics of 2-Isopropyl-5-(isoquinolin-3-yl)benzene-1,3-diol
Following a Single Topical Administration (1 g of Formulation/44 cm²) in Minipig

| Formulation | Animal ID | Epidermis/Upper Dermis (0-500 μm) | | | Dermis (500-1500 μm) | | |
|---|---|---|---|---|---|---|---|
| | | $C_{max}$ (μg/g) | $AUC_{168\,h}$ (μg * hr/g) | $T_{max}$ (hr) | $C_{max}$ (μg/g) | $AUC_{168\,h}$ (μg * hr/g) | $T_{max}$ (hr) |
| 1% cream formulation 1 | S0001 | 19.2 | 1659 | 48 | 0.55 | 36.7 | 72 |
| | S0002 | 27.5 | 2394 | 72 | 0.92 | 38.3 | 72 |
| | Mean | 23.4 | 2026 | 60 | 0.74 | 37.5 | 72 |
| 1% gel formulation 1 | S0101 | 23.9 | 2401 | 8 | 0.43 | 38.4 | 168 |
| | S0102 | 12.0 | 1056 | 48 | 0.35 | 31.0 | 48 |
| | Mean | 18.0 | 1729 | 28 | 0.39 | 34.7 | 108 |

TABLE 16

Skin Levels of 2-Isopropyl-5-(isoquinolin-3-yl)benzene-1,3-diol
Determined by MALDI IMS in Minipig Following a Single Topical
Administration (1 g of Formulation/44 cm²)

| Formulation | Animal ID | Epidermis (0-100 μm) | | Upper Dermis (100-500 μm) | |
|---|---|---|---|---|---|
| | | $C_{max}$ (μg/g) | $T_{max}$ (hr) | $C_{max}$ (μg/g) | $T_{max}$ (hr) |
| 1% cream formulation 1 | S0001 | 9.4 | 48 | 1.37 | 72 |
| 1% gel formulation 1 | S0101 | 21.8 | 8 | 1.67 | 8 |

Example 18: Estimation of Human Plasma Concentration Following Topical Administration The human plasma concentration at steady state ($C_{ss,human}$) following topical application of 2-isopropyl-5-(isoquinolin-3-yl)benzene-1,3-diol was predicted by assuming that the topically applied drug is absorbed through the skin at a constant rate, and $$C_{ss,human} = \frac{\text{Topical Skin Flux} \times \text{Dosing Area}}{CL_{human}}.$$

The plasma clearance ($CL_{human}$) was estimated from the in vitro and preclinical pharmacokinetic studies. Using allometric scaling, based on in vivo clearance in rat and minipig, liver blood flow rate method, and IVIVE approach with well-stirred model (assuming that hepatic metabolic clearance is the major elimination pathway), $CL_{human}$ was predicted to be between 6 to 25 mL/min/kg. The lowest predicted clearance (6 mL/min/kg predicted from allometric scaling with plasma protein binding correction) was selected to evaluate the potential systemic safety risk of 2-isopropyl-5-(isoquinolin-3-yl)benzene-1,3-diol in human.

In the in vitro human skin penetration evaluation of 2-isopropyl-5-(isoquinolin-3-yl)benzene-1,3-diol loaded at 0.1% cream formulation 1, 0.5% cream formulation 1 and 1% cream formulation 1, the receiving fluid levels were below the lower limit of quantification (LLOQ; 80 pg/mL) over 16 hours, therefore preventing the calculation of the skin flux values. An estimated skin flux prediction was conducted, assuming a 2-hour lag time and receiving fluid levels obtained every two hours at the LLOQ level for 16 hours, leading to a calculated flux of 0.048 ng/cm²/h.

Healthy skin is an effective protective barrier to most xenobiotics; therefore the relevance of a flux value derived from the ex vivo skin penetration assay, which uses healthy human skin from abdominoplasty surgeries, may not translate to what is observed following application onto unhealthy skin. In order to account for damaged skin barrier, a 10-fold increase in flux was incorporated in the initial prediction of human systemic exposure following topical administration of 2-isopropyl-5-(isoquinolin-3-yl)benzene-1,3-diol. Calculation of human systemic exposure with a 100-fold increase in flux has also been performed to account for the worst case estimation. A 10% body surface area (1800 cm²) in human was used for this estimation. Therefore, for the purpose of safety margin estimation and considering the conditions explained herein, the estimated $C_{ss,human}$ is 0.34 ng/mL with the corresponding $AUC_{ss,24h}$ is 8.2 ng*h/mL. In clinical practice, topical treatment for atopical dermatitis can be up to 50% BSA (9000 cm2) and therefore corresponding estimated $C_{ss,human}$ and $AUC_{ss,24h}$ with 10-fold increase in flux is 0.17 ng/mL and 4.1 ng*h/mL. Different simulated scenarios are summarized in Table 17.

TABLE 17

Estimated Human Plasma Concentration at Steady State
(Css,human) and Corresponding Area Under the Curve over 24 Hours
($AUC_{24h}$) Following Topical Application of 2-Isopropyl-5-
(isoquinolin-3-yl)benzene-1,3-diol (1% Cream Formulation 1)

| Topical Skin Flux (ng/cm²/h) | Dose Area (cm²) | Clearance (ml/min/kg) | Body Weight (kg) | Estimated $C_{ss}$ (ng/mL) | Estimated $AUC_{24h}$ (ng * hr/mL) |
|---|---|---|---|---|---|
| 0.048 (calculated) | 1800 | 6 | 70 | 0.003 | 0.08 |
| 0.48 (10-fold increase) | 1800 | 6 | 70 | 0.034 | 0.82 |
| 4.8 (100-fold increase) | 1800 | 6 | 70 | 0.343 | 8.23 |
| 0.048 (calculated) | 9000 | 6 | 70 | 0.015 | 0.36 |
| 0.48 (10-fold increase) | 9000 | 6 | 70 | 0.170 | 4.08 |
| 4.8 (100-fold increase) | 9000 | 6 | 70 | 1.715 | 41.2 |

Example 19: Integration of Preclinical Target Engagement Studies for Human Dose Selection Based on the combination of data from in vitro potency, ex vivo human skin target engagement and penetration, and minipig skin PK data, it is expected that the 1% cream formulation 1 following daily dosing will result in sufficient concentrations of 2-isopropyl-5-(isoquinolin-3-yl)benzene-1,3-diol at the target skin site (viable epidermis and upper dermis), resulting in AhR target engagement.

The free drug concentrations in the skin, obtained after topical application of the 1% cream formulation 1 and calculated from the ex vivo human skin and minipig skin PK studies (via MALDI-IMS analysis), suggest sufficient coverage of the effective concentration obtained via in vitro potency assays (50% of AhR activation in fluorescence-based reporter assay for CYP1A1 gene expression and 50% of IL-17A production inhibition in primary human peripheral blood CD4+ T-cells) shown in Table 18. These calculations assumed same skin binding between human and minipig and 100% dermal bioavailability after correction for unbound skin fraction.

TABLE 18

Calculated free skin concentrations (µM) of 2-isopropyl-5-(isoquinolin-3-yl)benzene-1,3-diol in the Epidermis and Upper Dermis Compartments (± SEM) as Determined by MALDI-IMS Analysis

| | | MALDI-IMS of ex vivo human skin (n = *) | | | | MALDI-IMS of in vivo minipig skin | | | |
| --- | --- | --- | --- | --- | --- | --- | --- | --- | --- |
| | | Epidermis | | Upper Dermis | | $C_{max}$ (n = 3 for one animal) | | | |
| | | Concentration at 24 h (0-100 µm) | | Concentration at 24 h (100-500 µm) | | | Epidermis $C_{max}$ (0-100 µm) | | Upper Dermis $C_{max}$ (100-500 µm) |
| Formulation | Dose (mg/cm$^2$) | Total | Free | Total | Free | Dose (mg/cm$^2$) | Total Free | Total | Free |
| 1% cream form. 1 | 0.1 (non-occluded) | 1448.2 ± 13.6 | 742.9 ± 7.0 | 28.3 ± 1.7 | 9.7 ± 0.6 (613-fold over AhR EC$_{50}$; 69-fold over IL17A IC$_{50}$) | 0.23 (semi-occluded) | 33.8 ± 17.3 ± 4.9 2.5 | 4.9 ± 0.5 | 1.7 ± 0.2 (108-fold over AhR EC$_{50}$; 12-fold over IL17A IC$_{50}$) |

Note:
AhR activation in fluorescence-based reporter assay for CYP1A1 gene expression EC50 = 0.0158 µM; IL-17A inhibition in primary human peripheral blood CD4+ T-cells IC50 = 0.14 µM.
Values reported for the MALDI-IMS analysis of ex vivo human skin are the average of 6 skin sections, taken from 2 skin penetration replicates (3 sections per skin replicate), using 1 skin donor All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A method of treating an inflammatory disorder selected from the group consisting of psoriasis, atopic dermatitis, vitiligo, acne, uveitis radiation dermatitis, COPD, asthma, multiple sclerosis, and inflammatory bowel disease, in a subject in need thereof, comprising administering to said subject a therapeutically effective amount of a compound which is 2-isopropyl-5-(isoquinolin-3-yl)benzene-1,3-diol of the formula:

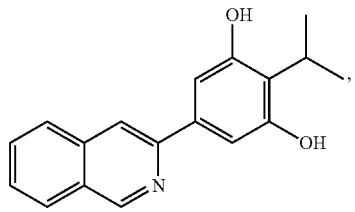 [SMILES: CC(C)c1c(O)cc(-c2cc3ccccc3cn2)cc1O]

or a pharmaceutically acceptable salt, solvate or hydrate thereof to thereby treat the inflammatory disorder.

2. The method of claim 1, wherein the compound is 2-isopropyl-5-(isoquinolin-3-yl)benzene-1,3-diol of the formula:

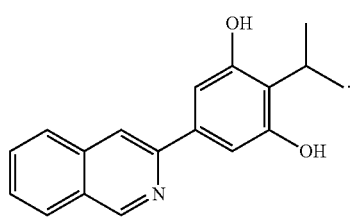 [SMILES: CC(C)c1c(O)cc(-c2cc3ccccc3cn2)cc1O]

3. The method of claim 1 wherein the inflammatory disorder is selected from the group consisting of psoriasis, atopic dermatitis, and acne.

4. The method of claim 1 wherein the compound, or a pharmaceutically acceptable salt, solvate or hydrate thereof, is administered topically.

5. The method of claim 1, wherein the compound is at least 90% pure by weight.

6. The method of claim 1, wherein the compound is at least 95% pure by weight.

7. The method of claim 1, wherein the compound is at least 98% pure by weight.

8. The method of claim 1, wherein the compound is at least 99% pure by weight.

9. A method of treating an inflammatory disorder selected from the group consisting of psoriasis, acne, and atopic dermatitis, in a subject in need thereof, comprising administering to said subject a pharmaceutical composition comprising therapeutically effective amount of a compound which is 2-isopropyl-5-(isoquinolin-3-yl)benzene-1,3-diol of the formula:

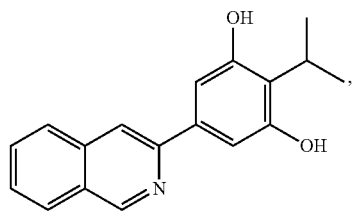 [SMILES: CC(C)c1c(O)cc(-c2cc3ccccc3cn2)cc1O]

or a pharmaceutically acceptable salt, solvate or hydrate thereof and a pharmaceutically acceptable carrier or diluent to thereby treat the inflammatory disorder.

10. The method of claim 9, wherein the compound is 2-isopropyl-5-(isoquinolin-3-yl)benzene-1,3-diol of the formula:

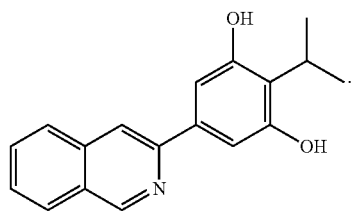 [SMILES: CC(C)c1c(O)cc(-c2cc3ccccc3cn2)cc1O]

11. The method of claim 9, wherein the pharmaceutically acceptable carrier or diluent is suitable for topical administration.

12. The method of claim 9, wherein the pharmaceutically acceptable carrier or diluent is suitable for a gel topical administration.

13. The method of claim 9, wherein the pharmaceutically acceptable carrier or diluent is suitable for a cream topical administration.

14. The method of claim 9, wherein the pharmaceutical composition is administered topically.

15. The method of claim 1 wherein the inflammatory disorder is selected from the group consisting of COPD and inflammatory bowel disease.

16. A method of treating an inflammatory disorder selected from the group consisting of COPD and inflammatory bowel disease, in a subject in need thereof, comprising administering to said subject a pharmaceutical composition comprising a therapeutically effective amount of a compound which is 2-isopropyl-5-(isoquinolin-3-yl)benzene-1,3-diol of the formula:

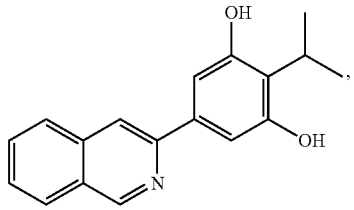 [SMILES: CC(C)c1c(O)cc(-c2cc3ccccc3cn2)cc1O]

or a pharmaceutically acceptable salt, solvate or hydrate thereof and a pharmaceutically acceptable carrier or diluent to thereby treat the inflammatory disorder.

17. The method of claim 16, wherein the compound is 2-isopropyl-5-(isoquinolin-3-yl)benzene-1,3-diol of the formula:

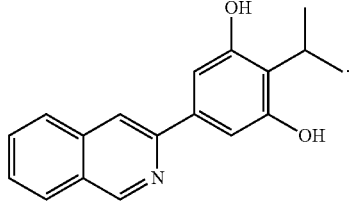 [SMILES: CC(C)c1c(O)cc(-c2cc3ccccc3cn2)cc1O]

18. The method of claim 16, wherein the pharmaceutically acceptable carrier or diluent is suitable for oral, parenteral or intranasal administration.

19. The method of claim 16, wherein the pharmaceutically acceptable carrier or diluent is suitable for oral administration.

20. The method of claim 16, wherein the pharmaceutically acceptable carrier or diluent is suitable for parenteral administration.

21. The method of claim 16, wherein the pharmaceutical composition is administered orally.

22. The method of claim 16, wherein the pharmaceutical composition is administered parenterally.

23. The method of claim 16, wherein the pharmaceutical composition is administered by intranasal or oral inhalation.

* * * * *